US012558521B2

(12) United States Patent
Korkuch et al.

(10) Patent No.: US 12,558,521 B2
(45) Date of Patent: Feb. 24, 2026

(54) EXPANDABLE INTRODUCER SHEATH FOR MEDICAL DEVICE

(71) Applicant: ABIOMED, Inc., Danvers, MA (US)

(72) Inventors: Christopher Nason Korkuch, Danvers, MA (US); Glen R. Fantuzzi, Danvers, MA (US); Alexander Ship, Danvers, MA (US); Robert Swierczek, Danvers, MA (US); Robert Fishman, Danvers, MA (US)

(73) Assignee: ABIOMED, Inc., Danvers, MA (US)

( * ) Notice: Subject to any disclaimer, the term of this patent is extended or adjusted under 35 U.S.C. 154(b) by 586 days.

(21) Appl. No.: 17/954,889

(22) Filed: Sep. 28, 2022

(65) Prior Publication Data

US 2023/0085812 A1     Mar. 23, 2023

Related U.S. Application Data

(63) Continuation of application No. 16/540,922, filed on Aug. 14, 2019, now Pat. No. 11,517,720.

(Continued)

(51) Int. Cl.
*A61M 25/06*      (2006.01)
*A61M 25/00*      (2006.01)
(Continued)

(52) U.S. Cl.
CPC .... *A61M 25/0662* (2013.01); *A61M 25/0023* (2013.01); *A61M 25/0045* (2013.01);
(Continued)

(58) Field of Classification Search
CPC .............. A61M 25/0662; A61M 60/13; A61M 60/865; A61M 60/165; A61M 60/216; A61M 25/0023; A61M 25/0045
(Continued)

(56) References Cited

U.S. PATENT DOCUMENTS

| | | | |
|---|---|---|---|
| 4,699,611 A | 10/1987 | Bowden |
| 5,139,486 A | 8/1992 | Moss |

(Continued)

FOREIGN PATENT DOCUMENTS

| | | |
|---|---|---|
| CN | 1494449 A | 5/2004 |
| CN | 101431963 A | 5/2009 |

(Continued)

OTHER PUBLICATIONS

International Preliminary Report on Patentability and Written Opinion for International Application No. PCT/US2018/021695 dated Sep. 10, 2019 (6 pages).

(Continued)

*Primary Examiner* — Phillip A Gray
(74) *Attorney, Agent, or Firm* — BOTOS CHURCHILL IP LAW LLP

(57)     ABSTRACT

An introducer sheath for the insertion of a medical device into a blood vessel having an expandable sheath. The sheath has a length, a thickness, and proximal and distal ends. The expandable sheath has a frame extending longitudinally between the proximal and the distal ends, and having an exterior surface and an interior surface that forms an interior lumen along the length of the frame. The frame is configured to achieve an expanded state and a contracted state, the expanded state forming an expanded cross-section in the lumen for passing a medical device therethrough. The frame has a smooth coating about the exterior surface and protrusions extending into the lumen along the interior surface. The introducer sheath can be introduced into a patient in the contracted state, with the distal end of the introducer sheath prevented from moving in the proximal direction by an abutment against a dilator end surface.

19 Claims, 87 Drawing Sheets

Related U.S. Application Data

(60) Provisional application No. 62/718,681, filed on Aug. 14, 2018.

(51) Int. Cl.

| | |
|---|---|
| *A61M 60/13* | (2021.01) |
| *A61M 60/165* | (2021.01) |
| *A61M 60/216* | (2021.01) |
| *A61M 60/865* | (2021.01) |
| *A61M 39/06* | (2006.01) |

(52) U.S. Cl.
CPC ...... *A61M 25/005* (2013.01); *A61M 25/0097* (2013.01); *A61M 60/13* (2021.01); *A61M 60/165* (2021.01); *A61M 60/216* (2021.01); *A61M 60/865* (2021.01); *A61M 2025/0024* (2013.01); *A61M 2025/004* (2013.01); *A61M 2025/0047* (2013.01); *A61M 2025/0681* (2013.01); *A61M 2039/0626* (2013.01)

(58) Field of Classification Search
USPC ........................................................ 604/508
See application file for complete search history.

(56) References Cited

U.S. PATENT DOCUMENTS

| | | | |
|---|---|---|---|
| 5,234,425 A | 8/1993 | Fogarty et al. |
| 5,304,142 A | 4/1994 | Liebl et al. |
| 5,320,611 A | 6/1994 | Bonutti et al. |
| 5,395,341 A | 3/1995 | Slater |
| 5,397,310 A | 3/1995 | Chu et al. |
| 5,407,430 A | 4/1995 | Peters |
| 5,488,960 A | 2/1996 | Toner |
| 5,492,530 A | 2/1996 | Fischell et al. |
| 5,536,255 A | 7/1996 | Moss |
| 5,573,517 A | 11/1996 | Bonutti et al. |
| 5,653,697 A | 8/1997 | Quiachon et al. |
| 5,814,058 A | 9/1998 | Carlson et al. |
| 5,911,702 A | 6/1999 | Romley et al. |
| 5,935,122 A | 8/1999 | Fourkas et al. |
| 5,943,462 A | 8/1999 | Schofield et al. |
| 5,944,691 A | 8/1999 | Querns et al. |
| 5,971,993 A | 10/1999 | Hussein et al. |
| 5,997,562 A | 12/1999 | Zadno-Azizi et al. |
| 6,120,480 A | 9/2000 | Zhang et al. |
| 6,197,016 B1 | 3/2001 | Fourkas et al. |
| 6,338,730 B1 | 1/2002 | Bonutti et al. |
| 6,428,556 B1 | 8/2002 | Chin |
| 6,458,867 B1 | 10/2002 | Wang et al. |
| 6,579,264 B1 | 6/2003 | Rossi |
| 6,613,038 B2 | 9/2003 | Bonutti et al. |
| 6,692,462 B2 | 2/2004 | Mackenzie et al. |
| 6,814,715 B2 | 11/2004 | Bonutti et al. |
| 6,989,003 B2 | 1/2006 | Wing et al. |
| 7,025,746 B2 | 4/2006 | Tal |
| 7,722,567 B2 | 5/2010 | Tal |
| 7,727,251 B2 | 6/2010 | Spurchise et al. |
| 7,927,309 B2 | 4/2011 | Palm |
| 8,323,350 B2 | 12/2012 | Nissl |
| 8,475,431 B2 | 7/2013 | Howat |
| 8,597,277 B2 | 12/2013 | Lenker et al. |
| 8,663,541 B2 | 3/2014 | Chun et al. |
| 8,672,888 B2 | 3/2014 | Tal |
| 8,758,402 B2 | 6/2014 | Jenson et al. |
| 8,814,832 B1 | 8/2014 | Al-Rashdan et al. |
| 9,126,015 B2 | 9/2015 | Krolik et al. |
| 9,320,508 B2 | 4/2016 | Carroux |
| 9,446,218 B2 | 9/2016 | Accisano |
| 9,474,884 B1 | 10/2016 | Aman et al. |
| 9,586,033 B2 | 3/2017 | Tegels |
| 9,693,800 B2 | 7/2017 | Aman et al. |
| 9,782,560 B2 | 10/2017 | Schaeffer |
| 9,895,245 B2 | 2/2018 | Puckett et al. |
| 9,974,561 B2 | 5/2018 | Benning et al. |
| 10,143,491 B2 | 12/2018 | Clancy et al. |
| 10,449,071 B2 | 10/2019 | Jordan |
| 10,499,895 B2 | 12/2019 | Anderson |
| 10,537,718 B2 | 1/2020 | Lederman et al. |
| 10,625,050 B2 | 4/2020 | Mcfarland |
| 10,682,157 B2 | 6/2020 | Bierman et al. |
| 10,695,531 B2 | 6/2020 | Suzuki |
| 10,874,511 B2 | 12/2020 | Ginn |
| 11,464,963 B1 | 10/2022 | Fishman et al. |
| 2001/0012946 A1 | 8/2001 | MacKenzie et al. |
| 2002/0052624 A1 | 5/2002 | Bonutti et al. |
| 2002/0072712 A1 | 6/2002 | Nool et al. |
| 2003/0014068 A1* | 1/2003 | Bonutti ................. A61M 25/06 606/190 |
| 2003/0153874 A1 | 8/2003 | Tal |
| 2005/0027257 A1 | 2/2005 | Davey |
| 2005/0149105 A1 | 7/2005 | Leeflang et al. |
| 2006/0041270 A1 | 2/2006 | Lenker et al. |
| 2006/0135981 A1 | 6/2006 | Lenker et al. |
| 2006/0212062 A1* | 9/2006 | Farascioni ......... A61B 17/3439 606/191 |
| 2006/0259051 A1 | 11/2006 | Nissl |
| 2006/0287574 A1 | 12/2006 | Chin |
| 2006/0287669 A1 | 12/2006 | Casey et al. |
| 2007/0144731 A1 | 6/2007 | Murray et al. |
| 2007/0169877 A1 | 7/2007 | Leeflang et al. |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0082165 A1 | 4/2008 | Wilson et al. |
| 2008/0183136 A1 | 7/2008 | Lenker et al. |
| 2009/0216232 A1 | 8/2009 | Buford et al. |
| 2009/0240202 A1 | 9/2009 | Drasler et al. |
| 2009/0259200 A1 | 10/2009 | Lampropoulos et al. |
| 2010/0051182 A1 | 3/2010 | Graham |
| 2010/0198160 A1 | 8/2010 | Voss |
| 2011/0144690 A1 | 6/2011 | Bishop et al. |
| 2011/0152763 A1 | 6/2011 | Bishop et al. |
| 2011/0166637 A1 | 7/2011 | Irwin et al. |
| 2012/0022617 A1 | 1/2012 | Tockman et al. |
| 2012/0035548 A1 | 2/2012 | Mackenzie et al. |
| 2012/0109056 A1 | 5/2012 | Rasmussen |
| 2012/0116354 A1 | 5/2012 | Heuser |
| 2012/0130192 A1 | 5/2012 | Rasmussen et al. |
| 2012/0310085 A1 | 12/2012 | Herweck et al. |
| 2013/0000551 A1 | 1/2013 | Guignon et al. |
| 2013/0014068 A1 | 1/2013 | Gangadharan et al. |
| 2013/0131718 A1 | 5/2013 | Jenson et al. |
| 2013/0131787 A1 | 5/2013 | Ginn |
| 2013/0138201 A1 | 5/2013 | Ginn |
| 2013/0184736 A1 | 7/2013 | Aman et al. |
| 2013/0317438 A1 | 11/2013 | Ellingwood et al. |
| 2013/0317481 A1 | 11/2013 | Ellingwood et al. |
| 2013/0338677 A1 | 12/2013 | Schwitzer et al. |
| 2014/0046425 A1 | 2/2014 | Cannon et al. |
| 2014/0073926 A1 | 3/2014 | Rajendran et al. |
| 2014/0173878 A1 | 6/2014 | Merk et al. |
| 2014/0275795 A1 | 9/2014 | Little et al. |
| 2014/0336752 A1 | 11/2014 | Ginn et al. |
| 2015/0025648 A1 | 1/2015 | Mctighe et al. |
| 2015/0094795 A1 | 4/2015 | Ginn et al. |
| 2015/0165158 A1 | 6/2015 | Ren et al. |
| 2015/0246203 A1 | 9/2015 | Ciurea et al. |
| 2016/0066948 A1 | 3/2016 | Ellingwood et al. |
| 2016/0067454 A1 | 3/2016 | Furnish et al. |
| 2016/0074011 A1 | 3/2016 | Johnson et al. |
| 2016/0074067 A1 | 3/2016 | Furnish et al. |
| 2016/0128723 A1 | 5/2016 | Ginn et al. |
| 2016/0220358 A1 | 8/2016 | Wilson et al. |
| 2016/0338828 A1 | 11/2016 | Ginn |
| 2016/0354583 A1 | 12/2016 | Ellingwood et al. |
| 2017/0000973 A1 | 1/2017 | Otake et al. |
| 2017/0014232 A1 | 1/2017 | Ginn et al. |
| 2017/0056063 A1 | 3/2017 | Ellingwood et al. |
| 2017/0080180 A1 | 3/2017 | Eilat |
| 2017/0095640 A1 | 4/2017 | Rogers et al. |
| 2017/0239443 A1 | 8/2017 | Abitabilo et al. |
| 2017/0265891 A1 | 9/2017 | Mcfarland |
| 2017/0281908 A1 | 10/2017 | Ellingwood et al. |

(56) References Cited

U.S. PATENT DOCUMENTS

| | | | |
|---|---|---|---|
| 2018/0055637 | A1 | 3/2018 | Von Oepen et al. |
| 2018/0071091 | A9 | 3/2018 | Ginn et al. |
| 2018/0256859 | A1 | 9/2018 | Korkuch |
| 2018/0271558 | A1 | 9/2018 | Bierman et al. |
| 2018/0325706 | A1 | 11/2018 | Hebert et al. |
| 2019/0030294 | A1 | 1/2019 | Mclaughlin et al. |
| 2019/0070394 | A1 | 3/2019 | Appling et al. |
| 2019/0183525 | A9 | 6/2019 | Ginn et al. |
| 2019/0247617 | A1 | 8/2019 | Farnan |
| 2019/0247627 | A1 | 8/2019 | Korkuch et al. |
| 2019/0307589 | A1 | 10/2019 | Goldberg et al. |
| 2020/0360140 | A1 | 11/2020 | Ginn et al. |
| 2020/0360165 | A1 | 11/2020 | Ginn et al. |
| 2020/0367929 | A1 | 11/2020 | Ginn et al. |

FOREIGN PATENT DOCUMENTS

| | | | |
|---|---|---|---|
| CN | 105163790 | A | 12/2015 |
| EP | 2133115 | A1 | 12/2009 |
| EP | 2676641 | A2 | 12/2013 |
| EP | 2962720 | A1 | 1/2016 |
| EP | 2995268 | A1 | 3/2016 |
| JP | 2003503164 | A | 1/2003 |
| JP | 2008011867 | A | 1/2008 |
| JP | 2009006117 | A | 1/2009 |
| JP | 2011517424 | A | 6/2011 |
| JP | 5199434 | B2 | 2/2013 |
| JP | 2016522032 | A | 7/2016 |
| JP | 2016189839 | A | 11/2016 |
| JP | 2019076330 | A | 5/2019 |
| KR | 20170029555 | A | 3/2017 |
| WO | 0102045 | A1 | 1/2001 |
| WO | 0211806 | A1 | 2/2002 |
| WO | 02055124 | A2 | 7/2002 |
| WO | 2004022148 | A1 | 3/2004 |
| WO | 2004037333 | A1 | 5/2004 |
| WO | 2013163366 | A1 | 10/2013 |
| WO | 2014186414 | A1 | 11/2014 |
| WO | 2016044854 | A1 | 3/2016 |
| WO | 2017110757 | A1 | 6/2017 |
| WO | 2019008922 | A1 | 1/2019 |

OTHER PUBLICATIONS

International Preliminary Report on Patentability and Written Opinion for International Application No. PCT/US2019/018275 dated Aug. 27, 2020 (14 pages).

International Search Report and Written Opinion for corresponding International Application No. PCT/US2019/018275 dated Jul. 15, 2019 (20 pages).

International Search Report and Written Opinion for International Application No. PCT/US2018/021695 dated Jun. 22, 2018 (9 pages).

International Search Report and Written Opinion for International Application No. PCT/US2019/018275 dated Jul. 15, 2019 (23 pages).

International Search Report and Written Opinion for International Application No. PCT/US2019/046543 dated Jan. 10, 2020 (23 pages).

Office Action for Chinese Application No. 201980026114.4 dated May 16, 2022 (22 pages).

Office Action from corresponding Japanese Patent Application No. 2023-208189 dated Dec. 9, 2024 (7 pp.).

Office Action from corresponding Japanese Patent Application No. 2024-038097 dated Feb. 3, 2025 (6 pp.).

Office Action dated Jan. 29, 2024 for KR Appln. No. 10-2020-7026652, (22 pp.).

Office Action issued in Japanese Patent Application No. 2021-507622 on Dec. 12, 2023 (9 pp.).

First Examination Report issued in corresponding Indian Patent Application No. 202017038059 dated Dec. 9, 2022 (7 pp.).

Office Action and Search Report from corresponding Chinese Application No. 2019800261144, dated Nov. 21, 2022, (14 pp.).

Office Action from corresponding Japanese Application No. JP2020-543644 dated Dec. 27, 2022. (10 pp).

Office Action from corresponding Korean Patent Application No. 10-2021-7007739 dated Apr. 23, 2024 (12 pp.).

First Examination Report issued in corresponding Indian Patent Application No. 202117009049 dated Nov. 11, 2022 (6 pp.).

Office Action from corresponding Chinese Application No. 2019800635496 dated Nov. 2, 2022 (17 pp.).

Search Report from corresponding Chinese Application No. 2019800635496 dated Nov. 10, 2022 (2 pp.).

Office Action from corresponding Japanese Patent Application No. 2021-507622 dated Jun. 14, 2023 (5 pp.).

Office Action from corresponding Japanese Patent Application No. 2020-543644 dated Sep. 11, 2023 (6 pp.).

Notice of Reasons for Refusal issued in corresponding Japanese Patent Application No. 2023-208189, dated Jun. 9, 2024 (7 pp.).

Examination Report No. 1 issued in New Zealand patent application No. 808070, dated Aug. 26, 2025 (4 pp.).

Examination Report No. 1 issued in New Zealand patent application No. 808071, dated Aug. 26, 2025 (4 pp.).

Office Action from corresponding Israeli Patent Application No. 305105 dated Sep. 4, 2025 (3 pp.).

Office Action from corresponding New Zealand Patent Application No. 766883 dated Aug. 26, 2025 (4pp.).

Office Action from corresponding New Zealand Patent Application No. 808063 dated Aug. 26, 2025 (4 pp.).

Office Action from corresponding New Zealand Patent Application No. 808066 dated Aug. 26, 2025 (4 pp.).

Hearing Adjournment Notice for Indian Patent Application No. 202117009049, Aug. 25, 2025 (2 pages).

Office Action from corresponding Chinese Patent Application No. 202310681676.0 dated Jul. 3, 2025 (20 pp.).

European search report for Application No. EP25187897 dated Oct. 21, 2025, 11 pp.

* cited by examiner

STRETCHED→RELAXED

RELAXED→EXPANDED

1100

1104   1106

1102

1100

1104   1106

1102

1100

1108   1110

1102

MANDREL
1302

BRAID
1306

SILICONE
1310

DIP CONTAINER
1308

1. PRE DIP STAGE

1304
MACHINE FEATURE
INTO DIP COAT MANDREL TIP

*Feature design shown is for illustration Proposes only*

POST DIP @ ITH MANDREL FEATURE TRANSFERRED

1306

B. POST DIP STAGE

1306

B. TIP DIP STAGE

1306

1500

Dip braid into polymer container

1502

Encapsulate braid with polymer

1504

Expose braid with polymer to hydrophilic coating

1506

Coat braid with polymer with hydrophilic coating

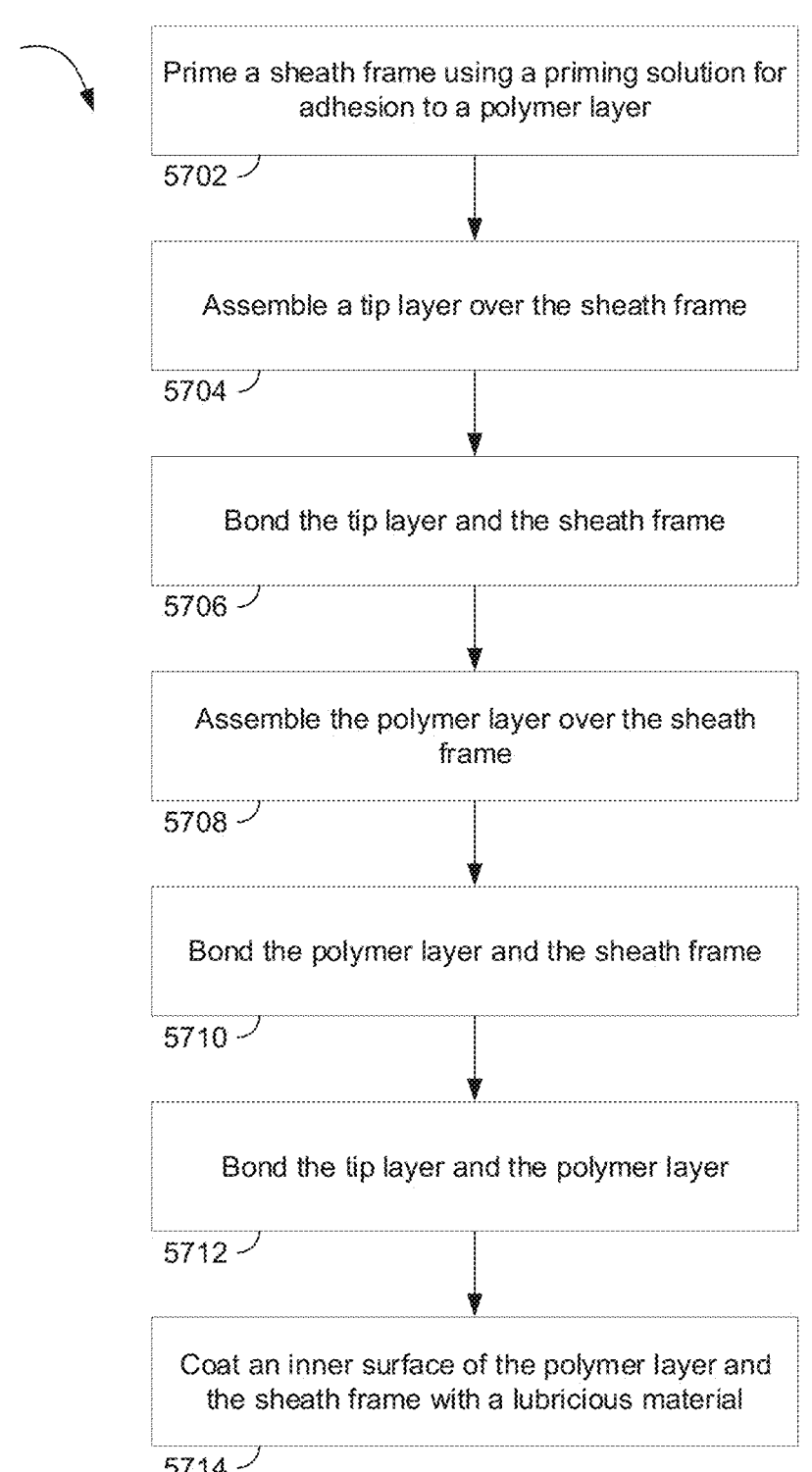

5700

Prime a sheath frame using a priming solution for adhesion to a polymer layer

5702

Assemble a tip layer over the sheath frame

5704

Bond the tip layer and the sheath frame

5706

Assemble the polymer layer over the sheath frame

5708

Bond the polymer layer and the sheath frame

5710

Bond the tip layer and the polymer layer

5712

Coat an inner surface of the polymer layer and the sheath frame with a lubricious material

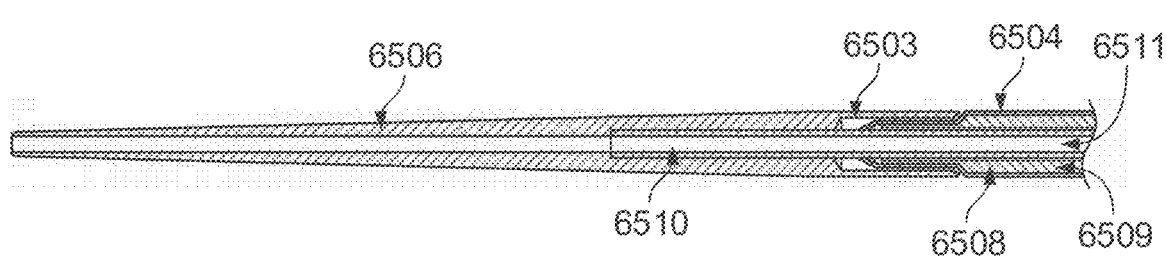
FIG. 65
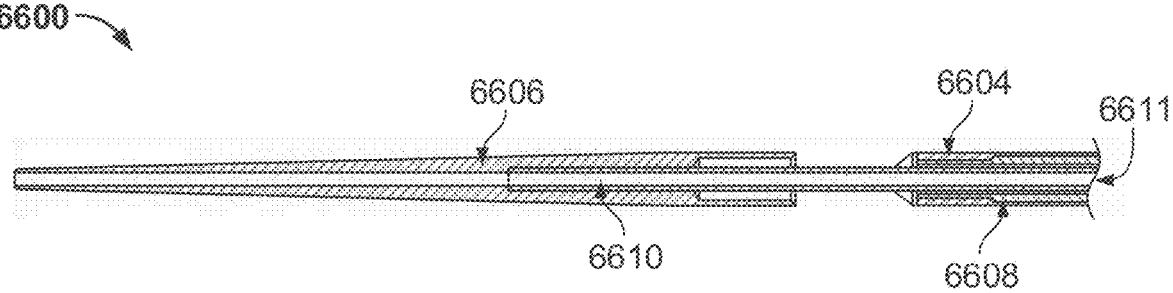
FIG. 66

6700

6706          6704          6711

6710          6708     6713

6800

6803     6804  6811

6810          6806   6808

6900

6906  6904          6911

6910          6908

7012

7004

7400

7500

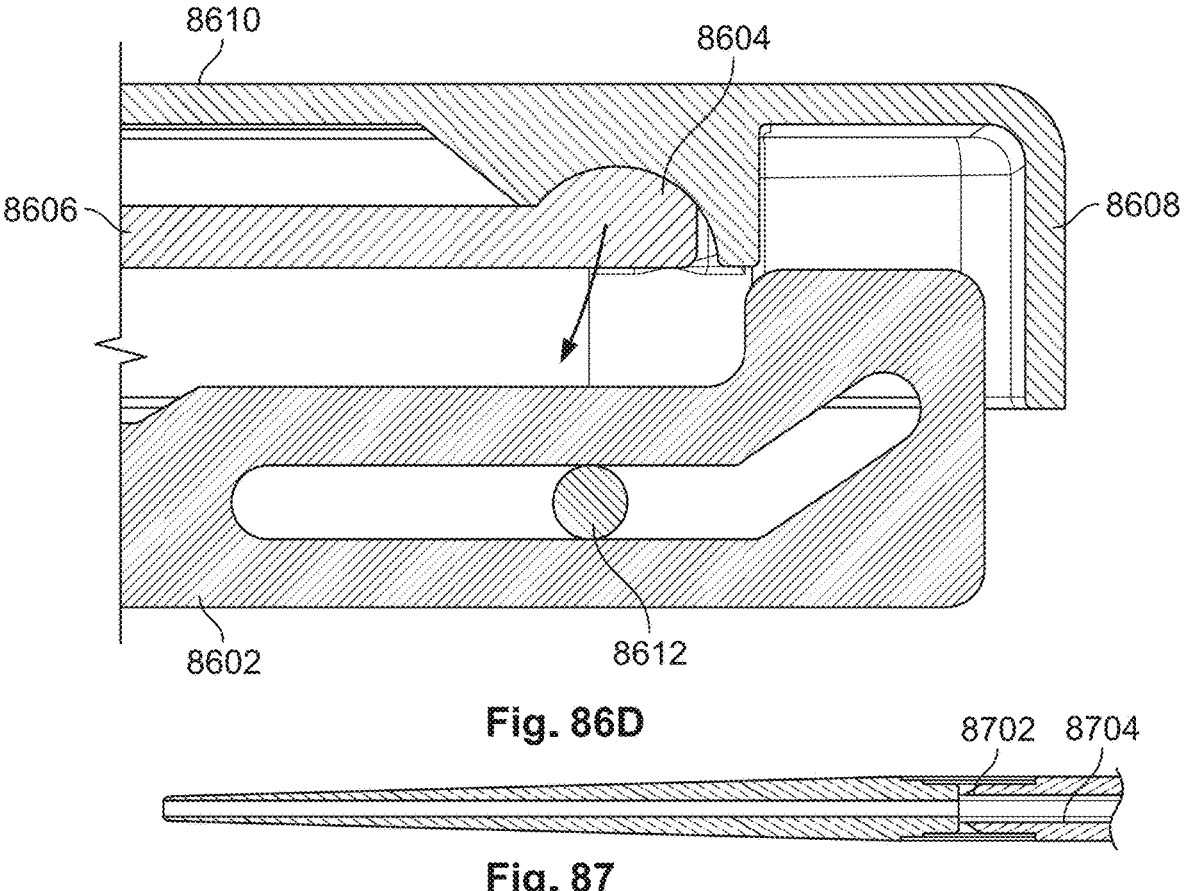
Fig. 86D
Fig. 87
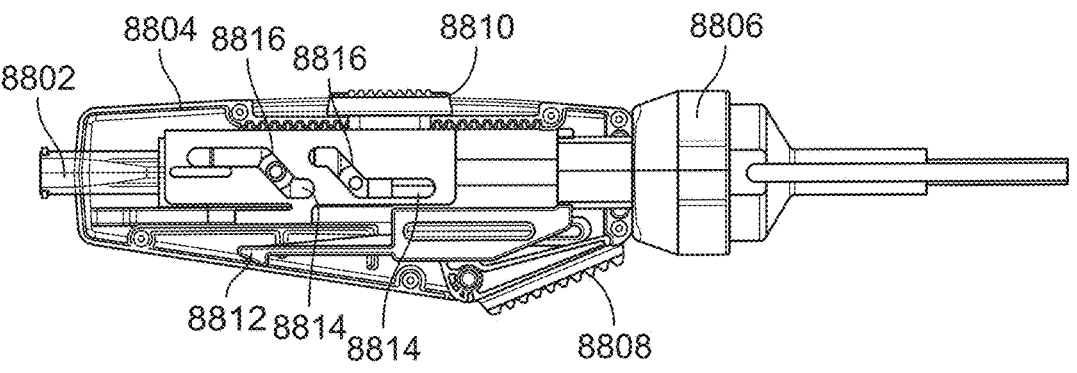
FIG. 88

9206

9204

9202

9204

9202

9402

9404

9406

9408

9502

9510

9504

9510

9506

9506

9508

EXPANDABLE INTRODUCER SHEATH FOR MEDICAL DEVICE

CROSS-REFERENCE TO RELATED APPLICATIONS

This application is a continuation of U.S. application Ser. No. 16/540,922, filed Aug. 14, 2019, which claims priority to U.S. Provisional Application No. 62/718,681, filed Aug. 14, 2018, the contents of each of which are hereby incorporated by reference in their entirety. This application is related to U.S. patent application Ser. No. 16/277,378, filed Feb. 15, 2019, which published on Aug. 15, 2019 as U.S. Patent Application Publication No. 2019/0247627 A1, the content of which is also hereby incorporated by reference in its entirety.

BACKGROUND

Intracardiac heart pump assemblies can be introduced into the heart either surgically or percutaneously and used to deliver blood from one location in the heart or circulatory system to another location in the heart or circulatory system. For example, when deployed in the heart, an intracardiac pump can pump blood from the left ventricle of the heart into the aorta, or pump blood from the inferior vena cava into the pulmonary artery. Intracardiac pumps can be powered by a motor located outside of the patient's body (and accompanying drive cable) or by an onboard motor located inside the patient's body. Some intracardiac blood pump systems can operate in parallel with the native heart to supplement cardiac output and partially or fully unload components of the heart. Examples of such systems include the IMPELLA® family of devices (Abiomed, Inc., Danvers Mass.).

In one common approach, an intracardiac blood pump is inserted by a catheterization procedure through the femoral artery using a sheath, such as a peel away introducer sheath. The sheath can alternatively be inserted in other locations such as in the femoral vein or any path for delivery of a pump for supporting either the left or right side of the heart.

The introducer sheath can be inserted into the femoral artery through an arteriotomy to create an insertion path for the pump assembly. A portion of the pump assembly is then advanced through an inner lumen of the introducer and into the artery. Once the pump assembly has been inserted, the introducer sheath is peeled away. A repositioning sheath can then be advanced over the pump assembly and into the arteriotomy. Replacing the introducer sheath with the repositioning sheath during insertion of a medical device can reduce limb ischemia and bleeding at the insertion site in the skin (and/or at the insertion site within the vessel) because of better fixation of the sheath to the patient when used with a hemostatic valve.

Since commercially available tear away introducer sheaths are not radially expandable, the inner diameter of the introducer sheath must always be large enough to accommodate the largest diameter portion of the pump assembly such as the pump head even if other parts of the pump assembly, such as the catheter, have a significantly smaller diameter. In this example, the introducer creates an opening that has an outer diameter wider than necessary to allow passage of the pump catheter into the vessel. Then, the introducer sheath is peeled or torn away and replaced with a lower-profile repositioning sheath. Removing the introducer sheath by peeling it away presents several challenges. For example, introducers can tear too easily and/or prematurely, leading to bleeding or vascular complications. Some introducers may require excessive force to tear away for removal. If a physician applies too much force, when the introducer finally tears, the physician may inadvertently shift the position of the pump within the heart. This configuration also complicates the design of the hemostatic valve located in the hub of the introducer which also needs to tear. Further, a peel away introducer sheath leads to a larger vessel opening after the system is removed, which can complicate vessel closure.

Medical introducers for other applications than inserting heart pumps have expandable sheath bodies which may expand radially to allow passage of percutaneous devices into the patient's vasculature. These existing expandable introducers are for relatively short-term use and may be designed to prevent thrombosis between the sheath body and an indwelling catheter. These introducers are inserted having inner diameters smaller than the outer diameter of the device being introduced. The introducers expand to allow passage of the device through the sheath and into the vasculature and then may shrink again after the device has passed. In the current state of the industry, these expandable introducers require a distinct expandable feature, e.g. a longitudinal fold or crease or a lumen for injection of a fluid (e.g. saline) to transition from a compressed state to an expanded state. Because these existing expandable introducers are intended for relatively short-term use, clot formation on the outside of the introducer sheath may be unlikely. However, if left in for longer periods of time (e.g. >1 hour, >2 hours, >6 hours, >1 day, >2 days, >1 week), clots may form on the outside surface of the expandable sheath mesh, and risk being dislodged into the blood stream at a later time. Additionally, some commercially available expandable sheaths are completely flexible and therefore do not provide any rigidity within their structure thereby leading to kinking or buckling during insertion or withdrawal of a percutaneous medical device.

BRIEF SUMMARY

Systems, devices and methods for insertion of a medical device (e.g., intravascular medical device) are presented. The devices are delivered through an expandable introducer sheath. The expandable introducer sheath is configured to remain in an insertion path (e.g., an arteriotomy) for relatively long durations (e.g., >1 hr, >2 hr, >6 hr, or any suitable duration). Use of an introducer sheath capable of expansion allows a smaller size sheath to be used for insertion and can allow the vessel opening to spend less time at a larger diameter, notwithstanding the sheath being used for longer durations. For example, the expandable introducer sheath can more easily recoil to a smaller diameter after insertion of the pump, which allows the opening of the vessel to recoil to a more natural position. Additionally, because the medical device only momentarily passes through the vessel wall, the opening in the vessel is expected to be smaller than if a larger non-expandable sheath is used. Still further, since the medical device only momentarily passes through the vessel, friction between the device, sheath, and vessel wall is minimized and there is a reduced axial load and reduced stress on the vessel. That is, the sheath is a smaller size and is therefore not pushing or pulling the vessel along the axis of the insertion/removal path. Instead, when the device passes through the vessel, the vessel is expanded outward radially.

An expandable introducer sheath structure comprises at least one frame and one coating. A coating is applied to the surface of the sheath to facilitate passage inside the patient. In some embodiments, the coating is applied on the inner surface of the sheath, which is an inner diameter biased approach. An inner-diameter biased coating advantageously provides for a thin coating thickness and, advantageously a relatively smaller force is required to expand the sheath compared to a force required to expand a sheath having a coating without any bias. In alternative embodiments, the coating is applied on the outer surface of the sheath, which is an outer diameter biased approach. An outer-diameter biased coating advantageously provides a smooth outer surface which reduces the risk of clot formation and minimizes friction when inserting a device through the expandable sheath. For example, the use of a smooth outer surface advantageously minimizes the risk of clots forming on the surface of the expandable sheath, and a corrugated inner surface minimizes the surface area of the expandable sheath in contact with a device being pushed through, thereby minimizing associated friction forces. The outer-diameter biased coating further advantageously provides for a thin coating thickness, and advantageously a relatively smaller force is required to expand the sheath compared to a force required to expand a sheath having a coating without any bias. The outer-diameter biased coating advantageously allows the sheath frame to expand and contract as desired, i.e. the outer-diameter biased coating does not immobilize the frame at a fixed diameter because the thin coating thickness is such that the coating does not encapsulate the portions of the frame where frame elements intersect. For example, for a braided frame having braided elements in an over-under braid pattern and an outer-diameter biased coating, the outer diameter biased coating advantageously is thin enough that it does not reach encapsulate an overlap of braided elements, i.e. the outer-diameter coating does not extend to the braided elements located under other braided elements in the over-under braided pattern.

The expandable sheath is configured for insertion into the vasculature of a patient with a dilator assembly. For example, the expandable sheath has a geometry that enables the expandable sheath to be held in a stretched configuration for insertion with the dilator assembly, and released after insertion into the vasculature of a patient. For example, the dilator assembly comprises an inner dilator and outer dilator, and the distal end of the expandable sheath is configured to interface with both dilators such that the distal end of the expandable sheath cannot move toward a proximal end of the pump assembly. For example, the distal end of the expandable sheath can have a larger thickness than a thickness of the remainder of the expandable sheath body. Advantageously, the thicker distal tip of the sheath abuts a distal end of dilator system, which prevents the distal end of the expandable sheath from slipping toward the proximal direction during insertion into the vasculature.

The expandable introducer sheath structure can be manufactured using thermal bonding or an outer-diameter biased dipping. Advantageously, thermal bonding or an outer-diameter biased dipping produce the smooth outer surface of the sheath, without losing the desired spring-like expandable nature of the sheath.

Since the expandable introducer sheath need not be removed and replaced by a secondary repositioning sheath, the risk of premature tearing/peeling is essentially eliminated and the risk of shifting the introduced device inadvertently (e.g., by overuse of force) is reduced or eliminated. Furthermore, allowing the expandable introducer sheath to remain in an insertion path simplifies the process of inserting the introduced device by reducing the number of steps in the insertion procedure, e.g. by eliminating a second step where the sheath and valve must be peeled away or torn before it is removed.

Such an expandable sheath also does away with the need for the conventional set up of having multiple sheaths, such as a peel away introducer sheath and a repositioning sheath for the introduction of a medical device (e.g. an intracardiac heart pump) into the vessel opening (e.g. arteriotomy). Such an expandable sheath allows a repositioning sheath to be used in conjunction with it, if necessary, but does not require one in all cases. Once the expandable sheath is positioned, it maintains access to a vessel even after the medical device is removed, should such access be required for other medical procedures. This increases procedural efficiency of any medical procedure as there is no need to peel away the introducer sheath for the insertion of a repositioning sheath each time access to the vessel opening is required. Furthermore, more accurate repositioning of the medical device can be achieved with the expandable introducer sheath as the expandable introducer sheath is fixed in position once inserted, whereas the insertion of a separate repositioning sheath involves multiple steps that increase the chances of misplacing the medical device.

The expandable sheath therefore removes the need for multiple sheaths (e.g. an introducer sheath and a repositioning sheath) during any medical procedure requiring access to an opening of a blood vessel of a patient. In particular, the use of a frame and coating assembly which can expand and collapse while being resistant to kinking, and return to its original shape after deformation, advantageously enables delivery and recovery of the medical device. The consolidation of the introducer sheath and the repositioning sheath into a single device can decrease the costs involved during a medical procedure. Further, since only a single sheath is required to gain arteriotomic access to a vessel, less bleeding may be involved during its long-term use with a percutaneous medical device, such as a heart pump. In addition, configuring the expandable sheath for compatibility with a dilator assembly and a stylet assembly reduces issues with dilator insertion and removal as well as improves hemostasis performance. Advantageously, the combination of a dual-dilator assembly, an expandable sheath and a hemostasis stylet provide a synergistic system which can be used relatively early in a procedure, e.g. in a catheterization lab rather than later in procedure, e.g. in surgery, when displacement of the pump could have more severe consequences for a patient. Because the system can be used relatively early in a procedure, potential pump migration can be addressed earlier, and vascular injury can be reduced. According to a first implementation of the present disclosure, there is provided an introducer sheath including an expandable sheath frame having a length, a first thickness, a proximal end and a distal end. The frame includes strands extending longitudinally between the proximal end and the distal end, and having an exterior surface and an interior surface that form an interior lumen along the length of the frame. The frame is configured to achieve an expanded state and a contracted state, the expanded state forming an expanded cross-section in the lumen for passing a medical device therethrough. The frame has a smooth coating about the exterior surface and protrusions extending into the lumen along the interior surface.

In some implementations, the cross-section of the expandable sheath body is circular. In certain implementations, the cross-section of the expandable sheath body is elliptical. A sheath having a circular cross-section may have a perimeter of the same length as a sheath having an elliptical cross-section. In further implementations, the cross-section of a given expandable sheath body may be configured to temporarily change. For example, the introduction of devices into the sheath or the exertion of forces on the sheath may cause the cross-section of the sheath to change between circular and elliptical. Such a temporary change in cross-section advantageously allows for the expandable sheath to accommodate blood pump elements having larger diameters, and upon passing them, to return to a cross-section having a smaller area.

In further implementations, the variation in cross-sectional area for an expandable sheath of a given perimeter or circumference advantageously allows for the simultaneous introduction of devices using a hub into the sheath that have larger diameters than devices accommodated by sheaths of an invariable cross-section. For example, an expandable sheath that is able to accommodate both a blood pump and a catheter could be employed for percutaneous coronary intervention. Such sheaths allow for dual access of devices by optimizing the space available within the introducer sheath. Additionally, such implementations involving variable cross-section expandable sheaths allow for a free shape (i.e., a shape of the expandable sheath within the vasculature of the patient and not containing a device) having a small diameter for insertion into the arteriotomy. This allows the arteriotomy to be kept small, as the width of the sheath is aligned with the formation of the resulting arteriotomy. An elliptical cross-section can also be used for insertion into the arteriotomy, while keeping the arteriotomy small. The elliptical cross-section helps to obtain distal flow, as the elliptical cross-section generally matches the shape of the arteriotomy. Additionally, the incorporation of a small, variable diameter expandable sheath improves hemostasis during procedures. The forces exerted on the vasculature by the sheath in implementations wherein the expandable sheath has a small diameter free shape mimic the way in which blood vessels naturally stretch, advantageously preventing damage unto the vasculature by the sheath.

In some implementations, the introducer sheath includes a polymer layer covering an outer circumference of the frame and forming the smooth coating. In some implementations, the polymer layer comprises at least one of polyether and polyurethane. In certain implementations, the polyurethane comprises TPU. In some implementations, the TPU has a durometer between about D20 and about D90. In certain implementations, the TPU has a durometer between about D30 and about D80. In further implementations, the TPU has a durometer between about D40 and about D70. In some implementations, the TPU has a durometer between about D50 and about D60. In further implementations, the TPU has a durometer of about D55. In some implementations, the expandable sheath frame has an expansion mechanism that allows the frame to expand and contract. In certain implementations, the strands are configured with a bias to expand or contract from a resting position. According to some implementations, the expansion mechanism permits the strands to slide relative to each other when the frame expands and contracts.

In some implementations, the strands include first and second overlapping strands, with the second strand extending radially inward from the first strand. In certain implementations, the second strand overlaps with the first strand and forms a plurality of peaks that project into the lumen.

According to certain implementations, the coating extends about the interior surface. In some implementations, the coating covers the protrusions along the interior surface. In certain implementations, the coating covering the protrusions has a first thickness and the coating extending about the exterior surface has a second thickness. In some implementations, the first thickness is less than the second thickness.

In certain implementations, the first strand is bounded on an upper side by the smooth exterior surface coating. In some implementations, the coating covers the second strand along a first longitudinal side of the second strand. According to certain implementations, the coating covers an exterior-facing side of the first strand and an interior facing side of the second strand.

In some implementations, the frame includes a braided mesh formed of first strands. In certain implementations, the diameter of the first strands is between about 1 millimeters and about 10 millimeters. In further implementations, the diameter of the first strands is between about 3 millimeters and about 8 millimeters. In some implementations, the diameter of the first strands is between about 5 millimeters and about 6 millimeters. In further implementations, the diameter of the first strands is about 5.5 millimeters. According to certain implementations, the first strands are wrapped in a spiral direction along the length. In certain implementations, the frame includes second strands. In some implementations, the second strands are wrapped in a counter-clock-wise direction along the length.

According to certain implementations, a thickness of the polymer layer is less than a thickness of the protrusions extending into the lumen along the interior surface. In some implementations, a thickness of the coating is less than the thickness of the polymer layer. In certain implementations, the thickness of the protrusions is less than a thickness of a strand of the first strands. In some implementations, the thickness of the protrusions is less than about 75 or 100 $\mu$m.

In some implementations, the introducer sheath includes a sheath tip at the distal end of the expandable sheath frame, the sheath tip having a thickness, wherein the sheath tip thickness is greater than the thickness of the expandable sheath frame.

In certain implementations, at least one of the frame, polymer layer, and coating of the sheath tip is thicker than the frame, polymer layer, and coating of the sheath. In some implementations, the sheath tip is polymer. In certain implementations, the polymer is co-molded with the coating of the sheath frame. According to certain implementations, the sheath tip is made of a first material and the expandable sheath is made of a second material different than the first material. In some implementations, the first material has a different stiffness than the second material. In certain implementations, the distal tip of the sheath is stiffer than the proximal end of the sheath.

According to a further implementation of the present disclosure, there is provided a dilator assembly for the insertion of a medical device into a blood vessel. The dilator assembly includes an inner dilator having a first length and a lumen between proximal and distal ends of the inner dilator, and an outer dilator having a second length and a lumen between proximal and distal ends of the outer dilator. The outer dilator is coaxial with the inner dilator and the first length is greater than the second length. The inner dilator and the outer dilator are configured to be spaced apart radially by a circumferential gap having a gap thickness. The inner dilator and outer dilator assembly in combination with the expandable sheath permit stretching of the expandable sheath into a smaller diameter increased length state, e.g. for insertion of the expandable sheath, without the need for multiple sheaths.

In certain implementations, the inner dilator of the dilator assembly includes a shaft extending through the lumen of the outer dilator and a distal tip forming a cavity about the distal end of the inner dilator. In some implementations, the cavity has an inner wall, a closed end, and an open proximal end sized to receive the distal end of the outer dilator. According to certain implementations, the inner wall has a diameter greater than the diameter of the inner dilator shaft. In some implementations, the distal end of the outer dilator extends axially along the inner wall within the cavity to a position between the closed end and the open proximal end, forming a sheath tip receptacle.

According to certain implementations, the outer dilator of the dilator assembly includes a proximal portion with a first diameter, a distal portion with a second diameter, and a conical transition portion between the proximal portion and the distal portion. In some implementations, the second diameter is smaller than the first diameter. In certain implementations, the first diameter of the outer dilator is substantially equal to an outer diameter of a tip of the inner dilator.

According to a further implementation of the present disclosure, there is provided a sheath assembly including the introducer sheath and the dilator assembly in combination. In some implementations, the inner dilator and the outer dilator are configured to be inserted into the first lumen of the expandable sheath frame to adjust a diameter of the expandable sheath frame. According to certain implementations, the head of the inner dilator is bonded to the distal end of the dilator.

In some implementations, the second thickness is greater than the thickness of the sheath frame such that the sheath frame fits within the circumferential gap, the sheath tip fits within the sheath tip receptacle, and the second thickness is smaller than the thickness of the sheath tip such that sheath tip is retained within the dilator tip.

According to a further implementation of the present disclosure, there is provided a method of manufacturing an expandable introducer sheath. The method comprises priming a sheath frame using a priming solution. The sheath frame can be primed for adhesion to a polymer layer. The method further comprises assembling the polymer layer over the sheath frame. The method further comprises bonding the polymer layer and the sheath frame by exposing the polymer layer and the sheath frame to air for a duration of time, wherein the air is heated to a first temperature. The method further comprises coating an inner surface of the polymer layer and the sheath frame with a lubricious material. In some implementations, the method further comprises coating an outer surface of the polymer layer and the sheath frame with the lubricious material.

In some implementations, the lubricious material may be hydrophobic. In other implementations, the lubricious material may be hydrophilic. In certain implementations, the method further comprises coating the inner surface of the polymer layer and the sheath frame with a hydrophobic lubricious material and coating the outer surface of the polymer layer and the sheath frame with a hydrophilic lubricious material. In some implementations, the method further comprises coating the inner surface of the polymer layer and the sheath frame with a hydrophilic lubricious material and coating the outer surface of the polymer layer and the sheath frame with a hydrophobic lubricious material.

According to another implementation of the present disclosure, there is provided an introducer sheath including an expandable sheath body having a first length, a longitudinal axis, and proximal and distal ends. The expandable sheath body includes a first lumen extending between the proximal and distal ends of the expandable sheath body, a braid forming the first lumen, and a polymer encapsulating at least a distal portion of the braid. The first lumen having a first diameter in a first elongated state and a second diameter in a second relaxed state, the second diameter in the second relaxed state is sized to accommodate the medical device. The braid formed of at least one strand of an elastic material (e.g. a metal) extending from the proximal end of the expandable sheath body at an acute angle relative to the longitudinal axis of the expandable sheath body. The polymer can expand or collapse along with the braid. The acute angle and the material forming the at least one strand can be selected such that the medical device can be passed through the expandable sheath body without the expandable sheath body buckling.

In some implementations, the braid includes first strands wrapped in a clock-wise spiral direction along the first length and second strands wrapped in a counter-clock-wise spiral direction along the first length, which can permit expansion and contraction of the braid while avoiding a finger-trapping effect and/or buckling of the sheath. In some implementations, the first strands and the second strands are radiopaque. In certain implementations, the diameter of at least one the first strands and the second strands is between about 1 millimeters and about 10 millimeters. In further implementations, the diameter of at least one of the first strands and the second strands is between about 3 millimeters and about 8 millimeters. In some implementations, the diameter of at least one of the first strands and the second strands is between about 5 millimeters and about 6 millimeters. In further implementations, the diameter of at least one of the first strands and the second strands is about 5.5 millimeters. According to certain implementations, an angle between the first strands and the second strands is about 35 degrees, 45 degrees, or 55 degrees. In other implementations, the braid includes a braid pattern of the first strands and the second strands. In some implementations, the braid pattern defines a rhombi, each rhombi including a first corner and a second corner adjacent the first corner. According to certain implementations, at least one strand of the first strands goes over at least one strand of the second strands at the first corner and the at least one strand of the first strands goes over the at least one strand of the second strands at the second corner. In other implementations, at least one strand of the first strands goes over at least one strand of the second strands at the first corner and the at least one strand of the first strands goes under the at least one strand of the second strands at the second corner. The braid and strand configurations enable the sheath to have sufficient flexibility to expand and contract as needed to insert the medical device, while having sufficient rigidity to maintain an open lumen and withstand axial forces when the medical device is inserted or withdrawn.

In certain implementations, the frame material comprises at least one of Nitinol round wire, Nitinol flat wire, Stainless steel round wire, stainless steel flat wire, liquid crystal polymer, polyamide, and polyether ether ketone (PEEK). In some implementations, the polymer encapsulating the frame comprises at least one of silicone and thermoplastic polyurethane. The frame and encapsulating material combination permits the sheath to expand and contract while having sufficient rigidity to maintain an open lumen and withstand axial forces when the medical device is inserted or withdrawn, and permits promoting a smooth flow of blood along the outer surface of the sheath to reduce the risk of clots forming.

In some implementations, the introducer sheath includes a hub having a second length and a second lumen extending between proximal and distal ends of the hub. The distal end of the hub can be bonded or attached to the proximal end of the expandable sheath body. The second lumen of the hub can be in communication with the first lumen of the sheath. In further implementations, the hub includes a hemostasis valve within the second lumen, the hemostasis valve being configured for insertion of a component. In other implementations, the hub includes a side-arm that allows for flushing and aspiration of the introducer sheath. The hub and valve configuration prevent blood from leaking outside of the patient during insertion and/or removal of the device, and also provide a structural anchor to minimize the risk of sheath eversion at the hub.

According to certain implementations, the polymer encapsulates the entire braid. In other implementations, the introducer sheath includes a hydrophilic material coating at least a portion of an inner surface of the polymer. In some implementations, the hydrophilic material coats at least a portion of an outer surface of the polymer. The hydrophilic coating on the inner surface of the polymer permits a reduction of the frictional forces during delivery of the medical device and to avoid clotting by allowing adequate blood flow along the sheath body. In certain implementations, the inner surface of the polymer has a smooth surface and the outer surface of the polymer has at least one trough. In other implementations, the inner surface of the polymer has at least one trough and the outer surface of the polymer has a smooth surface.

In certain implementations, the proximal end of the expandable sheath body lies outside of a body of a patient. In other implementations, the introducer sheath is configured for the insertion of a blood pump into a blood vessel.

In some implementations, the introducer sheath includes at the distal end of the expandable sheath body a distal portion of the first lumen, the distal portion shaped to reversibly lock with a distal end of a dilator. In other implementations, the distal portion allows movement with respect to the dilator in one direction but not the other. The distal portion of the introducer sheath locking with the distal end of the dilator permits stretching of the introducer sheath relative to an anchor point.

According to a further implementation of the present disclosure, there is provided a dilator assembly for the insertion of a medical device into a blood vessel. The dilator assembly includes an inner dilator having a first length and a first lumen between proximal and distal ends of the inner dilator, an outer dilator having a second length and a second lumen between proximal and distal ends of the outer dilator, and a hub attachment having a third length and a third lumen between proximal and distal ends of the hub attachment. The outer dilator can be axially aligned with the inner dilator and the first length can be greater than the second length. The inner dilator and the outer dilator are configured to be inserted into an expandable sheath of an introducer assembly to adjust a diameter of the expandable sheath. The hub attachment can be axially aligned with the outer dilator and the outer dilator can lie within the third lumen. The distal end of the hub attachment can be attached to a proximal end of the introducer assembly. In further implementations, adjusting the diameter of the expandable sheath comprises changing the diameter from a first diameter in a first relaxed state to a second diameter in a second expanded state. The inner dilator and outer dilator assembly in combination with the expandable sheath permit stretching of the expandable sheath into a smaller diameter increased length state, e.g. for insertion of the expandable sheath, without the need for multiple sheaths.

In some implementations, the dilator assembly includes a luer assembly having a fourth length and a fourth lumen between proximal and distal ends of the luer assembly. The distal end of the luer assembly can be bonded to the proximal end of the hub attachment. In certain implementations, the luer assembly comprises a compressible elastomer and a compression nut. In other implementations, the compressible elastomer includes a first state and a second state. The first state corresponds to minimum compression and the second state corresponds to maximum compression. In some implementations, the compression nut is loose and the compressible elastomer is in the first state, allowing the hub attachment to traverse with respect to the outer dilator. In certain implementations, the compression nut is tight and the compressible elastomer is in the second state, allowing the hub attachment to remain in place with respect to the outer dilator.

In other implementations, the distal end of the inner dilator is bonded to a tip and the proximal end of the inner dilator is bonded to a luer hub. In certain implementations, the inner dilator lies within the outer dilator such that the proximal and distal ends of the inner dilator are exposed. In some implementations, the hub attachment comprises a hub attachment cap at the distal end of the hub attachment.

According to a further implementation of the present disclosure, there is provided a hemostasis stylet assembly for controlling hemostasis with a blood vessel. The hemostasis stylet assembly includes a locking hub having distal and proximal ends, a hemostasis stylet hub having a lumen between distal and proximal ends of the hemostasis stylet hub, a first sterile layer having a first length and a first lumen between distal and proximal ends of the first sterile layer, a hemostasis stylet body having distal and proximal ends, and a second sterile layer having a second length and a second lumen between distal and proximal ends of the second sterile layer. The distal end of the locking hub can be configured to attach to a proximal end of an introducer assembly. The first sterile layer and a hemostasis stylet body can be attached to the distal end of the hemostasis stylet hub. The second sterile layer can be attached to the proximal end of the hemostasis stylet hub. The distal end of the first sterile layer can be attached to the locking hub. The distal end of the hemostasis stylet body can be configured to be inserted into an expandable sheath of the introducer assembly in order to control hemostasis between the expandable sheath and an opening of a blood vessel. The hemostasis stylet, in combination with the dual dilator assembly and the expandable sheath allows for control of the blood flow along the expandable sheath, to reduce potential ischemia. In some implementations, the hemostasis stylet can be a repositioning sheath, which is also used to control of the blood flow along the expandable sheath and minimize bleeding.

In some implementations, the locking hub has a first state corresponding to buttons in a compressed state and a second state corresponding to the buttons in an uncompressed state. In certain implementations, the locking hub in the first state allows the locking hub to be movable with respect to the hemostasis stylet hub. In other implementations, the locking hub in the second state allows the locking hub to be in a fixed state with respect to the hemostasis stylet hub. In further implementations, the locking hub includes a locking cap at the distal end of the locking hub.

In other implementations, the first sterile layer includes a first attachment component attached to the proximal end of the locking hub. In certain implementations, the second sterile layer includes a second attachment component attached to the proximal end of the hemostasis stylet hub. In some implementations, the proximal end of the hemostasis stylet hub is attached to an internal seal component.

According to a further implementation of the present disclosure, there is provided an introducer sheath including an expandable sheath body having a first length, a longitudinal axis, and proximal and distal ends. The expandable sheath body includes a first lumen extending between the proximal and distal ends of the expandable sheath body, a braid forming the first lumen, and a polymer encapsulating at least a portion of the braid. The first lumen having a first diameter in a first elongated state, the first diameter in the first relaxed state is sized to insert the introducer sheath into a vessel, a second diameter in a second relaxed state, and a third diameter in a third expanded state, the third diameter in the expanded state sized to accommodate the medical device. The braid formed of at least one strand extending from the proximal end of the expandable sheath body at an acute angle relative to the longitudinal axis of the expandable sheath body. The polymer can expand or collapse along with the braid. Selection of the acute angle and the material of the at least one strand can permit the medical device to pass through the expandable sheath body in its third expanded state without the expandable sheath body buckling.

According to a further implementation of the present disclosure, the first lumen has a first diameter in a first relaxed state and a second diameter in a second expanded state, the second diameter in the second expanded state being sized to accommodate the medical device. The acute angle and the material can be selected to allow the medical device to pass through the expandable sheath body, and the expandable sheath body will expand to its second expanded state to accommodate the medical device.

According to a further implementation of the present disclosure, there is provided a sheath assembly for the insertion of a medical device into a blood vessel. In some implementations, the sheath assembly includes an introducer sheath and a dilator assembly. In other implementations, the sheath assembly includes an introducer sheath and a hemostasis stylet assembly. In certain implementations, the sheath assembly includes an introducer sheath, a dilator assembly, and a hemostasis stylet assembly. The introducer sheath, dilator assembly and hemostasis stylet assembly permit insertion and withdrawal of a medical device in the introducer sheath without the sheath buckling, while keeping the opening required in a vessel to a minimum, and controlling leak path blood flow.

According to a further implementation of the present disclosure, there is provided a method of inserting a pump into a blood vessel. The method comprises attaching an introducer assembly to a dilator assembly. The introducer assembly comprises an expandable sheath having a first diameter and a first length. The method further comprises moving the dilator assembly with respect to the introducer assembly in the proximal direction such that the expandable sheath of the introducer assembly contracts to a second diameter and a second length, the second diameter being smaller than the first diameter and the second length being greater than the first length. The method further comprises inserting the introducer assembly and the dilator into a desired location in a blood vessel such that an opening of the blood vessel expands to accommodate the second diameter of the expandable sheath. The method further comprises moving the dilator assembly with respect to the introducer assembly in the distal direction such that the expandable sheath of the introducer assembly expands to a third diameter and a third length, and the opening of the blood vessel expands to accommodate the third diameter of the expandable sheath, the third diameter being greater than the second diameter and the third length being smaller than the second length. The method further comprises detaching the dilator assembly from the introducer assembly and removing the dilator assembly from the desired location in the blood vessel. The method further comprises inserting a pump through the introducer assembly such that the expandable sheath expands to a fourth diameter to accommodate the pump as the pump traverses within the introducer assembly, and the opening of the blood vessel expands to accommodate the fourth diameter of the expandable sheath, the fourth diameter being greater than the third diameter. The method further comprises inserting a hemostasis stylet through the introducer assembly such that the expandable sheath expands to a fifth diameter to accommodate the hemostasis stylet as the hemostasis stylet traverses within the introducer assembly, the fifth diameter being such as to achieve hemostasis between the opening of the blood vessel and the expandable sheath. The method of inserting the pump, including the introducer sheath, dilator assembly and hemostasis stylet assembly permits insertion of the medical device in the introducer sheath without the sheath buckling, while keeping the opening required in a vessel to a minimum, and controlling leak path blood flow.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIGS. 40A and 40B show cross-section views of an illustrative sheath capture configuration;

FIG. 57 shows an illustrative method for manufacturing the expandable sheath of FIG. 2;

FIG. 65 shows a cross-section of an illustrative sheath system tip in a first position;

FIG. 66 shows a cross-section of an illustrative sheath system tip in a second position;

FIG. 86D shows a second aerial cross-sectional view of the hub housing of an illustrative sheath delivery system;

FIG. 87 shows an illustrative view of a delivery mechanism tip;

FIG. 88 shows a cross-sectional view of an illustrative sheath delivery system in a third position;

DETAILED DESCRIPTION

Figures 1A, 1B:
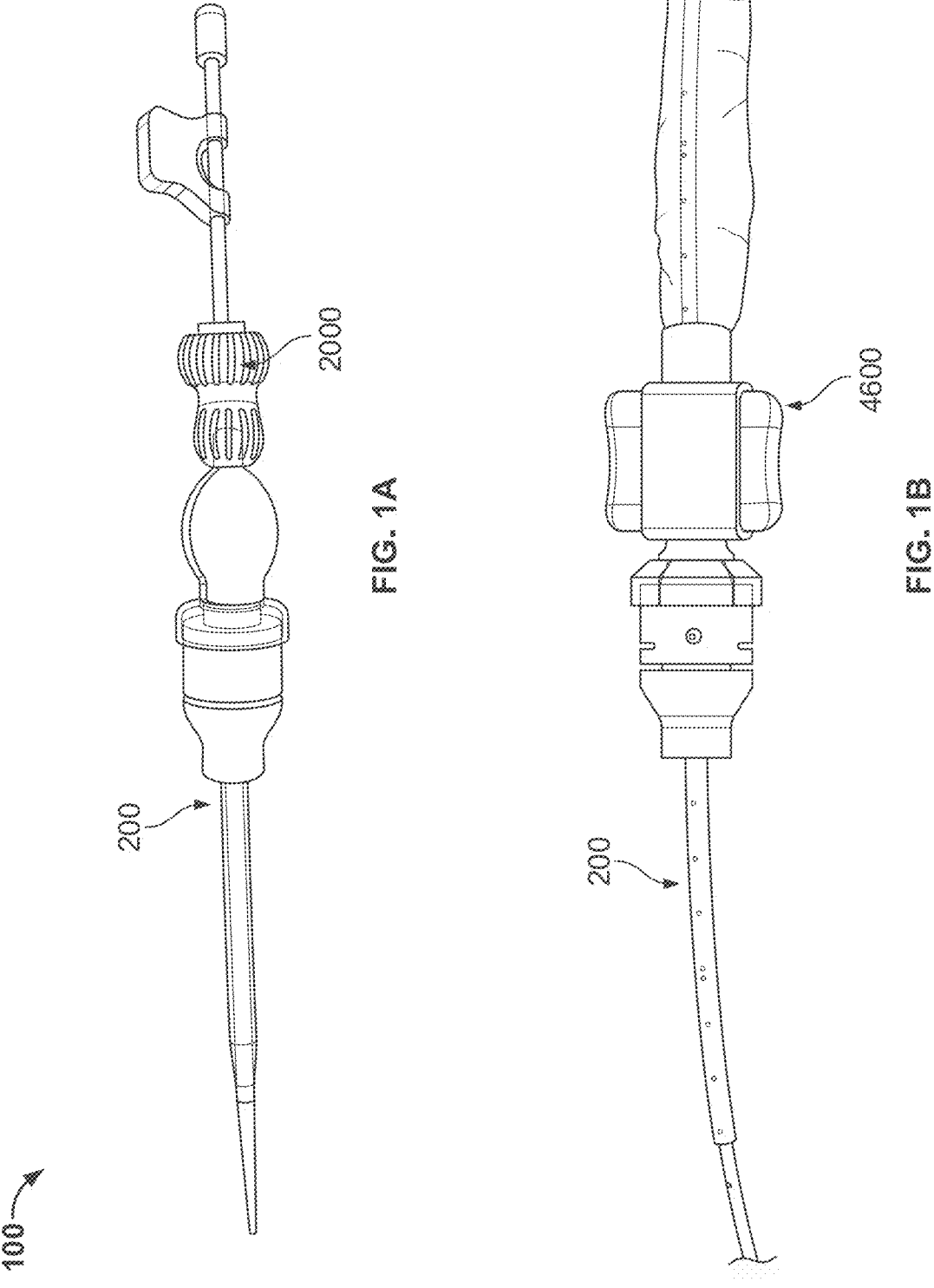
FIGS. 1A and 1B show an isometric view of an illustrative sheath assembly including an illustrative expandable sheath coupled to an illustrative dilator assembly, and an illustrative expandable sheath coupled to a hemostasis stylet assembly, respectively.

To provide an overall understanding of the systems, method, and devices described herein, certain illustrative embodiments will be described. Although the embodiments and features described herein are specifically described for use in connection with an intracardiac heart pump system, it will be understood that all the components and other features outlined below may be combined with one another in any suitable manner and may be adapted and applied to other types of medical devices such as electrophysiology study and catheter ablation devices, angioplasty and stenting devices, angiographic catheters, peripherally inserted central catheters, central venous catheters, midline catheters, peripheral catheters, inferior vena cava filters, abdominal aortic aneurysm therapy devices, thrombectomy devices, TAVR delivery systems, cardiac therapy and cardiac assist devices, including balloon pumps, cardiac assist devices implanted using a surgical incision, and any other venous or arterial based introduced catheters and devices.

The systems, methods and devices described herein provide an expandable sheath assembly for the insertion of a medical device (e.g., an intracardiac heart pump) into a blood vessel through a vessel aperture. The expandable sheath assembly comprises a dilator assembly and a sheath body having an inner surface and an outer surface, the inner surface defining a lumen that extends between proximal and distal ends of the sheath. Optionally, the expandable sheath assembly may include a hemostasis stylet. The expandable sheath assemblies (including the sheath body, dilator assembly, and optional hemostasis stylet) are especially advantageous over existing expandable sheath assemblies for patients with coronary artery disease (CAD) and peripheral artery disease, presenting with calcification and tortuosity of arteries, making delivery of introducer sheaths and catheters difficult. The expandable sheath assemblies herein are easier to insert than traditional assemblies because of their reduced insertion profile, increased flexibility, reduced friction, and reduced risk of kinking under loads. The reduced insertion profile minimizes insertion related complications, minimizes stretching and load on the vessel opening, and minimizes the risk of limb ischemia. The structure of the sheath body described herein provides sufficient axial stiffness for pushability and buckling resistance, while maintaining bending flexibility and kink resistance, reduces frictional force to prevent "finger trapping." Moreover, the structures of the sheath body described herein provides an improvement over existing introducer sheaths bodies by either, having a smooth inner surface with a thin coating thickness reducing the force required to expand the sheath compared to the force required to expand the sheath having a coating without any bias, or having a smooth outer surface reducing the risk of thrombus formation during use over longer durations while at the same time enabling the sheath to expand and contract as desired and reducing friction between the sheath body and devices being inserted through it. Furthermore, the structure of the sheath body described herein interfaces with a dilator assembly, such that the sheath body can be held in place for insertion into a body lumen by having a portion of the sheath body be constrained or entrapped in a longitudinal direction. This constraint or entrapment of the sheath body facilitates the expandable sheath body insertion in combination with a dilator assembly, without damaging the expandable sheath body or altering its properties.

The sheath body can expand between different states to accommodate the medical device. For example, the sheath body is elongated in a first smaller diameter state for insertion and relaxed into a second larger diameter state once at a desired location to allow the passage of a portion of a medical device through the lumen, the portion of the medical device having a transverse cross-sectional area larger than a transverse cross-sectional area of the lumen in the first state. In different configurations, the sheath is further expanded between a resting state when the sheath is at its desired location, and a larger diameter state when the medical device is passed through. In any configuration, the expandable sheath assemblies herein do not require additional elements relative to a standard introducer: no external balloon, no fold in the expandable sheath body, no second sheath for delivery. This can be advantageous over existing expandable sheath assemblies by simplifying the use of the expandable sheath assembly (e.g. requiring less steps, taking less time).

Moreover, the momentary expansion of the sheath body from the elongated state to the relaxed state (or from the relaxed state to the expanded state) minimizes the size of the opening, e.g. arteriotomy, required when inserting the sheath into the vasculature of the patient. Minimizing the amount of time the sheath body is in the expanded state also minimizes damage to a vessel wall as a smaller opening would be required to accommodate the sheath body in the relaxed or collapsed state, thereby minimizing thrombotic occlusion of the vessel. A smaller opening also minimizes the time to reach hemostasis after removal of the medical device. Such an expandable sheath does away with the need for the conventional set up of having multiple sheaths, such as a peel away introducer sheath and a repositioning sheath for the introduction of a medical device (e.g. an intracardiac heart pump) into the vessel. Such an expandable sheath also allows such a conventional set-up to be used in conjunction with it, if necessary. Once the expandable sheath is positioned in an opening of a blood vessel of a patient, it maintains access to the vessel even after the medical device is removed, should such access be required for other medical procedures. This increases procedural efficiency of any medical procedure as there is no need to re-gain alternative access or re-insert a second sheath in the same access site. The effective consolidation of the introducer sheath and the repositioning sheath into a single device decreases the costs involved during a medical procedure. Further, since only a single sheath is required to gain arteriotomic access to a vessel, less bleeding would be involved during long term use of a percutaneous medical device such as a heart pump. The integration of the sheath body and dilator assembly with the hemostasis stylet allows for titrated hemostasis at the vessel opening. In some implementations, the hemostasis stylet can be a repositioning sheath, which is also used to control of the blood flow along the expandable sheath and minimize bleeding.

Additionally, the expandable sheath assemblies herein are advantageous over existing expandable sheath assemblies because they maintain guidewire access throughout the full procedure by always allowing the user to remove the pump with the sheath in place.

FIGS. 1-6 show different aspects of an illustrative sheath assembly, and exemplary components and configurations. FIG. 1A shows an illustrative sheath assembly including an expandable introducer sheath 200 (further described in relation to FIG. 2) coupled to a dilator assembly 2000 (further described in relation to FIG. 20). FIG. 1B shows the illustrative sheath assembly of FIG. 1A with the expandable introducer sheath 200 coupled to a hemostasis stylet assembly 4600 (further described in relation to FIG. 46). As described further below in relation to FIG. 19, the expandable introducer sheath 200 is attached to the dilator assembly 2000 prior to insertion into a desired location in blood vessel. After the expandable introducer sheath 200 and dilator assembly 2000 are at the desired location in the blood vessel, the dilator assembly is removed from the blood vessel, and a medical device, e.g. a pump, is introduced through the expandable introducer sheath 200. After the medical device, e.g. the pump, has been introduced, the hemostasis stylet assembly 4600 can be coupled to the expandable introducer sheath 200 as shown in FIG. 1B to further control any retrograde bleeding. In some implementations, the hemostasis stylet can be a repositioning sheath, which is also used to control of the blood flow along the expandable sheath and minimize bleeding.

Figure 2:
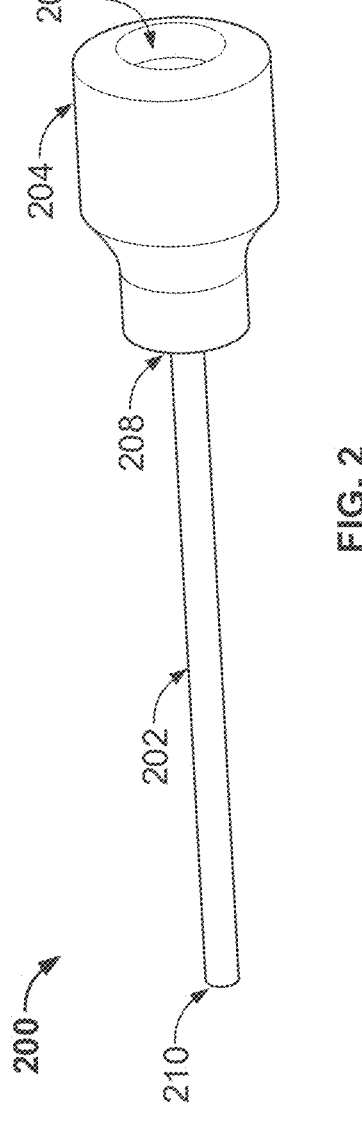
FIG. 2 shows an isometric view of an illustrative expandable sheath assembly.

FIG. 2 shows an illustrative expandable introducer sheath 200 (e.g. the expandable introducer sheath 200 of FIG. 1), comprising a hub 204 and expandable sheath body 202. As discussed further below in relation to FIGS. 16-18 and 49-52, the expandable sheath body 202 of the expandable introducer sheath 200 comprises a frame and one or more coatings. In one embodiment, the expandable sheath body 202 includes the frame, a polymer coating encapsulating the frame, and a hydrophilic coating on a portion of an inner surface and/or outer surface of the polymer-coated frame. The frame of the expandable sheath body 202 shown in FIG. 2 may be a braid, for example a woven braid (e.g. FIGS. 7A-B, FIG. 8, FIG. 9), a laser cut frame (e.g. FIG. 10), or a wire-wound frame (e.g. FIGS. 11A-C). Each of these frames is further described below. Alternatively, the frame of the expandable sheath body 202 may use any other structure such that the force to insert a device within the sheath body is minimized (e.g. below 5N), and such that the sheath can turn corners as required by patient anatomy (e.g. turn corners with a minimum bend configuration of 30 mm through 55-degree bend using a force less than 5N). At least one advantage of the hydrophilic coating is to reduce frictional forces on the sheath below a threshold that begins the process of "finger trapping", during which the device being inserted (e.g. an intracardiac heart pump) creates a positive feedback loop, due to the axial load caused by friction, wherein the sheath will compress upon the device being inserted and increase the frictional force and axial load resulting in the inserted device becoming seized and insertion not being able to be completed.

As shown in FIG. 2, the expandable sheath body 202 is defined by a proximal end 208, a distal end 210, and a lumen extending through between the proximal and distal end. On the proximal end 208, the expandable sheath body 202 is attached to the hub 204. The hub 204 comprises a proximal end and a distal end, with a lumen extending between the proximal end and the distal end. On its distal end, the hub 204 is attached to the expandable sheath body 202. On the proximal side of the hub 204 there is a hemostasis valve 206 within the sheath hub 204. The hemostasis valve 206 allows for insertion of components through the hub and sheath but prevents flow of fluid (i.e. blood) from the distal end of the expandable sheath body 202 to the outside of the expandable sheath body 202 and hub 204. The hub 204 contains a side-arm (not shown in FIG. 2) that allows for aspiration of fluid and flushing of the sheath. The distal end 210 of the expandable sheath body 202, as shown in FIGS. 26-33 and described below in relation to FIGS. 26-33, has a geometry configured to interface with a dilator assembly (e.g. dilator assembly 2000 of FIG. 20). The distal end 210 of the expandable sheath body 202 is also advantageously atraumatic—to avoid damaging the blood vessel wall or any other anatomy during insertion of the expandable introducer sheath assembly, and while the expandable introducer sheath assembly remains within a patient.

Figure 3:
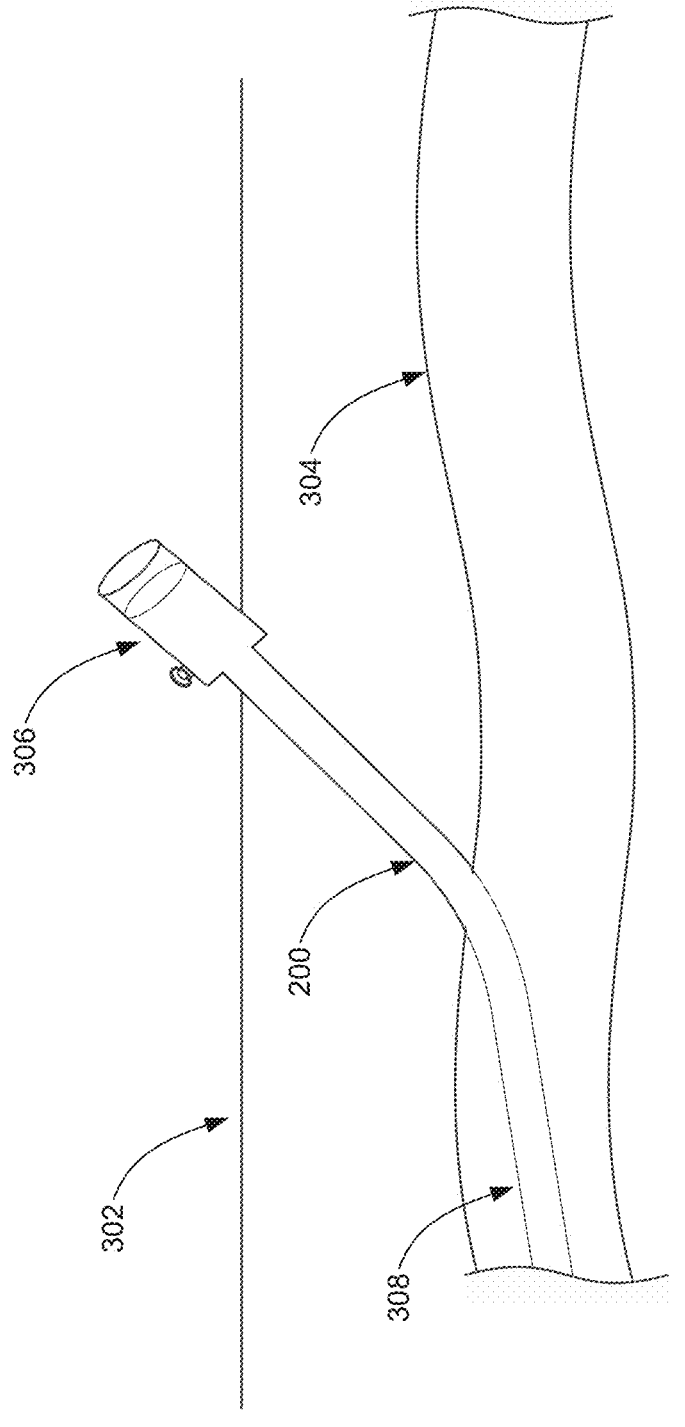
FIG. 3 shows the introducer sheath after insertion into the blood vessel.

FIG. 3 shows an illustrative expandable introducer sheath 200 (e.g. expandable introducer sheath 200 shown in FIG. 2) after insertion into the blood vessel 304 of a patient. As shown, the proximal portion 306 of the introducer sheath 200 is outside the skin 302 of the patient, while the distal portion 308 of the expandable introducer sheath 200 is within the vessel 304. As described further below in relation to FIGS. 16-18 and 49-52, at least a distal portion (e.g. portion 308) of the expandable introducer sheath 200 is coated with one or more coatings. Alternatively, the entire length of the expandable introducer sheath 200 is coated with one or more coatings. At least one advantage of the expandable introducer sheath 200 being coated includes minimizing friction between various materials of the sheath and the device being inserted. At least another advantage of the expandable introducer sheath 200 being coated and forming a closed-cell mesh is that the expandable sheath is not porous and blood is not diverted through the expandable sheath. At least another advantage of the expandable introducer sheath 200 being coated and forming a closed-cell mesh is that, when flushing the sheath from the sheath hub to clear the entire length of the sheath, the fluid goes along the entire length of the sheath rather than going through the mesh. At least another advantage of the expandable introducer sheath 200 being coated and forming a closed-cell mesh is that the expandable introducer sheath 200 is less sensitive to positioning relative to the arteriotomy because the closed-cell mesh reduces risk of bleeding across the arteriotomy. At least some additional advantages of the expandable sheath body (e.g. expandable sheath body 202 of FIG. 2) in the expandable introducer sheath 200 include providing sufficient stiffness for the sheath body to maintain an open lumen along its length, while remaining flexible enough to expand, as described below in relation at least to FIGS. 12 and 4. In any instances where the medical device being passed through the sheath is an intracardiac heart pump with a pigtail at its distal end, the pigtail has the potential to catch on a distal end of the sheath as the pump is being withdrawn. At least an additional advantage of the expandable sheath body is to have enough longitudinal resistance or column strength to counter the removal force and prevent the sheath from buckling and bunching up along its length during removal of the device.

As mentioned above after the expandable introducer sheath 200 is at a desired position in a vessel, a medical device, e.g. a pump, is introduced into and passes through the expandable introducer sheath 200 until the medical device is positioned distal of the expandable introducer sheath. At a later time the medical device may be in turn passed through the expandable introducer sheath in order to be withdrawn from the body of the patient. The expandable sheath body 202 of the expandable introducer sheath is designed to expand and contract to accommodate insertion and withdrawal of the medical device while avoiding buckling and/or kinking of the expandable introducer sheath. The structure of the sheath body allows for the sheath to expand during the passage of the medical device in the lumen of the sheath body.

Figures 4A, 4B:
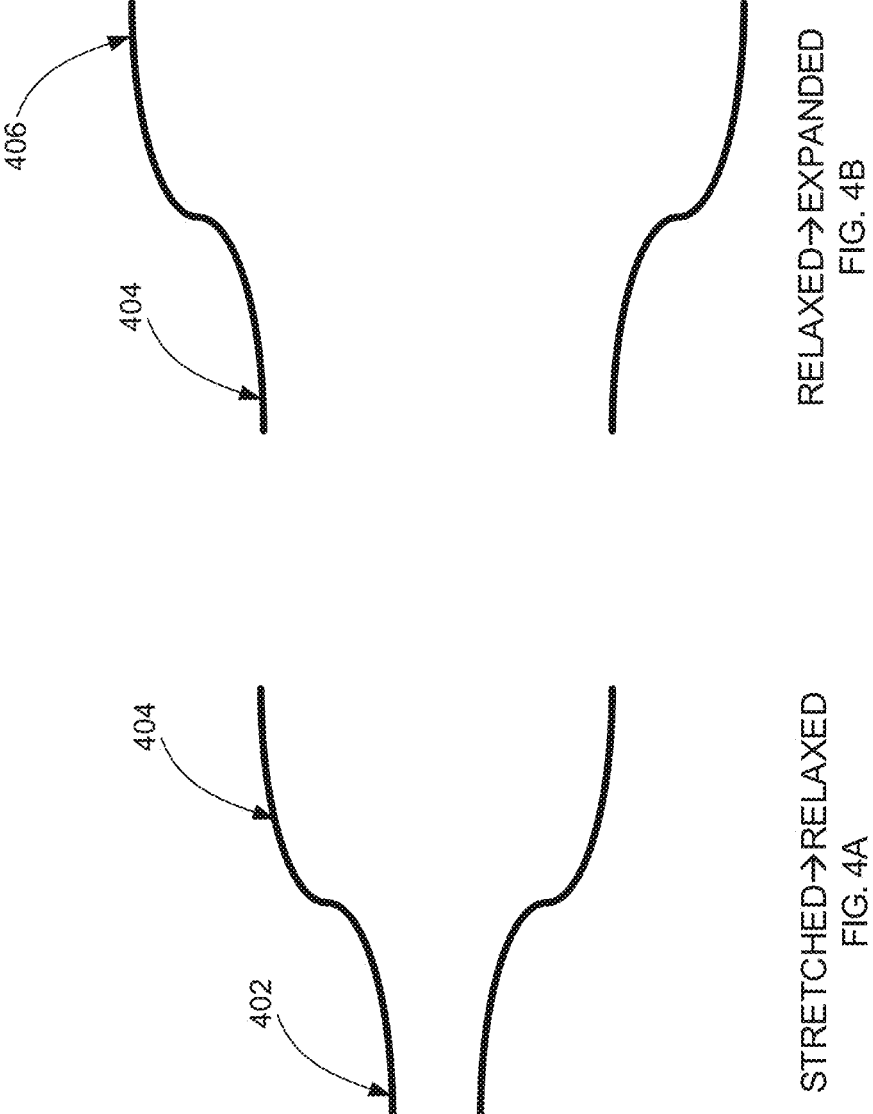
FIGS. 4A and 4B show schematic cross-sectional profiles of an expandable sheath having elongated, relaxed and expanded states.

The expandable introducer sheath can expand between an elongated state, a relaxed state and an expanded state according to at least three different configurations. FIGS. 4A and 4B show schematic profiles of an expandable sheath body (e.g. the expandable sheath body 202 shown in FIG. 2) transitioning between these states. The sheath body must be impermeable to blood through all expansion states. An elongated state is defined as a state in which tensile forces are applied to the expandable introducer sheath, such that the expandable sheath body is stretched, increasing in length and decreasing in diameter. A relaxed state is defined as a state the expandable introducer sheath is in when no external forces are applied to the expandable introducer sheath, e.g. no tensile forces, and or no radially expanding or compressing forces. An expanded state is defined as one in which radially outward forces may be applied to the expandable introducer sheath, such that its diameter increases. In some instances the expandable introducer sheath may also be in a second relaxed state, defined as a state in which the diameter of the expandable introducer sheath is reduced relative to a previous state.

In a first configuration, the expandable introducer sheath is inserted to a desired location in a first state, and the expandable introducer sheath relaxes to a second state. As shown for example in FIG. 4A, portion 402 of the sheath is in an elongated first state, whereas portion 404 of the sheath is in a second relaxed state. In the first state the expandable introducer sheath is stretched, increasing in length and decreasing in diameter relative to the second state—the diameter of portion 402 of the sheath is smaller than the diameter of the sheath in portion 404. Once the expandable introducer sheath is at the desired location and tensile forces are no longer applied to the expandable introducer sheath, the expandable introducer sheath relaxes to the second state, a resting state, with a diameter which is sufficiently large to allow passage of a medical device, e.g. a pump without further deformation. The diameter of portion 404 in FIG. 4A is greater than a diameter of a medical device.

In a second configuration, the expandable introducer sheath is inserted to a desired location in a first state, relaxes to a second state, and expands to a third state to accommodate a medical device. As shown for example in FIG. 4A, portion 402 of the sheath is in an elongated state, whereas portion 404 of the sheath is in a relaxed state. In turn, as shown in FIG. 4B, portion 406 of the sheath is in an expanded state. In the first state, similar to the first configuration, the expandable introducer sheath is stretched, increasing in length and decreasing in diameter relative to the second state. Once the expandable introducer sheath is at the desired location and the expandable introducer sheath is no longer stretched (tensile forces are no longer applied to the expandable introducer sheath), the expandable introducer sheath relaxes to the second state, a resting state, with a diameter which is larger than the diameter of the expandable introducer sheath in the first state, but smaller than a diameter of the medical device to be inserted. In this configuration, a diameter of a medical device to be inserted would be larger than a diameter of the expandable introducer sheath in its relaxed state, i.e. larger than a diameter of portion 404 of the expandable introducer sheath in FIG. 4B. In the third state, the expandable introducer sheath expands further as the larger-diameter medical device is inserted, and expands to accommodate the medical device.

In a third configuration, the expandable introducer sheath is inserted to a desired location in a first state, a resting state, and expands to a second state to accommodate the medical device. The expandable introducer sheath expands to a larger diameter in the second state. As shown for example in relation to FIG. 4B, the diameter of portion 404 of the sheath in its first resting state is smaller than the diameter of portion 406 of the sheath in its second expanded state, and the diameter of portion 406 would accommodate the diameter of a medical device to be inserted. At least one advantage of these configurations is that they allow for a small insertion profile which minimizes insertion related complications and minimizes stretching and load on the access opening formed in the blood vessel.

In some configurations in each state the sheath has a constant diameter along its length. In some configurations in any state the sheath may have a diameter which varies along its length. For example, in a relaxed state the expandable sheath body may have a larger diameter in the proximal portion and a smaller diameter in the distal portion with a taper between the larger diameter and the smaller diameter.

Figure 5:
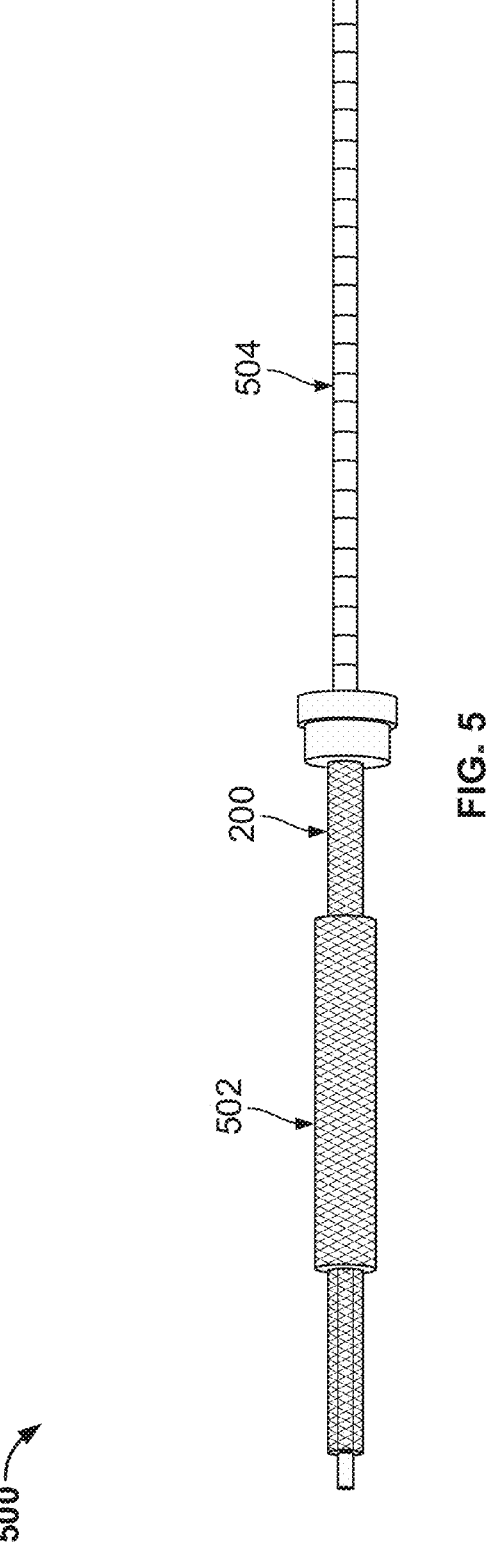
FIG. 5 shows an isometric view of a pump insertion through an expandable sheath.
Figure 6:
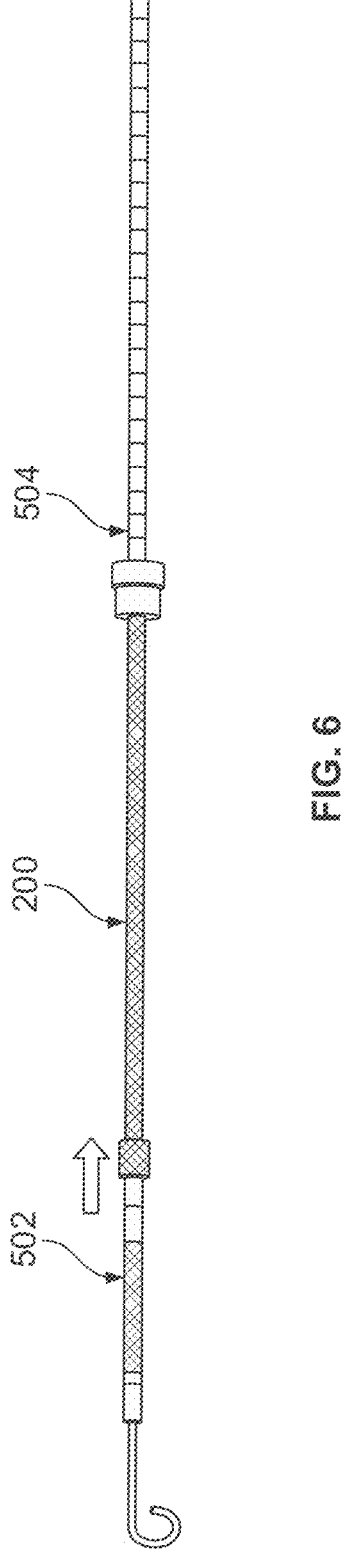
FIG. 6 shows an isometric view of a pump partially removed from an illustrative expandable sheath.

As an example, FIG. 5 shows the insertion of a heart pump 502 through an introducer sheath 200 in the third configuration. As shown in FIG. 5, the outer diameter of the pump 502 is larger than the inner diameter of the expandable sheath body 202 causing the expandable sheath body 202 to expand as the pump passes through—the sheath 202 is in an expanded second state over the length of the pump 502. The outer diameter of catheter 504 may be larger than the inner diameter of the expandable sheath body 202, where the expandable sheath body 202 collapses back down on the catheter 504 (e.g. in a second relaxed state) after passage of the pump 502 and the expandable sheath body 202 tight on the catheter 504 in this second relaxed state. As an example, FIG. 6 shows the removal of the pump 502. The distal end of the introducer sheath 200 expands as the pump 502 is pulled through. The introducer sheath 200 must have enough column strength to resist buckling due to the frictional loads of the pump 502 and of the uncurl force of the pigtail.

Figure 7B:
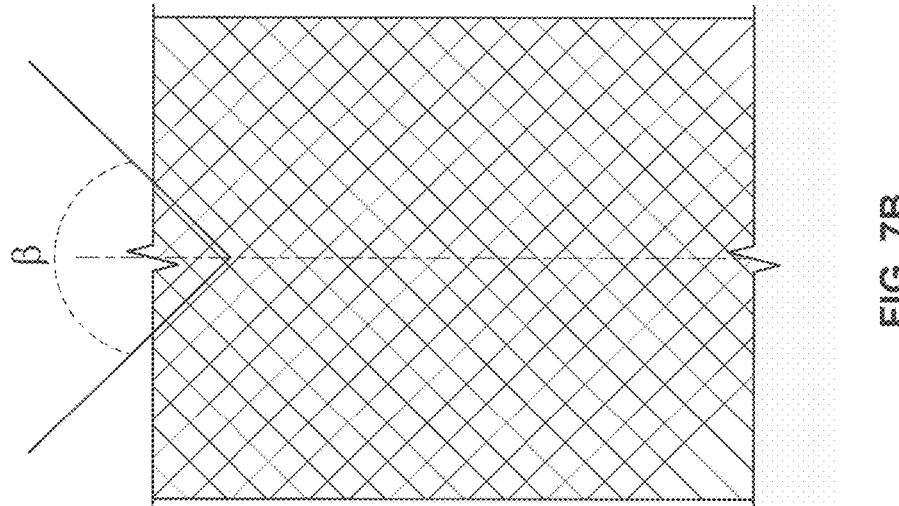
FIGS. 7A and 7B show illustrative braid patterns for an illustrative expandable sheath body.
Figure 7A:
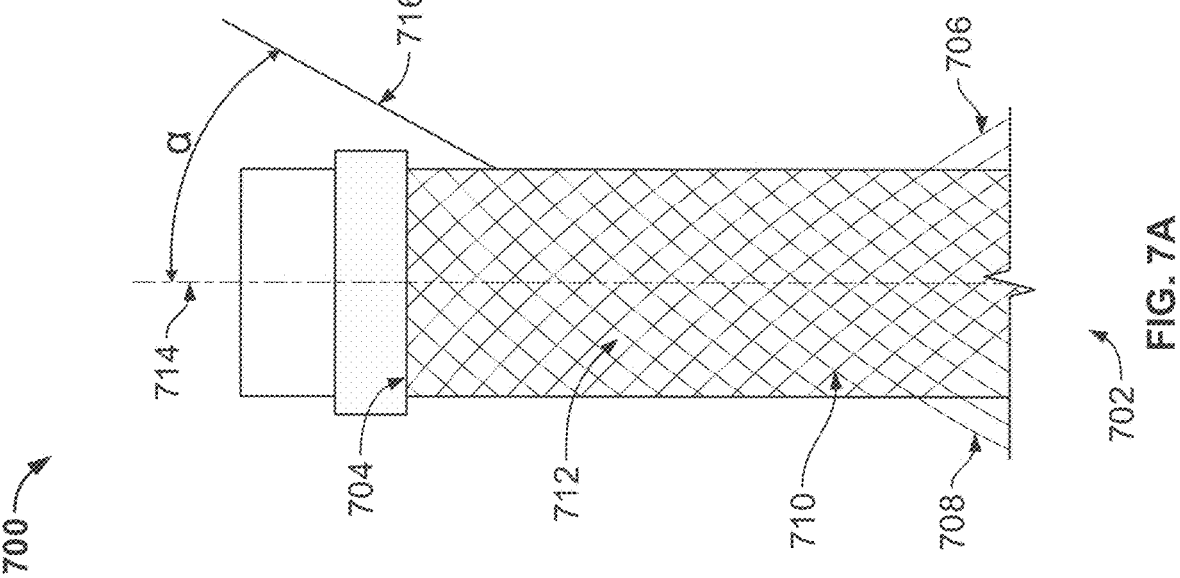
Figure 10:
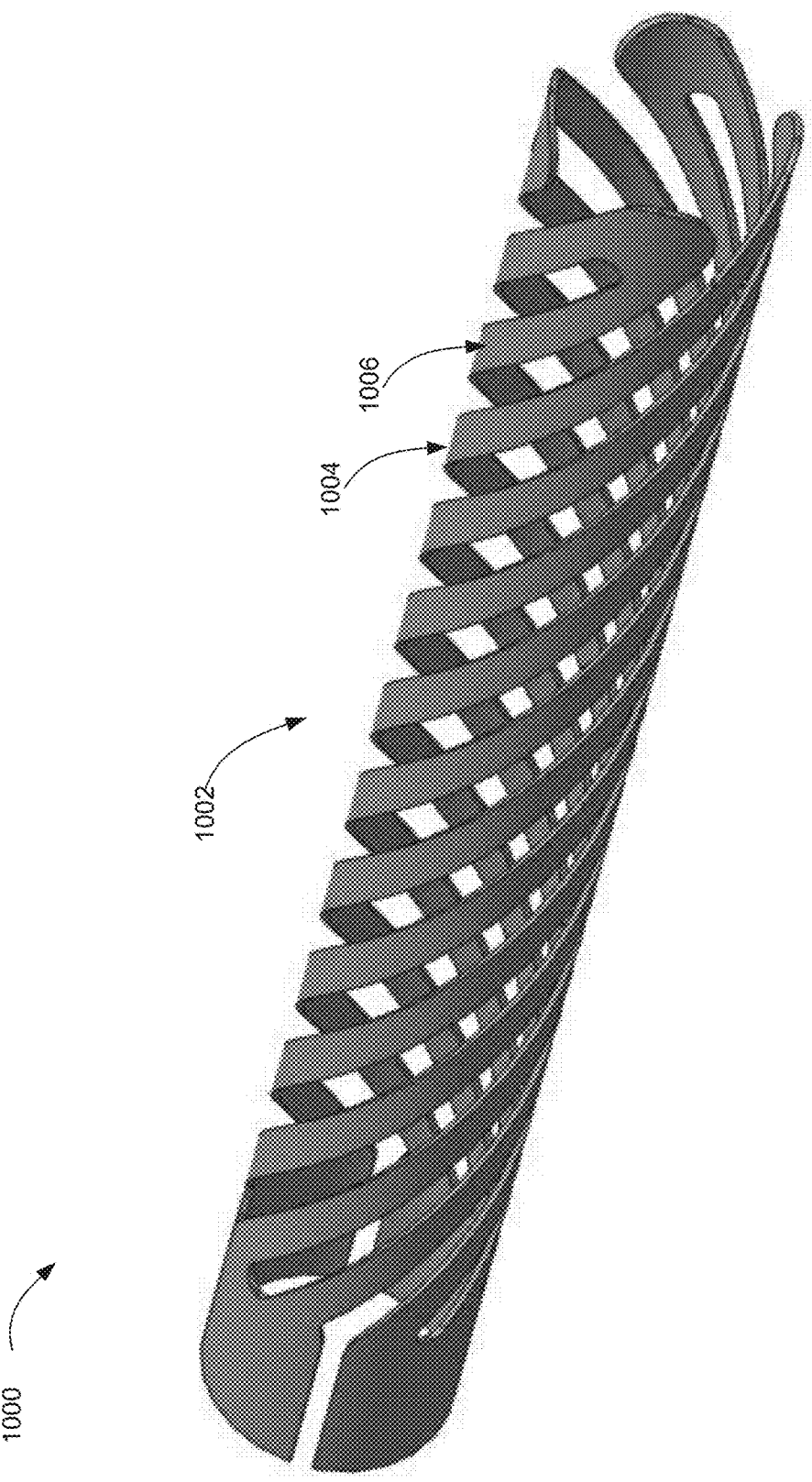
FIG. 10 shows an illustrative view of a laser cut frame for an illustrative expandable sheath.
Figures 11A, 11B, 11C:
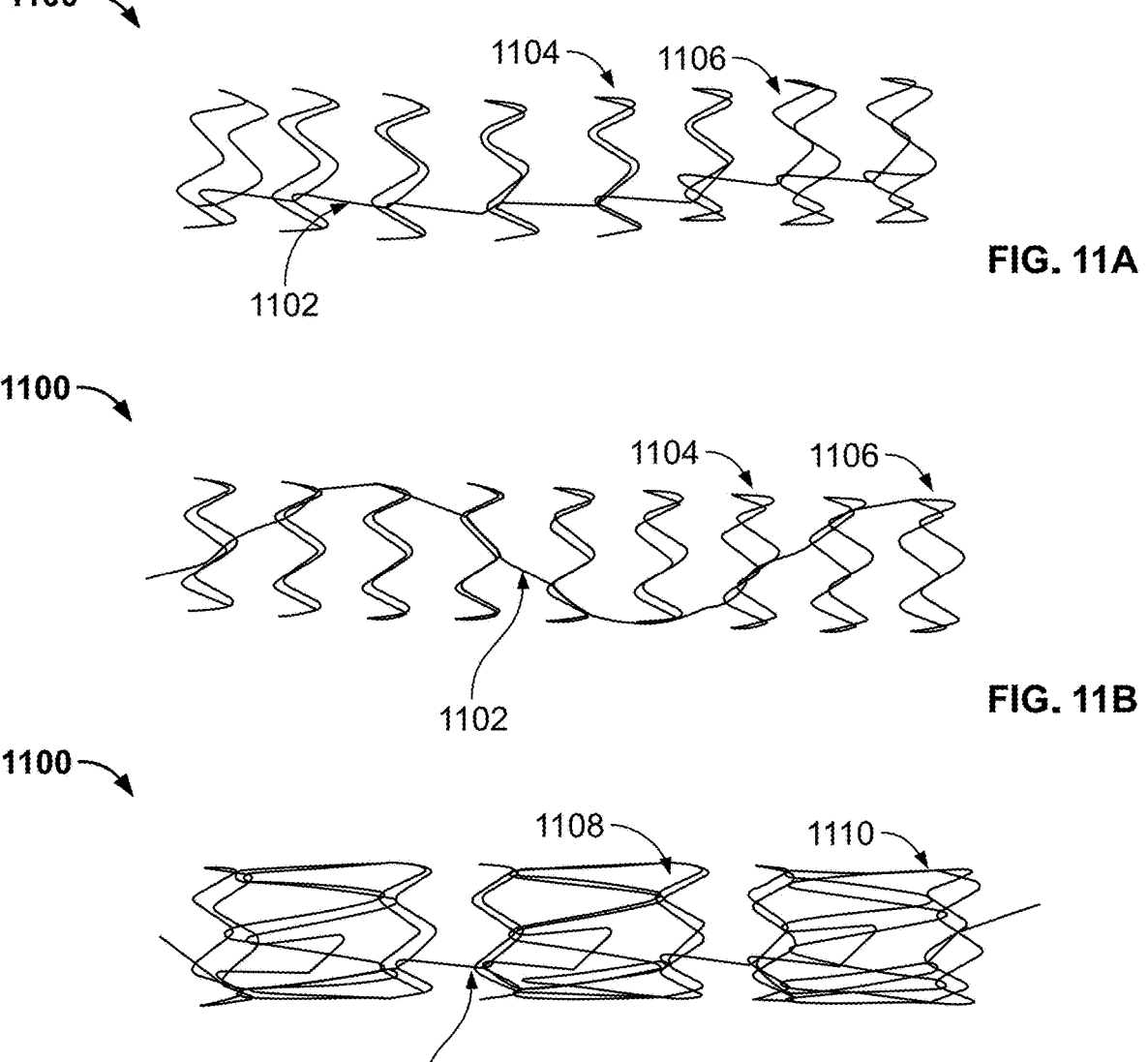
FIGS. 11A-C show an illustrative view of a single wire frame for an illustrative expandable sheath.

As mentioned above, the frame component of the expandable sheath body may be at least one of a braid (e.g. FIGS. 7A-B, FIG. 8, FIG. 9), a laser cut frame (e.g. FIG. 10), or a wire-wound frame (e.g. FIGS. 11A-C). In one embodiment, the frame component of the expandable sheath body 202 is a braid, e.g. as shown in FIG. 7. The braid may comprise threads of braid material that form a pattern. A braid is defined herein as an interlace of two or more strands or threads, with the two or more strands or threads crossing each other at least once along a length of the braid. In contrast to a mesh, in which connection points are fixed, the crossings between threads in the braid are not fixed, i.e. the crossings between threads may shift along the length of the braid, and/or the angles of the threads at the crossing may vary as well. Some examples of the braid material include Nitinol round wire, Nitinol flat wire, stainless steel round wire, stainless steel flat wire, other metals, or other rigid polymers such as PEEK. At least one advantage of using Nitinol for the frame, e.g. braid, is that the frame will be visible under medical imaging, e.g. fluoroscopy, and will assist a user with placement of the device. In some embodiments, the braid threads of expandable sheath body 202 are radioactive. At least one advantage of using superelastic nitinol as a metallic frame is having a frame that resists kinking and that enables recovery from any mechanical deformation the sheath may encounter.

Figure 8:
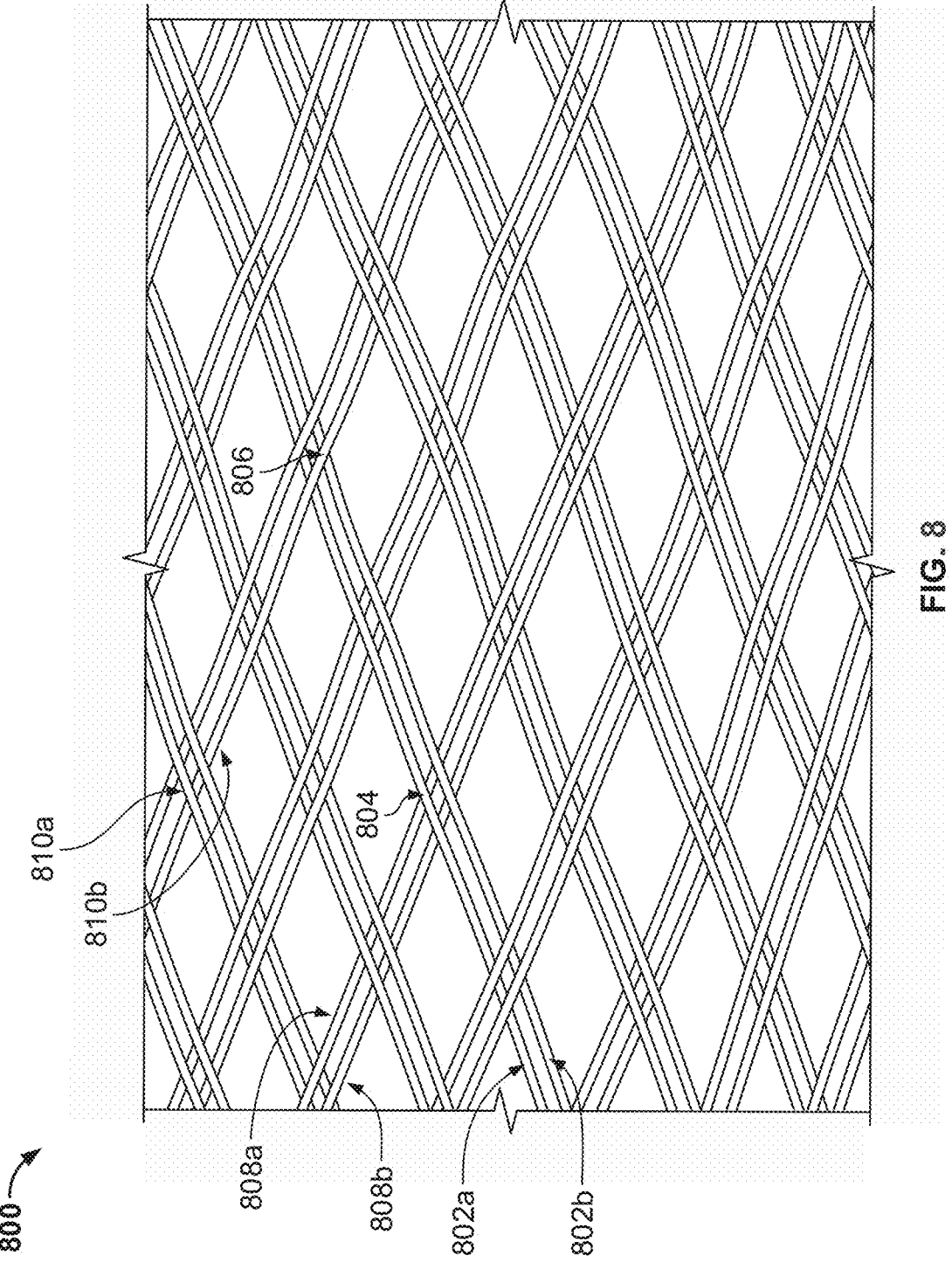
FIG. 8 shows an isometric view of an illustrative introducer sheath body with pairs of opposed threads in a first pattern.
Figure 9:
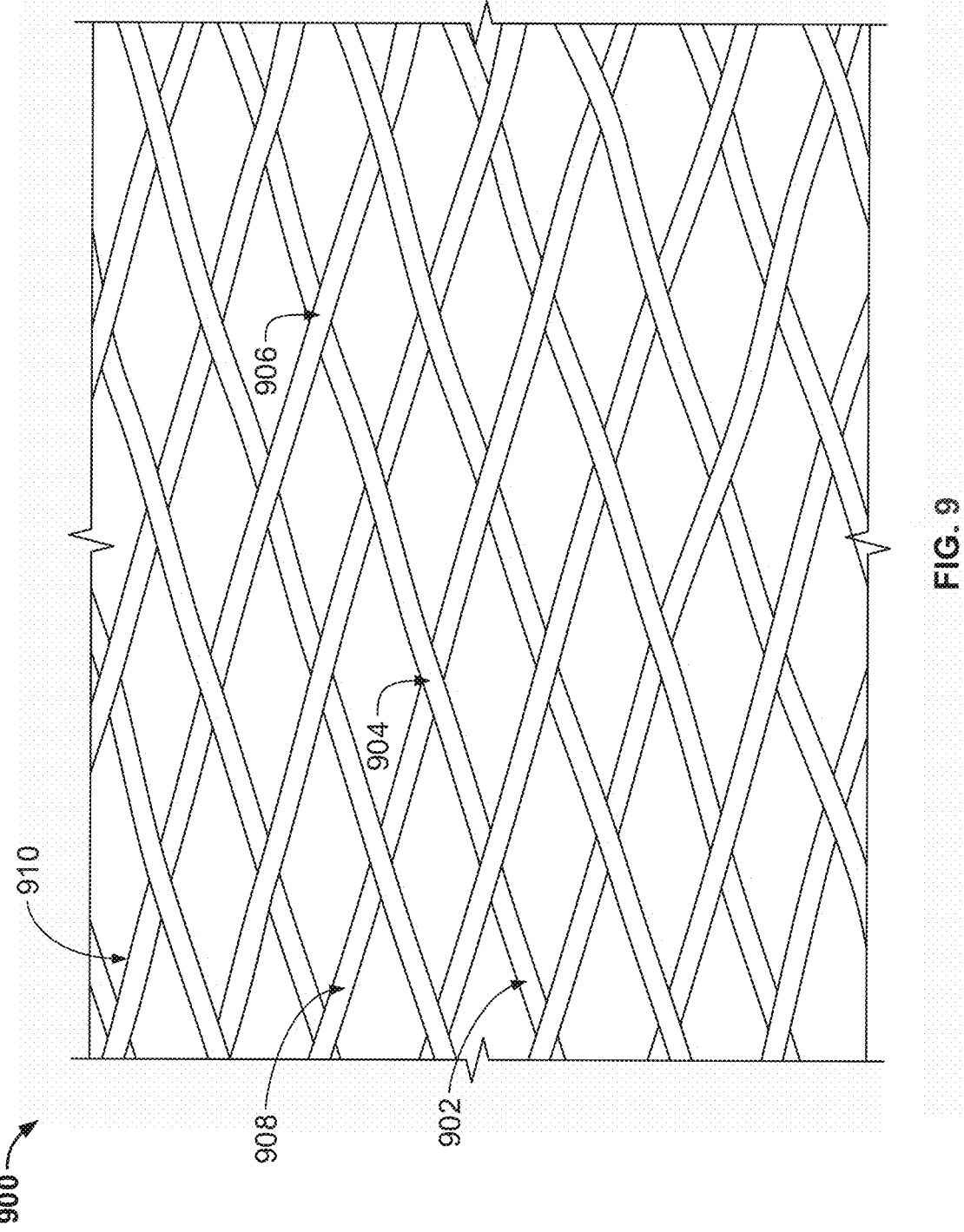
FIG. 9 shows an illustrative view of a braid of an expandable sheath with opposed threads in a second pattern.

FIGS. 7-9 show illustrative representations of an expandable sheath body using a braid as its frame. FIG. 7 shows an illustrative representation of the expandable sheath body 202 including a braid 700 having a distal end 704 and a proximal end 702, and a lumen extending between the proximal end 702 and the distal end 704. Braid 700 can be made out of various materials and geometry. The braid 700 of FIG. 7 comprises a group of threads wrapped in a clock-wise spiral direction along the length 706 and a counter-clock-wise spiral direction along the length 708. In some configurations, the groups of threads are wrapped in one spiral direction, clock-wise or counter-clock-wise, along the length. The angle alpha (α) is defined herein as the angle between the axis of the braid 714 and the direction 716 of the threads. The angle beta (ß) defines the angle between the clock-wise and counter-clock-wise threads. The value of ß may be 55 degrees, 45 degrees, 35 degrees, or another magnitude (as further described in relation to FIG. 9 below). As shown in FIG. 7, thread 706 crosses with thread 708 at a corner 710: thread 706 can cross on top or below thread 708. The space created between threads, e.g. between thread 706 and thread 708 in FIG. 7 define a window 712. The window 712 may have a rhombus shape as shown in FIG. 7. Alternatively, the window 712 may be shaped as a parallelogram, square, or other geometry. In some configurations the braid has a constant pattern down the length of the sheath body 202. In some configurations, there is a variable braid angle along the sheath body 202. In some configurations the diameter of the braid is consistent along the sheath body 202. In some configurations, the braid threads are of the same diameter. In certain implementations, the diameter of the braid material is between about 1 millimeters and about 10 millimeters. In further implementations, the diameter of the braid material is between about 3 millimeters and about 8 millimeters. In some implementations, the diameter of the braid material is between about 5 millimeters and about 6 millimeters. In further implementations, the diameter of the braid material is about 5.5 millimeters. In some configurations one or more of the threads may be of a different diameter than the rest. In one configuration there is a subset of large threads that are spaced evenly throughout the braid comprising smaller diameter threads.

A braid configuration is shown in FIG. 8 which shows a braid 800 of the expandable sheath body 202 with thread pairs 802a, 802b, 808a, 808b, 810a, and 810b. Each thread pair (e.g. thread pair 802a, 802b) travels "over two" opposing thread pairs (e.g. threads 808a, 808b) at a first corner 804, then "under two" opposing thread pairs (e.g. threads 810a, 810b) at a second corner 806. Accordingly, the construction shown in FIG. 8 is referred to as a "2 over 2" or "2 strands per thread over two opposing strands" pattern.

FIG. 9 shows an alternative braid configuration which includes a braid 900 of the expandable sheath body 202 with threads 902, 908, and 910 of one strand each. Each thread (e.g. thread 902) travels "over two" opposing threads (e.g. threads 908) starting at corner 904, then "under two" opposing threads (e.g. threads 910) starting at corner 906. The construction shown in FIG. 9 is refer to as a "1 over 2" or "1 strand per thread over two opposing threads" pattern. There may be a total of 96 strands, 72 strands, 48 strands, or another quantity of strands. The angle β may be between 5 and 175 degrees. The braid construction can be defined as 1 over 1, 1 over 2, 1 over 3, 1 over 4, 2 over 2, 2 over 4, 2 over 6, or another braid pattern. At least one advantage of a braid pattern of "1 over 1" is that the "1 over 1" is axially stiffer and allows for a larger minimum diameter expandable sheath body 202 compared to a braid pattern of "1 over 2." Alternatively, a braid pattern of "1 over 2" allows for larger flexibility compared to a braid pattern of "1 over 1."

FIGS. 9 and 10 show illustrative representations of an expandable sheath body using a laser cut or single wire frame. As mentioned above, instead of a braid, the frame component of the expandable sheath body may be a laser cut frame (e.g. FIG. 10), or a wire-wound frame (e.g. FIGS. 11A-C). FIG. 10 shows another alternative expandable sheath body configuration 1000 with a laser cut frame 1002. The laser cut frame 1002 defines a strand which wraps in a spiral direction along the length of the expandable sheath body 202. In the embodiment shown in FIG. 10 each spiral strand (e.g. 1004, 1006) extends along the entire length of the expandable sheath body 202. Alternatively, the laser cut frame may define windows between strands, similar to the braid patterns described in relation to FIG. 7 and FIG. 9.

FIGS. 11A-C show another alternative expandable sheath body configuration with a wire-wound frame 1100. FIG. 11A shows a single wire frame where the wire 1102 is straight between stages 1104 and 1106. FIG. 11B shows a single wire frame where the wire 1102 form a helix along the length of the frame, as visible between stages 1104 and 1106. FIG. 11C shows an alternative single wire frame where the wire 1102 connects stages 1108 and 1110, and stages 1108 and 1110 are formed differently from stages 1104 and 1106 in FIGS. 11A-B. Any of the frame elements for the expandable sheath body (braid, laser cut or wire-wound) can be combined with one or more coatings. At least one advantage of a single wire results is having blunted wire crowns or loops (e.g. states 1104 and 1106 in FIGS. 11A-B) at the distal end of the frame that loop back and forth. The wire-wound frame provides a high degree of flexibility while controlling the level of foreshortening and "finger-trapping" by adjusting the pattern to have fewer crossover points. The wire-bound frame also increases kink resistance while a winding pattern that includes a lower braiding angle or extended longitudinal members would reduce risk of buckling during pump removal. A number of winding tool and winding pattern concepts were developed to demonstrate the most likely patterns to solve the previously presented design problems. The tooling models varied by the number of pin arrays and the number of pins per array. The patterns developed for this application have been designed to contribute to a higher column strength to help prevent buckling and allow for an even tension across coating materials during expansion.

In one embodiment, the expandable sheath body 202 includes the frame (braid, laser cut or wire-bound), a polymer coating encapsulating the frame, and a hydrophilic coating on an inner surface and/or outer surface of the polymer-coated frame.

Figure 12:
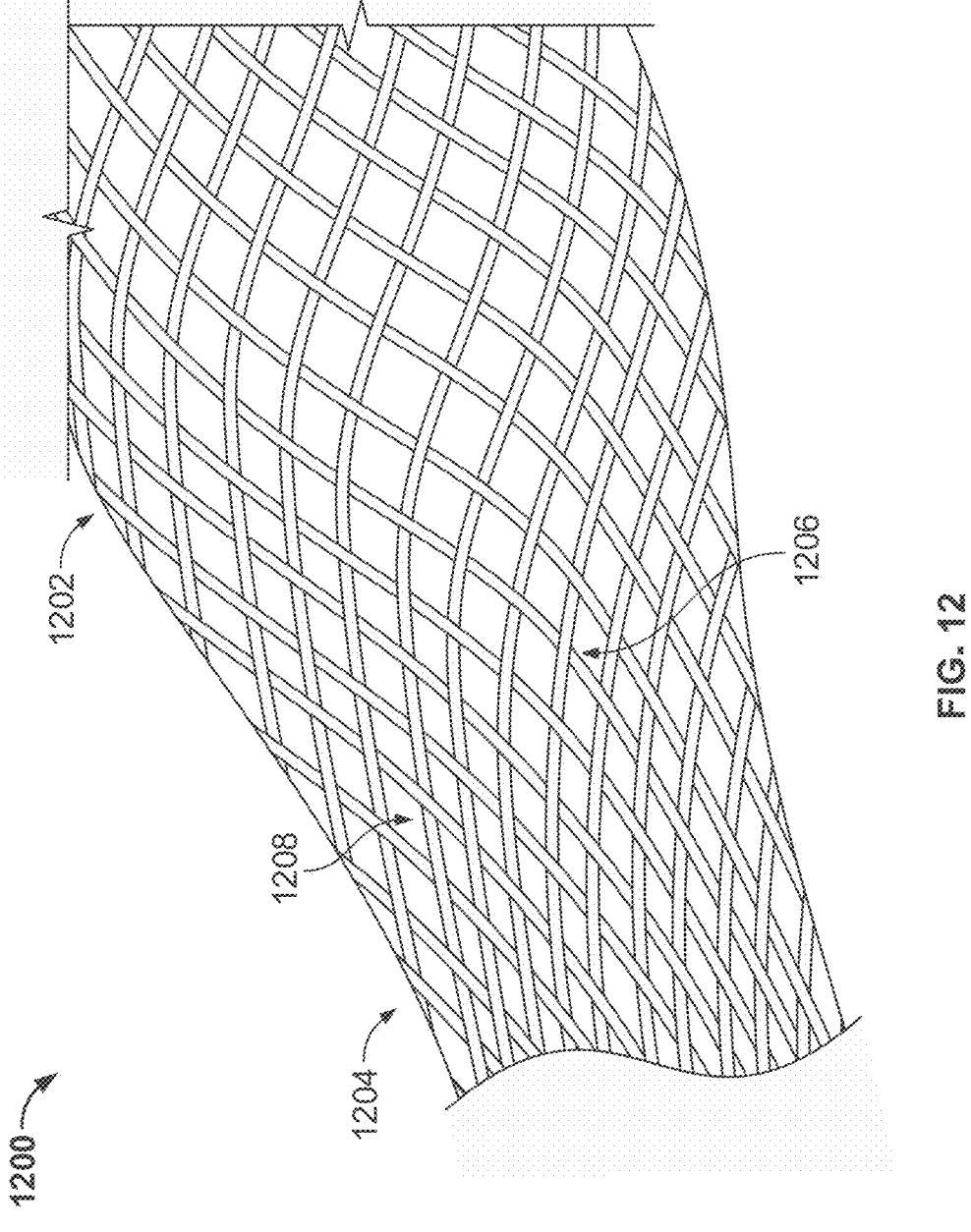
FIG. 12 shows an illustrative view of a braid of an expandable sheath having a first portion in a relaxed state and a second portion in an expanded state.

FIG. 12 and FIGS. 49-54 show illustrative expandable sheaths with different frame and coating configurations. FIG. 12 shows an example of a coated frame for an expandable sheath body (e.g. a braid as shown in FIGS. 7-9) having a first portion 1204 in a first state (e.g. relaxed state 404 of FIG. 4B) and a second portion 1202 in a second state (e.g. expanded state 406 of FIG. 4B). A coating 1206, e.g. a polymer coating, fully encapsulates the braid. The polymer coating may be biased to be substantially along an inner diameter of the frame (e.g. the braid), to create a smooth inner surface. Alternatively, the polymer coating may be biased to be substantially along the outer diameter of the frame (e.g. the braid) to create a smooth outer surface, as discussed in greater detail in relation to FIGS. 51 and 52 below. As shown in FIG. 12, the polymer encapsulation covers the windows 1208, i.e. the area between the braid strands. A hydrophilic coating is added over at least a portion of the inner surface of the polymer encapsulated frame.

Optionally, a hydrophilic coating may also be added over at least a portion of the outer surface of the polymer encapsulated frame. At least one advantage of the frame, the polymer coating and the hydrophilic coating combination is to reduce friction during delivery and to avoid clotting by allowing adequate blood flow along the sheath body.

Figures 49, 50, 51:
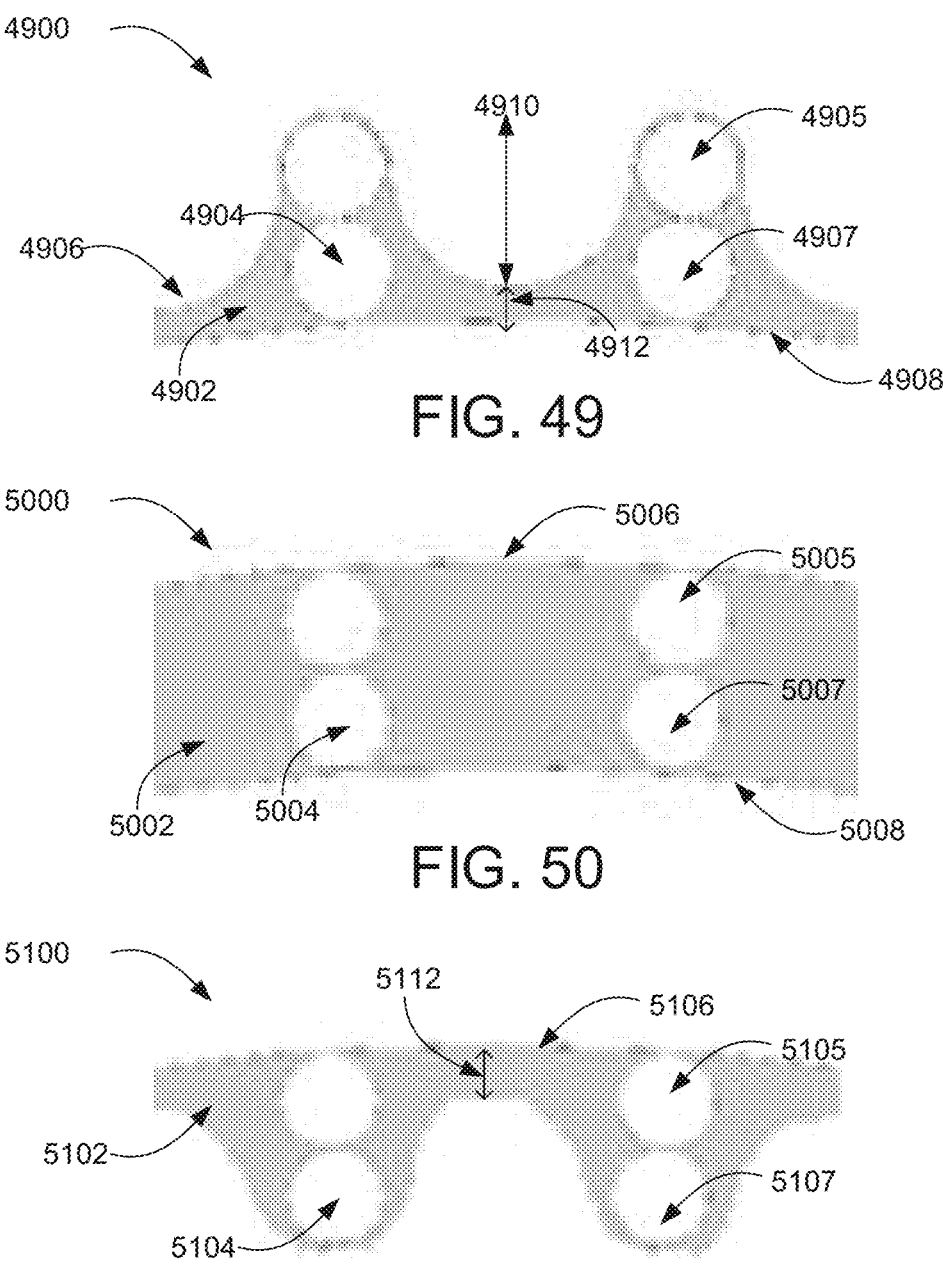
FIG. 49 shows a cross-section of the braid material surrounded by the polymer encapsulation forming a textured outer surface and a smooth inner surface.
FIG. 50 shows a cross-section of the braid material surrounded by the polymer encapsulation forming a smooth outer surface and a smooth inner surface.
FIG. 51 shows a cross-section of the braid material surrounded by the polymer encapsulation forming a smooth outer surface and a textured inner surface.

FIG. 49 shows a cross-section of an expandable sheath biased towards the inner diameter of the sheath. The sheath cross-section includes a frame 4904 and a coating layer 4902. The frame 4904 in FIG. 49 is a braided mesh, with wire strands 4905 and 4907. Alternatively, the frame 4904 can be a laser cut mesh or a single-wire mesh. As shown in FIGS. 49, frame 4904 with strands 4905 and 4907 of the braid material is fully encapsulated by coating layer 4902, forming a textured outer (i.e., abluminal) surface 4906 and a smooth inner (i.e., endoluminal) surface 4908. The braids of the frame 4904 extend longitudinally along the frame but the coating positions the braids so they protrude away from the lumen of the sheath, so the frame 4904 forms peaks and valleys which form a corrugated outer surface while the inner surface is smooth, the sheath thus having an inner-diameter bias configuration. A depth difference 4910 is the difference between a peak and valley. This combination of a low friction surface that can easily expand radially facilitating easy passage of a medical devise, thanks to the sheath. The textured outer surface 4906 includes troughs having a depth 4910 between adjacent strand pairs 4902 and 4904. At the trough, only the coating layer 4902 is present, with a thickness 4912. Advantageously, the smooth inner surface of the sheath in this configuration allows a medical device to be inserted through the sheath, and the coating layer 4902 with a relatively small thickness 4912 at the trough does not prevent frame 4904 from expanding, e.g. wire strands 4905 and 4907 remain free to move relative to one another. The depth difference 4910 is selected to reduce the risk of clot formation on the sheath. For example, the risk of clot formation on the sheath is reduced if the depth difference 4910 is less than around 100 μm. In yet another example, the risk of clot formation on the sheath is significantly reduced if the depth difference 4910 is less than around 60 μm.

FIG. 50 shows a cross-section of an expandable sheath in an alternative configuration with no bias. The cross-section includes a frame 5004 and a coating layer 5002. The frame 5004 in FIG. 50 is a braided mesh, with wire strands 5005 and 5007. Alternatively, the frame 5004 can be a laser cut mesh or a single-wire mesh. As shown in FIG. 50, the frame 5004 is fully surrounded (also referred to as encapsulated) by the coating layer 5002, forming both a smooth outer surface and a smooth inner surface. In this configuration, a thickness of the coating layer 5002 is effectively constant throughout the sheath and equal to or greater than a thickness of the frame 5004. For example, the thickness of the coating layer 5002 is twice the thickness of one strand of the braid material. As shown in FIG. 50, both the inner surface 5008 and the outer surface 5006 of the sheath are smooth. At least one advantage of this configuration with respect to the configuration shown in FIG. 49 is the ability to prevent blood collection and clotting on the sheath. The thickness of the coating layer 5002, and the coating layer 5002 fully encapsulating the frame 5004 may require a larger force to be applied to expand the sheath. For example, the coating layer 5002 may limit the sheath wire strands 5005 and 5007 in their relative motion and their ability to expand or contract.

FIG. 51 shows a cross-section of an expandable sheath biased towards the outer diameter of the sheath. The sheath cross-section includes a frame 5104 and a coating layer

5102. The frame 5104 in FIG. 51 is a braided mesh, with wire strands 5105 and 5107. Alternatively, the frame 5104 can be a laser cut mesh or a single-wire mesh. As shown in FIG. 51, the coating layer 5102 creates a smooth outer surface 5106, similar to the outer surface 5006 of the sheath of FIG. 50, advantageously minimizing clotting on the outside of the sheath. The braids of the frame extend longitudinal along the frame but the coating positions the braids so they protrude into the lumen of the sheath. The interior coating is thin and creates a thin surface around the interior face of the braids. The thin coating extends around the braids forming peaks and valleys/troughs along the interior lumen of the sheath. The peaks correspond to the height of the overlapping strands of the braid, whereas the valleys/troughs correspond to the space between the overlapping strands of the braid. A depth difference 5110 is the difference between a peak and valley. The textured inner surface 5106 includes valleys/troughs having a depth 5110 between two adjacent strand pairs 5105 and 5107. At the trough, only the coating layer 5102 is present, with a thickness 5112. Because the interior peaks are covered with the thin film, they are low in friction, and have limited constraints for moving relative to each other, facilitating easy radial expansion. This combination of a low friction surface that can easily expand radially facilitates easy passage of a medical device through the sheath. Advantageously, the inner surface of the sheath in this configuration allows a medical device to be inserted through the sheath while contacting only the peaks of the sheath on the sheath inner diameter. Advantageously, a device inserted through the sheath is in contact with a smaller surface area of the sheath than the configurations of FIGS. 49 and 50. As shown in FIG. 51, the coating layer 5102 advantageously provides both a smooth outer surface, and a reduced surface area on the inner surface of the sheath.

Figure 52:
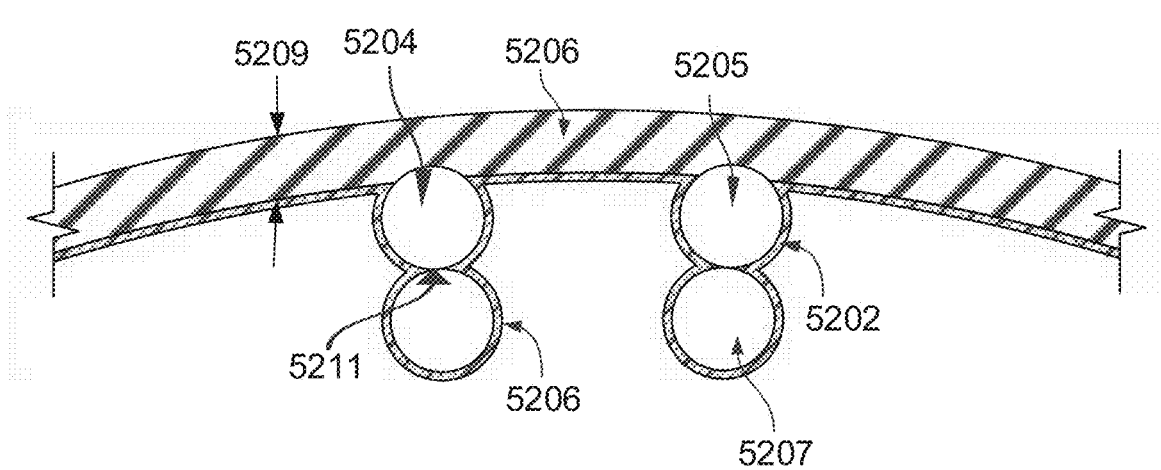
FIG. 52 shows a cross-section of the braid material surrounded by a coating and having a smooth outer surface and a textured inner surface.

FIG. 52 shows a cross-section of an alternative expandable sheath (e.g. expandable introducer sheath 200 of FIG. 2) having an outer-diameter biased arrangement. The sheath cross-section includes a frame 5204, an outer coating layer 5206, and an inner coating layer 5202. The outer coating layer 5206 is an elastomer or similar material. For example, the outer coating layer 5206 may be a polymer. In some implementations, the polymer layer comprises at least one of polyether, and polyurethane. In certain implementations, the polyurethane comprises TPU. In some implementations, the TPU has a durometer between about D20 and about D90. In certain implementations, the TPU has a durometer between about D30 and about D80. In further implementations, the TPU has a durometer between about D40 and about D70. In some implementations, the TPU has a durometer between about D50 and about D60. In further implementations, the TPU has a durometer of about D55. The frame 5204 in FIG. 52 is a mesh, for example, a braided mesh, with wire strands 5205 and 5207. Alternatively, the frame 5204 can be a laser cut mesh or a single-wire mesh. As shown in FIG. 52, the outer coating layer 5206 covers an outer surface of the frame 5204. Advantageously, the outer coating layer 5206 defines a smooth outer surface of the expandable sheath, and covers the open spaces (also referred to as "windows") created by frame 5204. The smooth outer surface of outer coating layer 5206 further reduces the risk of trauma to the vessel when the sheath is inserted, and reduces the risk of blood clots forming on the surface of the expandable sheath.

As shown in FIG. 52, the inner surface of the expandable sheath is coated with a coating 5202. This coating 5202 extends over an inner surface of the outer coating 5206, as well as over the perimeter of the frame 5204 not already covered by coating 5206. The coating 5202 is thin and is applied tightly about the mesh interior surface so as to share the contoured shape of the mesh strands on the outer side. The inner coating 5202 extends around the braids forming peaks and valleys/troughs along the interior lumen of the sheath. The peaks correspond to the height of the overlapping strands 5205 and 5207, whereas the valleys/troughs correspond to the space between the overlapping strands 5205 and 5207. The coating 5202 can be silicone and/or a hydrophobic or hydrophilic material, or any other coating that is suitable to provide a low friction surface for passage of a medical device through the lumen. The coating is thin so the sheath can readily expand to facilitate passing of the medical devise while the low friction outer surface facilitates sliding of the device. A thickness of the coating 5202 is on the order of a few microns. For example a thickness of the coating 5202 is about 5-20 microns. As shown in FIG. 52, the textured inner surface of the sheath advantageously minimizes a surface area in contact with devices inserted through the sheath. Furthermore, as shown in FIG. 52, a thickness 5209 of the outer coating layer 5206 is less than a thickness of the frame 5204, and less than a thickness of one wire strand 5205 or 5207. For example, a thickness 5209 of the outer coating layer 5206 is on the order of about 80-100 microns.

Figure 55:
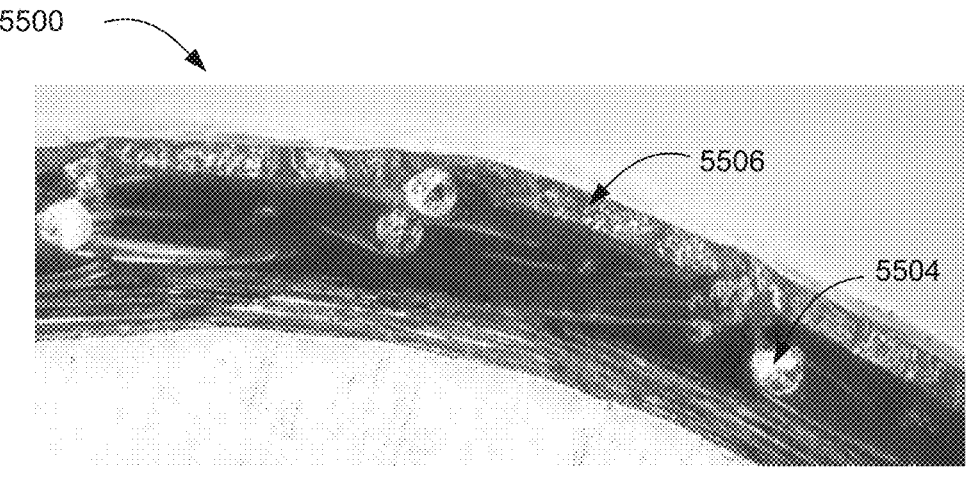
FIG. 55 shows a cross-section of the braid material surrounded by the polymer encapsulation.
Figure 56:
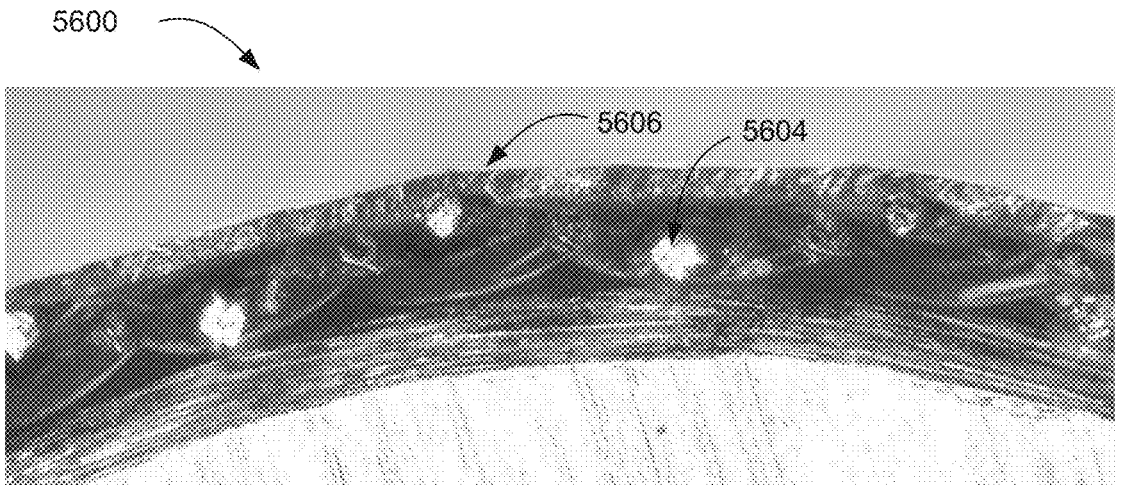
FIG. 56 shows a cross-section of the braid material surrounded by the polymer encapsulation.

The coating is thin so the sheath can readily expand to facilitate passage of the medical device, while the low friction outer surface facilitates sliding passage of the device. As shown in FIG. 52, the outer coating layer 5206 contacts and covers an outer portion of the wire strands 5205 and 5207, but does not fully encapsulate the wire strands, and does not encapsulate the interface 5211 between wire strand 5205 and 5207. FIGS. 55 and 56, described in further detail below show this configuration, with coating layer 5506 (or 5606) being in contact with some but not all of the frame elements 5504 (or 5604) reduces the thickness. The coating layer 5206 may be in contact with only a portion of the frame 5204. For example, the coating layer 5206 may be in contact with less than about 50% of the outer surface of frame 5204. In another example, the coating layer 5206 may be in contact with less than about 25% of the outer surface of frame 5204. In yet another example, the coating layer 5206 may be in contact with less than about 10% of the outer surface of frame 5204. The configuration of the outer coating layer 5206 as shown in FIG. 52 (contacting but not fully encapsulating the frame) is advantageous in preserving the ability of the frame (e.g. wire strands 706 and 708, as described in relation to FIG. 7) to expand and contract such that the expandable sheath (e.g. expandable sheath 200 in FIG. 2) can expand and contract as desired. The outer coating layer is a silicone and/or hydrophobic or hydrophilic coating. As described in relation to FIGS. 57 and 58 for manufacturing of an expandable sheath, the sheath may be formed by various processes. For example, the coating 5206 may be a separate layer heat bonded to the frame 5204 (e.g. as described further in relation to FIG. 57), or may be formed using an outer-diameter biased dipping process with a solvent-polymer coating solution (e.g. as described further in relation to FIG. 58). In some configurations, a separate hydrophobic coating may be applied to the outer surface and/or inner surface of the sheath.

Figure 53:
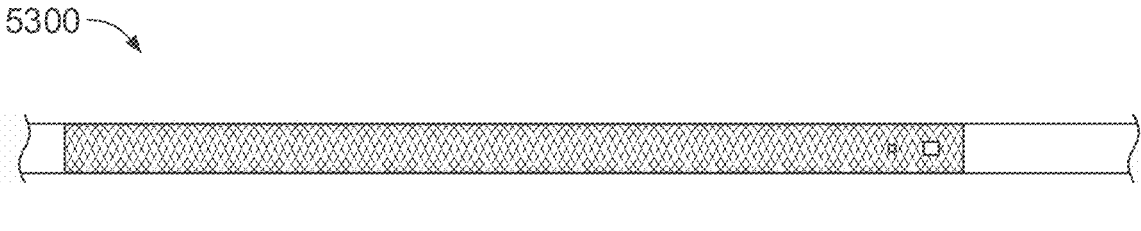
FIG. 53 shows the results of thrombogenicity testing on a first test expandable sheath having a cross-section as shown in FIG. 49.
Figure 54:
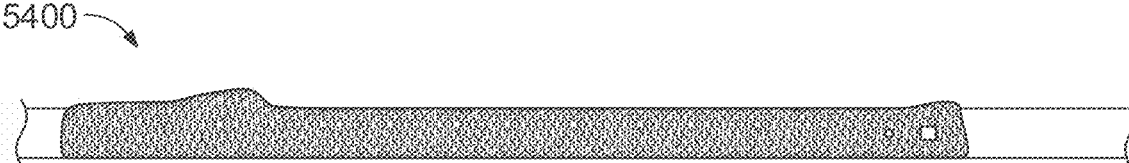
FIG. 54 shows the results of thrombogenicity testing on a second test expandable sheath having a cross-section as shown in FIG. 47.

FIGS. 53 and 54 show example prototypes of an expandable sheath (e.g. expandable sheath 200 of FIG. 2) after use. FIG. 53 shows a prototype of an expandable sheath 5300 representative of a used sheath with a smooth outer surface (e.g. configured according to FIG. 50, 51, or 52) or a sheath with an inner diameter biased geometry (e.g. configured according to FIG. 49) with a depth difference 4910 selected to minimize clotting but maximize flexibility. As shown in FIG. 53, the sheath 5300 has been used (e.g. either placed in a patient or subjected to thrombogenicity testing in a laboratory setting), FIG. 53 shows a prototype with a smooth outer surface, having negligible thrombus growth and adhesion on the outer surface of the sheath 5300. In contrast, FIG. 54 shows an exemplary prototype of an expandable sheath 5400 representative of a used sheath either without a coating layer (e.g. an open cell wire mesh sheath) or a sheath with an inner diameter biased geometry with an inadequate depth difference 5110. The sheath of FIG. 54 has significant build-up on its surface. It also has an expandable sheath with a trough depths greater than a thickness of the frame strand, e.g. greater than 100 μm. As shown in FIG. 54, the sheath shown 5400 has been used (e.g. either placed in a patient or subjected to thrombogenicity testing in a laboratory setting), FIG. 54 shows significant thrombus growth and adhesion on sheath 5400 due to the larger trough depth.

As discussed earlier in relation to FIG. 12, a coated frame for an expandable sheath body (e.g. a braid as shown in FIGS. 7-9) can have different portions of the sheath body in different states. The different states can be achieved or accommodated by varying the properties and/or positioning of the sheath frame (e.g. by varying the relative position of threads forming a braid frame). For example, as shown in FIG. 12 a first portion 1204 in a first state (e.g. relaxed state 404 of FIG. 4B) and a second portion 1202 in a second state (e.g. expanded state 406 of FIG. 4B). A relaxed state (e.g. relaxed state 404 of FIG. 4B) is defined as a state the expandable introducer sheath is in when no external forces are applied to the expandable introducer sheath, e.g. no tensile forces, and or no radially expanding or compressing forces. An expanded state (e.g. expanded state 406 of FIG. 4B) is defined as one in which radially outward forces may be applied to the expandable introducer sheath, such that its diameter increases. In the embodiment of FIG. 12, the diameter of the second portion of the sheath 1202 is larger than the diameter of the first portion of the sheath 1204. Accordingly, the beta angle—the angle between the threads, discussed above in relation to FIG. 7, is larger for the second portion 1202 than the beta angle of the first portion 1204. The strain in the coating 1206 across each window 1208 is higher in the expanded state than the relaxed state 1204. The expansion from a relaxed state 1204 to the expanded state 1202 through an increase in diameter also causes a length shortening caused by the increase in beta angle. As the diameter expands, the braid threads shift causing an increase in the beta angle, the angle between the threads, as previously described in relation to FIG. 7. The beta angle is selected to both reduce the force of insertion required to insert device (with a low beta angle the braid contributes less radial resistance to expansion as a medical device is passed through) and to ensure that a braid reduction in length as the device is passed through does not reduce the braid length to be less than a length of the device itself. A braid with the described structure and functionality defines one concept of the expandable sheath body 202.

The frame material and coating material are selected to allow for thin frame walls while maintaining axial stiffness and elasticity. The coating may be made of a material such as a polymer. The polymer coating can be silicone or thermoplastic polyurethane. In some instances, the polymer fully covers the entire length of the frame and the sheath body exhibits a homogenous construction (frame and coating) along the entire length of the sheath. In other instances, the coating extends over a proximal portion of the braid, covering between 5 and 50% in length of the proximal portion of the braid. Alternatively, the coating extends over a distal portion of the frame, covering between 5 and 50% in length of the distal portion of the braid. In other instances, the coating extends over any portion of the frame, and covers between 5 and 95% of the length of the frame. In other instances, the coating extends over multiple portions of the frame, and the portions can be discontinuous in length, and/or discontinuous in circumference. The polymer encapsulation should be of a low elastic modulus as exhibited by typical Shore A Silicones and Shore A and Shore D thermoplastic polyurethanes. The material for coating the frame can be varied specific to the performance requirements of the expandable sheath body 202. A material with a lower elastic modulus allows for lower radial strength to promote expansion while a material with a higher elastic modulus allows for stronger durability to prevent coating failure during use. Elastomers that are urethane based may allow for additional hydrophilic coatings on the inner and outer layer to reduce frictional forces experienced by the opening and inner surface of the blood vessel. Thicker elastomer coatings are beneficial for the durability of the coating and increase the stiffness of the expandable sheath body 202. Thinner elastomer coatings promote radial expansion and allows for delivery of the heart pump through smaller sheath profiles. Materials are further selected to be biocompatible such that they can be in direct and continuous contact with blood within the circulatory system for up to 28 days. Any of the materials described above can be used in any expandable sheath frame configuration, including for example any of the configurations discussed above in relation to FIGS. 51 and 52.

At least one advantage of a metallic and polymer/elastomer composite construction for the frame and coating of the sheath body is the ability to have a thin-walled construction≤200 microns (0.008"), minimizing arteriotomy size, improving vessel closure, and minimizing vascular complications (i.e. bleeding/oozing). In contrast, conventional polymer sheaths capable of passing a 14 Fr device have wall thicknesses around ~400 micron and conventional sheaths capable of passing a 23 Fr device have wall thicknesses around ~680 micron. At least another advantage of the metallic and polymer/elastomer composite construction from the frame and coating is the ability to retain axial stiffness (for pushability and buckling resistance) while maintaining bending flexibility and kink resistance that would not be possible with a thin-walled construction of either a polymer/elastomer sheath or a metallic sheath.

Figure 58:
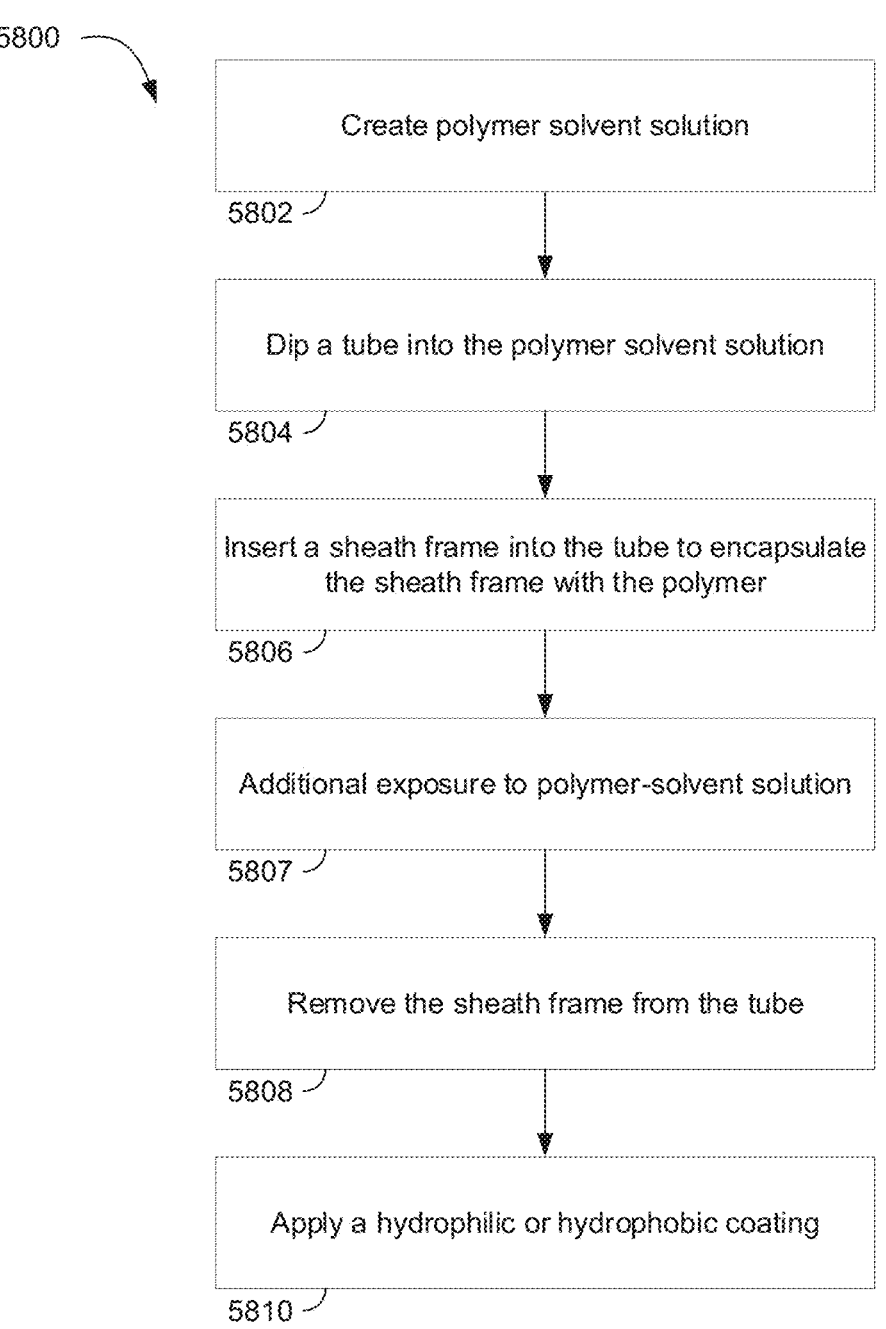
FIG. 58 shows an illustrative method for manufacturing the expandable sheath of FIG. 2 using a polymer solvent solution.

FIGS. 57 and 58 outline examples of different processes 5700 and 5800 for coating a sheath body 202 (e.g. expandable sheath 202 of FIG. 2) to provide an outer-diameter biased expandable sheath (e.g. as shown in FIG. 52). For example, processes 5700 or 5800 can be carried out instead of or in combination with process 1500 described in relation to FIGS. 13-15 below.

FIG. 57 shows a process 5700 of encapsulating and coating an expandable sheath (e.g. sheath 202 of FIG. 2) using thermal bonding. At step 5702, a sheath frame is primed for adhesion to a polymer layer. For example, the sheath frame is primed for adhesion using a priming solution. The priming solution can be a low bodied TPU solvent with the TPU being Lubrizol Tecoflex SG-80A and the solvent being THF. The priming can be done with Kommerling Cilbond 49SF. The polymer layer to which the sheath frame is to be adhered is formed separately. For example, the polymer layer can be extruded, or dip cast. The polymer layer can be Tecoflex EG-80A or SG-80A. The polymer layer can have an inner diameter between around 1 mm and 8 mm. For example, the polymer layer can have an inner diameter between around 3 Fr and 27 Fr. The wall thickness of the polymer layer can be between 20 μm and 150 μm.

At step 5704, a tip layer is assembled over the sheath frame. The tip layer may be slid over the distal end of the sheath frame. At step 5706, the tip layer is bonded to the sheath frame. The tip layer and the sheath frame are bonded by heating at a specified temperature over a specified time duration.

At step 5708, the polymer layer is assembled over the sheath frame. The polymer layer may be slid over the sheath frame. Alternatively, a polymer sheet may be wrapped around the sheath frame and sealed into a layer.

At step 5710, the polymer layer and the sheath frame are bonded by heating at a specified temperature over a specified time duration. Advantageously, the specified temperature and specified duration are selected to adequately fuse the sheath frame and polymer layer but reduce or avoid over-penetration of the polymer layer and the sheath frame. In some configurations, the specified temperature and specified time duration may comprise a range of temperatures and a range of time durations, applied in sequence. For example, the specified temperature may range between 300 F and 500 F. For example, the specified time duration may range between 5 seconds to 5 minutes. Heating may take place in an oven, with heated air being fed from a hot air nozzle onto the sheath frame and polymer layer assembly. For example, hot air from the hot air nozzle may be dispensed at 0.1 mm/min to 1 mm/min. Similarly, at step 5712, the tip layer and the polymer layer are bonded by heating at a specified temperature over a specified time duration.

After the polymer layer and the sheath frame are bonded to one another, at step 5714, an inner surface of the expandable sheath (e.g. the inner surface as shown in FIG. 52) is coated with a lubricious material. Alternatively or additionally, a hydrophilic or hydrophobic silicone layer may be further applied on the inner surface of the expandable sheath. The hydrophilic material may be applied to the inner surface of the expandable sheath in combination with a solvent, and the solvent evaporated. Alternatively or additionally, at least a portion of the outer surface of the expandable sheath (e.g. the outer surface as shown in FIG. 52) is coated with a hydrophilic material.

FIG. 58 shows an alternate process 5800 of encapsulating and coating an expandable sheath (e.g. sheath 202 of FIG. 2) by using an outer-diameter biased dipping process. At step 5802, a polymer solvent solution is created. The polymer can be silicone, specifically Nusil MED10-6600 or MED10-6400. The solvent can be xylene. At step 5804, a tube is dipped into the polymer solvent solution. The inner diameter of the tube can be equal to the desired outer diameter of the finished expandable sheath. At step 5806, a sheath frame is inserted into the tube to encapsulate the sheath frame with the polymer solvent solution present on the inner diameter of the tube. At step 5807 an additional amount of polymer solvent solution is inserted into the sheath frame, to coat the inner surface of the sheath frame. At step 5808, the sheath frame is removed from the tube. Similar to step 5714 described above, at step 5810, a hydrophilic or hydrophobic coating is applied. The characteristics of the polymer solvent solution can be used to control the thickness of the outer-diameter biased polymer layer on the sheath frame. For example, the viscosity of the polymer solvent solution can be used to control the thickness of the applied polymer, with high viscosity yielding thicker solution. Additionally, the speed of the removal of the solvent can be used to control the thickness of the outer-diameter biased polymer layer. For example, slower removal creates a thinner polymer layer. At both steps 5804 and 5807, the polymer solvent solution can be introduced by dipping or by injecting the solution. Using Silicone as the polymer in the polymer solvent solution is advantageous because Silicone is a thermoset which allows for cross-linking between the polymer chains and the frame, making it easier to use during bonding and other manufacturing steps.

Processes 5700 and 5800 may be used to manufacture all of the expandable sheath, or a portion of the expandable sheath. For example, a sheath body may be formed using either process 5700 or 5800. A sheath tip may be formed using a different process. The sheath tip may be formed integrally with the sheath body. Alternatively, the sheath tip may be formed separately from the sheath body, and later attached to the sheath body, e.g. via bonding.

FIGS. 55 and 56 show cross-sections of exemplary prototypes of an expandable sheath on a mandrel. FIG. 55 shows a cross section where the thickness of the coating is equal or greater to twice the wire diameter. As shown in FIG. 55 the inner surface of the expandable sheath 5500 is smooth—there are no peaks or valleys. The sheath shown in FIG. 55 can be manufactured by traditional dipping, or by laminating. Traditional dipping results in the inner diameter biased configuration (e.g. as shown in FIG. 49). In some examples, when laminating a heat shrink tube may be used. FIG. 56 shows a cross section with an outer diameter biased coating (e.g. as described in relation to FIG. 52). As shown in FIG. 56, the inner surface of the expandable sheath 5600 is smooth—there are no peaks or valleys. In addition, as shown in FIG. 56, the relatively thin coating layer 5602 does not fully encapsulate the sheath frame 5602. The sheath shown in FIG. 56 can be manufactured using a dipping technique such as the outer-diameter dipping technique described in relation to FIG. 58, or by using a thermal bonding technique such as the thermal bonding technique described in relation to FIG. 57.

Figure 13B:
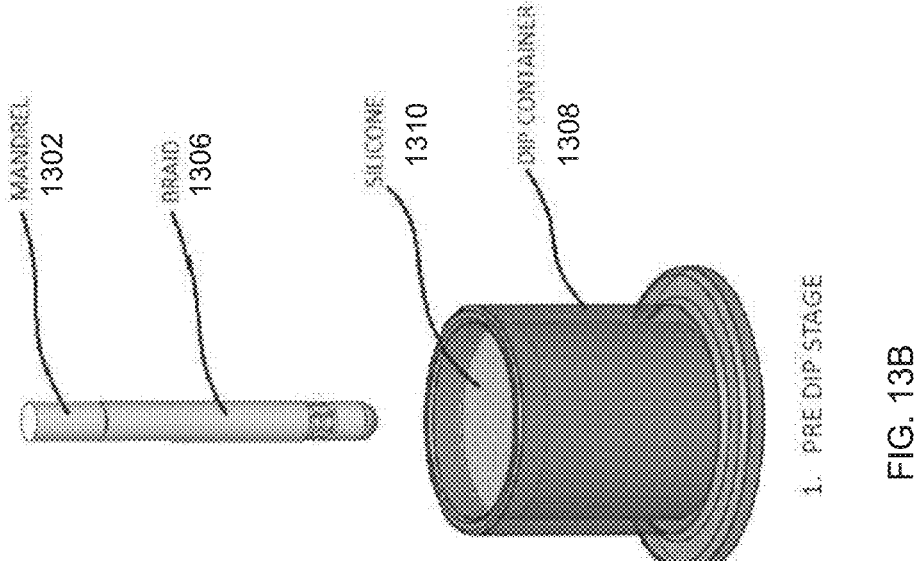
FIGS. 13A and 13B show isometric views of braid manufacturing stages.
Figure 13A:
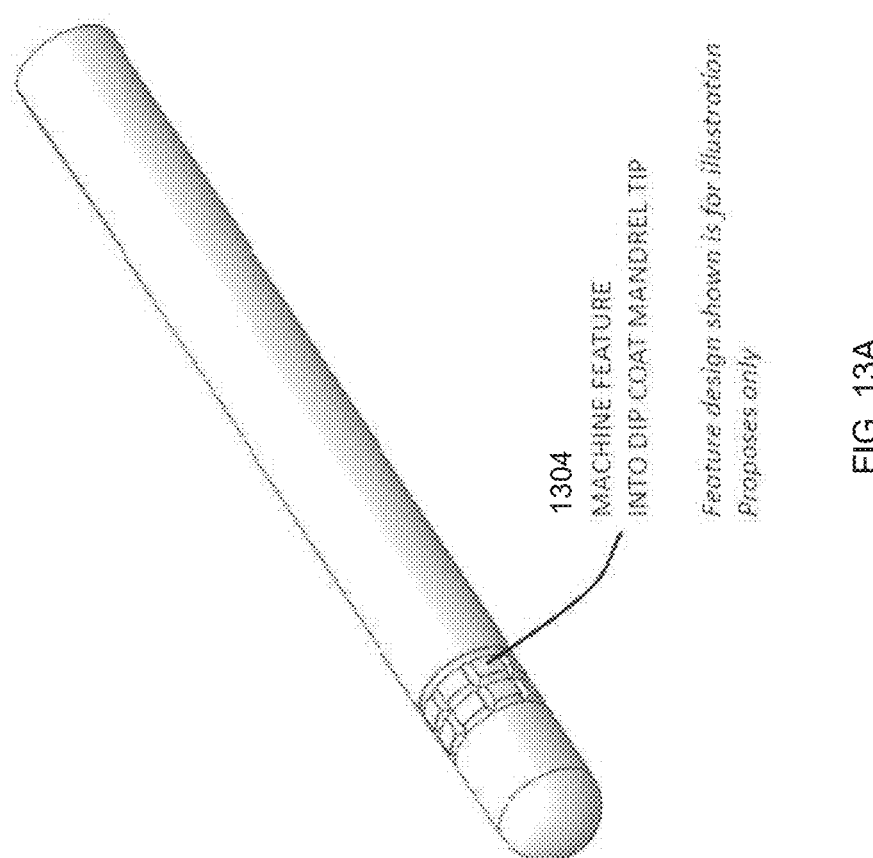
Figures 14A, 14B, 14C:
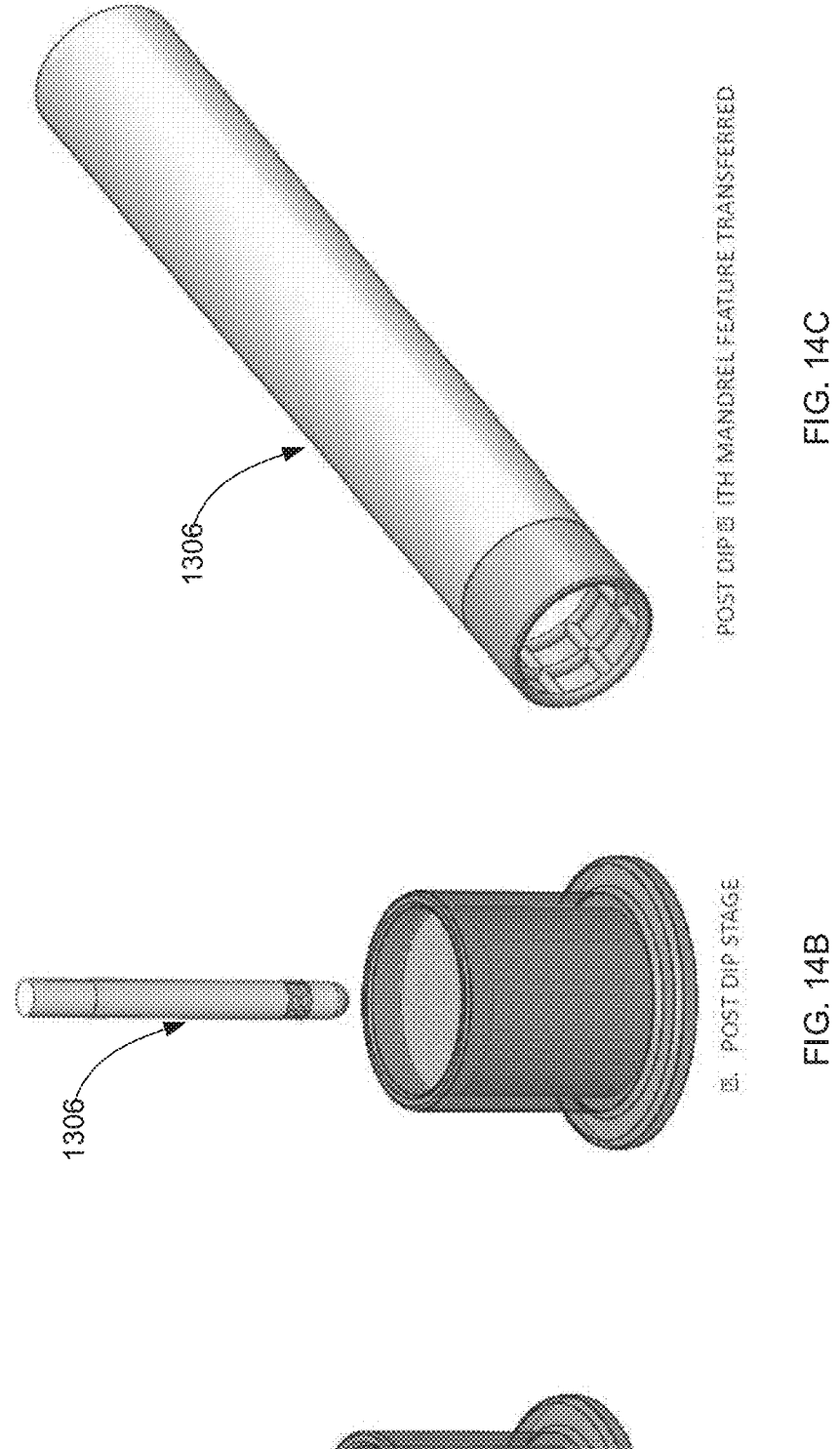
FIGS. 14A to 14C show isometric views of braid manufacturing stages.

FIGS. 13 and 14 illustrate isometric views of braid tip manufacturing stages. FIG. 13A illustrates a mandrel 1302 having a design machined onto the tip 1304. A braid 1306 can then be loaded onto the mandrel 1302 such that the distal tip of the braid 1306 is adjacent to the tip of the mandrel 1304. FIG. 13B illustrates the stage before the mandrel 1302 is lowered into a dip container 1308 containing silicone 1310. FIG. 14A illustrates the stage when the tip of the mandrel 1304 is lowered into the dip container 1308. FIG. 14B illustrates the stage when the tip of the mandrel 1304 is removed from the dip container 1308. After the braid 1306 is unloaded from the mandrel 1302, the design machined onto the tip 1304 is transferred to the distal tip of the braid 1306.

Figure 15:
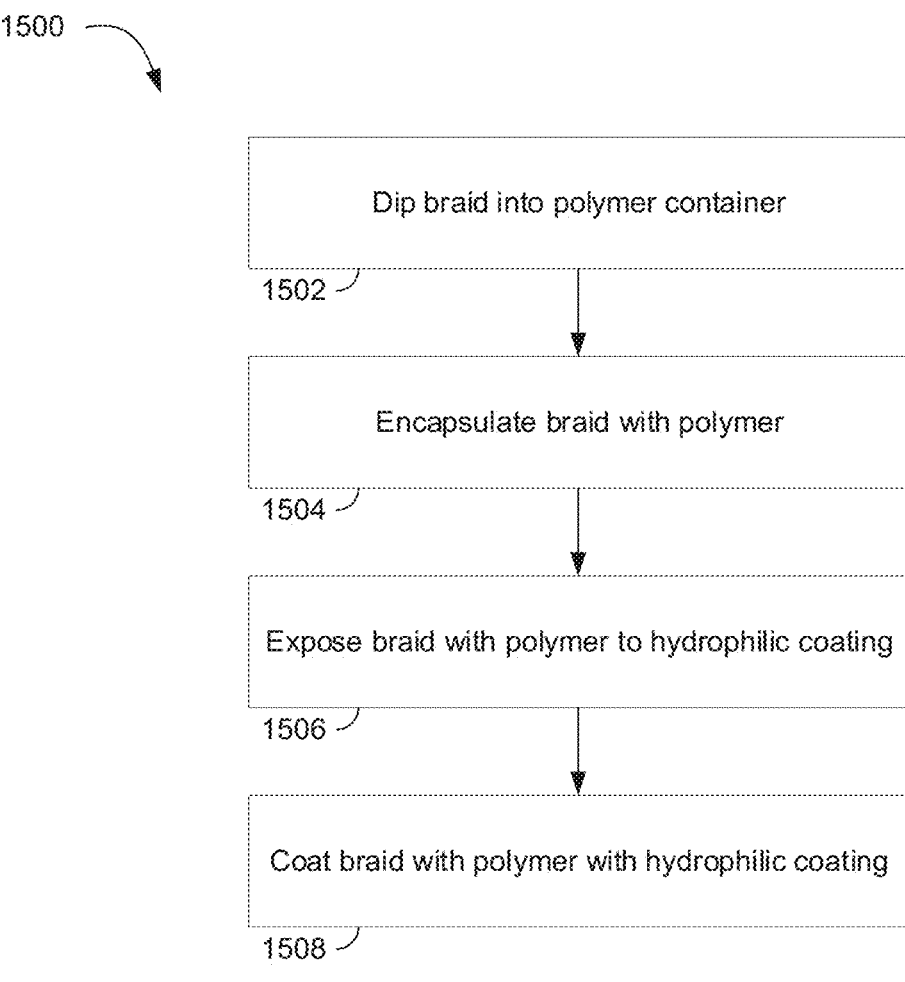
FIG. 15 shows an illustrative method for manufacturing the expandable sheath assembly of FIG. 2.

FIG. 15 shows a process 1500 of encapsulating and coating a sheath body 202, described above in relation to FIGS. 8, 9, and 12. At step 1502, a sheath body 202 is dipped into a polymer container. At step 1504, the braid of the sheath body 202 is encapsulated with the polymer. At step 1506, the polymer encapsulating the braid of the sheath body 202 is exposed to a hydrophilic coating. At step 1508, the polymer encapsulating the braid of the sheath body 202 is coated with the hydrophilic coating, and a chemical reaction between the polymer and hydrophilic coating results in bonding between both. The result of process 1500 is shown illustrated in FIGS. 16-18 and 49-52.

Figures 16, 17, 18:
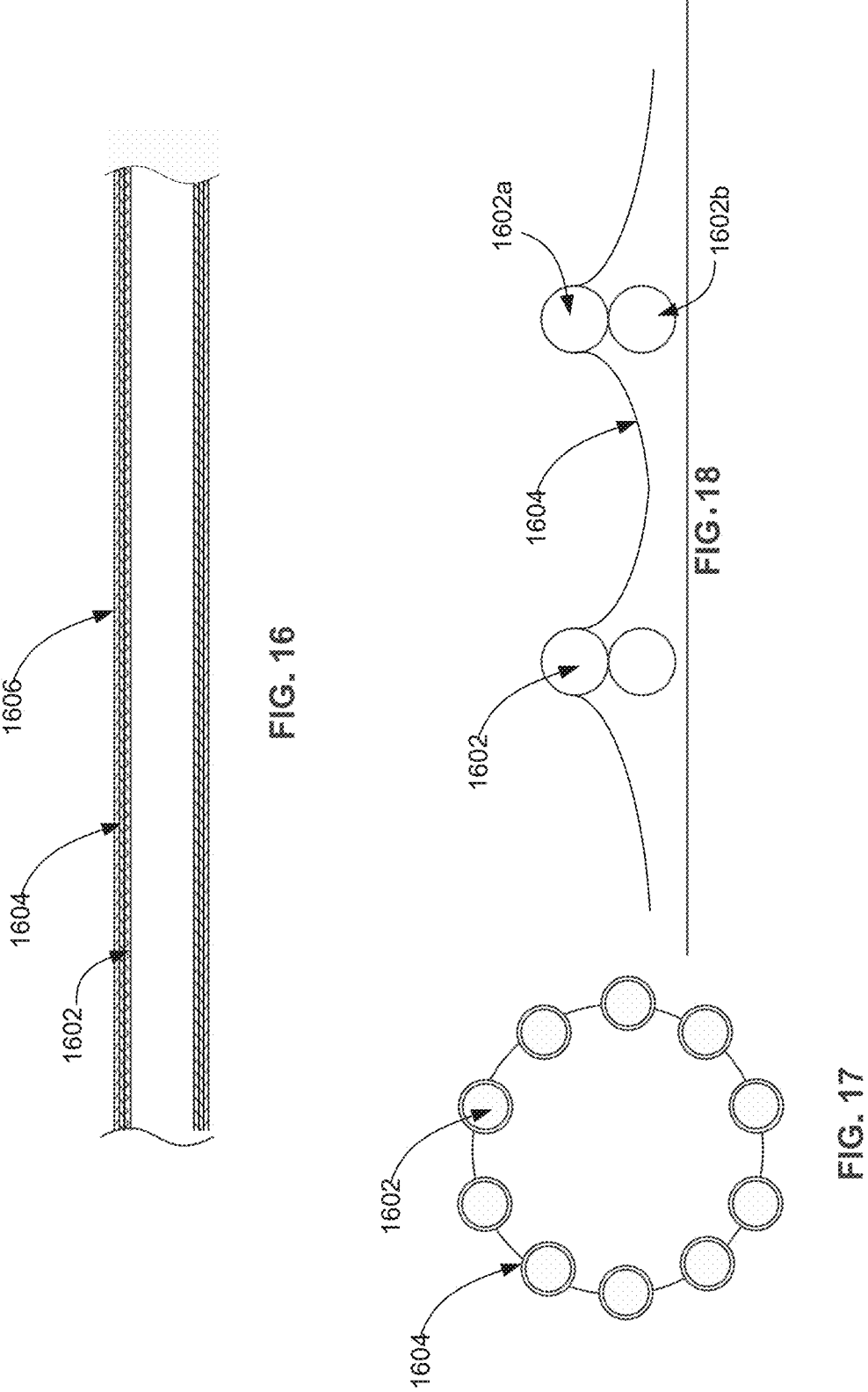
FIG. 16 shows an illustrative expandable sheath body comprising a braid, a polymer, and a hydrophilic coating.
FIG. 17 shows a cross-section of the expandable sheath body demonstrating the braid material surrounded by the polymer encapsulation.
FIG. 18 shows a cross-section of the braid material surrounded by the polymer encapsulation.

FIG. 16 shows an isometric view of a sheath body 202 having a braid 1602, encapsulated by a polymer 1604, which in turn is coated with a hydrophilic coating 1606. FIGS. 17 and 18 show cross-sectional views of the braid 1602 (e.g. with overlapping threads 1602*a* and 1602*b*) encapsulated by the polymer 1604. The distance between the peak of the braid 1602 and the trough of the polymer 1604 in the windows of the braid may range between 0 μm, when the polymer thickness is twice the thread diameter and 200 μm, when the thread diameter is 100 μm and two threads are stacked, assuming a near-zero polymer thickness. As discussed in relation to FIG. 12, the polymer encapsulates the frame of the expandable introducer sheath 202, including the threads but also forming a layer over the windows. As shown in FIG. 18, one surface of the polymer encapsulation is flat. In one embodiment and as further described in relation to FIG. 49 below, the inner surface the sheath body has a smooth surface and the outer surface of the sheath body has troughs 1604. In another embodiment and as further described in relation to FIGS. 50 and 51 below, the outer surface of the sheath body can be smooth to prevent blood collection and clotting thereon and reduce hemolysis. This configuration can also provide a minimal thickness of the sheath body which is desirable to minimize the size of the opening in the vessel through which the sheath body must pass through. In another embodiment and as further described in relation to FIG. 51 below, the inner surface of the sheath body has troughs 1604 and the outer surface of the sheath body has a smooth surface.

Introducer sheath 200, dilator assembly 2000, and hemostasis stylet assembly 4600 can be used in combination to form a sheath assembly for the insertion of a medical device into a blood vessel. In some implementations, the sheath assembly includes an introducer sheath 200 and a dilator assembly 2000. This configuration allows for the insertion of the introducer sheath 200 into an opening of the blood vessel and the expansion of the opening using the dilator assembly 2000. In other implementations, the sheath assembly 100 includes an introducer sheath 200 and a hemostasis stylet assembly 4600. This configuration allows for the regulation of hemostasis between the opening of the blood vessel and the introducer sheath 200. In certain implementations, the sheath assembly 100 includes an introducer sheath 200, a dilator assembly 2000, and a hemostasis stylet assembly 4600.

Figure 21:
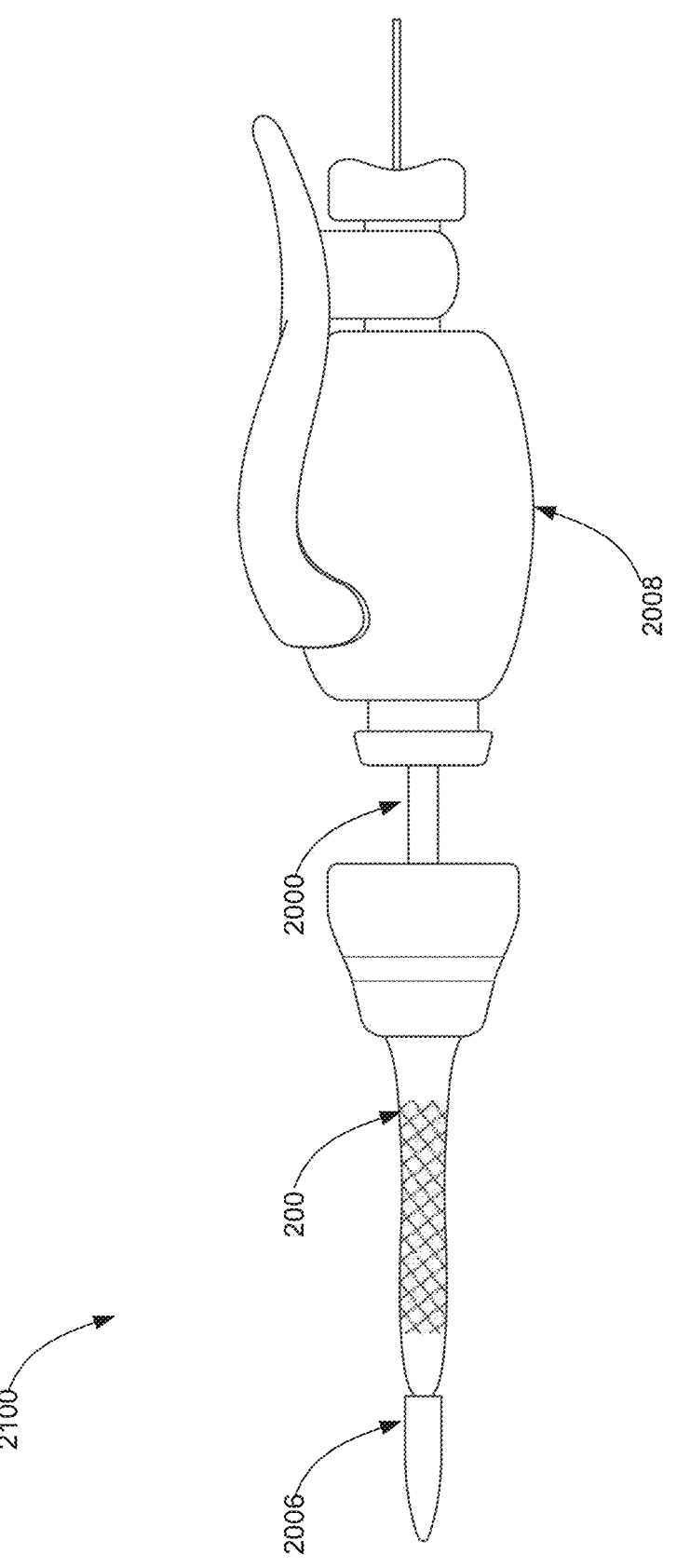
FIG. 21 shows an illustrative view of an introducer sheath and dilator assembly.
Figure 59:
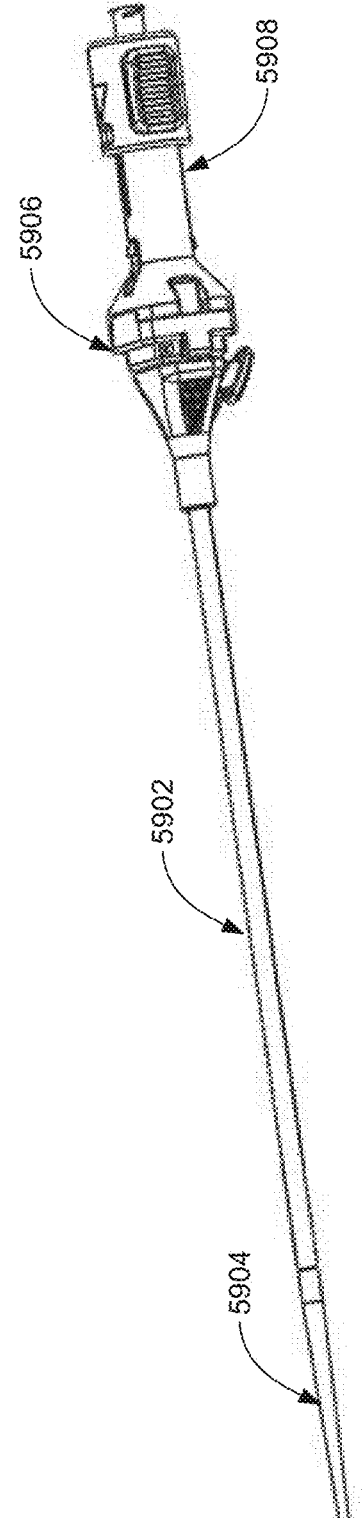
FIG. 59 shows an isometric view of the expandable sheath system of FIG. 21.
Figure 60:
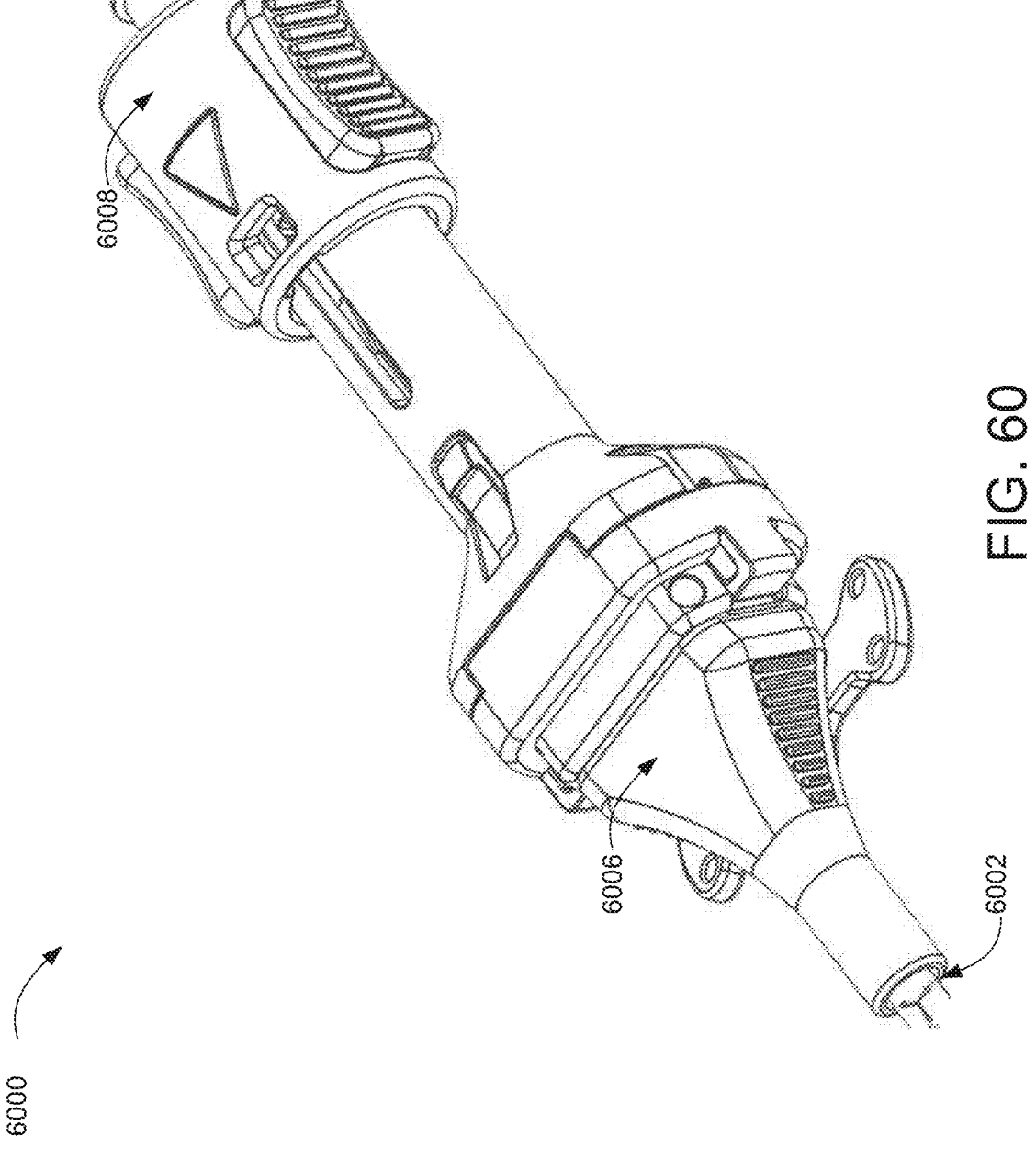
FIG. 60 shows an isometric view of an illustrative delivery system and sheath hub.
Figure 61:
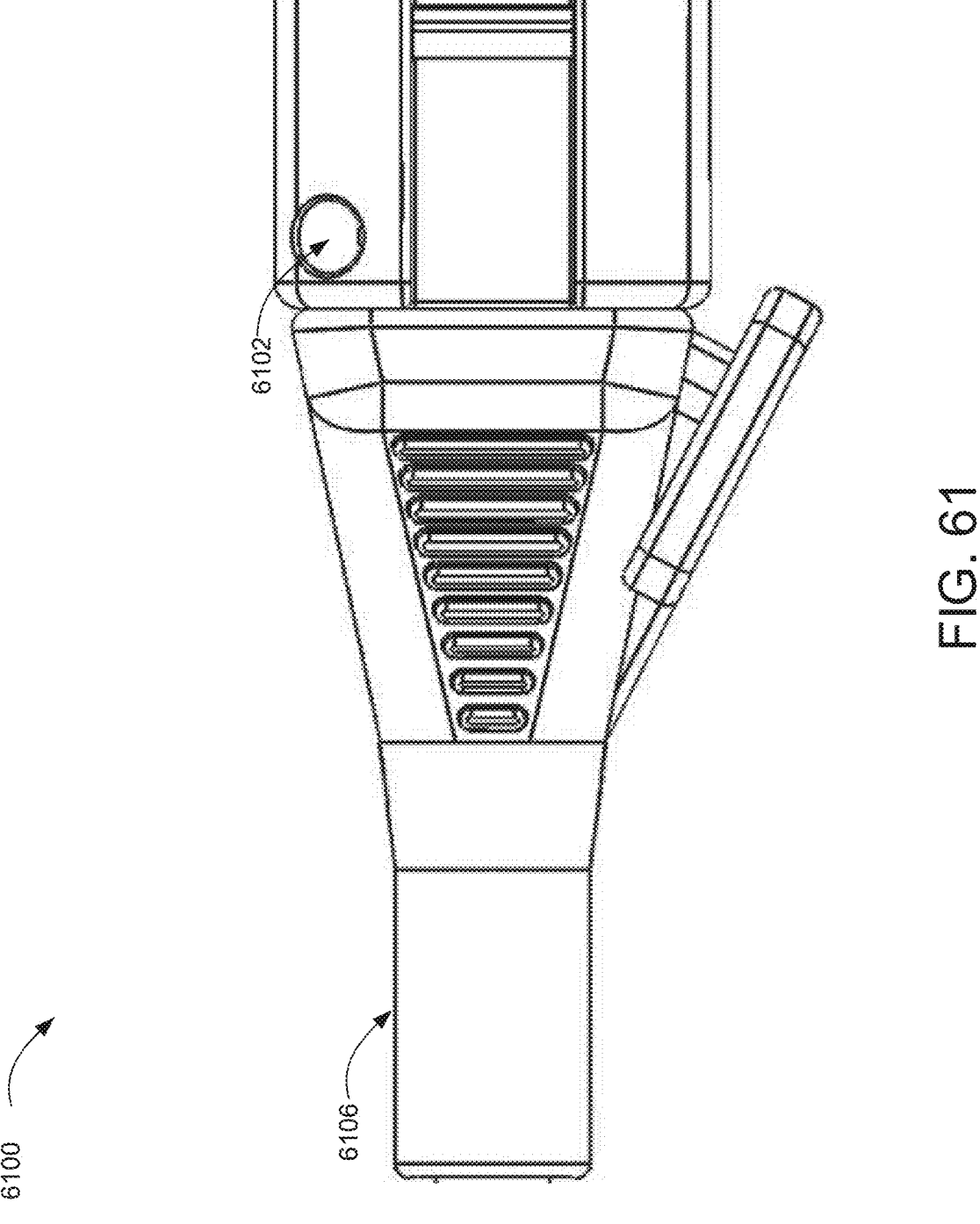
FIG. 61 shows an isometric view of an illustrative sheath hub.
Figure 62:
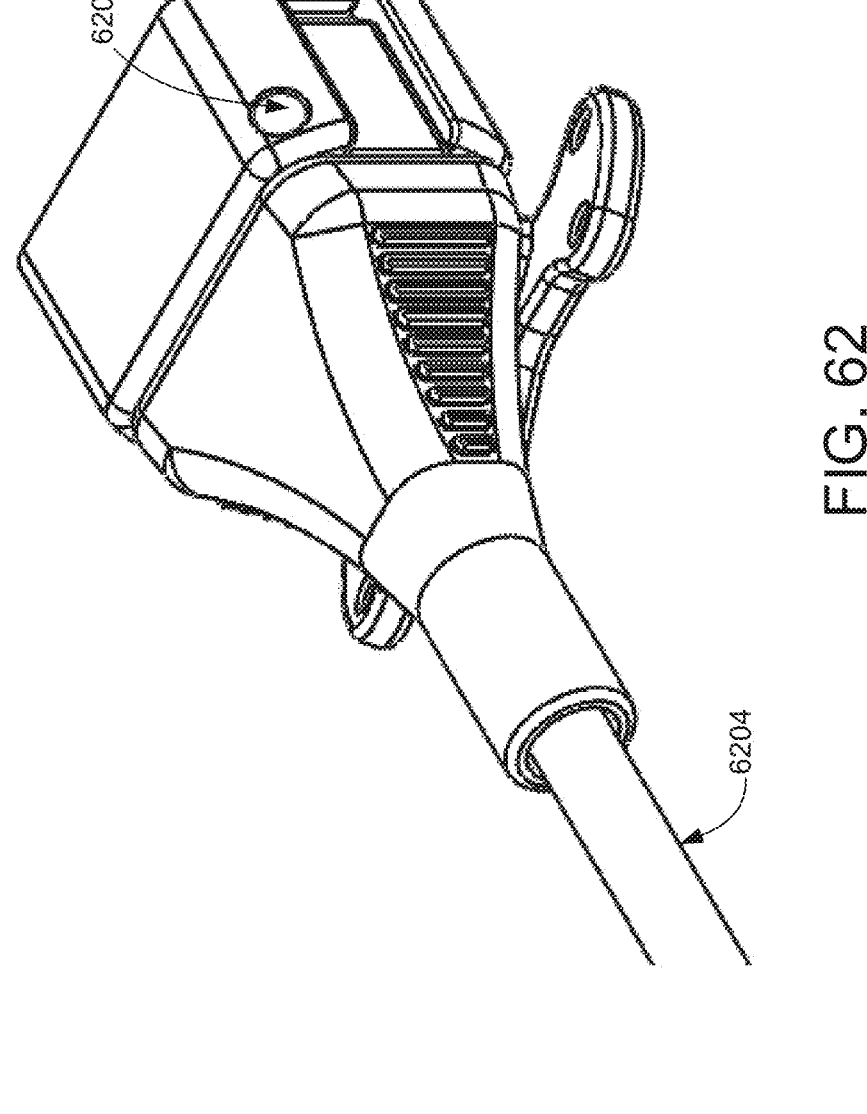
FIG. 62 shows an isometric view of an illustrative sheath hub.
Figure 63:
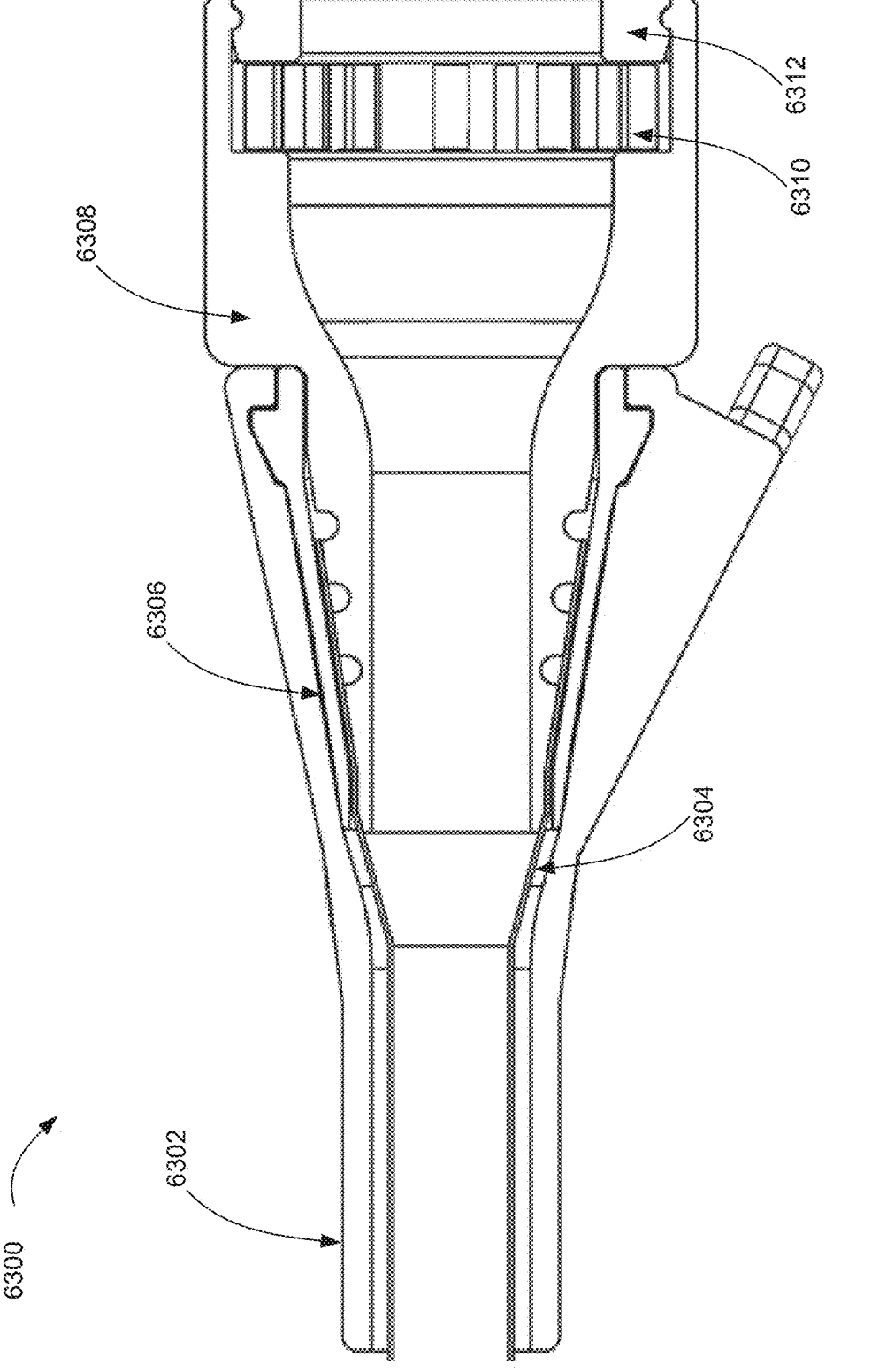
FIG. 63 shows a cross-section of an illustrative sheath hub.

FIGS. 59 and 60 show isometric views of the expandable sheath system of FIG. 21, including an illustrative delivery system and illustrative sheath hub. FIGS. 61 and 62 show isometric views of the illustrative sheath hub of FIGS. 59 and 60. In one embodiment, sheath hub 6200 includes a sidearm port 6202 which provides connection to a sidearm (not shown). FIG. 63 shows a cross-section of an illustrative sheath hub 6300 including a strain relief 6302, an expandable sheath 6304, a compression cap 6306, a hub 6308, a hemostasis valve 6310, and a retainer cap 6312.

Figure 19:
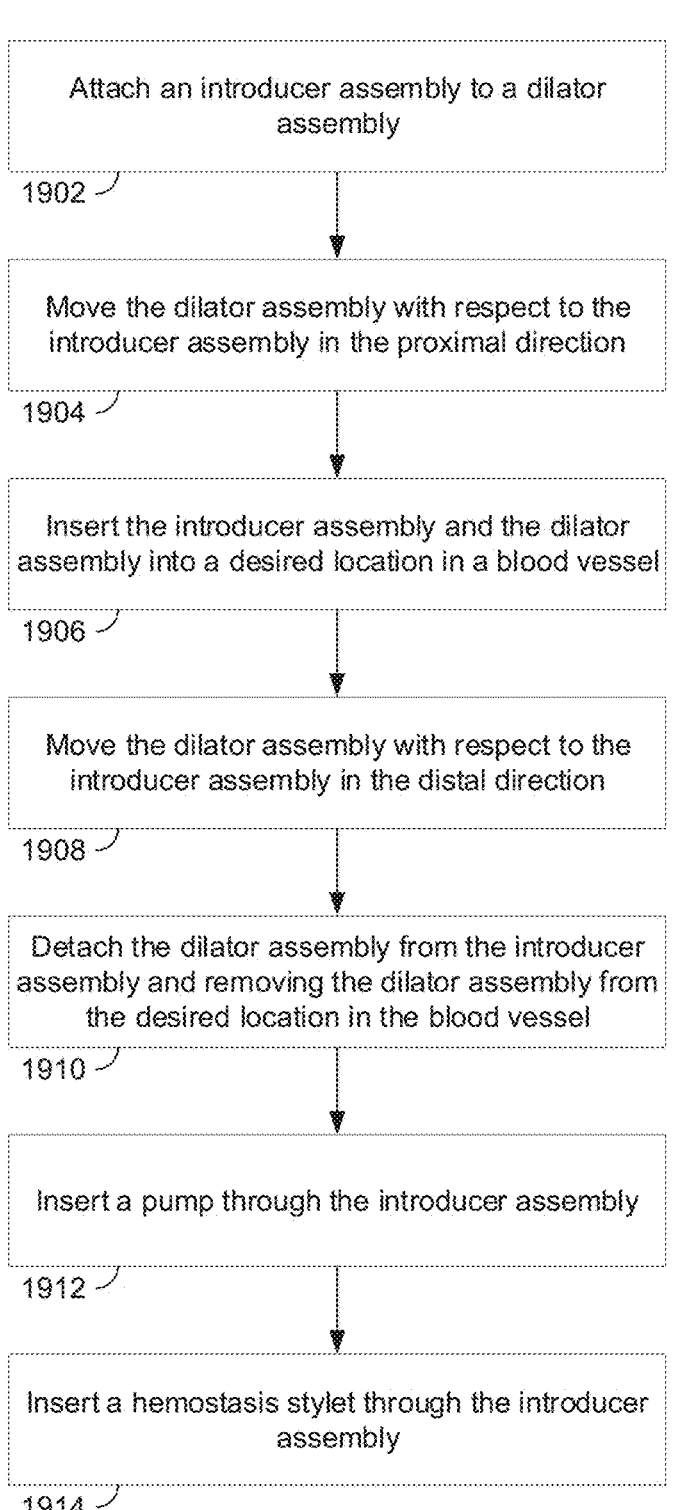
FIG. 19 shows an illustrative method for inserting a medical device into a vessel opening using the illustrative sheath assembly of FIG. 1.
Figure 29:
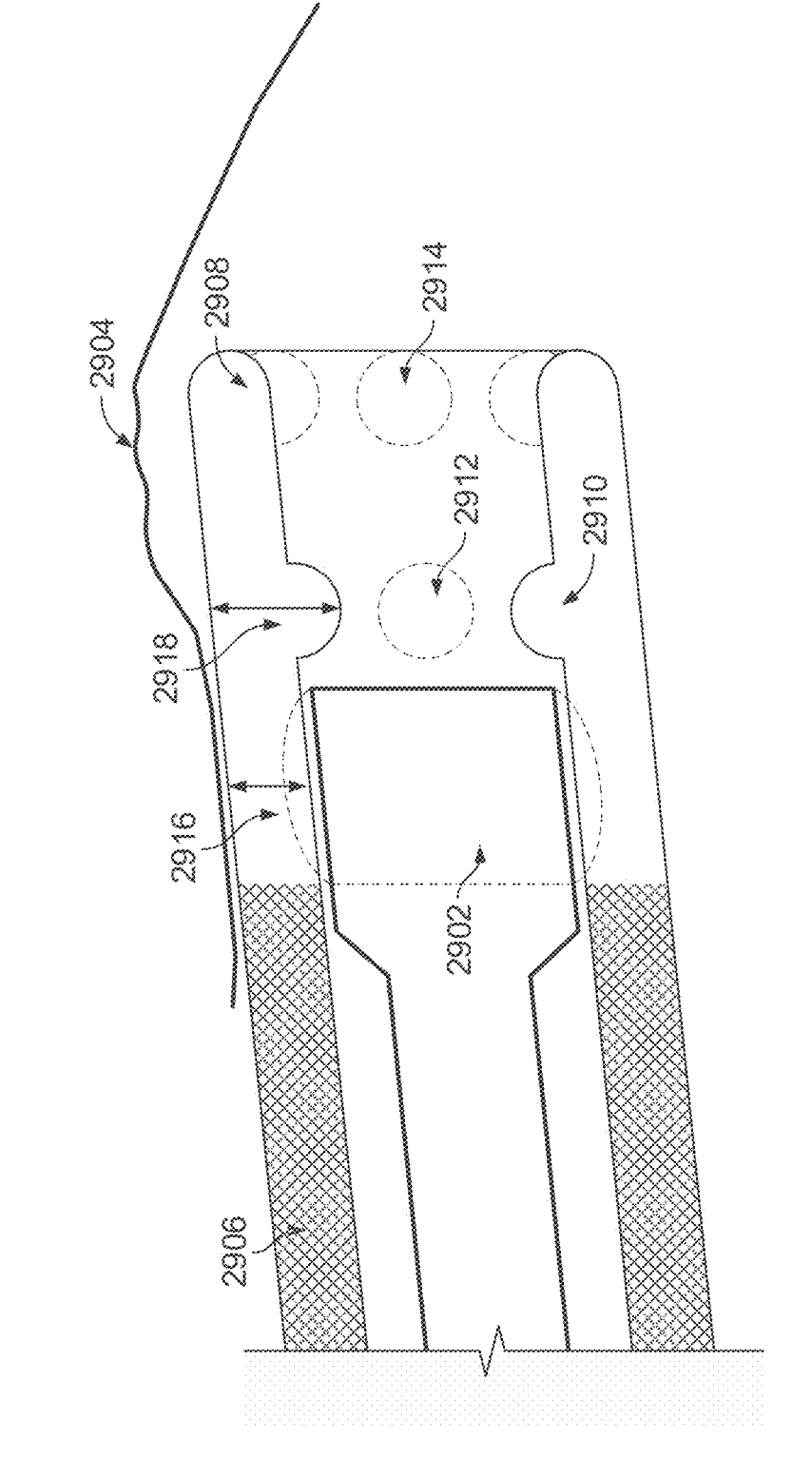
FIG. 29 shows a cross-section view of an illustrative sheath tip.

FIG. 19 shows a process 1900 of inserting a pump into a blood vessel using an introducer sheath 200, a dilator assembly 2000, and a hemostasis stylet assembly 4600, described above in relation to FIGS. 2, 20, and 46, respectively. At step 1902, an introducer sheath 200 is attached to a dilator assembly 2000. The introducer sheath 200 can include an expandable sheath body 202 having a first diameter D1 and a first length L1. FIG. 29 (described above) illustrates the introducer sheath 200 and dilator assembly 2000 with the sheath 200 attached to the dilator assembly 2000.

At step 1904, the dilator assembly 2000 moves in the proximal direction with respect to the introducer sheath 200 such that the expandable sheath body 202 of the introducer sheath 200 contracts to a second diameter D2 and a second length L2. The second diameter D2 is smaller than the first diameter D1 and the second length L2 is greater than the first length L1.

At step 1906, the introducer sheath 200 and the dilator assembly 2000 are inserted into a desired location in a blood vessel. The opening of the blood vessel expands to accommodate the second diameter D2 of the expandable sheath body 202.

At step 1908, the dilator assembly 2000 moves with respect to the introducer sheath 200 in the distal direction. The expandable sheath body 202 of the introducer sheath 200 expands to a third diameter D3 and a third length L3. The third diameter D3 is greater than the second diameter D2 and the third length L3 is smaller than the second length L2. The opening of the blood vessel expands to accommodate the third diameter of the expandable sheath body 202.

At step 1910, the dilator assembly 2000 is detached from the introducer sheath 200 and removed from the desired location in the blood vessel. FIG. 25 (described below) shows the dilator assembly 2000 being removed from the introducer sheath 200.

At step 1912, a pump is inserted through the introducer sheath 200. The expandable sheath body 202 expands to a fourth diameter D4 to accommodate the pump as the pump traverses within the introducer sheath 200. The fourth diameter D4 is greater than the third diameter D3. The opening of the blood vessel expands to accommodate the fourth diameter D4 of the expandable sheath body 202. FIG. 5 (further described above) shows the insertion of a pump 502 through the introducer sheath 200.

At step 1914, a hemostasis stylet assembly 4600 is inserted through the introducer sheath 200. The expandable sheath body 202 expands to a fifth diameter D5 to accommodate the hemostasis stylet assembly 4600 as the hemostasis stylet assembly 4600 traverses within the introducer assembly 200. The fifth diameter D5 is such as to achieve hemostasis between the opening of the blood vessel and the expandable sheath body 202.

As discussed above in relation to steps 1902-1910 of FIG. 19, a dilator assembly is used in combination introducer sheath 200 and hemostasis stylet 4600 to form a sheath assembly for the insertion of a medical device into a blood vessel. FIGS. 20-25C show various components of the dilator assembly and their relative motions while carrying out steps 1902-1910 as discussed in relation to FIG. 19.

Figure 20:
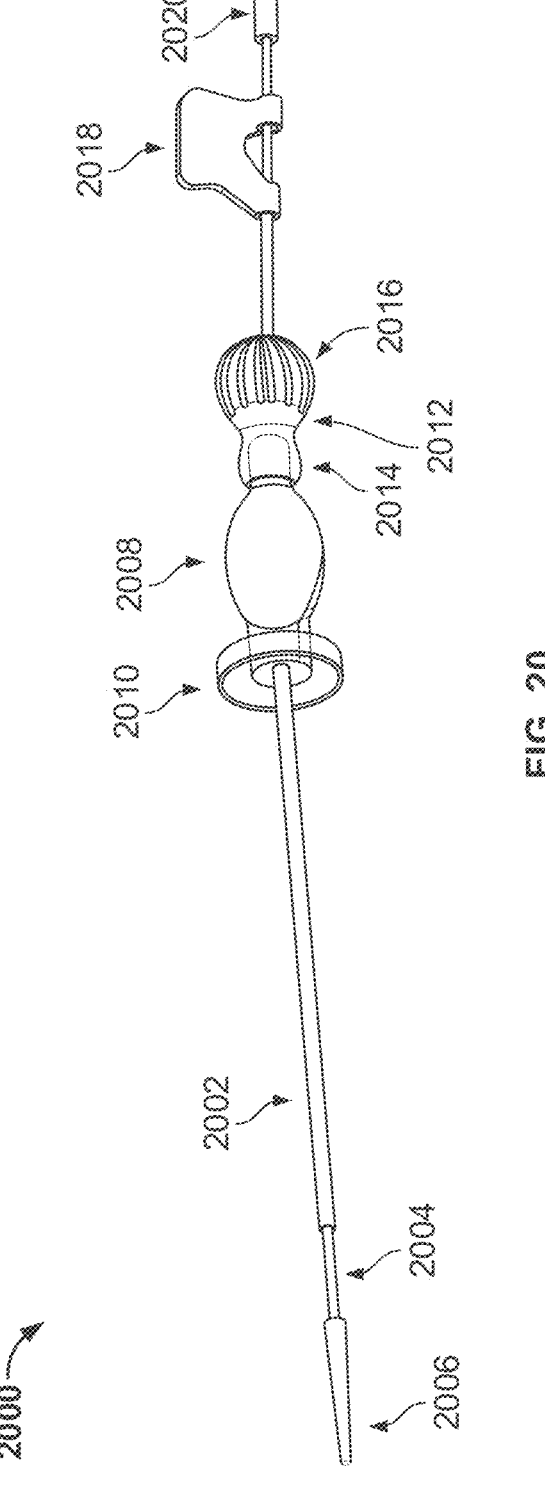
FIG. 20 shows an illustrative view of a dilator assembly.

FIG. 20 shows a dilator assembly 2000 with an outer dilator 2002, inner dilator 2004, hub attachment 2008, and tip interlock 2018. The distal end of the inner dilator 2004 consists of a tube with a distal end, a proximal end, and a lumen defined through. It is bonded to a tip 2006, with the proximal end of the inner dilator 2004 bonded to a luer hub 2020. The outer dilator 2002 is axially aligned with the inner dilator 2004 and has a length less than the inner dilator 2004 such that the inner dilator 2004 is exposed on either end and slides within the outer dilator 2002. The hub attachment 2008 consists of a hub attachment cap 2010 that contains features to attach to the hub 204 of a sheath on the distal end and is bonded to a luer assembly 2014 containing a compressible elastomer 2012 and a compression nut 2016. When the compression nut 2016 is loose the compressible elastomer 2012 is in a first state of minimum compression allowing the hub attachment 2008 to slide along the outer dilator 2002. When the compression nut 2016 is tightened the compressible elastomer 2012 is in a second state of maximum compression preventing the hub attachment 2008 from sliding on the outer dilator 2002 and locking the hub attachment 2008 in place with respect to the outer dilator 2002. FIG. 21 shows illustrative example of an introducer sheath assembly 2100 comprising an expandable introducer sheath 200 (as described in FIG. 2) and dilator assembly 2000 (as described in FIG. 20), with a distal tip 2006 and a sheath handle mechanism 2008.

At least one advantage of the integration of the introducer sheath 200 and the dilator assembly 2000 is that the integration allows for expansion of the opening of the blood vessel while using the same introducer sheath 200 for insertion of a pump. This removes the necessity of the peel away introducer and sheath exchanges, reducing the risk of migration and bleeding. In addition, an additional sheath does not need to be advanced into the blood vessel for pump insertion, reducing the risk of further damage to the blood vessel. Finally, guidewire access is maintained throughout the procedure allowing the pump to be removed with the introducer sheath 200 in place.

Figure 64:
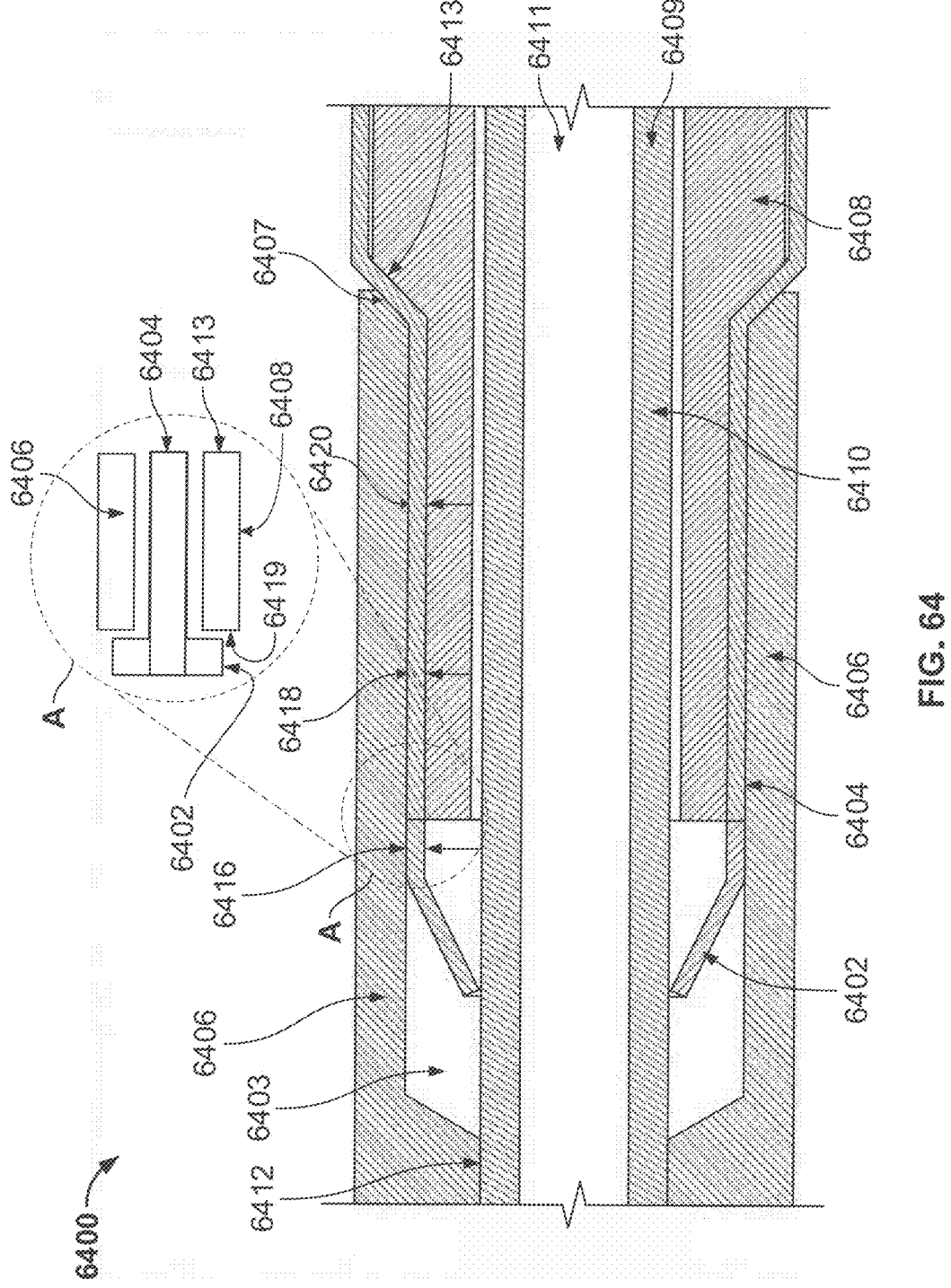
FIG. 64 shows a cross-section of an illustrative sheath system tip.

FIGS. 64-69 show cross sections of a sheath and dilator system configured for insertion into a body lumen, and changes in relative positions of the sheath and dilators between insertion on one hand, and when the sheath is relaxed at a desired location and both dilators are withdrawn on the other hand. FIG. 64 shows detail regarding relative positions of the sheath and dilators when configured for insertion, e.g. as shown in FIG. 65.

The dilator system of FIGS. 64-69 is configured so the dilators can be used to position the sheath by assembling the sheath and the dilators and then inserting the assembly into the patient. FIG. 64 shows a cross-section of a mechanism by which the combination of inner dilator 6410 and outer dilator 6408 retains or entraps the distal tip 6402 of the expandable sheath. As shown in FIG. 64, the combination of inner dilator 6410 with its inner dilator tip 6405 and outer dilator 6408 entraps a distal tip 6402 of an expandable sheath (e.g. sheath 202 of FIG. 2). The inner dilator 6410 has a shaft with an inner lumen 6411 extending along the shaft. The inner dilator 6410 is connected at its distal end to an inner dilator tip 6405. The inner dilator tip 6405 has a shape including inner dilator tip wings 6406 which extend proximally of a distal end of the inner dilator. For example, the inner dilator tip wings 6406 have a greater diameter than the diameter of the shaft of the inner dilator 6410. For example, the inner dilator tip 6405 is the shape of a cone, or an arrow-head. The inner dilator has an interior lumen 6411 which extends through the length of the inner dilator shaft and through to the end of the inner dilator tip 6405, to allow passage of a guidewire.

The outer dilator 6408 has an inner lumen 6409 which extends throughout the outer dilator 6408. The outer dilator and the inner dilator are coaxial, one over the other. As shown in FIG. 64, the inner dilator lies within the outer dilator inner lumen 6409. The outer dilator 6408 has a proximal portion and a distal portion, separated by a transition portion 6413, which transitions from the outer dilator proximal portion diameter to the outer dilator distal portion diameter. For example, the outer dilator proximal portion has a diameter which is greater than a diameter of the distal portion of the outer dilator. The transition portion 6413 may be in the shape of a frustum, a cone, a concave or convex shape. The transition portion 6413 on the outer dilator corresponds to a surface 6407 at the proximal end of the inner dilator tip wings 6406. For example, the surface 6407 may be in the shape of a frustum, a cone, a concave or convex shape. The outer dilator distal tip terminates with a surface 6419. In one example, end surface 6419 is substantially radial. In another example, end surface 6419 has a partial radial component. The shaft of inner dilator 6410 is attached to the inner dilator tip 6405 at connection element 6412. For example the shaft and the inner dilator tip may be bonded together, or may be molded together, or affixed by a connector.

To obtain the assembly shown in FIG. 64, the sheath is inserted into the dilator tip, and then the inner dilator tip, inner dilator 6410, and the sheath subassembly is retracted back until the outer dilator 6408 is in place within the sheath and the inner dilator tip, trapping the tip of the sheath. This is the configuration shown in FIGS. 64 and 65. If the sheath is being introduced into the vasculature in a relaxed state, the sheath inner dilator and sheath is retracted until the sheath hub locks into the delivery system hub. If the sheath is being introduced into the vasculature in a compressed state, the user draws back the sheath hub into the delivery system hub, drawing the diameter of the sheath down to the prescribed amount. This allows for the sheath tip to be delivered to the customer assembled and the sheath has no stress of assembly. The materials of the sheath are sensitive to stress, viscoelastic, and subject to high creep, and therefore would likely have significant permanent deformation after sterilization or shelf life.

As shown in FIG. 64, when the inner dilator shaft is placed within the inner lumen 6409 of the outer dilator 6408, and the transition surface 6413 of the outer dilator is pushed as far as possible distally, there is a free space 6403 between the distal end of the outer dilator 6408 and the portion of the inner dilator 6410 between the outer surface of the shaft of the inner dilator 6410 and the inner surface of the inner dilator tip wings 6406. Additionally, as shown in FIG. 64, and in detail A of FIG. 64, there is an annular gap 6417 between the outer surface of outer dilator 6408 and the inner surface of the inner dilator tip wings 6406. As shown in FIG. 64, the sheath body 6404 has a thickness 6420 which is less than the height of annular gap 6417. Accordingly, absent any forces, the sheath body 6404 can move in a distal direction within the annular gap 6417, and can move radially within annular gap 6417. However, as also shown in detail A of FIG. 64, the distal tip 6402 of the sheath has a thickness 6416 which is greater than the height of the annular gap 6417, such that the sheath distal tip 6402 cannot be pulled in a proximal direction into the annular gap 6417. As shown in detail A of FIG. 64, when the sheath is pulled in a proximal direction, e.g. when the sheath is in a stretched or tensioned configuration (e.g. configuration 6500 as shown in FIG. 65, for insertion into a body lumen), the sheath distal tip 6402 abuts the end surface 6419 of outer dilator 6408. The sheath distal tip 6402 is entrapped in the free space 6403—the sheath distal tip can move in a distal direction, but is prevented from moving in a proximal direction past the end surface 6419 of outer dilator 6408. The sheath distal tip 6402 is released from the entrapped configuration shown in FIG. 64 by moving the inner dilator 6410 and the outer dilator 6408 relative to each other in a longitudinal direction, as shown and described in relation to FIGS. 65-69. The sheath distal tip 6402 may additionally have a taper, as shown in FIG. 64. Alternatively the sheath distal tip 6402 may have a constant diameter.

Because the thickness 6416 of the sheath distal tip 6402 is greater than the thickness 6420 of the sheath body, the sheath distal tip 6402 is stiffer than the sheath body 6404. Alternatively, even in configurations where the sheath distal tip 6402 does not have an increased thickness 6416 relative to a thickness of the sheath body, the sheath distal tip may be made stiffer than the sheath body by increasing the volume ratio of frame to coating, or by selecting materials with a higher stiffness. For the entrapment configuration shown in FIG. 64, the thickness 6416 of the sheath distal tip 6402 may be obtained by varying the thickness of at least one of the sheath frame, the sheath polymeric cover layer, and/or the additional coating (e.g. hydrophobic and/or silicone coating). Alternatively, the sheath distal tip 6402 may be formed without a frame element, of at least one of the polymeric cover element and/or the additional coating (e.g. hydrophobic and/or silicone coating). Alternatively, materials used for the sheath distal tip 6402 may be different from the materials used for the sheath body (e.g. described in FIGS. 22-25).

In the configuration shown in FIG. 64, although the sheath is stretched and in tension, the abutment between the sheath distal tip 6402 having an increased thickness 6416 and the end surface 6419 of the outer dilator is what prevents the sheath from sliding toward a proximal direction. Although a portion of the sheath body is present between the transition 6413 on the outer surface of the outer dilator 6408 and the corresponding geometry 6407 at the proximal end of the inner dilator wings 6406, there is no pinching or gripping of the sheath between 6407 and 6413.

FIG. 65 shows a cross-section of an initial configuration 6500 for insertion of a sheath and dilator assembly into a body lumen. The dilator assembly includes inner dilator 6510 and outer dilator 6508. Outer dilator 6508 is coaxial with and located around inner dilator 6510. The outer dilator is configured to fit within the distal region of the sheath 6504, so the sheath is located over the outer dilator 6508. Outer dilator 6508 has an interior lumen 6509 through which the inner dilator 6510 passes. Inner dilator 6510 has an interior lumen 6511 extending through both the shaft and the distal tip 6505 of the inner dilator, and which can accommodate a guidewire for insertion of the dilator and sheath assembly. At a proximal end of the dilator and sheath assembly (not shown in FIG. 65), a proximal end of the sheath is secured in place at a hub (e.g. hub 204 of FIG. 2). Movement of the sheath distal tip in a longitudinal direction is prevented by the inner dilator 6510 and outer dilator 6508 combination, and the sheath is stretched over the dilators 6508 and 6510 toward a proximal direction. As a result, the sheath shown in FIG. 65 is stretched and in tension. As shown in FIG. 64, the sheath distal tip 6402 is entrapped in the free space 6403 defined by an inner diameter of the inner dilator tip wings 6406, an outer diameter of the inner dilator shaft, and a distal end of the outer dilator 6408. An entrapment mechanism by which the combination of inner dilator 6510 and outer dilator 6508 retain or entrap the sheath distal tip 6402 is shown and described in greater detail in relation to FIG. 64. The inner dilator 6510 includes a distal tip proximally extending flange that optimally mates with the distal portion of the outer dilator 6508. Prior to the loaded configuration shown in FIG. 65, the sheath, inner dilator and outer dilator are assembled outside of the patient body. This assembly prior to the loaded configuration shown in FIG. 65 is also discussed in greater detail in relation to FIG. 64.

Returning to FIGS. 65-69, to release the sheath from its stretched and tensioned configuration as shown in FIGS. 64 and 65, the inner dilator and outer dilator are moved relative to each other, as shown in FIG. 66. FIG. 66 shows the configuration 6600 of the sheath system tip in a second position. In configuration 6600, the inner dilator 6610 is pushed toward a distal direction independently of the outer dilator 6608, resulting in a longitudinal gap between the inner dilator tip wings 6606 and the outer dilator distal end. As a result of the relative displacement of the inner dilator 6610 with respect to the outer dilator 6608, the sheath tip 6602 is no longer entrapped within free space 6603. Because the sheath distal tip 6602 is no longer entrapped, the sheath in turn relaxes to its natural unstretched state in which the sheath expands, having a greater inner (and outer) diameter than in the stretched tensioned state. In its unstretched state the sheath can also have a shorter length than in its stretched tensioned state. In its relaxed unstretched state, the sheath relaxes over the outer dilator 6608. The devices can be pulled through the sheath in a similar way, expanding the sheath to the stretched state as the devices go through the sheath and relaxing the sheath to the unstretched state after the devices pass through.

Figure 67:
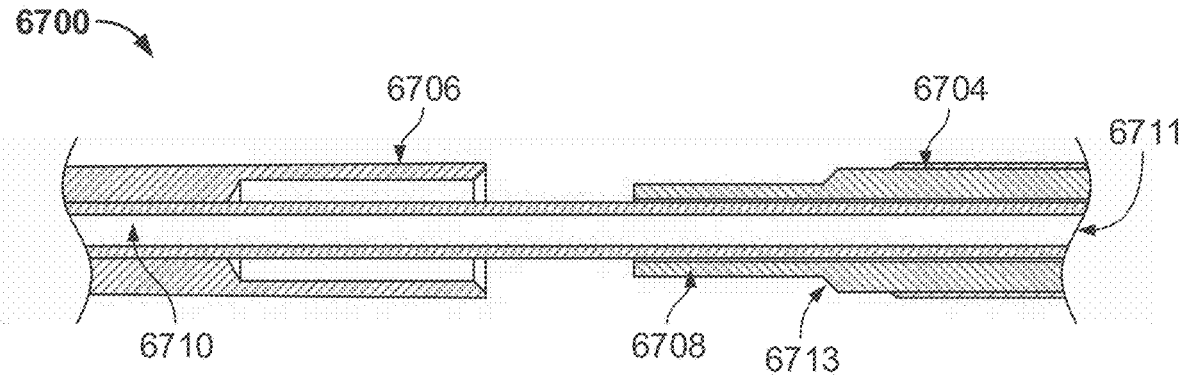
FIG. 67 shows a cross-section of an illustrative sheath system tip in a third position.

FIG. 67 shows the configuration 6700 of the sheath system tip in a third position. In configuration 6700, the inner dilator 6710 and the outer dilator 6708 is pushed toward a distal direction, such that the distal tip of the outer dilator 6708 extends beyond the sheath distal tip 6702. As shown in FIG. 67 there may still be a longitudinal gap between the inner dilator tip wings 6706 and the outer dilator distal end.

Figure 68:
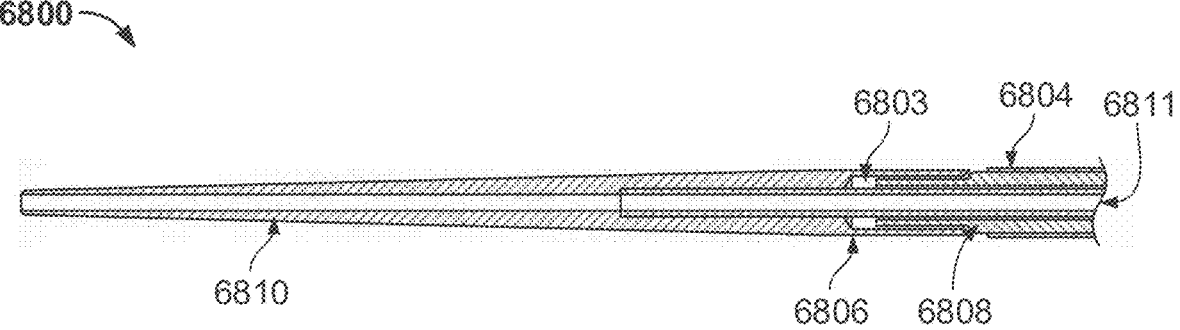
FIG. 68 shows a cross-section of an illustrative sheath system tip in a fourth position.

FIG. 68 shows the configuration 6800 of the sheath system tip in a fourth position. In configuration 6800, the outer dilator 6808 has been further pushed toward a distal direction such that the outer dilator 6808 is now mated with the geometry of the inner dilator tip 6805, the inner dilator tip 6805 being held in place in its most distal position. As shown in FIG. 67, outer dilator 6708 has a proximal portion and a distal portion, separated by a transition portion 6713, which transitions from the outer dilator proximal portion diameter to the outer dilator distal portion diameter. For example, the outer dilator proximal portion has a diameter which is greater than a diameter of the distal portion of the outer dilator 6708. For example, the transition portion 6713 may be in the shape of a frustum, a cone, a concave or convex shape, or any other geometry. The transition portion 6713 may consist of a substantially radial surface. The transition portion 6713 on the outer dilator corresponds to a surface 6707 at the proximal end of the inner dilator tip wings 6706. For example, the surface 6707 may be in the shape of a frustum, a cone, a concave or convex shape. For example, the surface 6707 may consist of a substantially radial surface. Contact between the surface 6707 and the surface 6713 prevents further motion of the outer dilator in the distal direction, and indicates that the inner dilator 6710 and outer dilator 6708 can be extracted as a whole. As shown in FIG. 68, when the surface 6807 and the surface 6813 are in contact, there may still be a longitudinal gap or free space between the outer dilator distal end and the inner dilator tip wings. Configuration 6800 advantageously provides a relatively smooth or flush outer surface distal of the sheath distal tip 6802. This minimized lip allows for smooth retraction of the delivery system from the expandable sheath hub, as shown in FIG. 69.

Figure 69:
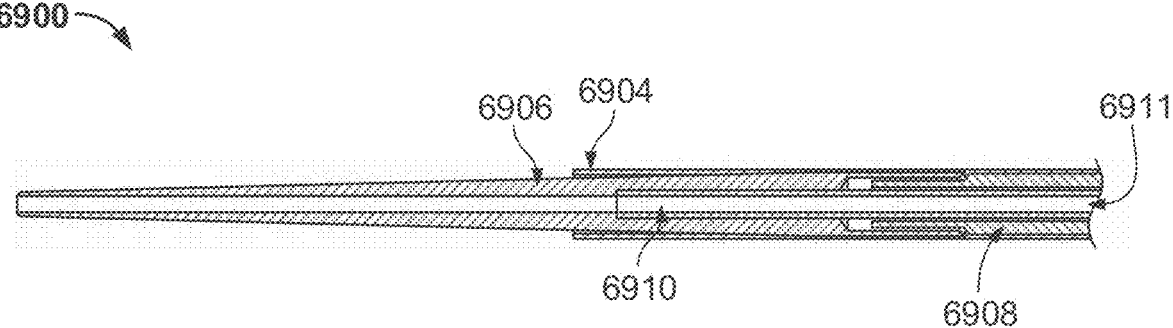
FIG. 69 shows a cross-section of an illustrative sheath system tip in a fifth position.

FIG. 69 shows the configuration 6900 of the sheath system tip in a fifth position, where the inner dilator 6910 and outer dilator 6908 have been pulled toward a proximal direction and are passing through the sheath body, to be removed from the patient body.

Figure 89:
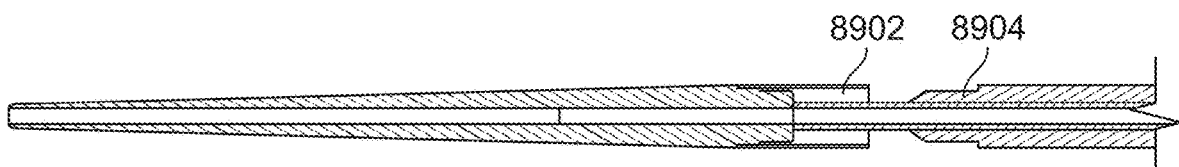
FIG. 89 shows an illustrative view of a delivery mechanism tip.

In another implementation, the proximal end of the distal tapered tip of the inner dilator comprises a tapered diameter. FIG. 87 shows an additional implementation of the delivery system tip in the configuration shown in FIGS. 65, 68, and 69, while FIG. 89 shows an additional implementation of the delivery system tip in the configuration shown in FIGS. 66 and 67. FIG. 87 includes inner dilator 8702 and outer dilator 8704. The proximal end of the distal tip of inner dilator 8902 as a tapered diameter. The tapered diameter allows for inner dilator 8702 to be pulled into outer dilator 8704 upon the release of the sheath from the delivery system tip, as discussed below in FIG. 88. As described below in relation to the delivery mechanism illustrated in FIGS. 83A-86D, in a first state, a second state, and a fourth state of such implementations, the sheath is held in place between inner dilator 8702 and outer dilator 8704. Thus, the closing of the delivery tip system allows for the system to hold on to the sheath during introduction of the sheath, until the sheath is inserted into the vasculature of a patient. Further, as described below in relation to FIGS. 90-93B, in a fourth state of the system, the closing of the delivery tip system advantageously provides a seamless transition between the dilators from which the sheath may be removed without getting caught on the tip of the delivery system.

FIG. 89 shows the delivery system tip in a third state, described below in relation to FIG. 88. FIG. 89 similarly comprises inner dilator 8702 and outer dilator 8704. In the third state, the inner dilator has been moved distal relative to the outer dilator. This motion between the inner dilator and the outer dilator may be attained using the tip interlock described below in relation to FIGS. 22A-B, or using the inner and outer dilator hub described below in relation to FIGS. 83-85. The changes in relative position of the elements of the sheath assembly as described above in relation to FIGS. 65-69 can be attained by incorporation of the delivery mechanism shown in FIGS. 70-93B, and described below.

Figure 22A:
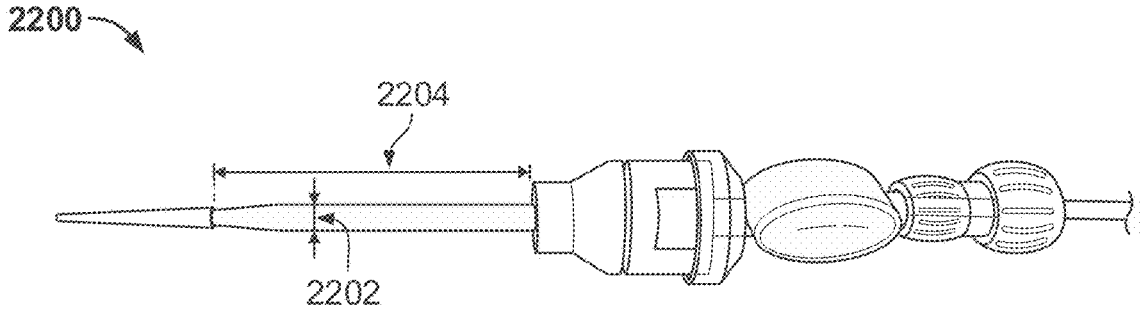
FIGS. 22A and 22B show isometric views of the expandable sheath assembly of FIG. 2 in a relaxed or resting state.
Figure 22B:
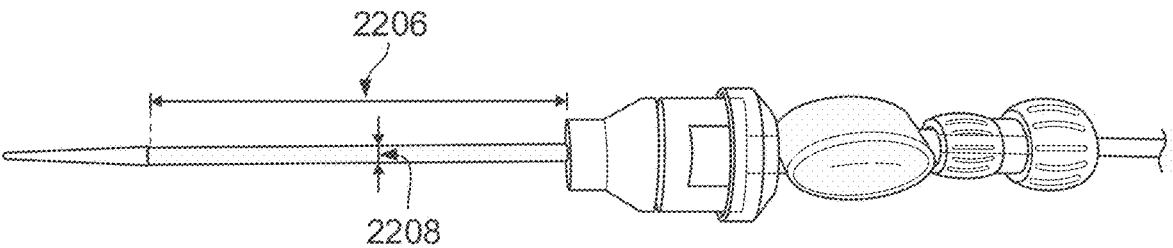

FIGS. 22A and 22B show an introducer sheath assembly 2200 in two different states. As shown in a first state in FIG. 22A (e.g. relaxed state 404 of FIGS. 4A-B) expandable sheath body 202 has a first diameter 2202 and a first length 2204. In one embodiment, the first diameter is between 3 mm and 8 mm, preferably between 3 mm and 6 mm, and preferably 5.2 mm. In one embodiment, the first length is between 10 cm and 40 cm, preferably between 13 cm and 35 cm. Tensioning the introducer sheath 200 into the elongated state shown in FIG. 22B, i.e. applying tensile forces on the introducer sheath via the dilator assembly 2000, reduces the sheath diameter to a second diameter 2208 and elongates the expandable sheath body 202 to a second length 2206. The expandable sheath body 202 is locked into this configuration through tightening of the compression nut 2016. Both the introducer sheath 200 and the dilator assembly 2000 are inserted over a wire and into the desired position within the vasculature in this configuration, e.g. via a "Seldinger" or "modified Seldinger" technique.

Figure 23A:
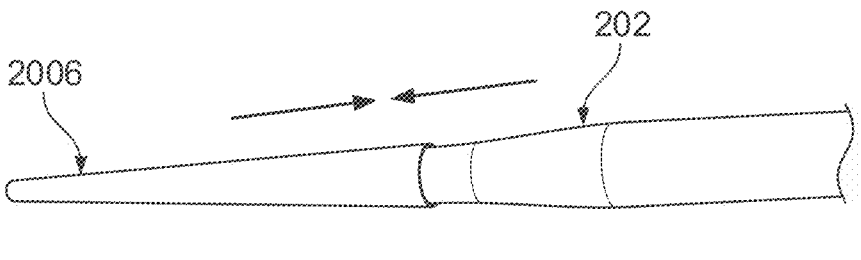
FIG. 23A shows an isometric view of a sheath tip interlock for inner and outer dilators of the dilator assembly.
Figure 23B:
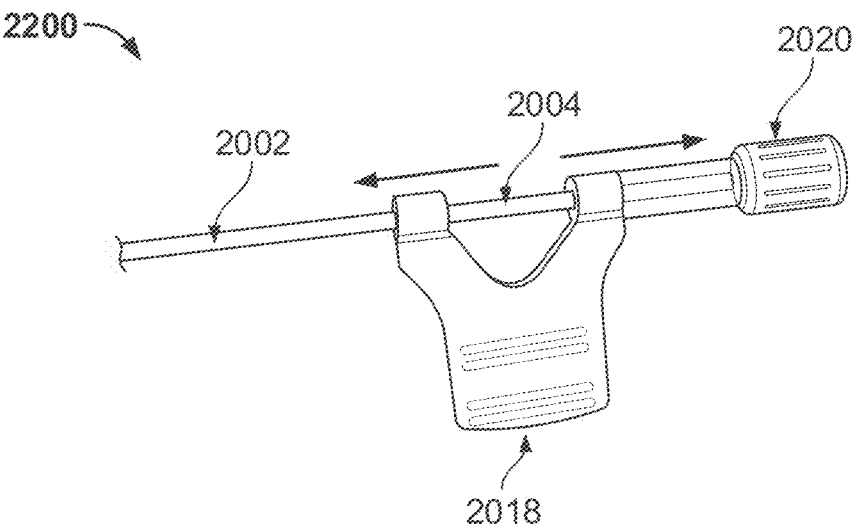
FIG. 23B shows an isometric view of an exemplary dilator tip to sheath connection.

In order to prevent movement of the inner dilator 2004 with respect to the outer dilator 2002 during the movement of the introducer sheath 200 with respect to the dilator assembly 2000 during the elongation setup step described in relation to FIGS. 22A-B, a tip interlock is used to lock the tip 2006 with respect to the expandable sheath body 202. FIG. 23A shows the distal end of the assembly with distal tip 2006 abutting the expandable sheath 202, while FIG. 23B shows the proximal end of the assembly, including a tip interlock 2018, inner dilator 2004, luer hub 2020, and outer dilator 2002. The tip interlock 2018 has a width such that, when placed as shown in FIG. 23B onto the inner dilator 2004 and the outer dilator 2002, at the distal end as shown in FIG. 23A, the distal tip 2006 is locked in place against the expandable sheath 202. With the expandable sheath body 202 residing between the tip 2006 and the outer dilator 2002, it is secured through a pinching force. Finally, locking the tip also prevents movement of the inner dilator 2004 with respect to the outer dilator 2002.

Figure 24A:
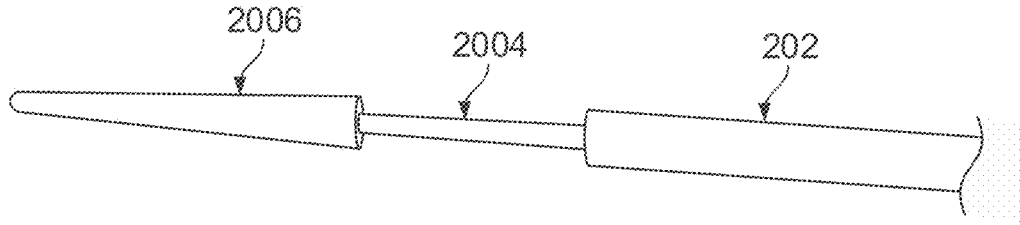
FIG. 24A shows an isometric view of a released dilator tip to sheath connection in a first state.
Figure 24B:
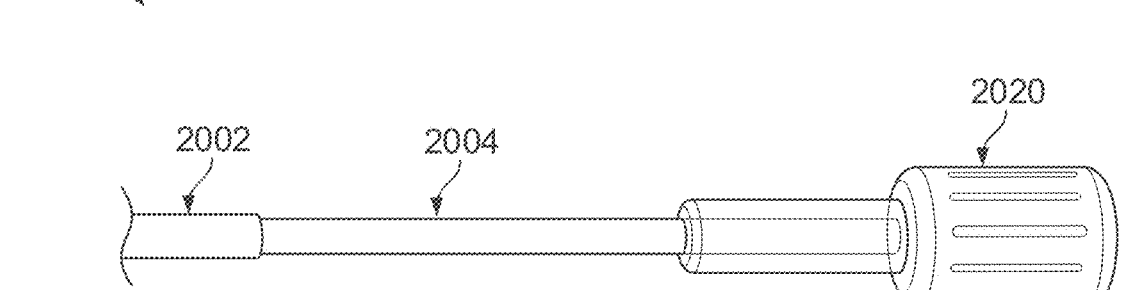
FIG. 24B shows an isometric view of a released dilator tip to sheath connection.

FIGS. 24A-B show the next step in sheath deployment after the tip interlock 2018 has been removed. When the tip interlock 2018 is removed from the inner dilator 2004, the pinching force holding the tip 2006 is removed and the inner dilator 2004 is allowed to freely slide within the outer dilator 2002, as shown in FIG. 24B. On the proximal end of the dilator assembly 2000, as shown in FIG. 24A, the inner dilator 2004 is pushed forward with respect to the outer dilator 2002. Advancement of the inner dilator 2004 from proximal to distal causes the tip 2006 to separate from the inner dilator 2004 and move distal to the expandable sheath body 202 on the distal end. Additional distal movement of the inner dilator 2004 independently of the outer dilator 2002 is not possible—further forward movement results in inner dilator 2004 and outer dilator 2002 moving forward together.

Figure 25A:
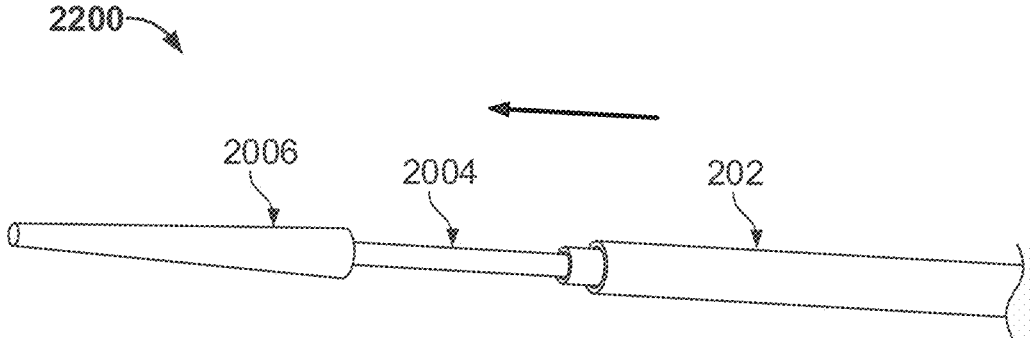
FIG. 25A shows an isometric view of a dilator removal distal preparation.
Figure 25B:
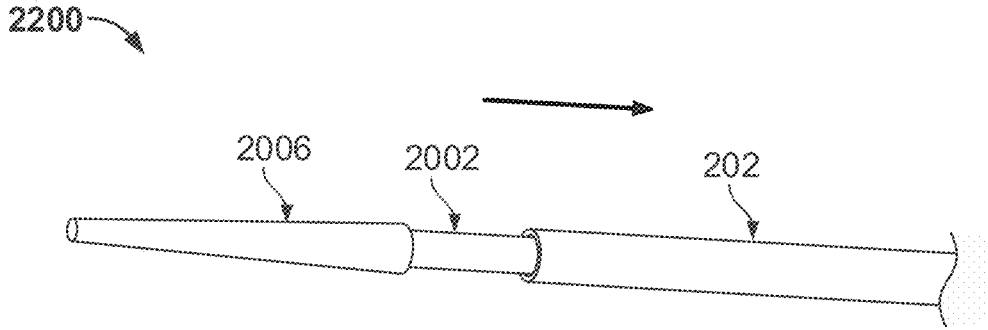
FIG. 25B shows an isometric view of a dilator removal distal preparation.
Figure 25C:
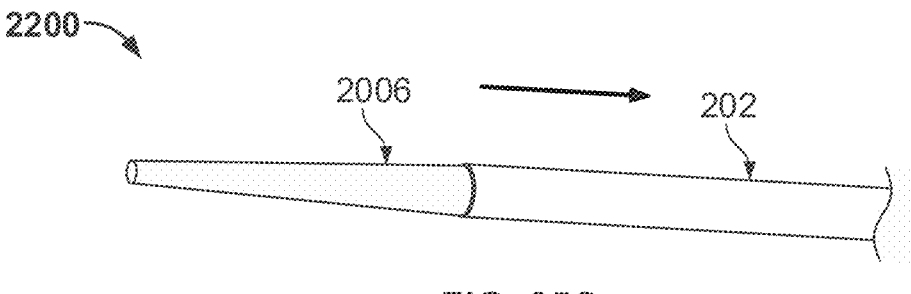
FIG. 25C shows an isometric view of a dilator being removed through the expandable sheath body.

FIGS. 25A-25C show removal of the dilator assembly, during which the distal tip 2006 moves proximally back together against the outer dilator 2002, resulting in a minimal proximal facing lip. FIG. 25A shows inner dilator 2004 and tip 2006 being moved distally in the direction of the arrow. FIG. 25B shows the inner dilator 2004 and tip 2006 being pulled back proximally until the tip 2006 abuts outer dilator 2002. FIG. 25C shows the tip 2006, inner dilator and outer dilator being pulled back proximally until the tip 2006 abuts the expandable introducer sheath body 202. Minimization of the lip between the tip 2006 and the outer dilator 2002 also minimizes the risk of the dilator assembly catching on the expandable introducer sheath body 202 upon removal.

At least one advantage of the configuration discussed in relation to FIGS. 25A-C is being able to capture the distal tip of the expandable introducer sheath while minimizing interference between the dilators and the sheath upon removal (e.g. preventing buckling or kinking). Additional mating geometry on the outer surface of the outer dilator 2002 may improve the lip further.

Figure 26:
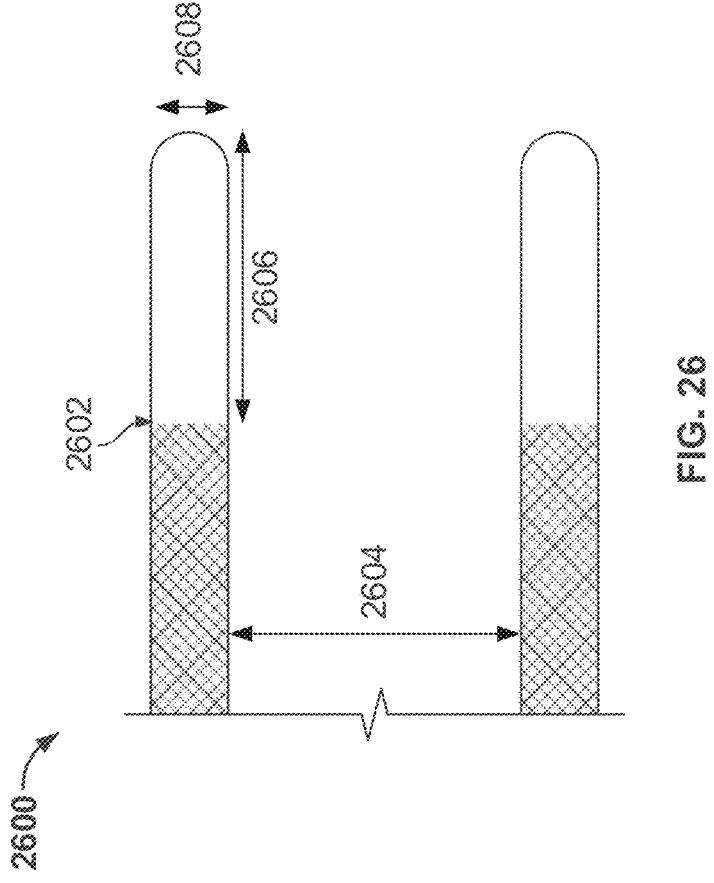
FIG. 26 shows a cross-section view of an illustrative sheath tip.

At the distal end of the sheath assembly, capture of the distal tip of the expandable sheath, as discussed above, can be achieved via various distal tip configurations. FIGS. 26-33 illustrate cross-sectional views of exemplary embodiments of the distal end, or tip, of the expandable sheath body 202. FIG. 26 illustrates a location marked as "last pick" 2602 marking an end to the braid portion of the expandable sheath body 202. In alternative configurations, the "last pick" 2602 may mark an end to a braid or an alternative expandable sheath body 202 material. There exists an additional length 2606 after the termination of the braid comprising solely the polymer matrix material. This length can be equal to the inner diameter 2604. As shown in FIG. 26, the thickness of this region 2608 can be equal to the wall thickness of the braid section of the expandable sheath body 202. Also shown, the inner diameter 2604 of the expandable sheath body 202 can be consistent throughout this transition.

Figure 27:
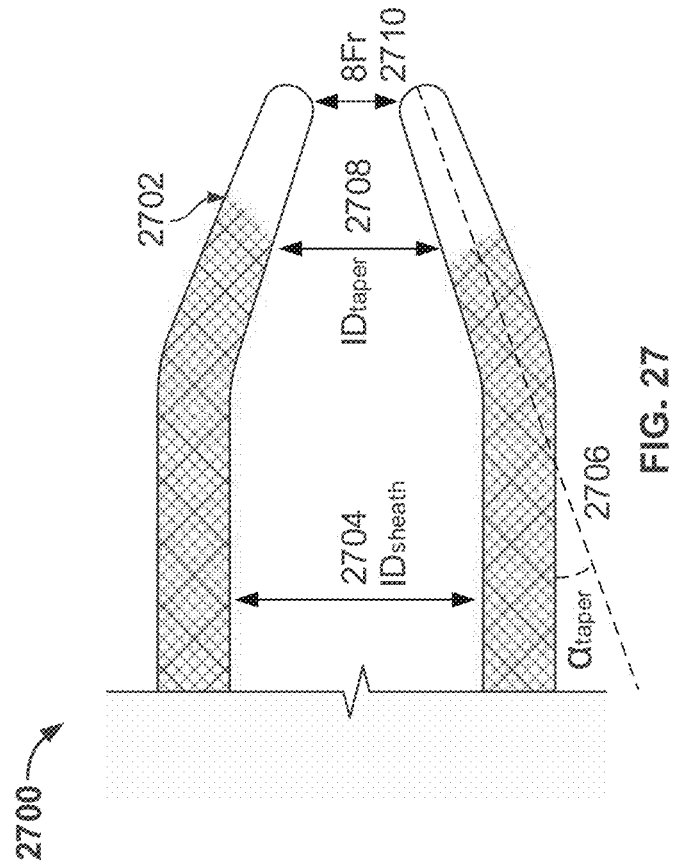
FIG. 27 shows a cross-section view of an illustrative sheath tip.
Figure 28:
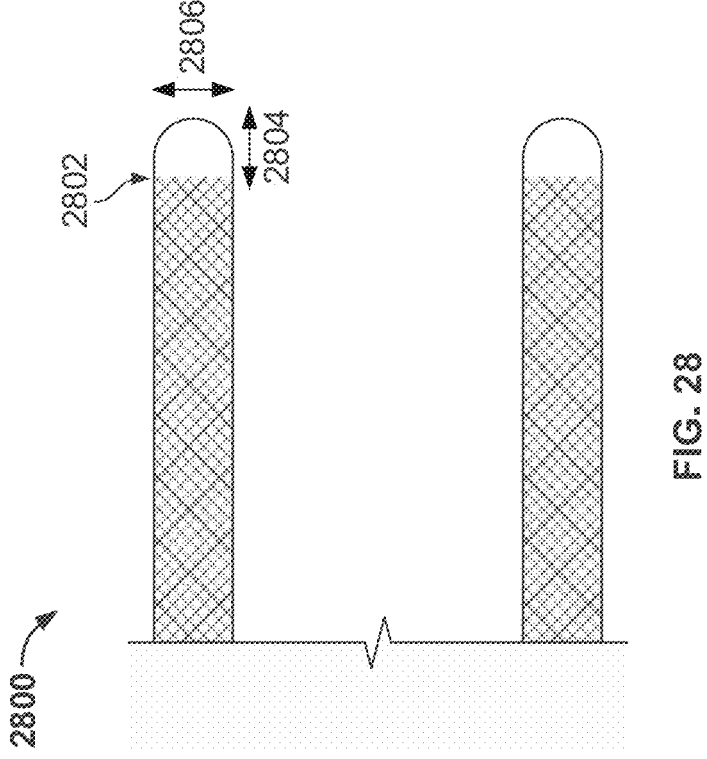
FIG. 28 shows a cross-section view of an illustrative sheath tip.

FIG. 27 shows a cross-sectional view of the distal end, or tip, of the expandable sheath body 202. The inner diameter 2704 of the expandable sheath body 202 is labeled $ID_{sheath}$. Also shown is a region comprising braid and polymer that reduces in diameter and wall thickness, ending at a final wall thickness and diameter 2708 labeled as $ID_{taper}$. This section is also defined by a taper angle 2706 labeled a taper. There exists an additional length after the termination of the braid comprising solely the polymer matrix material terminating at a diameter 2710 labeled as 8 Fr. Alternatively, FIG. 28 shows a cross-sectional view of the tip where the braid terminates at the end of the tip. The "last pick" 2802 may mark an end to a braid or an alternative expandable sheath body 202 material. Similar to the implementation shown in FIG. 26, there exists an additional length 2804 after the termination of the braid comprising solely the polymer matrix material. This length 2804 can be equal to the final wall thickness 2806.

FIG. 29 shows a cross-sectional view of the delivery system distal tip where an inner supporting member 2902 and inner geometry of a distal tip 2904 is assembled with the expandable sheath comprising a braided section 2906 and a polymer section 2908. The supporting member 2902 and the distal tip 2904 create a gap 2910. Within the polymer section 2908 there is a bump geometry 2912 that is also shown as a circular bump 2914 when on the opposing wall of the sheath. The thickness of the polymer section 2908 and bump 2912 creates a thickness that is greater than the gap 2910. When the delivery system is at rest, there is no load on the components. When there is axial strain on the expandable sheath, the distal tip of the sheath is trapped inside of the volume created by the supporting member 2902 and distal tip 2904 as the thickness cannot fit through the gap 2910. There may be a second set of bump 2914 further to the distal end. The bump can be of a polymer that is the same as the encapsulating polymer.

Figure 30:
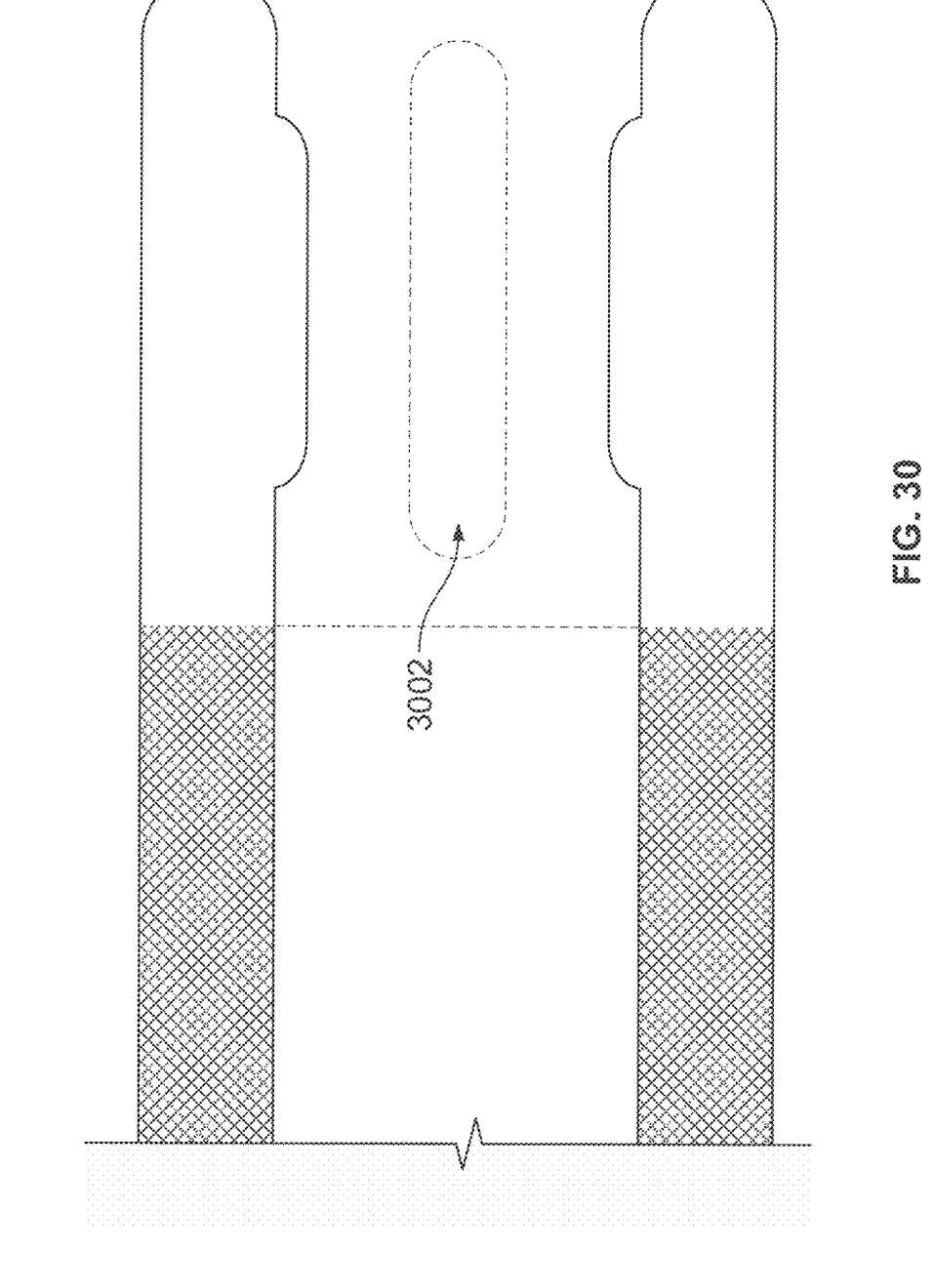
FIG. 30 shows a cross-section view of an illustrative sheath tip.

FIG. 30 shows a cross-sectional view of the delivery system distal tip as shown in FIG. 29 as a variation where the previous bump 2912 is an elongate member 3002 within the polymer section 2908. The elongate member 3002 has the advantage of having more material volume to fit through the gap 2910, decreasing the chances that the sheath can compress and escape through with minimal impact to the sheath tip ability to expand in the radial direction.

Figure 31:
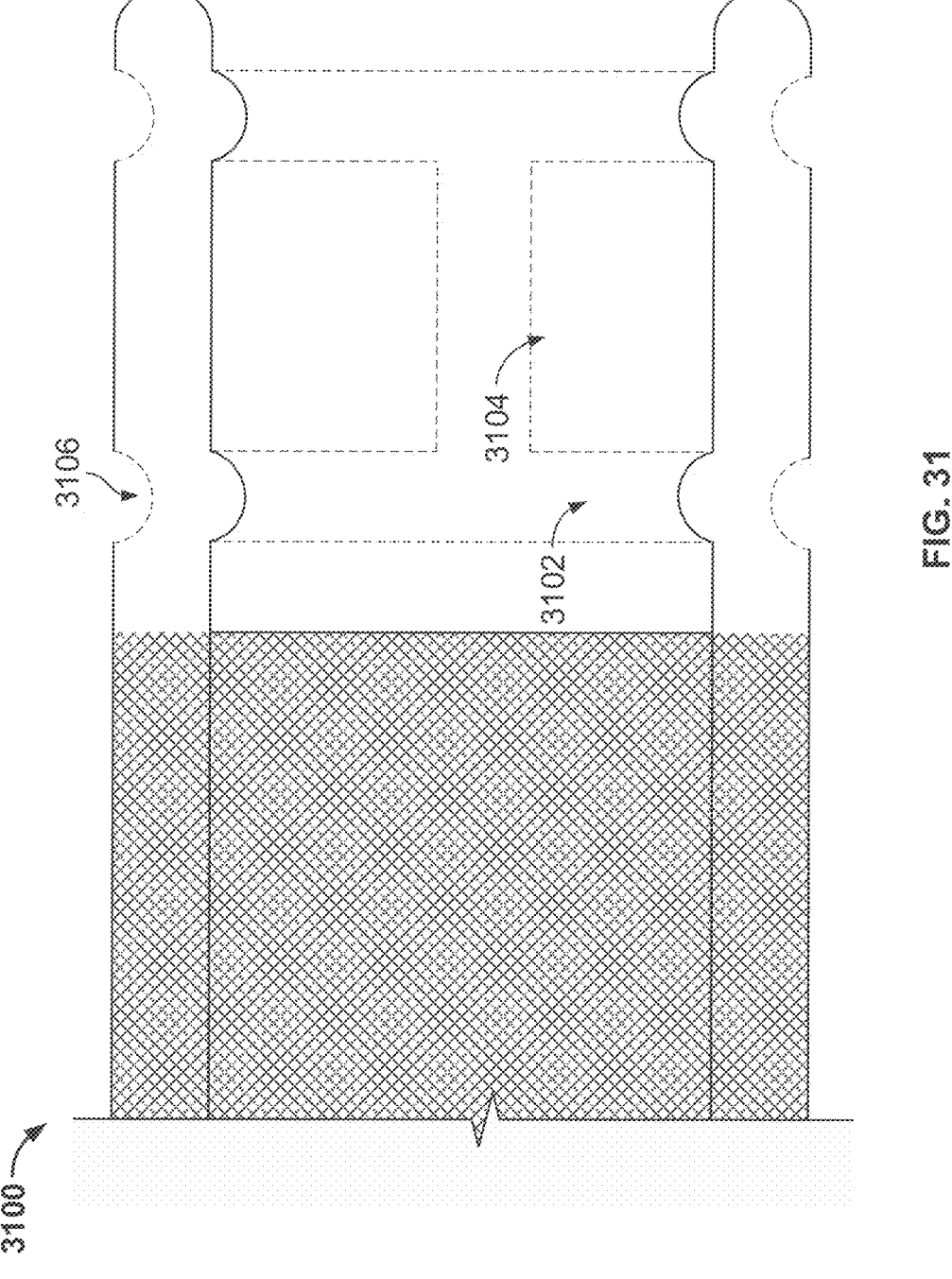
FIG. 31 shows a cross-section view of an illustrative sheath tip.

FIG. 31 shows a cross-sectional view of the delivery system distal tip as shown in FIG. 29 as a variation where the previous bump 2912 consists of at least one circumferential ridge 3102 and lengthwise members 3104. The presence of the circumferential ridges 3102 is anticipated to potentially create pockets on an outer surface 3106 due to some processing methods. This embodiment further increases the volume and decreases the chances that the sheath tip can compress and escape through the gap 2910 with some impact to the sheath ability to expand in a radial direction.

Figure 32:
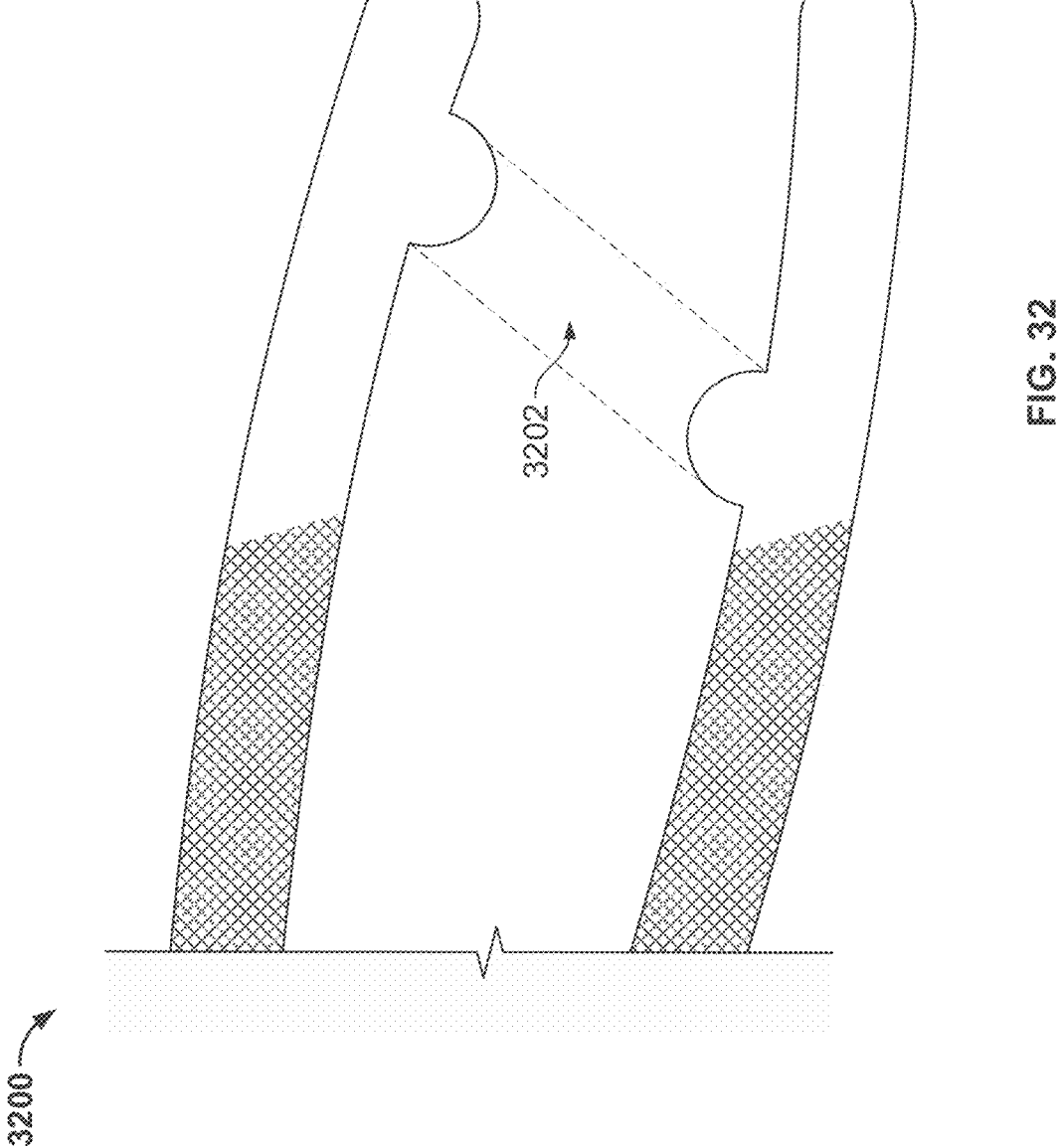
FIG. 32 shows a cross-section view of an illustrative sheath tip.

FIG. 32 shows a cross-sectional view of the delivery system distal tip as shown in FIG. 29 as a variation where the previous bump 2912 is a spiral elongate member 3202. This embodiment further increases the volume and decreases the chances that the sheath tip can compress and escape through the gap 2910 with a minimized impact to the sheath ability to expand in a radial direction.

Figure 33:
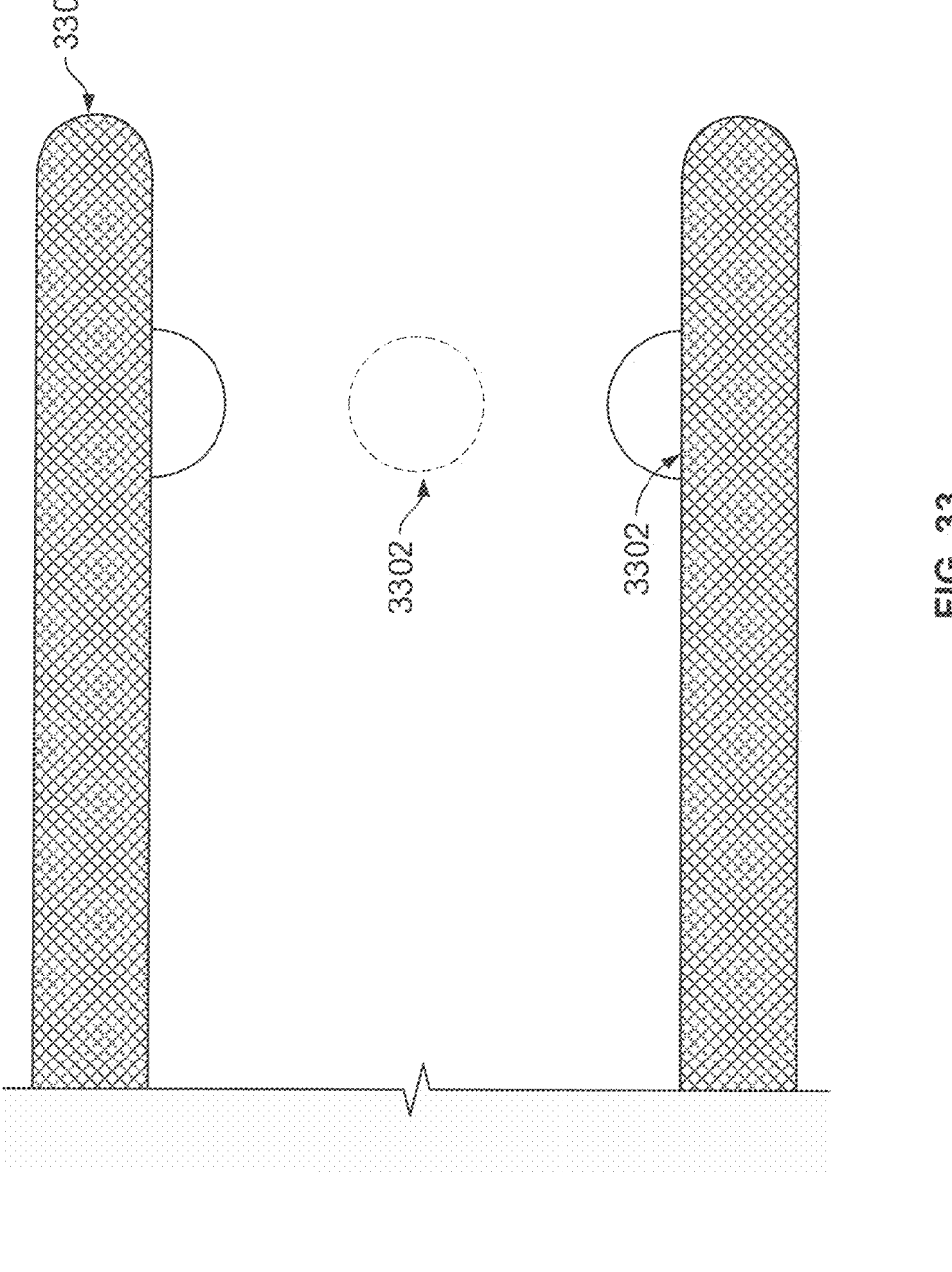
FIG. 33 shows a cross-section view of an illustrative sheath tip.

FIG. 33 shows a cross-sectional view of the delivery system distal tip as shown in FIG. 29 as a variation where any of the previous concepts as presented in FIGS. 29-32 could be in the braid area of the sheath. It is also anticipated that the features described in FIGS. 29-32 could exist in conjunction with FIGS. 26-28. The bump 3302 can be a radio-opaque marker that is welded to the braid. There can exist a section distal to the feature that consists of the encapsulating polymer.

In order to facilitate the compatibility between the introducer sheath 200 and dilator assembly 2000, the tip of the expandable sheath body 202 may be configured to be compatible with the dilator tip interlock configurations discussed in relation to FIGS. 34-42. FIGS. 34-42 illustrate cross-section views of dilator tip and sheath capture configurations. The tip capture mechanism may comprise a detent (a catch preventing motion until release), layer, slug, or o-ring configuration, described in relation to FIGS. 34-37.

Figures 34A, 34B:
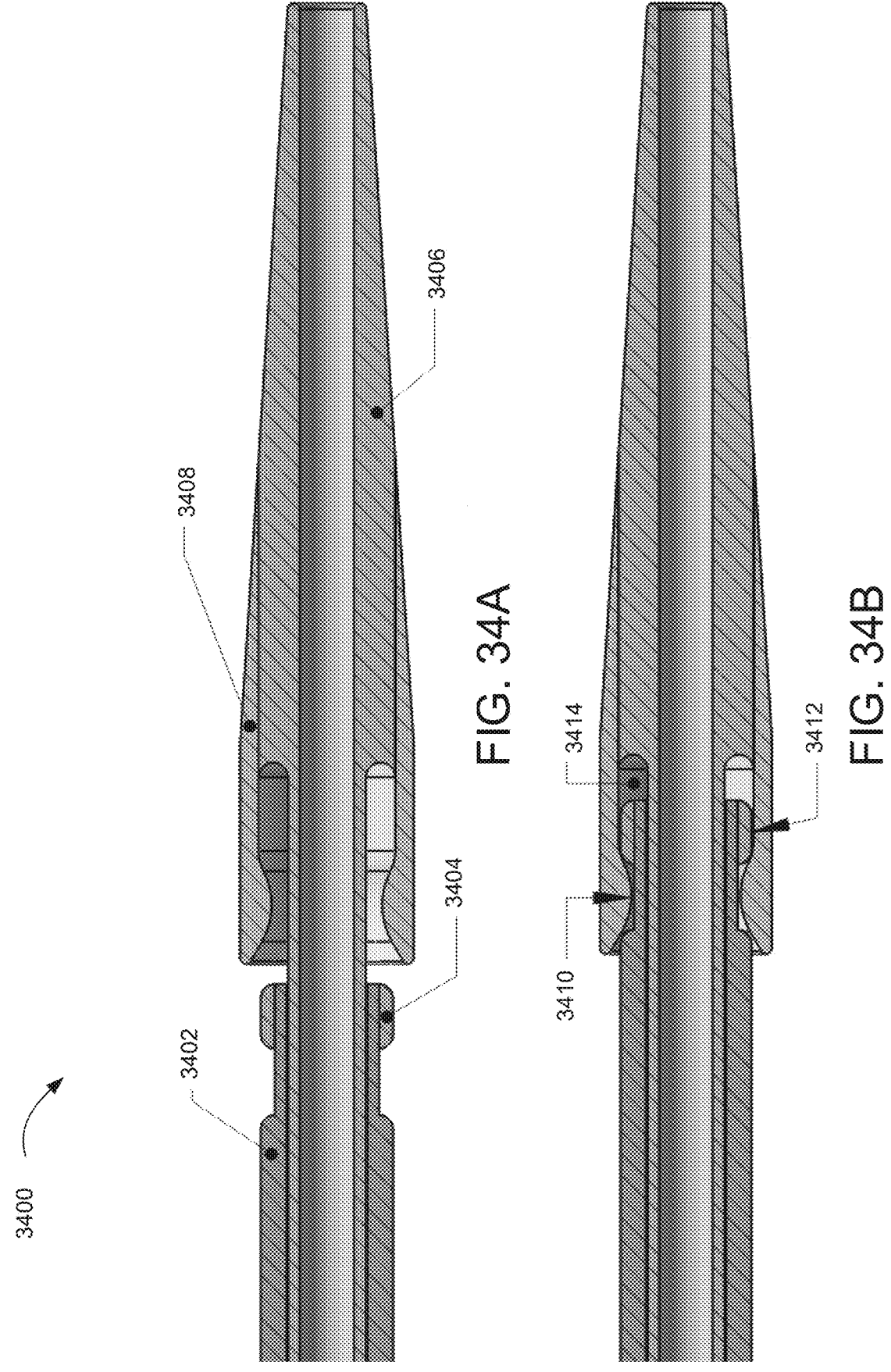
FIGS. 34A and 34B show cross-section views of an illustrative dilator tip configuration.

For example, FIG. 34 shows a detent configuration 3400 both before (A) and after (B) tip capture, with a dilator body 3402 being inserted into a dilator tip 3406. The dilator body 3402 may be rigid while the dilator tip may be semi-rigid. The dilator body 3402 has a semi-elastic compression band 3404 that is captured by the dilator tip 3406 after insertion. Protrusion 3410 and pocket 3414 allow for capture and retention of the distal end of sheath body 202 by providing circumferential compression 3412. The outer portion 3408 of the semi-rigid dilator tip 3406 can comprise a soft material for flexibility or a rigid material for inflexibility.

Figures 35A, 35B:
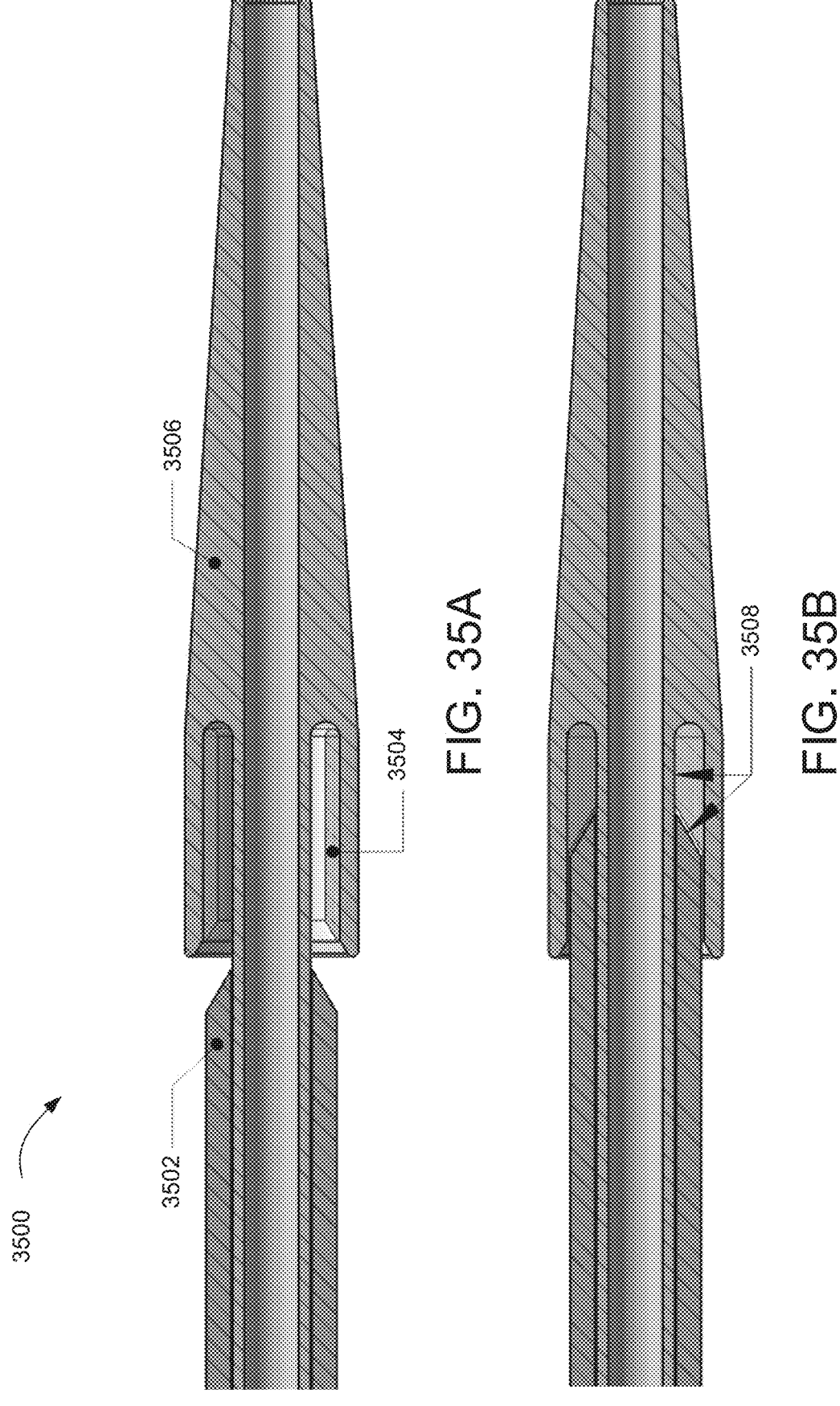
FIGS. 35A and 35B show cross-section views of an illustrative dilator tip configuration.

FIG. 35 shows a layer configuration 3500 before (A) and after (B) a rigid dilator body 3502 is inserted into a semi-rigid dilator tip 3506. The semi-rigid dilator tip 3506 has a semi-elastic compression layer 3504 that captures the rigid dilator body 3502 after insertion. The semi-elastic compression layer 3504 allows for capture and retention of the distal end of sheath body 202 by providing compressive retention with two faces 3508.

Figures 36A, 36B:
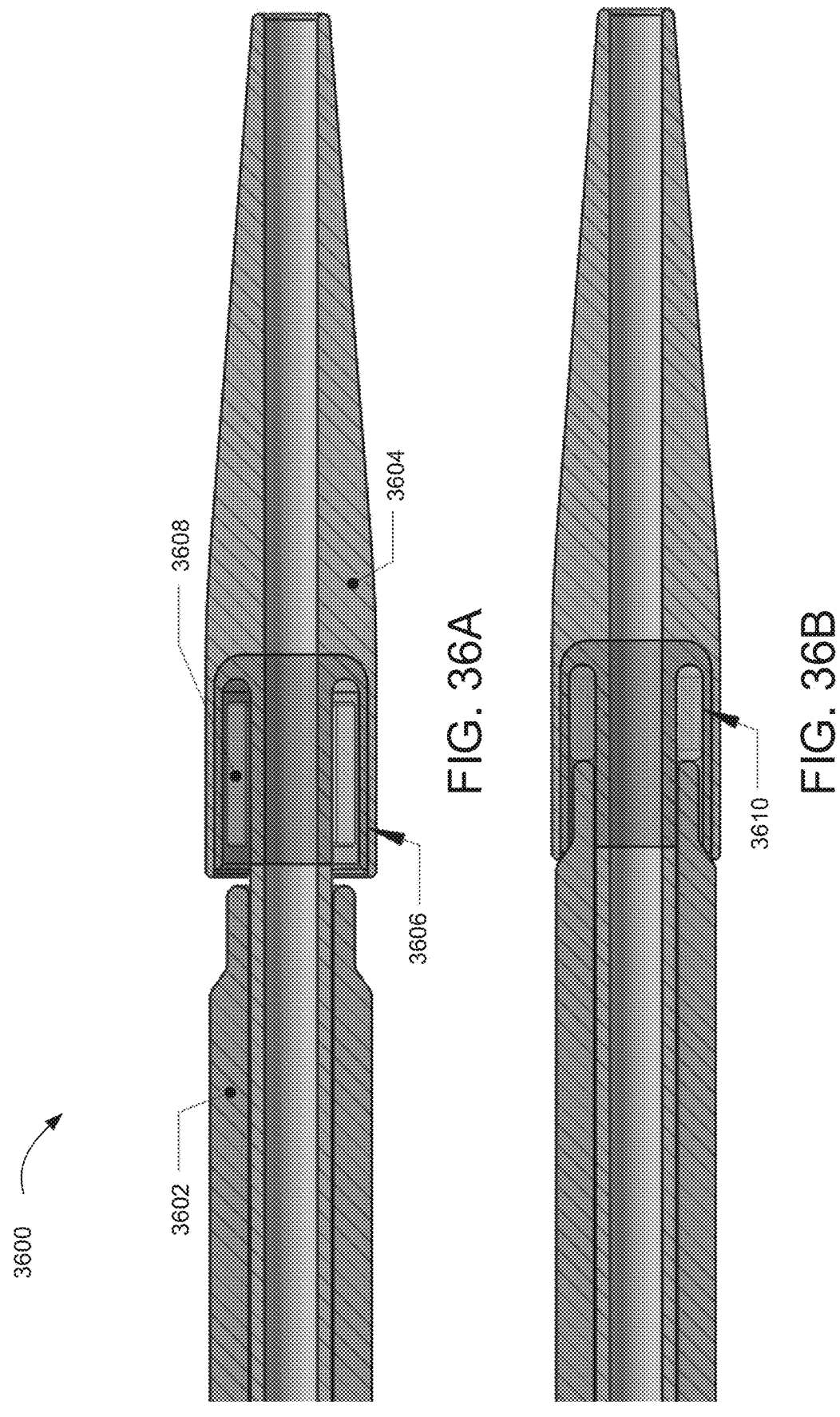
FIGS. 36A and 36B show cross-section views of an illustrative dilator tip configuration.

FIG. 36 shows a slug configuration 3600 before (A) and after (B) a rigid dilator body 3602 is inserted into a soft-flexible dilator tip 3604. The soft-flexible dilator tip 3604 has an elastomeric slug 3608 within a semi-rigid reinforcement 3606 that captures the rigid dilator body 3602 after insertion. The elastomeric slug 3608 is compressed to allow for space during insertion of the rigid dilator body 3602. Once inserted into the semi-rigid reinforcement 3606, the distal end of the sheath body 202 is retained by the compressive forces of the face 3610 of the semi-rigid reinforcement.

Figures 37A, 37B:
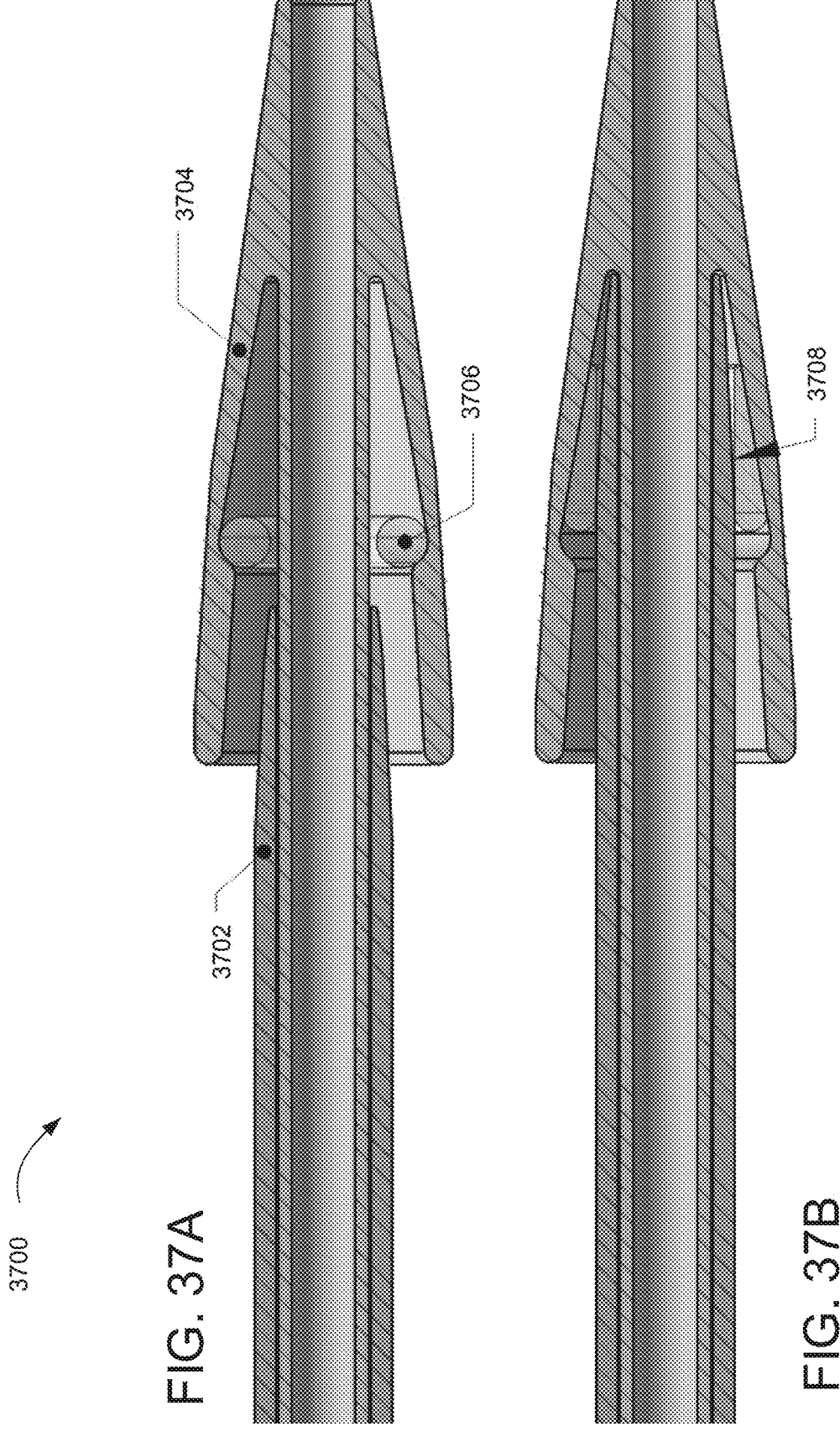
FIGS. 37A and 37B show cross-section views of an illustrative dilator tip configuration.

FIG. 37 shows an o-ring configuration 3700 before (A) and after (B) a rigid dilator body 3702 is inserted into a rigid dilator tip 3704. The rigid dilator tip 3704 has a floating o-ring 3706 that flexes to allow for the rigid dilator body 3702 to be inserted into the rigid dilator tip 3704. Once inserted, the floating o-ring 3706 applies circumferential compression 3708 which retains the distal end of the sheath body 202 when inserted.

Figures 38A, 38B:
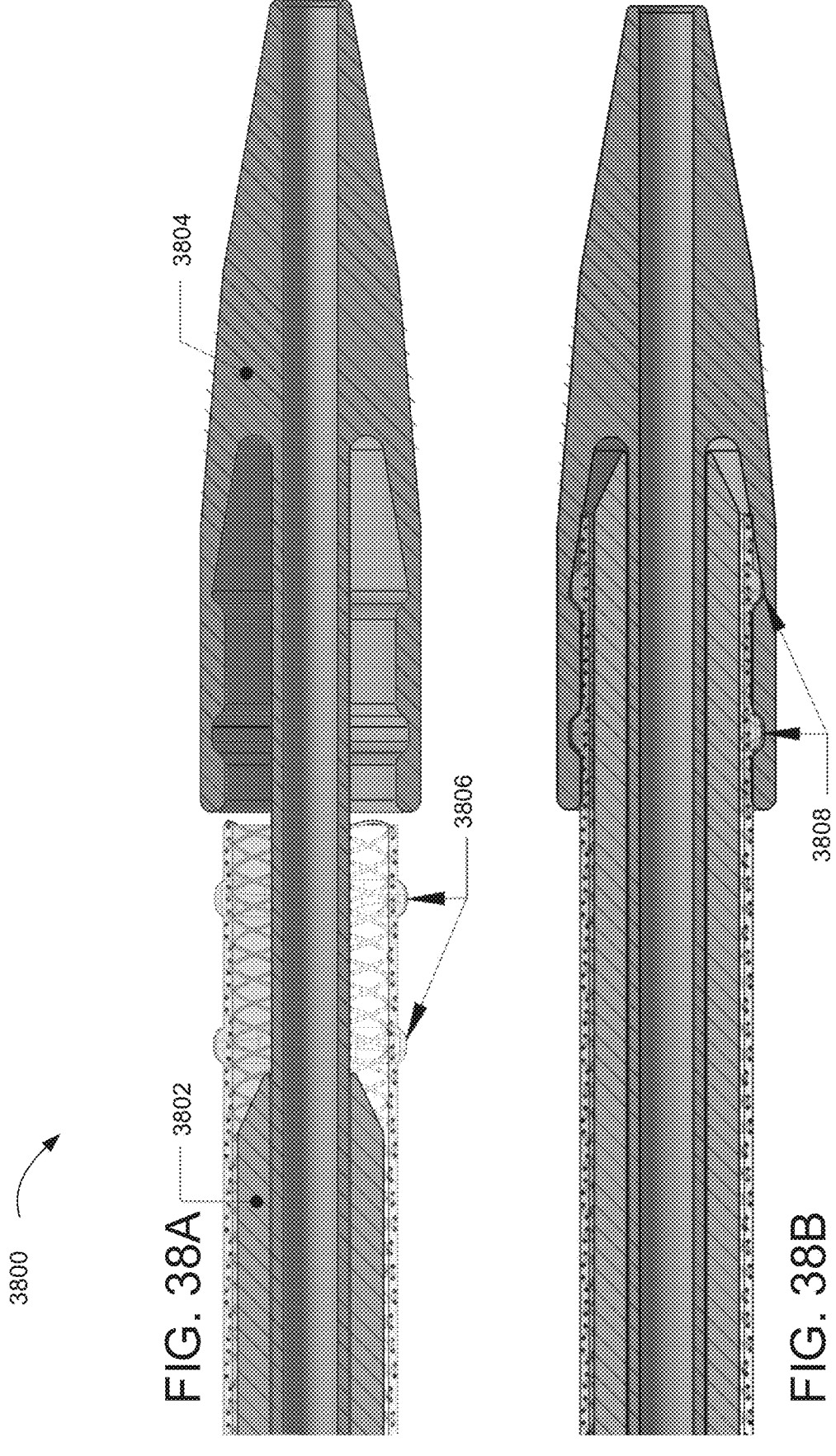
FIGS. 38A and 38B show cross-section views of an illustrative sheath capture configuration.

Alternatively, the tip capture mechanism may also comprise a ribbed, beaded, or split ring configuration, described in relation to FIGS. 38-41. FIG. 38 shows a ribbed configuration 3800 before (A) and after (B) a distal end of a sheath body 202 and a rigid dilator body 3802 are inserted into a rigid dilator tip 3804. The distal end of the sheath body 202 has soft thermoplastic ribs 3806 that are sized to fit into cavities 3808 inside the rigid dilator tip 3804. Once inserted, the cavities 3808 capture the soft thermoplastic ribs 3806 and retain the sheath body 202 within the rigid dilator tip 3804.

Figures 39A, 39B:
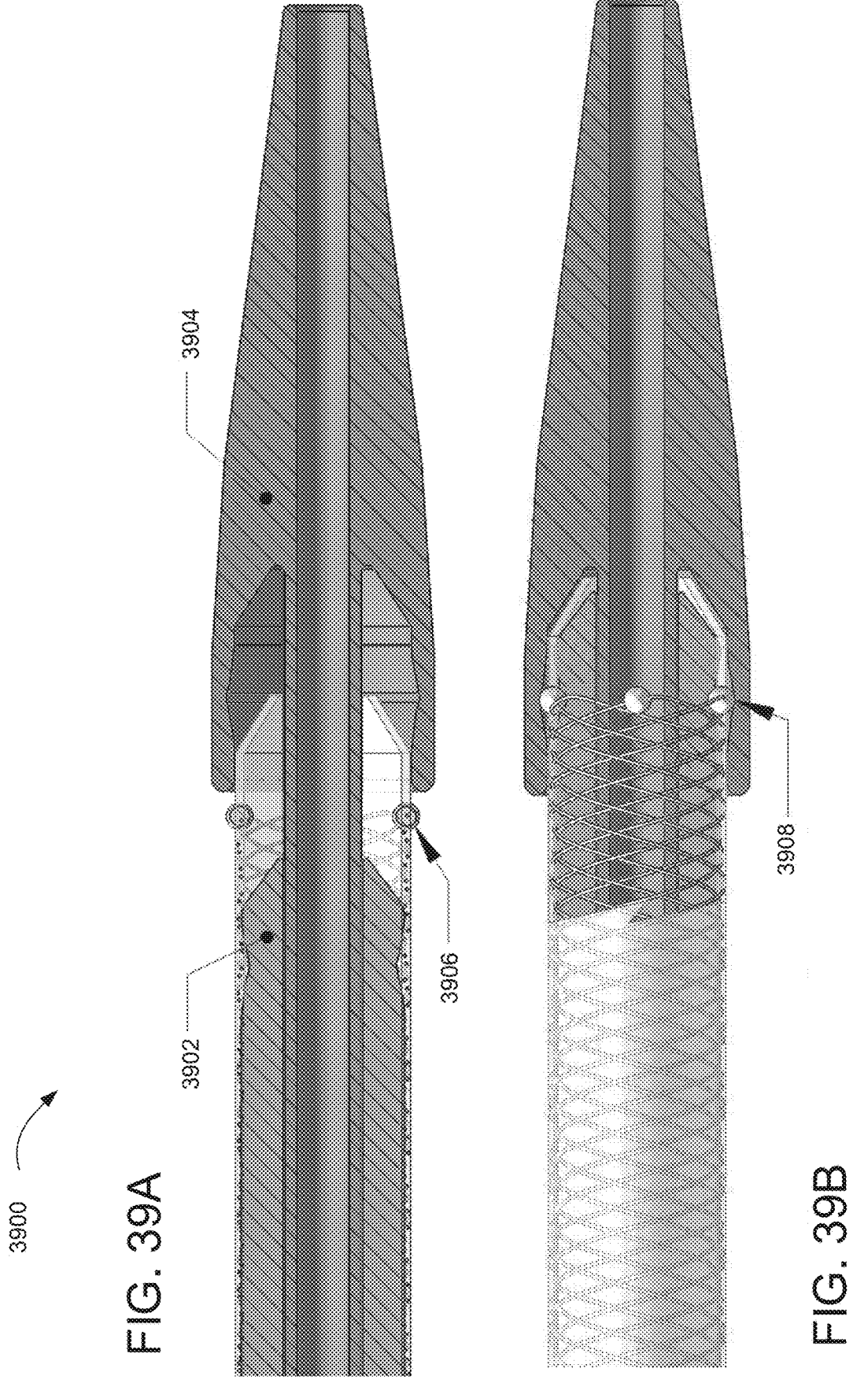
FIGS. 39A and 39B show cross-section views of an illustrative sheath capture configuration.

FIG. 39 shows a beaded configuration 3900 before (A) and after (B) a distal end of a sheath body 202 and a rigid dilator body 3902 are inserted into a rigid dilator tip 3904. The distal end of the sheath body 202 has beads 3906 that are sized to fit into pockets 3908 inside the rigid dilator tip 3904. In one configuration, the beads 3906 are welded to the sheath body 202. Once inserted, the pockets 3908 capture the beads 3906 and retain the sheath body 202 within the rigid dilator tip 3904.

Figures 40A, 40B:
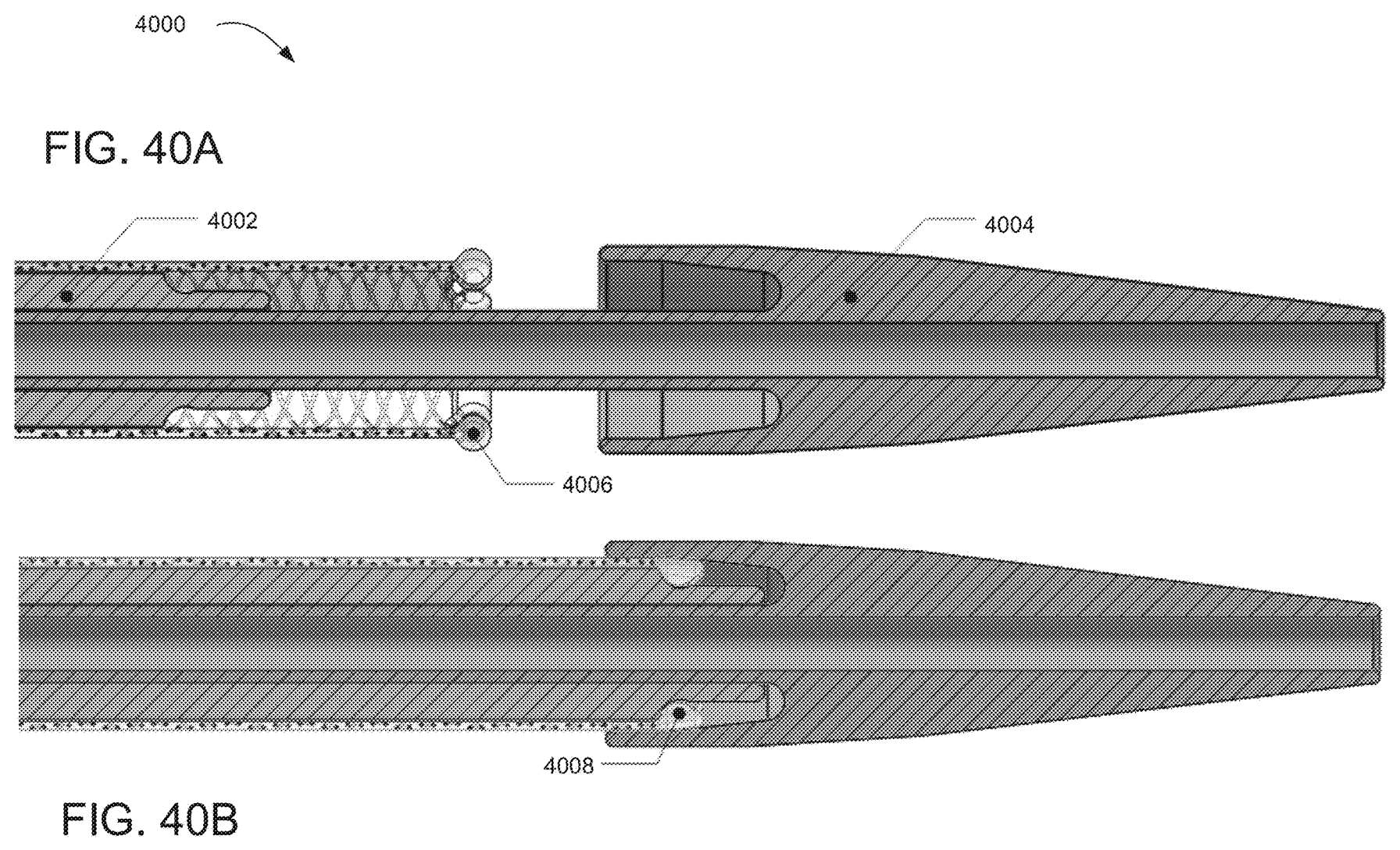

FIG. 40 shows a split ring configuration 4000 before (A) and after (B) a distal end of a sheath body 202 and a rigid dilator body 4002 are inserted into a rigid dilator tip 4004. The distal end of the sheath body 202 has a semi-elastic split ring 4006. Once inserted, the semi-elastic split ring 4006 is captured between an inner wall 4008 of the rigid dilator tip 4004 and the rigid dilator body 4002.

Figures 41A, 41B:
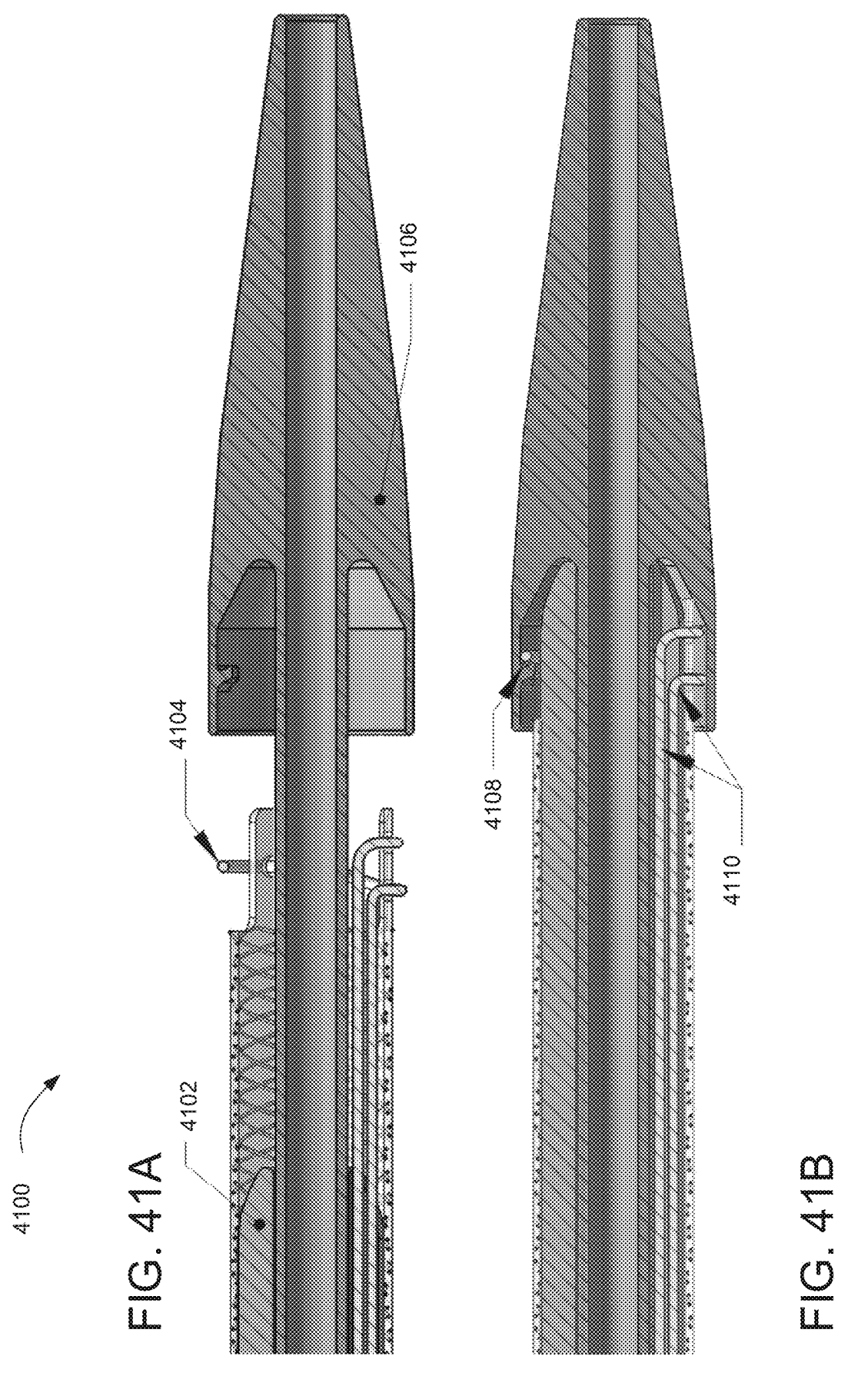
FIGS. 41A and 41B show cross-section views of an illustrative sheath capture configuration.

FIG. 41 shows a suture loop configuration 4100 before (A) and after (B) a distal end of a sheath body 202 and a rigid dilator body 4102 are inserted into a rigid dilator tip 4106. The distal end of the sheath body 202 has a suture loop 4104 that is trapped or captured in a detent 4108 inside the rigid dilator tip 4106 once inserted. The suture loop feeds 4110 run along the outer portion of the sheath body 202.

Figure 42:
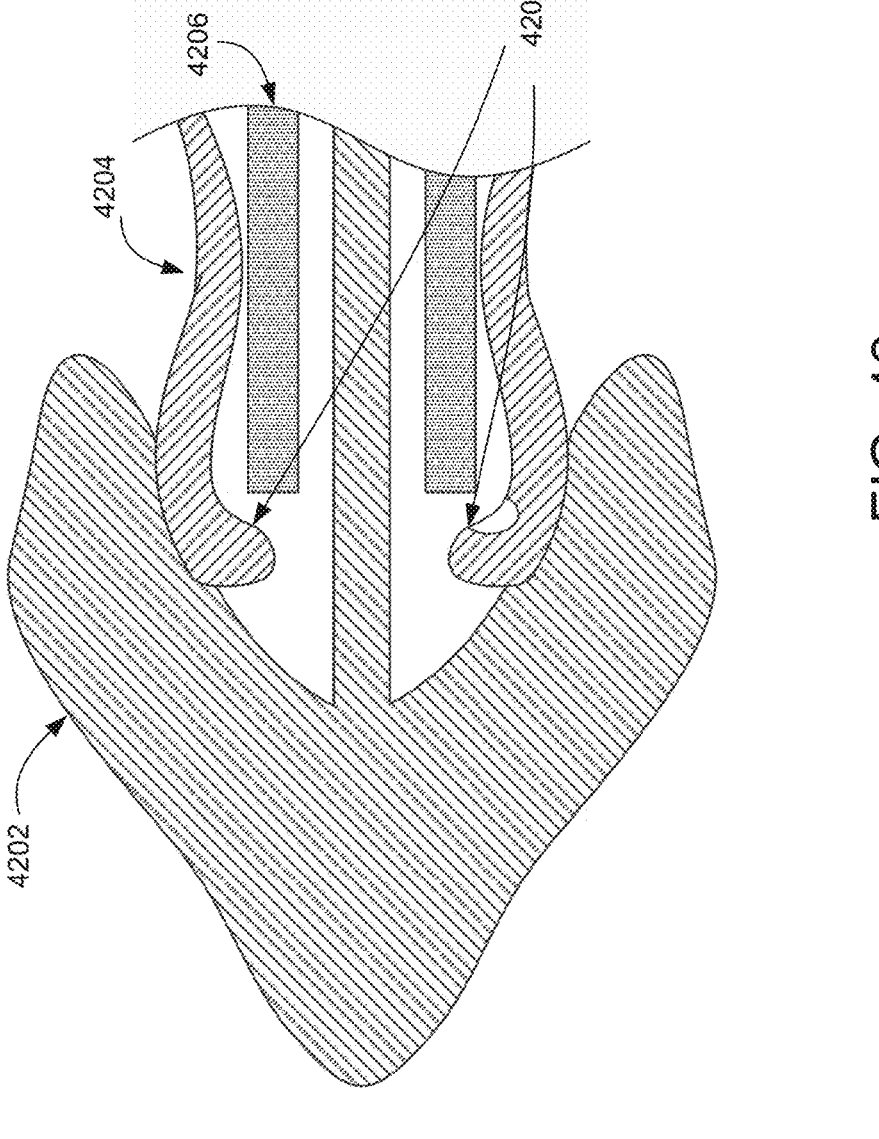
FIG. 42 shows a cross-section view of the distal tip shown in FIG. 29 with a dilator tip interlock.

FIG. 42 shows a cross-section view of a configuration 4200 using a distal end of a sheath body 4204 (as shown in FIG. 29) with a dilator body 4206 and a dilator tip 4202. The distal end of the sheath body 4204 has a bump geometry 4208 that may have a range of movement in a proximal-distal direction, but this range of movement is limited by contact between the bump geometry 4208 against the dilator tip 4202, and/or contact between the bump geometry 4208 against the distal end of the dilator body 4206. Configuration 4200 allows for the sheath body 4204 to be trapped or captured between the dilator body 4206 and the dilator tip 4202. The bump geometry 4208 may be any geometry that limits the range of motion of the sheath body 4204 by abutting against the dilator body 4206.

Figures 43A, 43B, 43C:
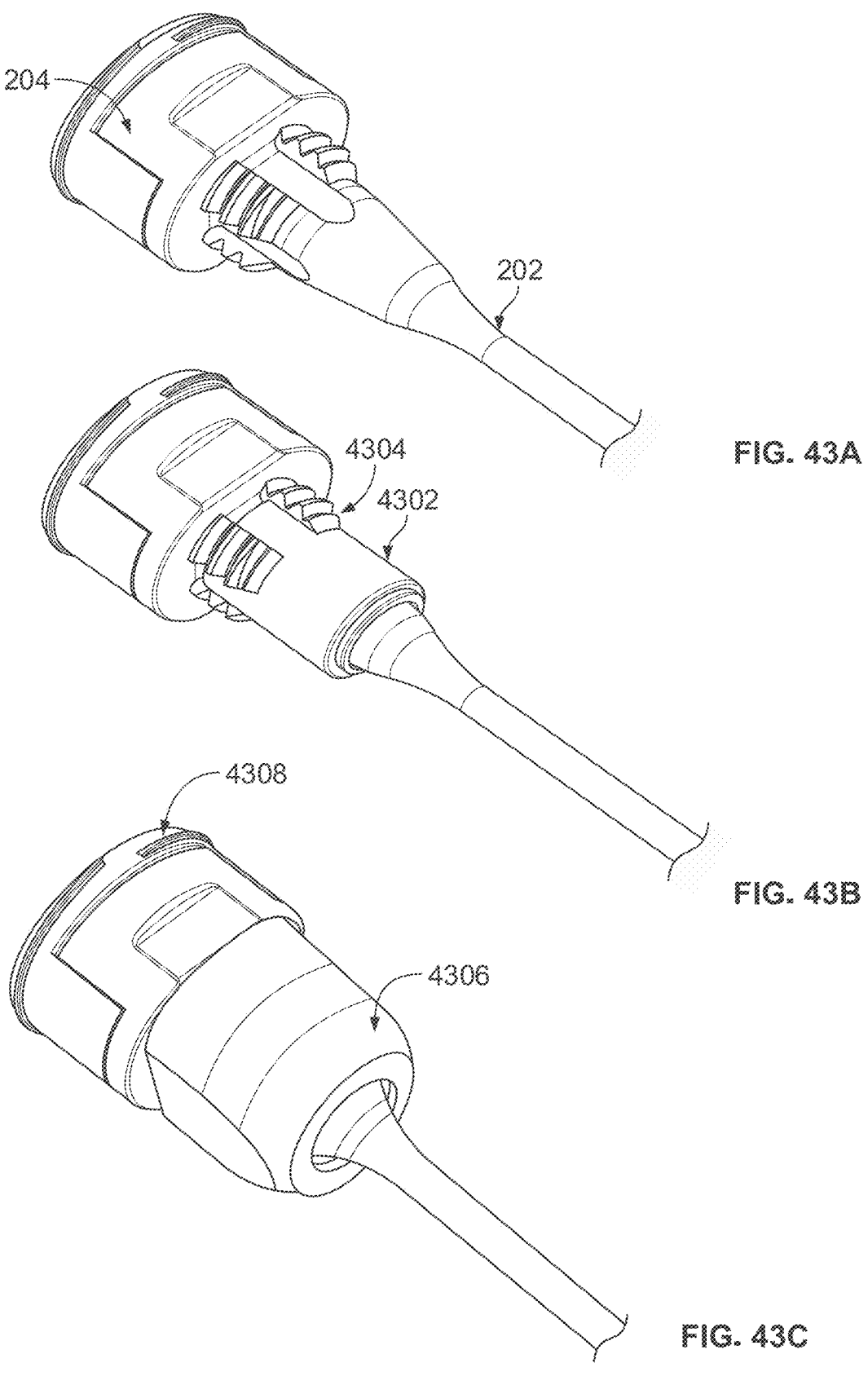
FIGS. 43A to 43C show isometric views of illustrative hub components of the expandable sheath assembly.
Figure 44:
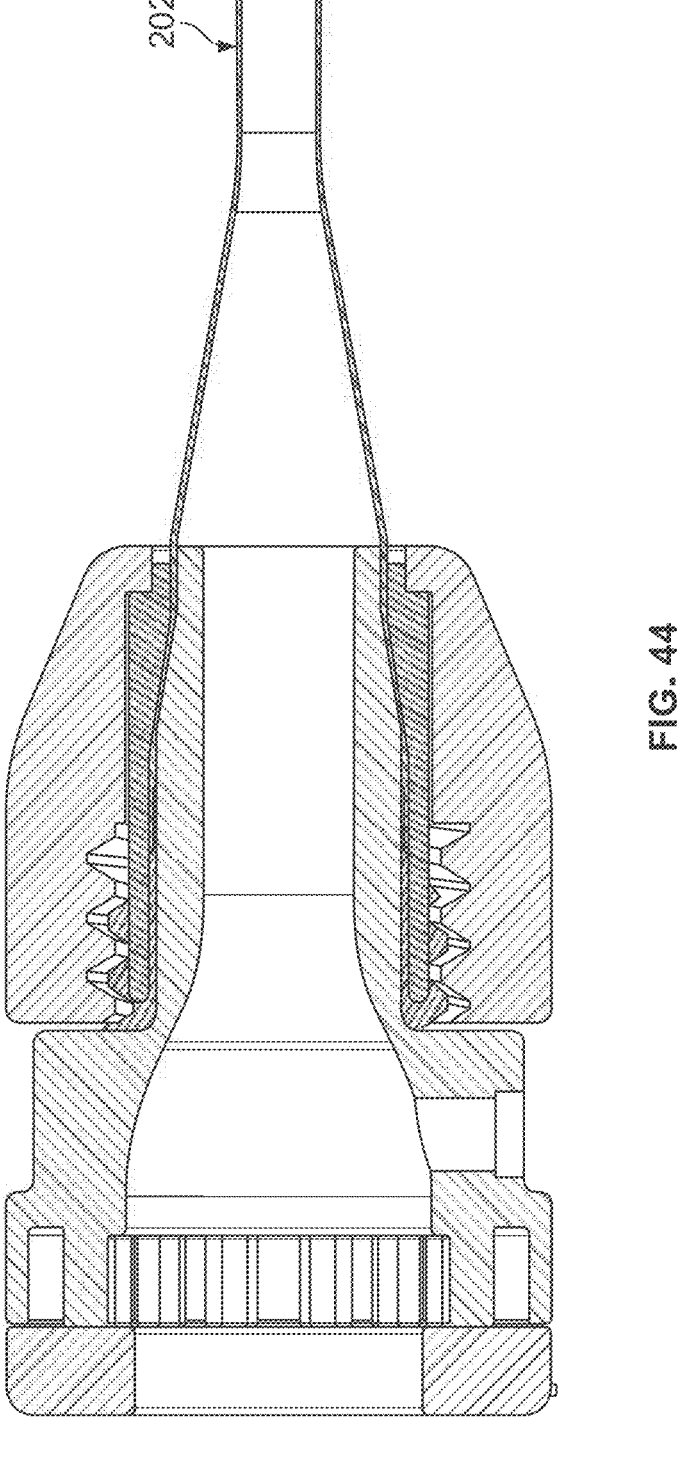
FIG. 44 shows a cross-section view of an illustrative hub.

At the proximal end of the sheath assembly, connection of the sheath is achieved via a hub. As discussed in relation to FIG. 1, the introducer sheath 200 has a hub 204 that allows for connection with a dilator assembly 2000 and a hemostasis stylet assembly 4600. In addition, the hub 204 attaches to the expandable sheath body 202. FIG. 43 shows the attachment of the expandable sheath body 202 to the hub 204 of the introducer sheath 200. First, the expandable sheath body 202 is slid up a taper of the hub 204 (A). Second, a locking ferule 4302 is inserted which has fingers 4304 that interlock with geometry on the hub 204 (B). A locking cap 4306 is then twisted on which creates a pinching force between the hub 204 and the locking ferule 4302. The fingers of the locking ferule 4302 prevent rotation, therefore preventing rotational loading on the sheath body 202 during the locking cap attachment. Also shown is a cap 4308 to provide containment of the hemostasis valve which is not shown. FIG. 44 shows a cross-sectional side view of the introducer sheath hub 204 and introducer sheath 202.

Figure 45:
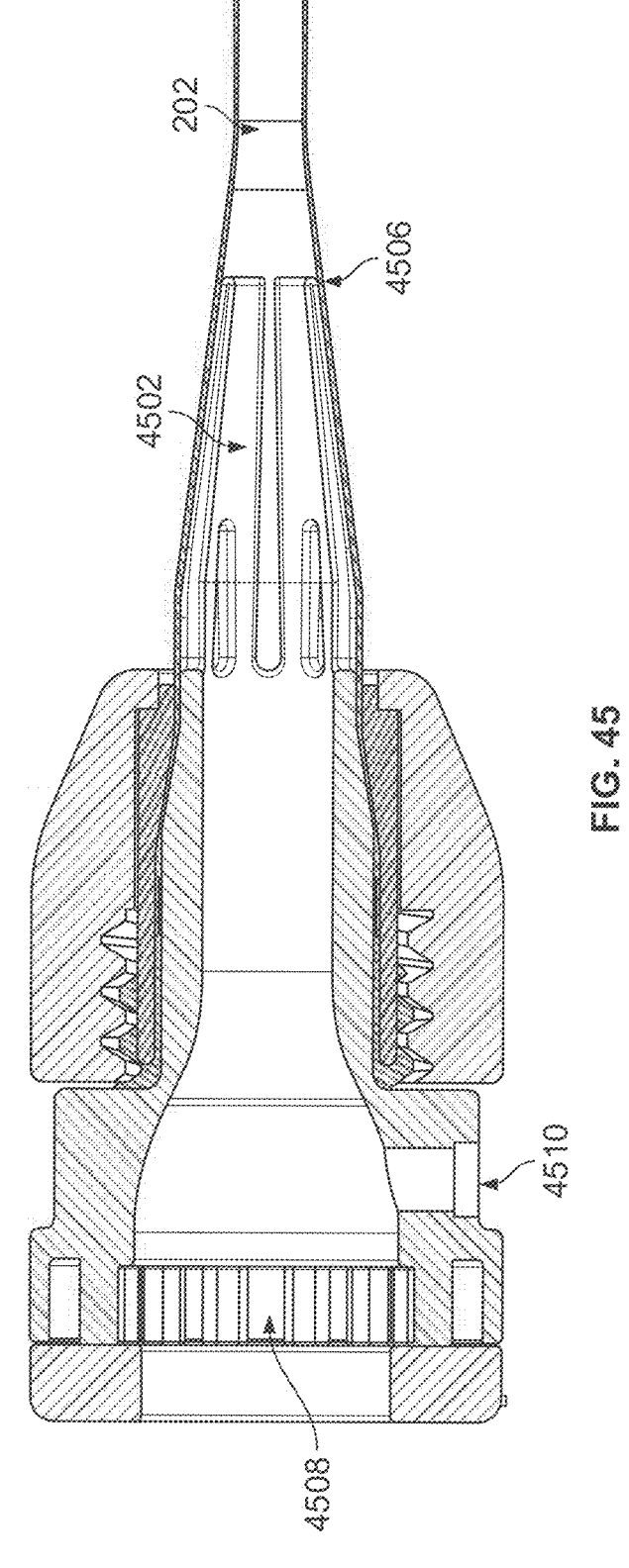
FIG. 45 shows a cross-section view of an illustrative hub with support fingers.

FIG. 45 shows a second expandable sheath hub 204 with a series of fingers 4502. The fingers 4502 are design to provide additional support through the region of the expandable sheath body 202 where it transitions form the large diameter secured on the hub 204 to a second smaller diameter. This area is typically an area of low mechanical integrity due to the transition. The fingers 4502 contain geometry that allows them to flex open to pass the pump 4504. The fingers 4502 contain a curved distal edge 4506 to allow for the withdrawal of the pump 4504. The fingers 4502 contain a geometry that prevents them from collapsing past a minimum diameter as the fingers 4502 make contact with each other. The hub 204 has an area that contains a hemostasis valve 4508. Also shown is a port 4510 for a sidearm (not shown) and luer connection (not shown) used for flushing and aspirating the introducer sheath 200.

At least one advantage of the hub and sheath assembly is to minimize the risk of sheath eversion at the hub, i.e. reduce the risk during removal of the device for the sheath to either ever and fold inside out from the hub or gather around the inside edge and bunch up, preventing further removal.

Figure 70:
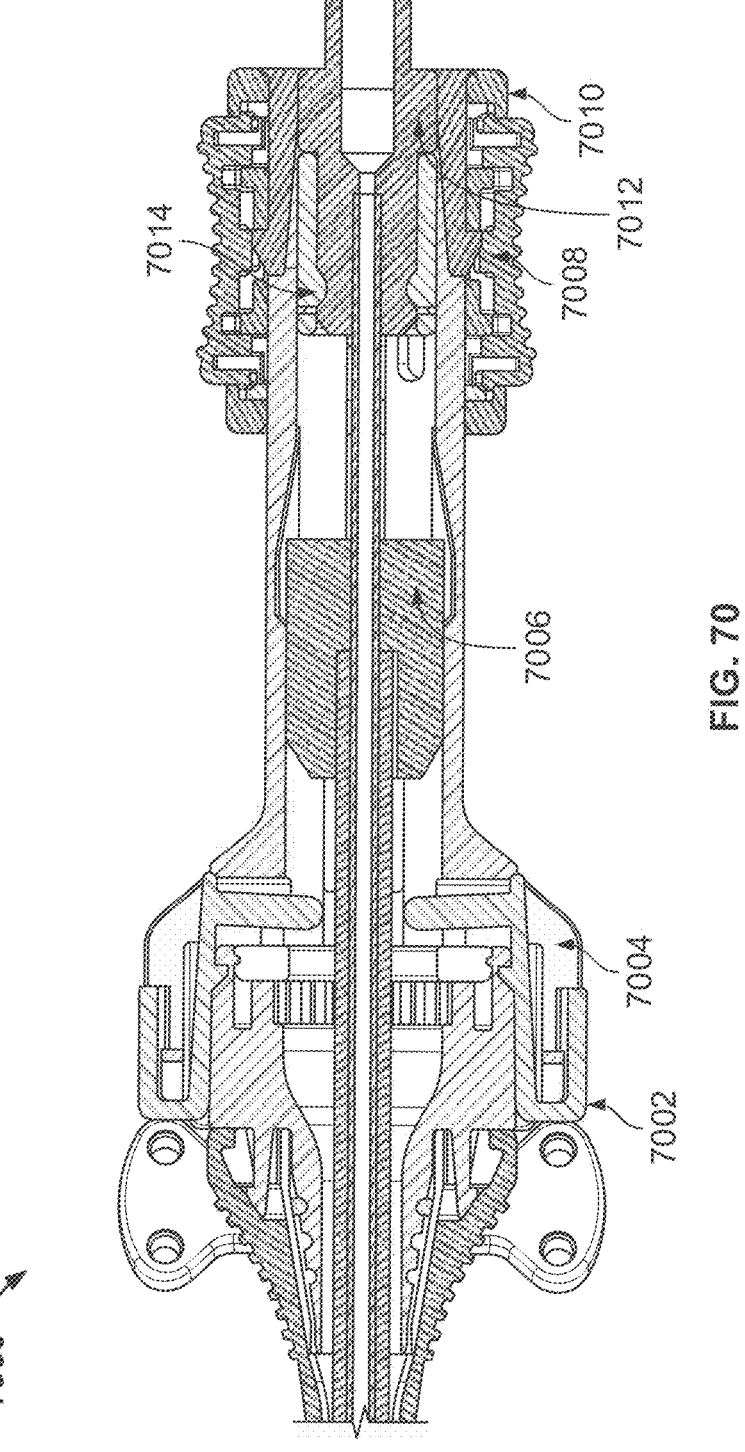
FIG. 70 shows a cross-section of an illustrative sheath delivery system in a first position.

FIGS. 70-81 show cross-sections of an illustrative sheath delivery system. FIG. 70 shows a cross-section of a configuration 7000 of the expandable sheath delivery system in a first position. Sheath delivery system 7000 includes snap ring 7002, handle 7004, outer dilator hub 7006, a pair of actuators 7008, a slider 7010, an inner dilator hub 7012, and a carrier 7014. Not shown in configuration 7000 are a pair of connectors 7016 that connects the slider to the carrier.

Figure 71:
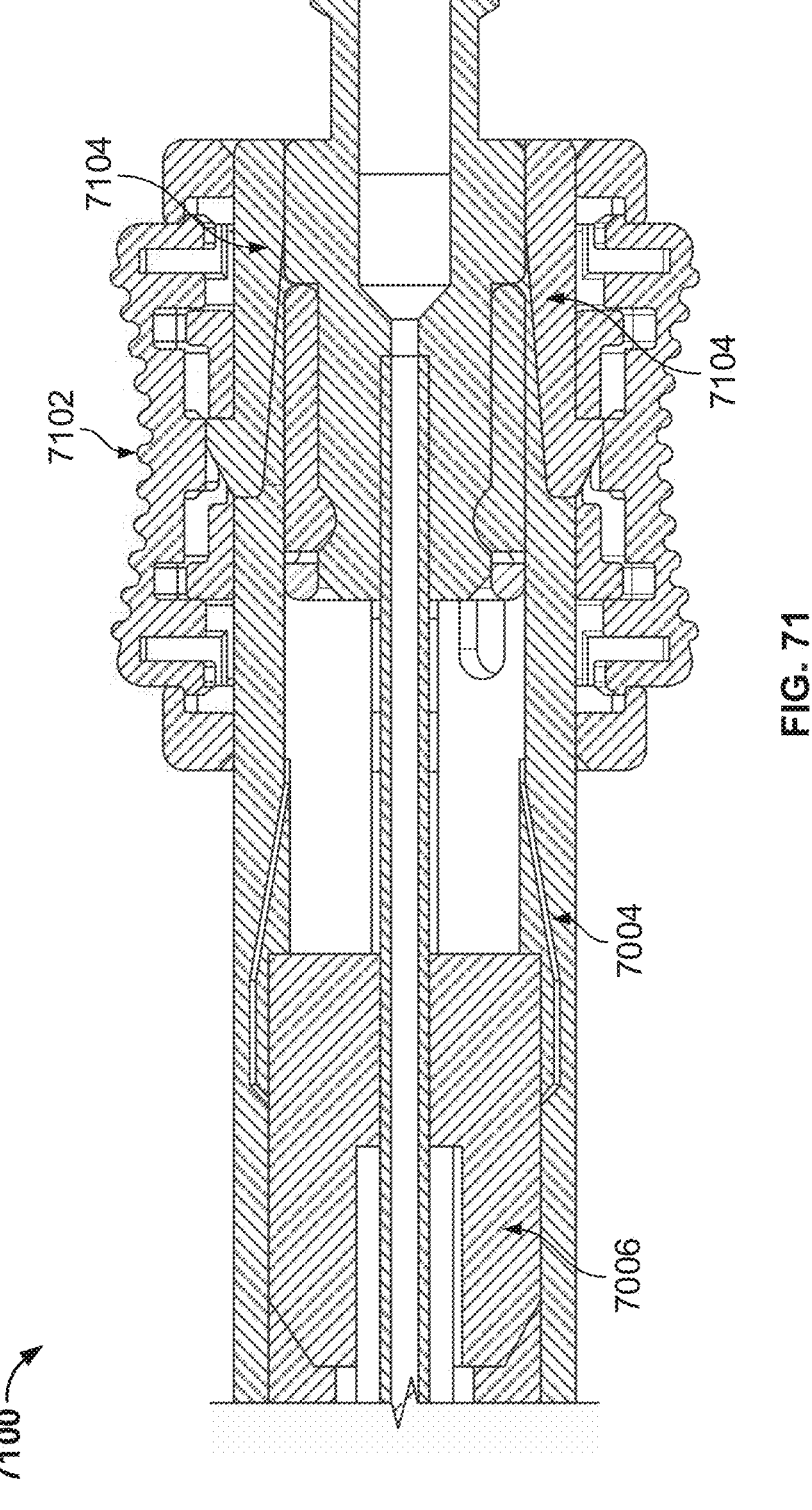
FIG. 71 shows a cross-section of an illustrative sheath delivery system in a first position.
Figure 72:
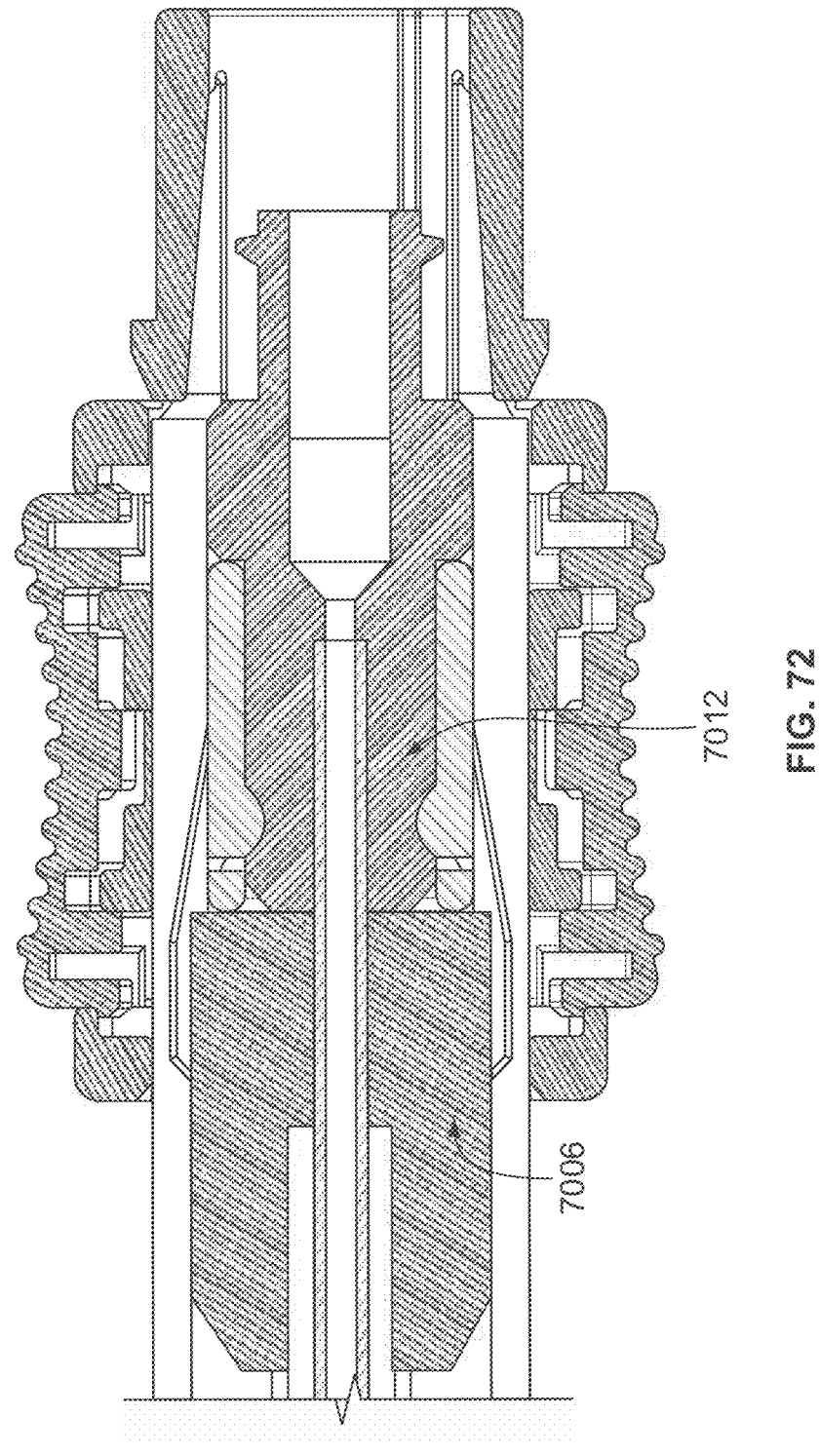
FIG. 72 shows a cross-section of an illustrative sheath delivery system in a second position.
Figure 73:
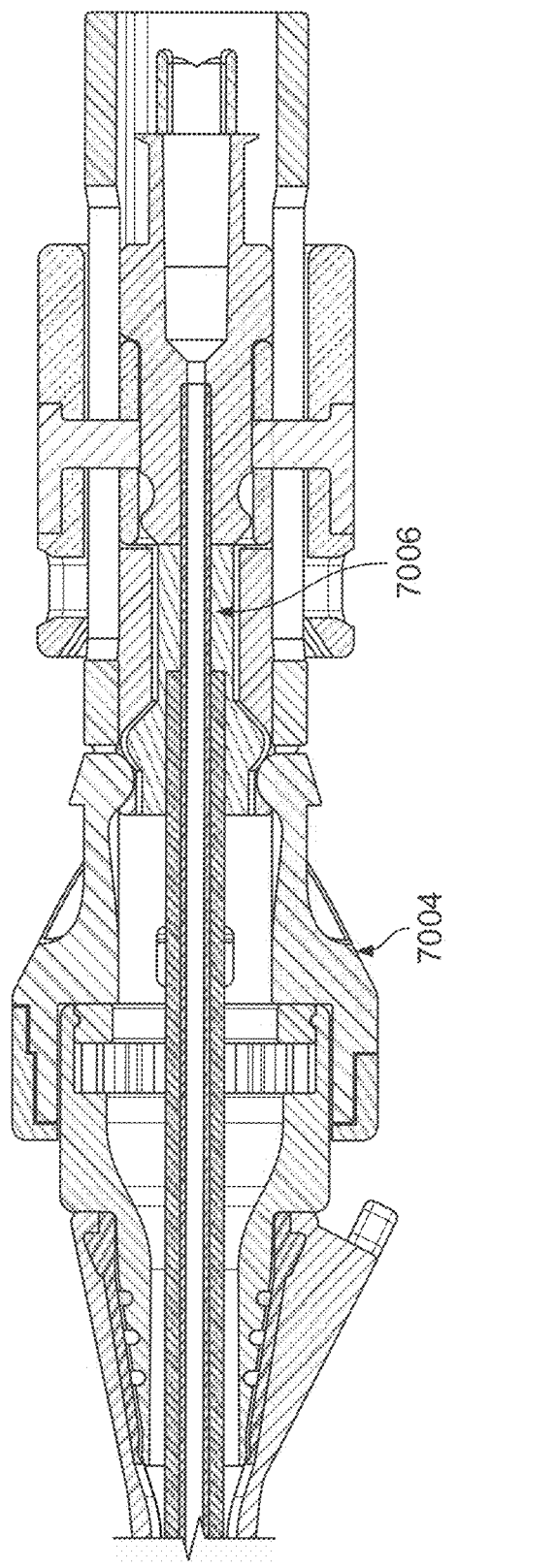
FIG. 73 shows a cross-section of an illustrative sheath delivery system in a second position.

FIG. 71 shows a cross-section of a configuration 7100 of the expandable sheath delivery system in a transitional position between the first position of configuration 7000 and a second position of configuration 7200, shown in FIG. 72. In configuration 7100, the user pinches the actuators 7102 which depresses latches 7104 on the handle 7004 that allows the slider 7010 to move. While the actuators 7102 are depressed, the user slides the slider forward to the second position in FIG. 72.

In configuration 7200, shown in FIG. 72, the sheath delivery system is in the second position and shows the point in which the inner dilator hub 7012 makes contact with the outer dilator hub 7006. FIG. 72 shows a cross-section of another configuration 7300 of the sheath delivery system in the second position. In the second position, the outer dilator hub 7006 is constrained by a feature on the inside of the handle 7004. A force is required to overcome the feature which serves to keep the outer dilator from moving forward during the transition from the first position to the second position.

Figure 74:
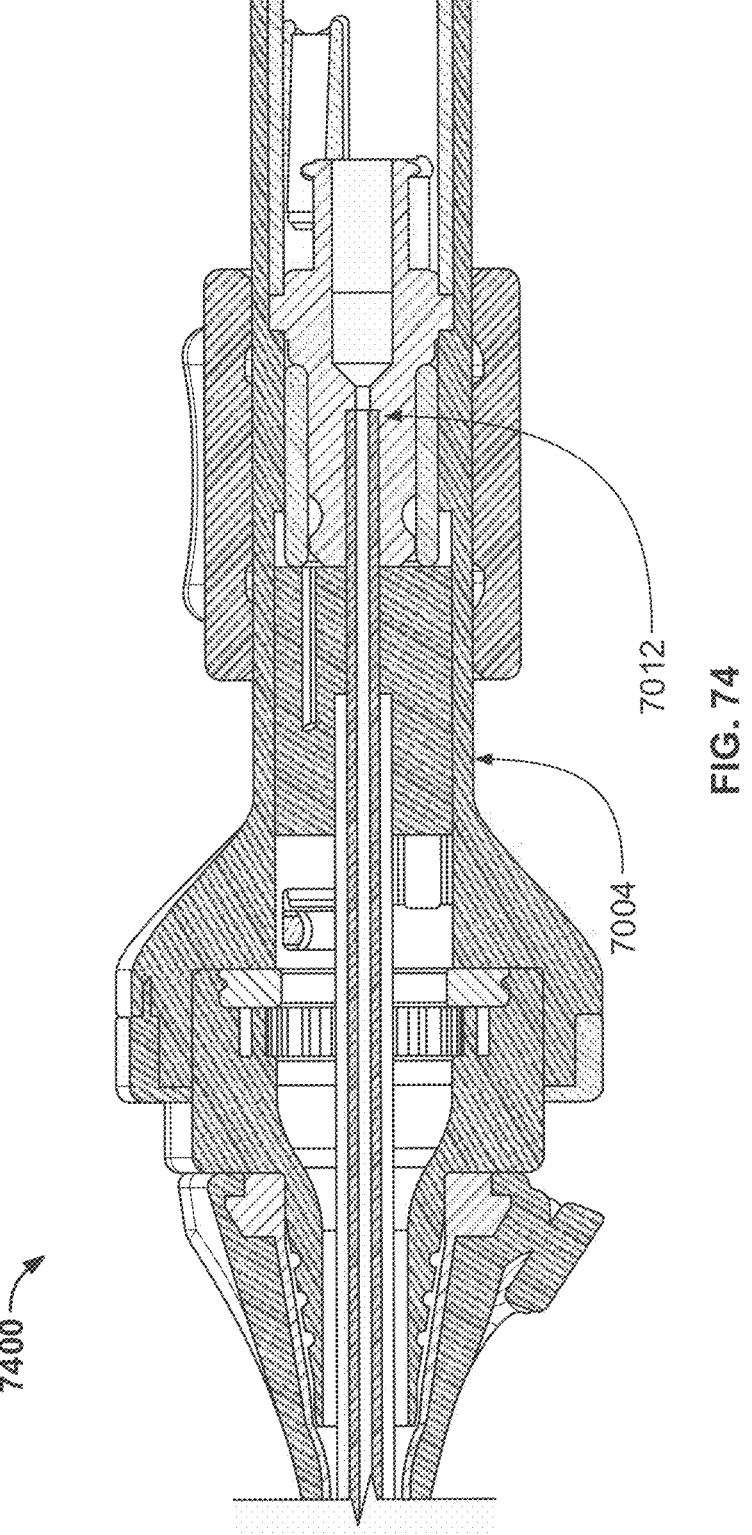
FIG. 74 shows a cross-section of an illustrative sheath delivery system in a third position.

FIG. 74 shows a cross-section of a configuration 7400 of the sheath delivery system in a third position. A positive stop on the inner diameter of the handle 7004 is shown which prevents the movement of the inner dilator hub 7012 forward.

Figure 75:
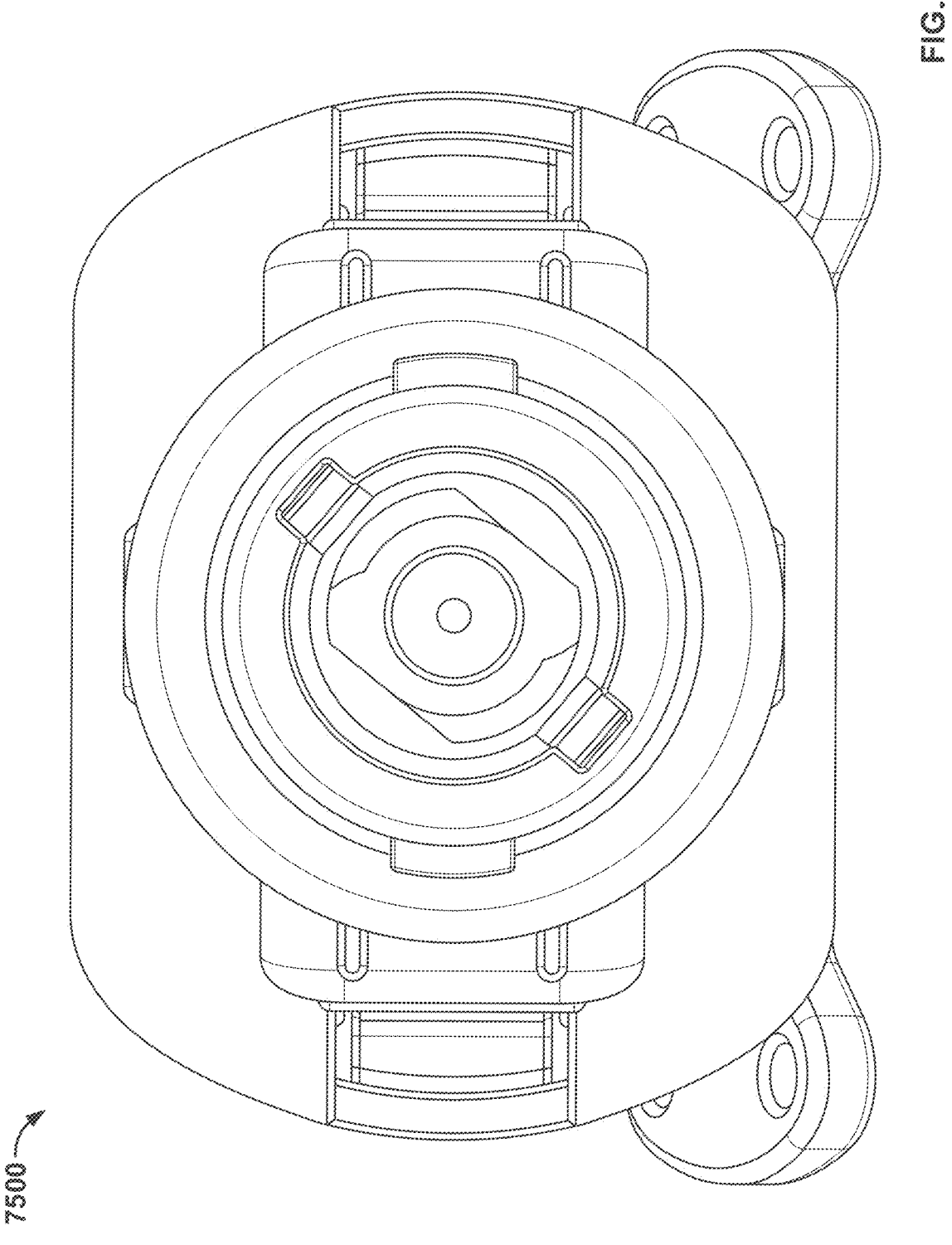
FIG. 75 shows a proximal view of the expandable sheath system.
Figure 76:
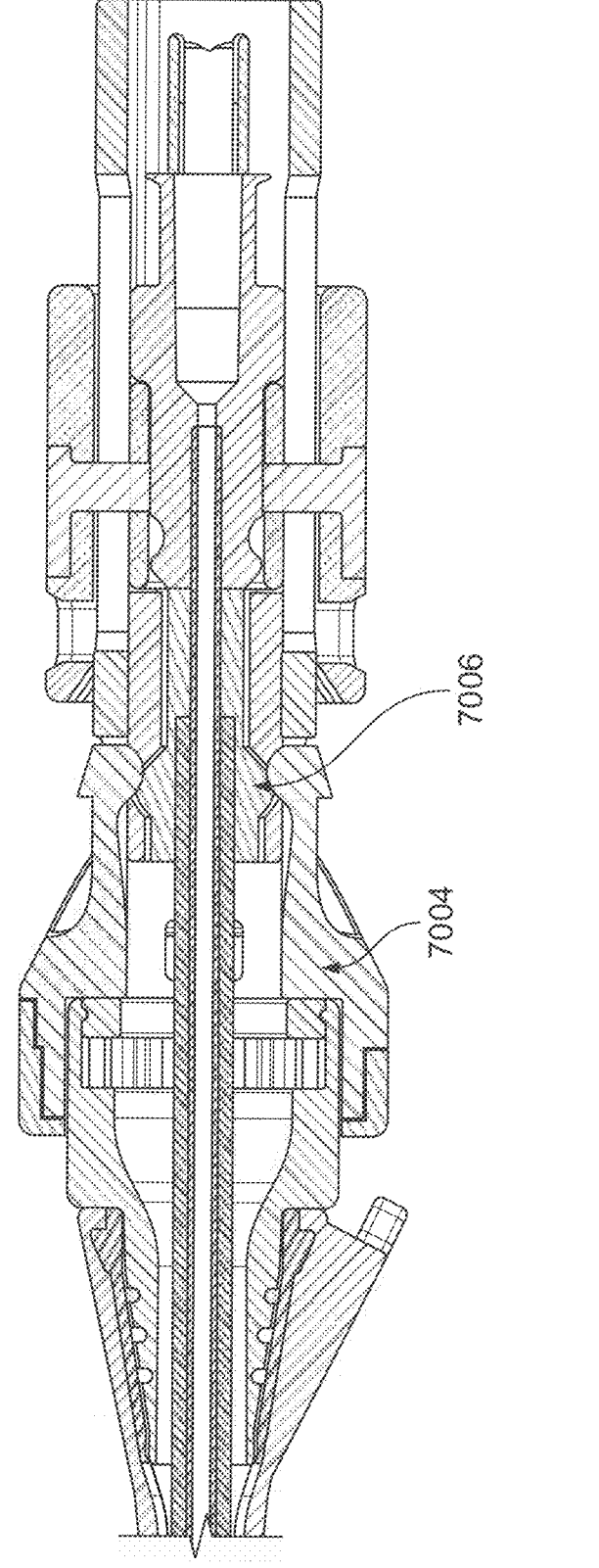
FIG. 76 shows a cross-section of an illustrative sheath delivery system in a third position.

FIG. 75 shows an illustrative view of a line defining the off-vertical cross-section of FIG. 74. FIG. 76 shows the delivery system in the third position where the outer dilator hub 6906 has overcome the feature on the inner diameter of the handle 7004.

Figure 77:
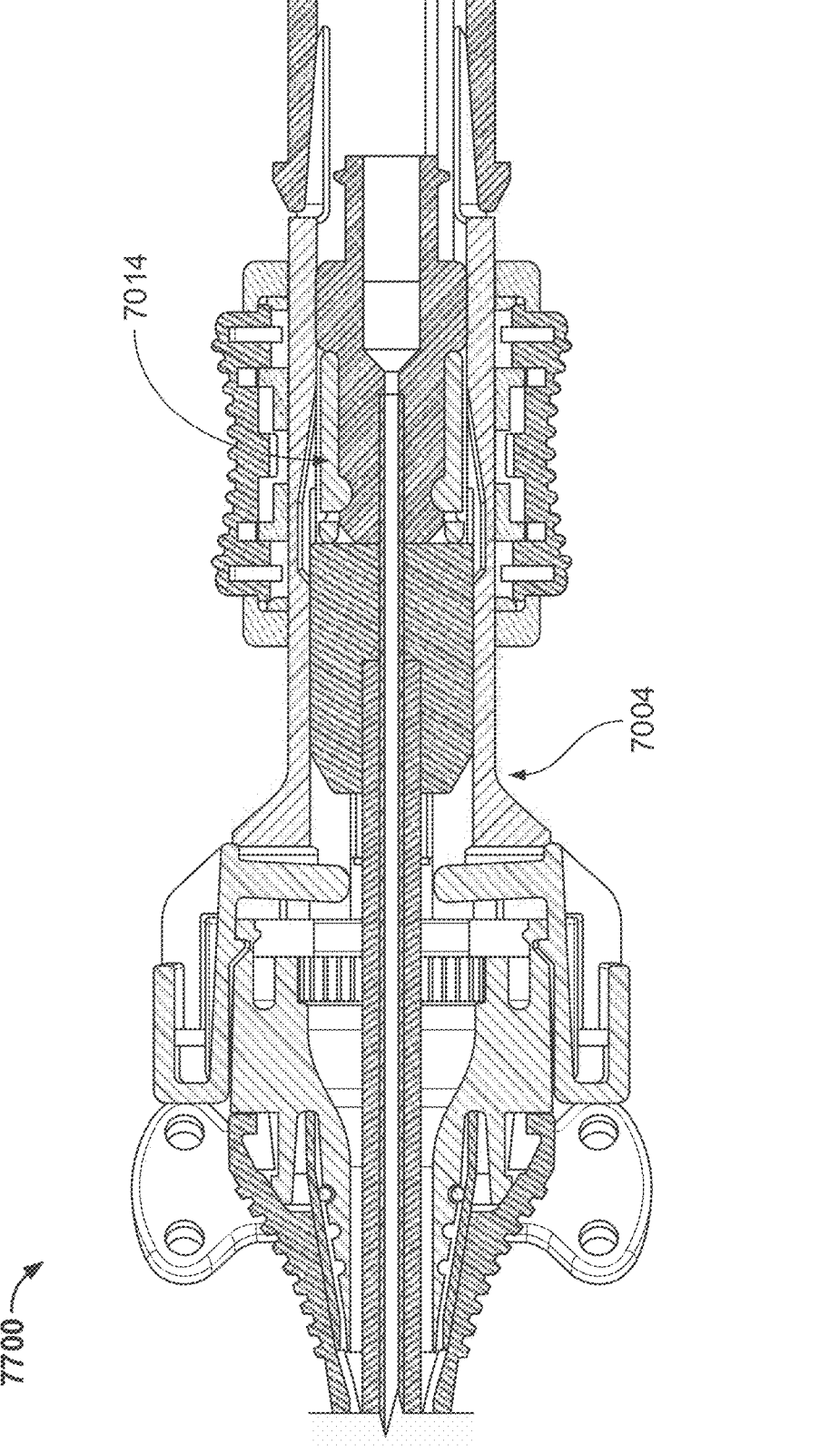
FIG. 77 shows a cross-section of an illustrative sheath delivery system in a third position.

FIG. 77 shows the delivery system with a horizontal cross-section, having a pocket in the delivery system handle 7004 that allows latches on the carrier 7014 to open and detach from the inner dilator hub.

Figure 78:
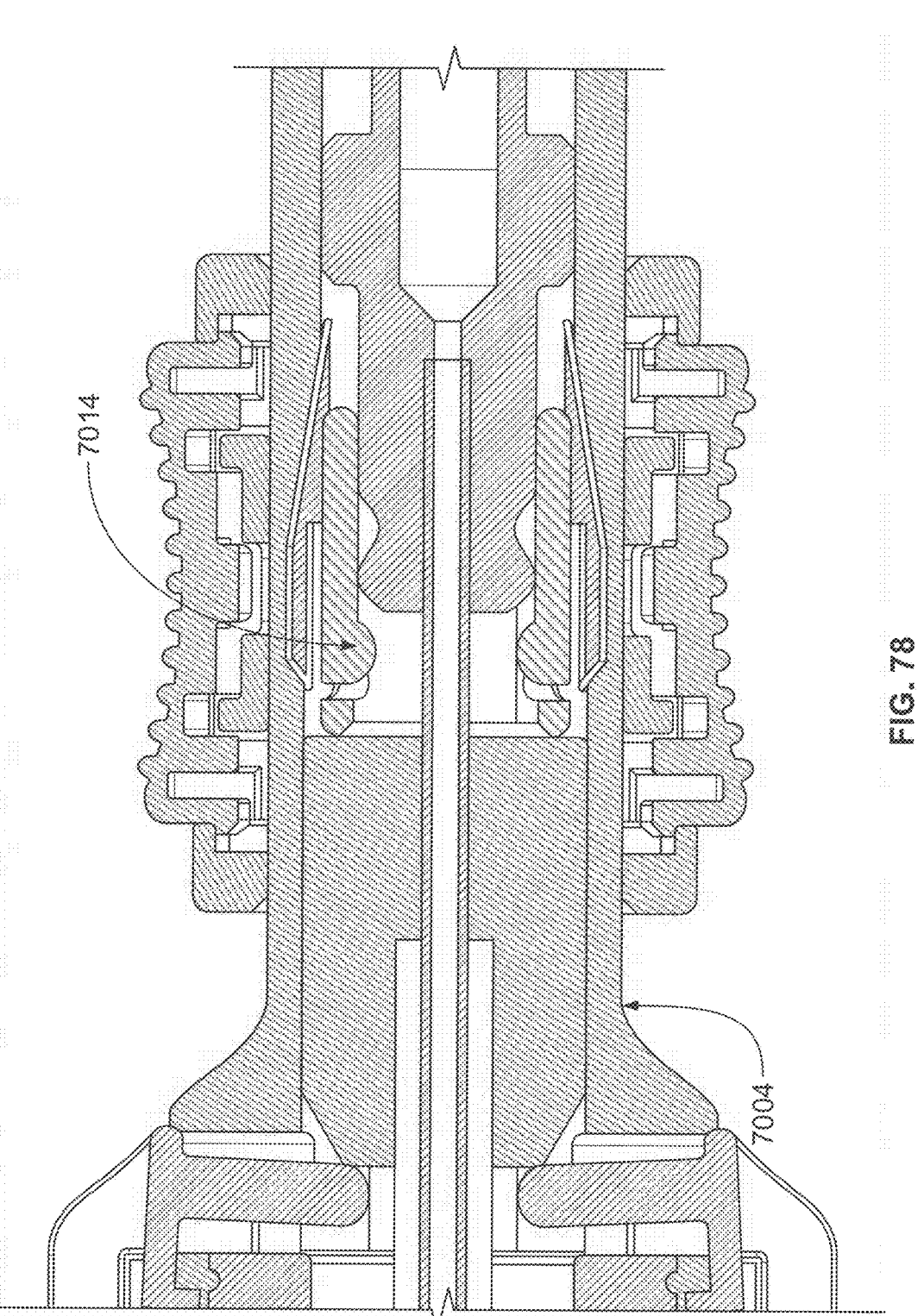
FIG. 78 shows a cross-section of an illustrative sheath delivery system in a fourth position.

FIG. 78 shows the delivery system in a fourth position where the forward movement of the slider now creates movement forward of the outer dilator assembly only and the inner dilator assembly no longer moves.

Figure 79:
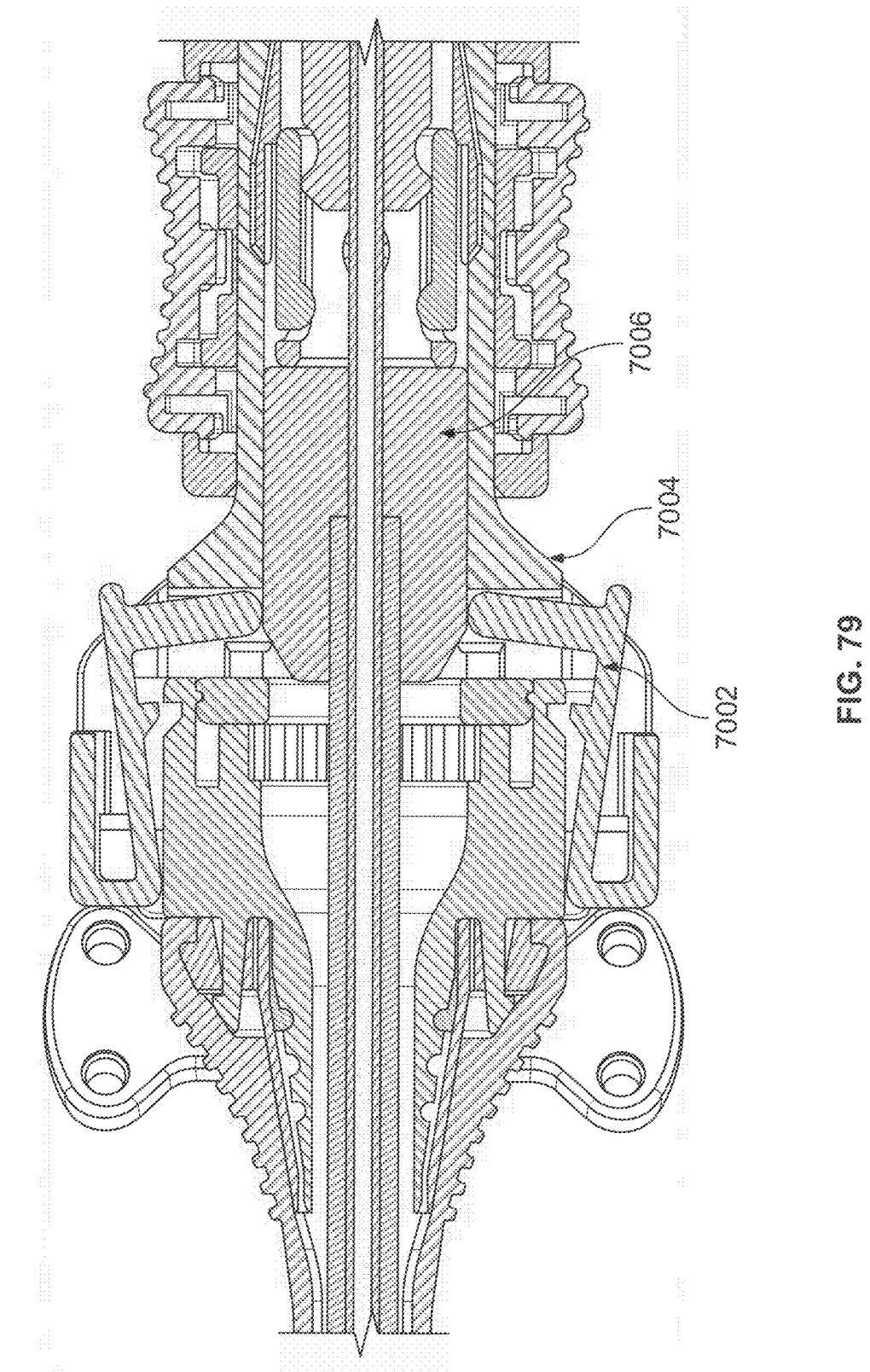
FIG. 79 shows a cross-section of an illustrative sheath delivery system in a fourth position.

FIG. 79 shows the delivery system in a fifth position where the outer dilator hub 7006 has been moved to its most forward location and has made contacts with features on the snap ring 7002 that causes the arms to flex and features on the inner surface to no longer constrain the sheath hub.

Figure 80:
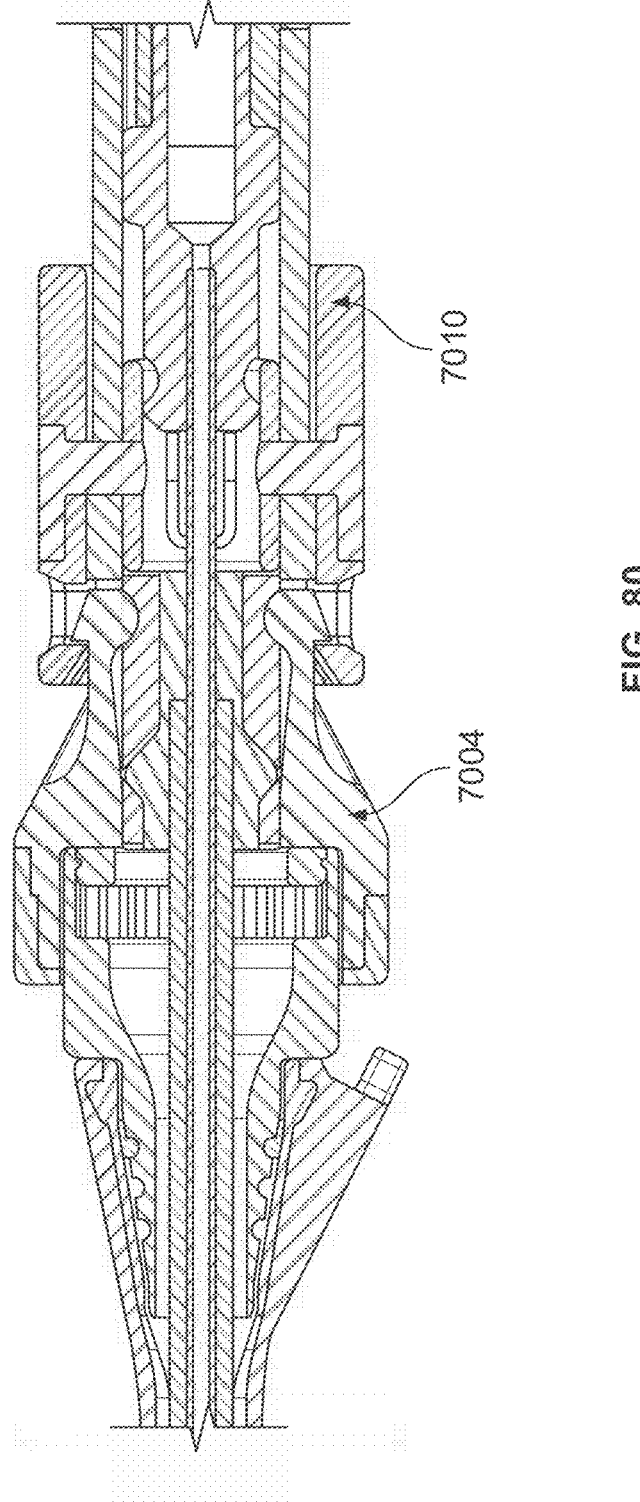
FIG. 80 shows a cross-section of an illustrative sheath delivery system in a fourth position.
Figure 81:
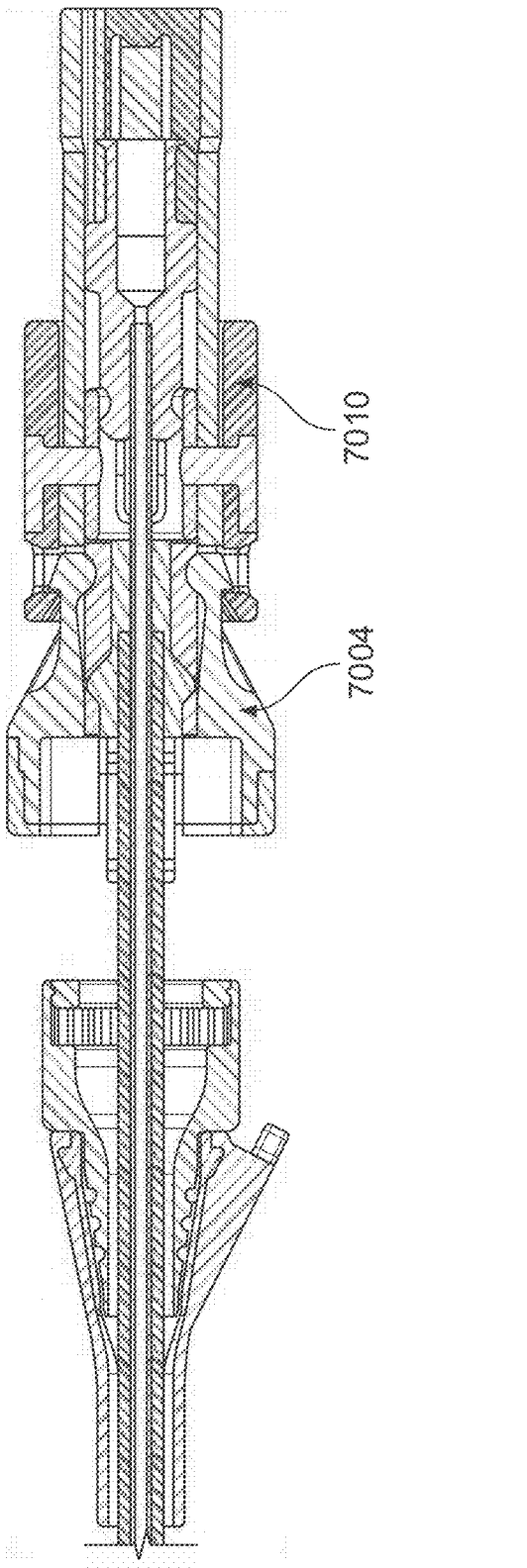
FIG. 81 shows a cross-section of an illustrative sheath delivery system in a fifth position.

FIG. 80 shows a vertical cross-section including the final position of the slider 7010 where latches on the handle 7004 engage an opening on the slider 7010, preventing further movement in either direction. FIG. 81 shows the retraction of the delivery system in the proximal direction from the expandable sheath hub.

Figure 82:
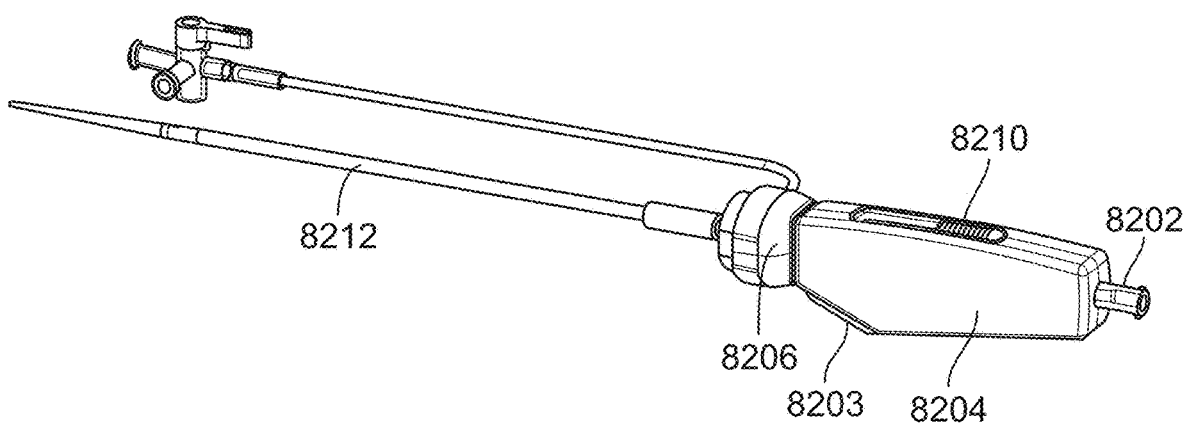
FIG. 82 shows an isometric view of an illustrative sheath delivery system.

FIG. 82 shows an isometric view of an illustrative delivery mechanism 8200 comprising sheath 8202, hub 8204, hub housing 8206, trigger 8208, slider 8210, and outer dilator 8212. Delivery mechanism 8200 may be any one of system 6000 of FIG. 60, system 6100 of FIG. 61, system 6200 of FIG. 62, or Figure system 6300 of FIG. 63. Delivery mechanism 8200 is configured to insert sheath 8202 (e.g., expandable sheath 200 of FIG. 2 or sheath 2200 of FIGS. 22A-22B) into the vasculature of a patient by means of a series of dilators and respective hubs, namely an inner dilator (not shown) and outer dilator 8212. Such implementations having dilator hubs differ from previously discussed implementations having a dilator tip interlock used to adjust the relative motion of the dilators. Hub 8204 and hub housing 8206 contain elements that are configured to adjust the relative positions of sheath 8202 and the series of dilators, including outer dilator 8212. The dilators are configured to extend from a distal end of hub 8204. Hub housing 8206 extends in a proximal direction from hub 8204. Hub housing 8206 is affixed to trigger 8208 and slider 8210. Trigger 8208 is configured to be depressed, and trigger 8208 is connected to hub housing 8206 at the distal end of trigger 8208. When trigger 8208 is depressed, it rotates about the point at which it is connected to hub housing 8206. In the illustrative state shown in FIG. 82, trigger 8208 is depressed, such that the proximal end of trigger 8208 is in contact with a proximal portion of hub housing 8206. The depression of trigger 8208 draws down sheath 8202 prior to the insertion of sheath 8202 into a patient. Slider 8210 is configured to adjust the relative positions of the dilators and sheath 8202. FIG. 82 shows a state in which sheath 8202 is attached to the distal end of the hub 8204. The combination of these elements advantageously ensure that the sheath is drawn down prior to the insertion of the sheath into the patient, preventing the possibility that the operator of the device forgets to draw down the sheath prior to attempting to insert the device into the vasculature of the patient. Additionally, these elements, as described below in relation to FIGS. 83A-92, advantageously prevent the accidental deployment of the sheath during preparation for insertion.

Figure 83A:
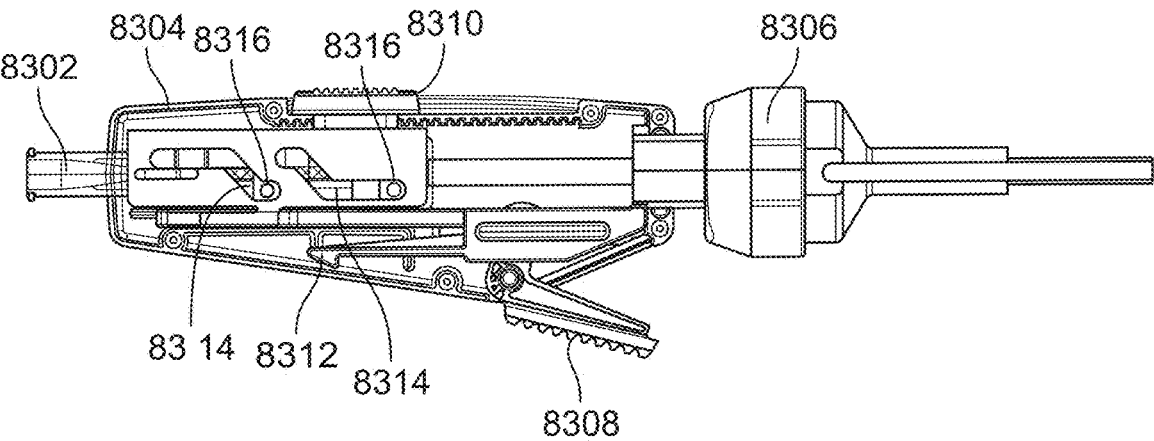
FIG. 83A shows a cross-sectional view of an illustrative sheath delivery system in a first position.
Figure 83B:
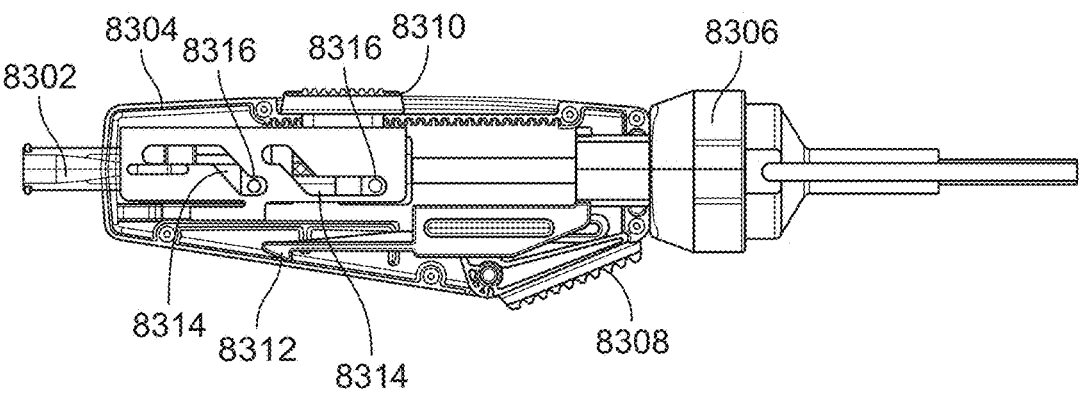
FIG. 83B shows a cross-sectional view of an illustrative sheath delivery system in a second position.

FIGS. 83A and 83B show two illustrative cross-sectional views of an illustrative delivery mechanism 8300 for an expandable sheath (i.e., sheath 200 of FIG. 2 or sheath 2200 of FIGS. 22A-22B). FIG. 83A shows a cross-sectional view of an illustrative delivery mechanism 8300 comprising sheath 8302, hub 8304, hub housing 8306, trigger 8308, slider 8310, clip 8312, slider slots 8314, and pins 8316. Illustrative delivery mechanism 8300 may, for example, be delivery mechanism 8200 of FIG. 82. In FIG. 83A, delivery mechanism 8300 is shown in a first state. In this first state, trigger 8308 is undepressed. Further, in this state, sheath 8302 is in a free state, hub 8304 is locked to hub housing 8306 and slider 8310 is locked in position. As described further below in relation to FIGS. 88-93B, the motion of slider 8310 is configured to direct pins 8316 through slider slots 8314. Each of pins 8316 is affixed to a dilator hub (an inner dilator hub and an outer dilator hub). When slider 1310 is moved in a distal direction, the forces exerted on pins 8316 by slider slots 8314 cause pins 8316, and thus the respective dilator hubs to which each of pins 8316 is connected (described below in relation to FIGS. 84A-85B), to move relative to each other. The relative motion of the dilator hubs in turn causes relative motion of the inner and outer dilators. This simplifies the motion that is required relative motion between the two dilators, as the entirety of the desired motion is attained upon the sliding of slider 8310.

Figure 84A:
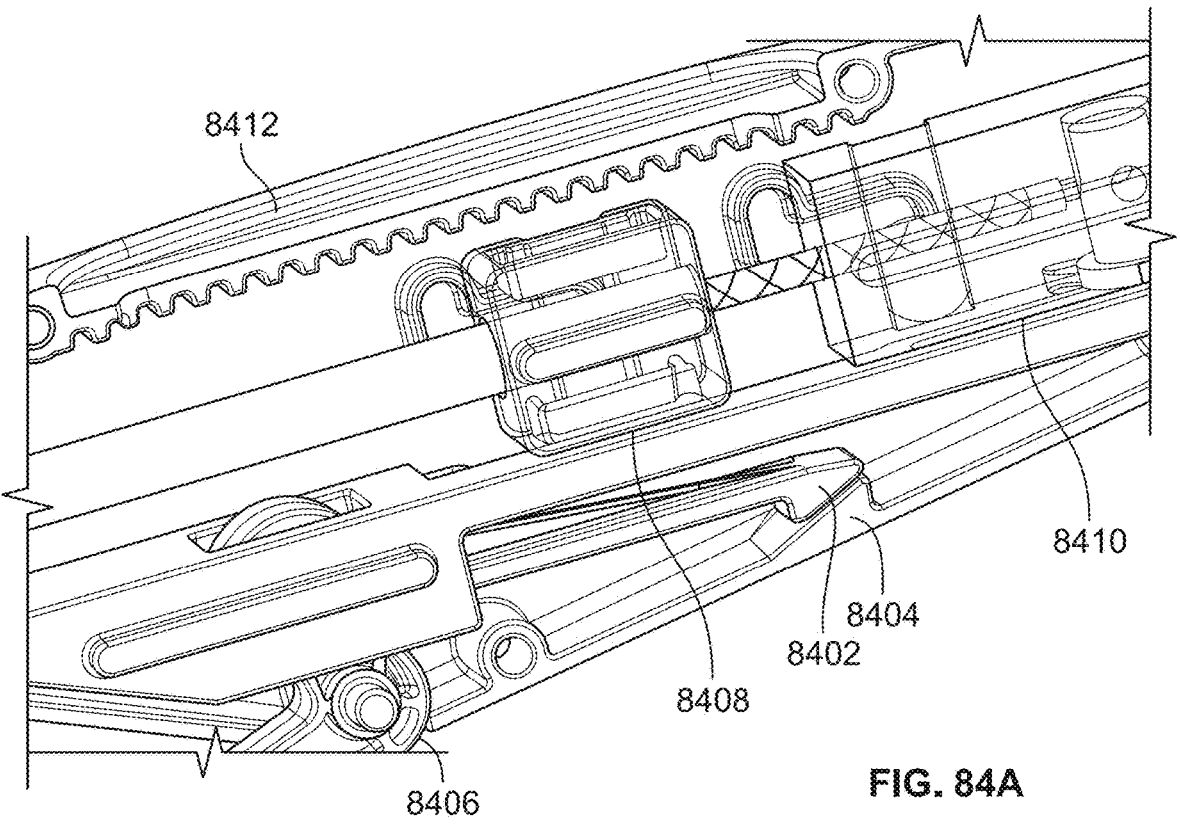
FIG. 84A shows a cross-sectional view of an illustrative sheath delivery system.

FIG. 84A shows an illustrative cross-sectional view of an illustrative delivery mechanism 8400 for the insertion of an expandable sheath having an inner dilator hub and an outer dilator hub wherein the system is in the first state described above in relation to FIG. 83A. Illustrative delivery mechanism 8400 may be, for example, one of illustrative delivery mechanism 8200 of FIG. 82 or illustrative delivery mechanism 8300 of FIG. 83. Illustrative delivery mechanism 8400 comprises clip 8402, housing lock 8404, trigger 8406, outer dilator hub 8408, inner dilator hub 8410, and hub housing 8412. As previously discussed in relation to FIG. 83B, outer dilator hub 8408 and inner dilator hub 8410 are each connected to pins within the hub housing (e.g., pins 8316 of FIG. 83B). Clip 8402 is configured to engage housing lock 8404 when hub housing 8412 is moved in a proximal direction as the device is moved from the first state to the second state. Depression of trigger 8406 while the system is in the first state causes hub housing 8412 to move in a proximal direction. The depression of trigger 8406 and the relative motion of the dilators attained by the motion of the slider (not shown) simplifies the burden of the practitioner to position the dilators correctly relative to one another, while simultaneously preventing the device from being inserted into the patient prior to the sheath being drawn down. This in turn prevents undue injury unto the patient during the insertion of an expandable sheath or other device into the vasculature of the patient.

FIG. 83B shows a cross-sectional view of illustrative delivery mechanism 8300 comprising sheath 8302, hub 8304, hub housing 8306, trigger 8308, slider 8310, clip 8312, slider slots 8314, and pins 8316 in a second state. In this second state, trigger 8308 is depressed, and, correspondingly, sheath 8202 is drawn down. Depression of trigger 8308 causes hub housing 8306 to move in the proximal direction. As shown in FIG. 83, the center of rotation about which trigger 8308 rotates is below the point of contact between trigger 8308 and the proximal surface of hub housing 8306. When trigger 8308 is depressed, the proximal end of trigger 8308 pushes against a proximal surface of hub housing 8308.

Figure 84B:
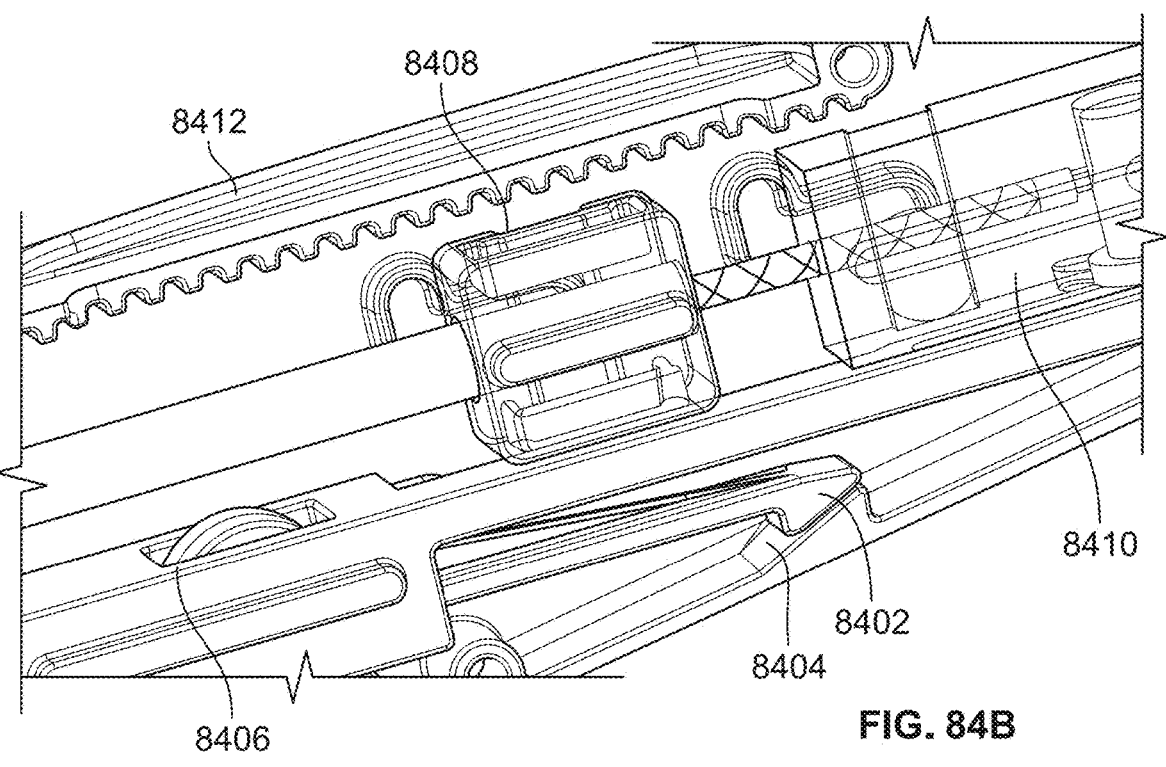
FIG. 84B shows a cross-sectional view of an illustrative sheath delivery system.

FIG. 84B shows an illustrative cross-sectional view of an illustrative delivery mechanism 8400 for the insertion of an expandable sheath having an inner dilator hub and an outer dilator hub wherein the system is in the second state described above in relation to FIG. 83B. FIG. 84B shows illustrative delivery mechanism 8400 wherein trigger 8406 has been depressed and hub housing 8412 has moved in a proximal direction. The proximal motion of hub housing 8412 causes the pins attached to outer dilator hub 8408 and inner dilator hub 8408 to move, causing relative motion between outer dilator hub 8408 and inner dilator 8410. Additionally, the proximal motion of hub housing 8412 causes clip 8402 to engage housing lock 8404. The engaging of housing lock 8404 by housing 8412 advantageously keeps the sheath drawn down after the operator of the delivery mechanism depresses the trigger.

Figure 85A:
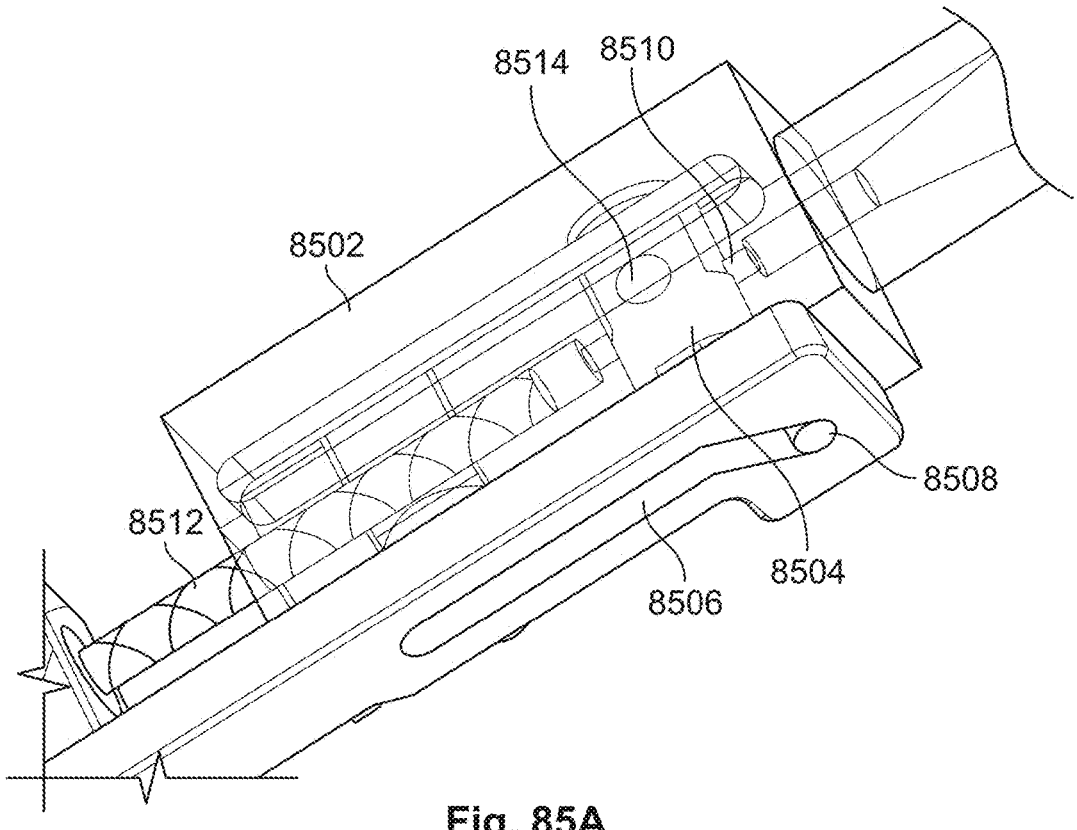
FIG. 85A shows a view of an illustrative luer-blocking mechanism.
Figure 85B:
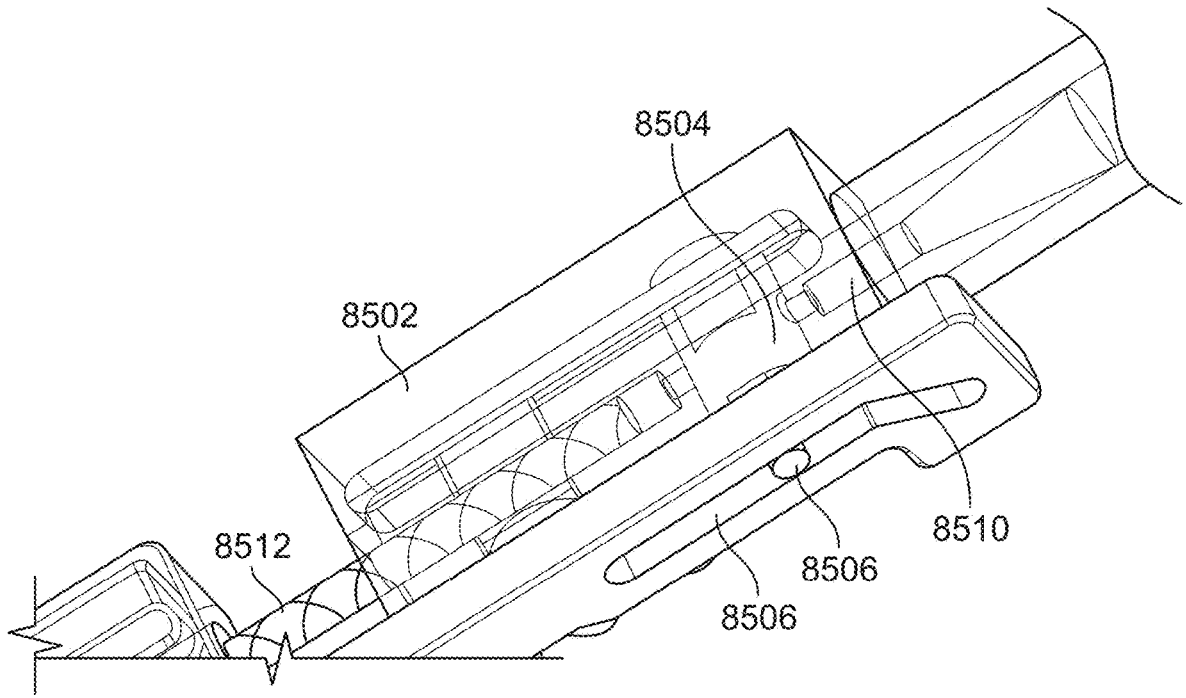
FIG. 85B shows a second view of a luer-blocking mechanism.

FIGS. 85A and 85B show two illustrative views of an illustrative delivery mechanism for the insertion of an expandable sheath wherein the inner dilator hub contains a luer blocker. FIG. 85A shows an illustrative luer-blocking mechanism comprising inner dilator hub 8502, luer blocker 8504, housing cam slot 8506, luer blocker camshaft 8508, inner dilator 8510, and outer dilator 8512. Inner dilator hub 8502 contains luer blocker 8504. Luer blocker 8504 comprises luer slot 8514 and luer blocker camshaft 8508 which extends into housing cam slot 8506. Luer blocker 8504 is shown in a first state in FIG. 85A, in which luer blocker camshaft 8508 is disposed at the proximal end of housing cam slot 8506. In this first state of luer blocker 8504, luer slot 8514 is not aligned with an axis of the dilators. As a result, in the first state of luer blocker 8504, it is not possible to insert a guidewire through the device. As shown in FIG. 85B, in a second state, luer blocker camshaft 8508 is moved in the distal direction. Movement of luer blocker camshaft 8508 in the distal direction within housing cam slot 8506 from the first state to the second state causes a quarter rotation of luer blocker 8504. The quarter rotation of luer blocker 8504 causes luer slot 8514 to align with an axis of the dilators, allowing the insertion of a guidewire through the mechanism. Luer blocker 8504 and luer slot 8514 thus together advantageously prevents the accidental passage of a guidewire through the device prior to the sheath being drawn down. This is beneficial to the patient, as insertion of the guidewire through the device prior to the sheath being drawn down reduces the benefits of inserting the sheath at a low profile. As such, the guidewire is inserted once the sheath is drawn down, leading to lower rates of vascular injury and damage, lower required insertion forces, and less necessary predilation.

Figure 86A:
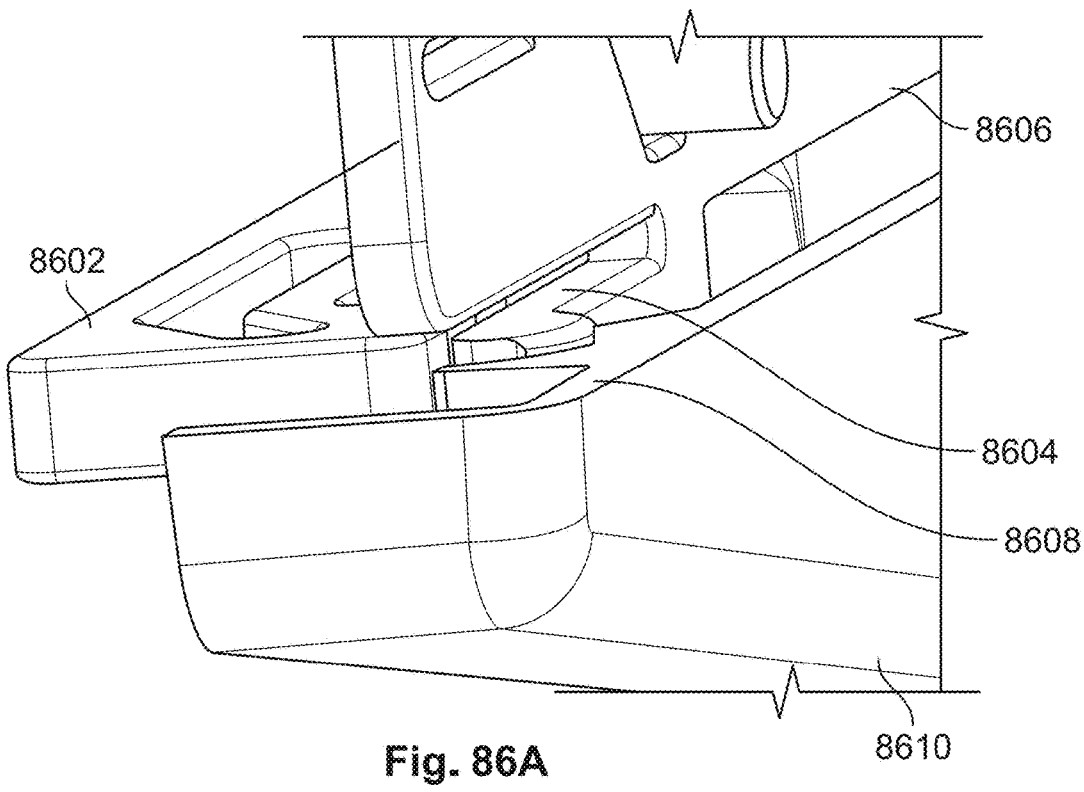
FIG. 86A shows a first cross-sectional view of the hub housing of an illustrative sheath delivery system.

FIGS. 86A-8D show illustrative cross-sectional views of the hub housing of an illustrative delivery system for an expandable sheath, the hub housing containing a locking mechanism on the slider of the hub housing. FIG. 86A shows an illustrative cross-sectional view of the hub housing 8600 of a delivery mechanism for the insertion of an expandable sheath. For example, section view of the hub housing 8600 may show a section view of hub housing 8206 of FIG. 82, hub housing 8306 of FIG. 83, hub housing 8412 of FIG. 84. Hub housing 8600 comprises hub housing component 8602, slider locking feature 8604, slider 8606, sectioned plane 8608, and housing side 8610. In the illustrative example shown, housing side 8610 is the right side of the housing when viewed from the proximal direction. Slider locking feature 8604 can, for example, be seen below slider 8310 of FIG. 83A. In general, the delivery mechanism may be constructed such that slider locking feature 8604 is disposed on either the left side or the right side of the delivery mechanism when viewed from the distal direction. In other words, the delivery mechanism may be constructed as a mirror image of the illustrative implementations discussed herein. Slider locking feature 8604 engages with a portion of hub housing 8600. In the first state of slider 8606, as discussed previously in relation to FIG. 83A, slider locking feature 8604 of slider 8606 is trapped by the portion of the hub housing 8600 and is unable to move. Additionally, FIG. 86A shows hub housing component 8602 in abutment with slider 8606. As previously discussed in relation to FIGS. 83B and 84A, hub housing component 8602 is configured to move in the proximal direction upon depression of the trigger of the delivery system. The proximal motion of hub housing component 8602 allows slider locking feature 8604 to move. This advantageously prevents the motion of the slider prior to the sheath being drawn down.

Figure 86B:
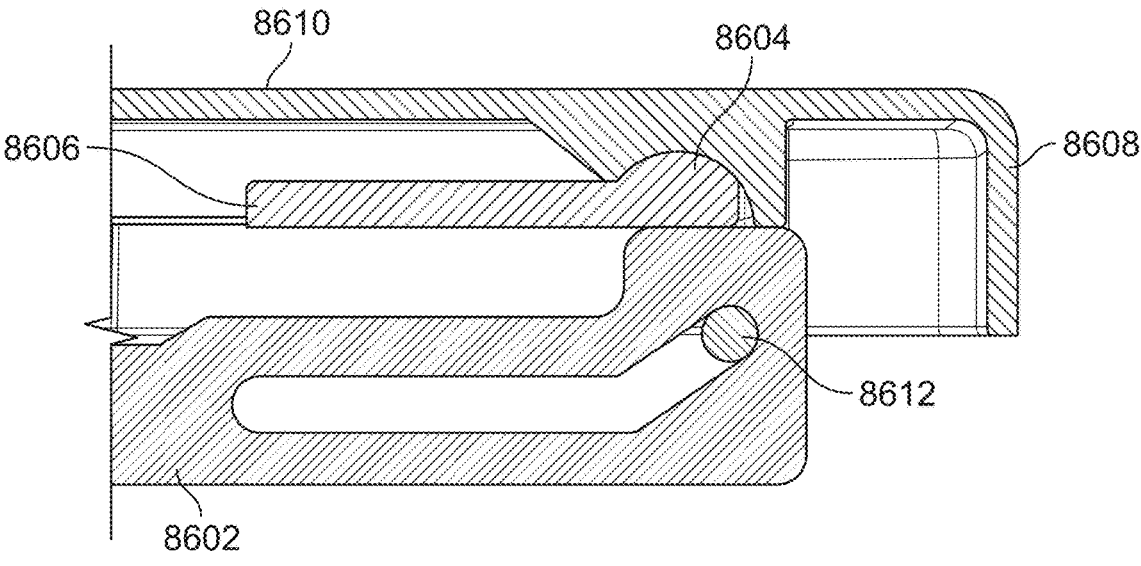
FIG. 86B shows a first aerial cross-sectional view of the hub housing of an illustrative sheath delivery system.

FIG. 86B shows an illustrative top view of the cross-sectional view of hub housing 8600 of a delivery mechanism for the insertion of an expandable sheath shown in FIG. 86A. Hub housing 8600 comprises hub housing component 8602, slider locking feature 8604, slider 8606, sectioned plane 8608, housing side 8610, and hub housing pin 8612. The movement of hub housing component 8602 in the proximal direction is constrained such that hub housing pin 8612 slides through the gap in hub housing component 8602.

Figure 86C:
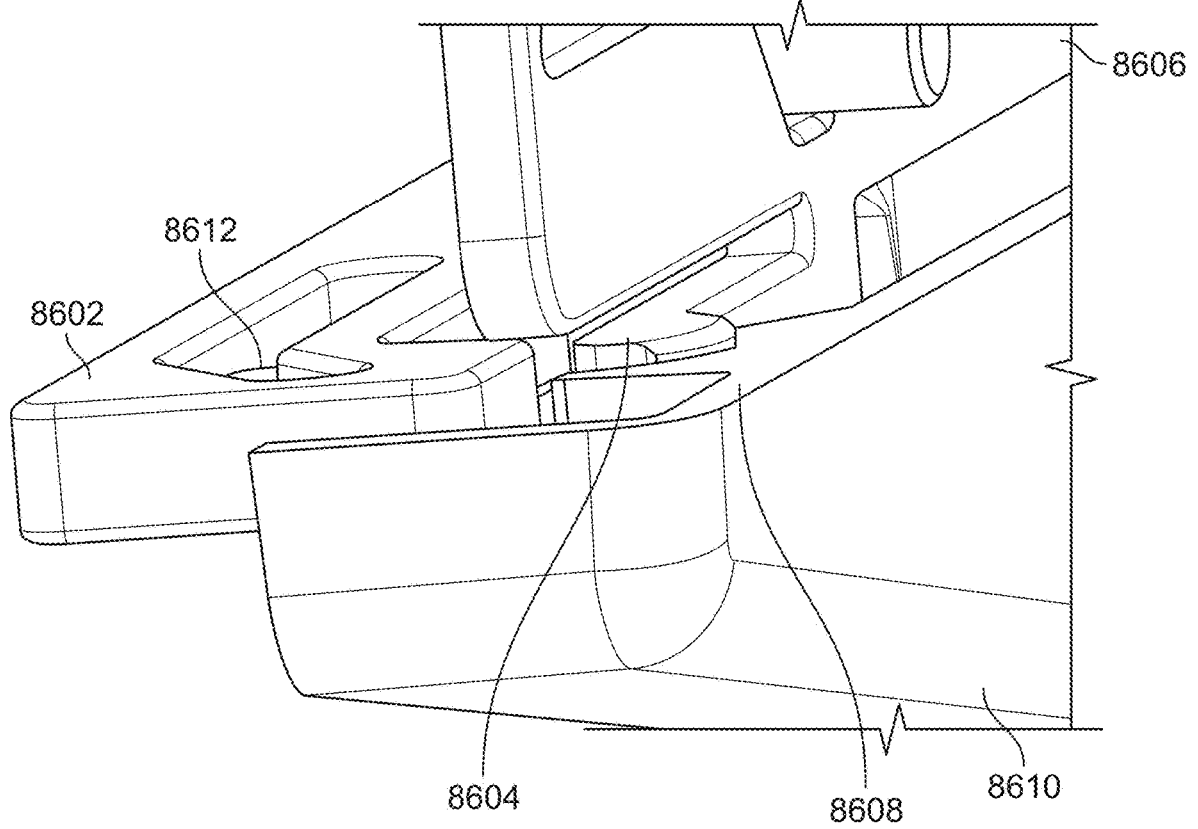
FIG. 86C shows second a cross-sectional view of the hub housing of an illustrative sheath delivery system.

FIGS. 86C and 86D show an illustrative cross-sectional view and an illustrative aerial cross-sectional view, respectively, of the hub housing 8600 of a delivery mechanism for the insertion of an expandable sheath. For example, section view of the hub housing 8600 may show a section view of hub housing 8206 of FIG. 82, hub housing 8306 of FIG. 83, hub housing 8412 of FIG. 84. Hub housing 8600 comprises hub housing component 8602, slider locking feature 8604, slider 8606, sectioned plane 8608, housing side 8610, and pump housing pin 8612. The movement of hub housing component 8602 in the proximal direction eliminates the abutment of hub housing component 8602 with slider 8606. Housing component 8602 thus slides in the proximal direction towards the gap formed in housing side 8610. The proximal motion of housing component 8602 thus enables slider locking feature 8604 to be released and allows the motion of the slider, and thus the adjustment of the relative position of the two dilators, after the trigger is depressed and the sheath is drawn down.

FIG. 88 shows a cross-sectional view of an illustrative delivery mechanism 8800 for the introduction of an expandable sheath in a state wherein the inner and outer dilator hubs are positioned to release an expandable sheath. Delivery mechanism 8800 comprises sheath 8802, hub 8804, hub housing 8806, trigger 8808, slider 8810, clip 8812, slider slots 8814, and pins 8816. Illustrative delivery mechanism 8800 may, for example, be delivery mechanism 8200 of FIG. 82. In FIG. 88, delivery mechanism 8800 is shown in a third state. In this third state, trigger 8808 is depressed, hub housing 8806 has moved in a proximal direction relative to the first state (as described above), and slider 8810 has moved in the distal direction. Movement in the distal direction of slider 8810 causes relative motion of the inner and outer dilators, as slider slots 8814 guide pins 8816 through slider slots 8814 as hub housing 8806 moves in a proximal direction. The relative geometries of slider slits 8814 can be configured to adjust the relative motion between the inner and the outer dilators. In certain implementations, the inner dilator moves forward by an amount, as discussed previously in relation to FIG. 89, while the outer dilator remains stationary relative to hub housing 8806. The relative motion between the two dilator hubs allows the sheath to be released from between the inner dilator hub and the outer dilator hub. As such, the inner dilator hub and outer dilator hub can be withdrawn in order to remove the delivery system mechanism. In some implementations, the inner dilator moves forward by between about 2 millimeters and about 10 millimeters. In certain implementations, the inner dilator moves forward by between about 4 millimeters and about 8 millimeters. In further implementations, the inner dilator moves forward by about 6 millimeters. The relative motion of the inner and the outer dilators can be adjusted based on the respective lengths of the dilators.

Figure 90:
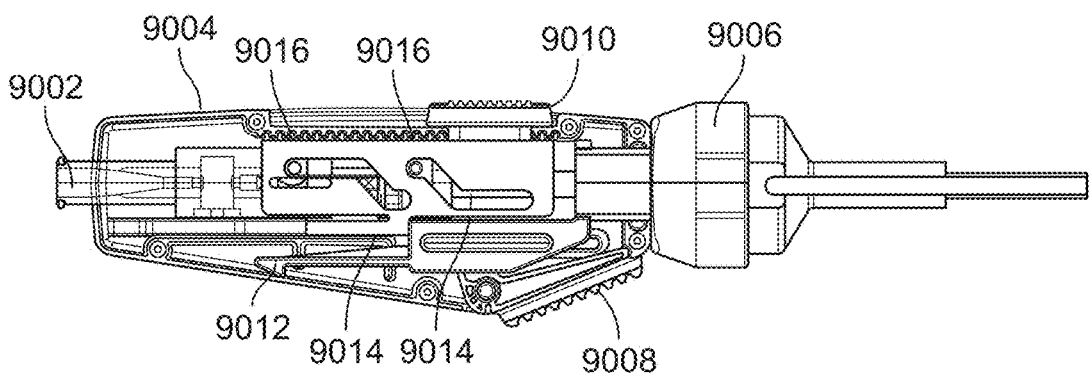
FIG. 90 shows a cross-sectional view of an illustrative sheath delivery system in a fourth state.

FIG. 90 shows a cross-sectional view of an illustrative delivery mechanism 9000 for the introduction of an expandable sheath in the fourth state wherein the inner and outer dilator hubs are positioned to be withdrawn from the sheath. Delivery mechanism 9000 comprises comprising sheath 9002, hub 9004, hub housing 9006, trigger 9008, slider 9010, clip 9012, slider slots 9014, pins 9016, inner dilator hub 9018, and outer dilator hub 9020. Illustrative delivery mechanism 9000 may, for example, be delivery mechanism 8200 of FIG. 82. In FIG. 88, delivery mechanism 9000 is shown in a fourth state. In this fourth state, trigger 8808 is depressed, slider 8810 has moved as far as possible in the distal direction, and hub housing 9006 has moved in a proximal direction relative to the first state, described above. As discussed, movement in the distal direction of slider 9010 causes relative motion of the inner and outer dilators, as slider slots 9014 guide pins 9016 connected to inner dilator hub 9018 and outer dilator hub 9020 through slider slots 9014 as hub housing 9006 moves in a proximal direction. The relative geometries of slider slits 9014 can be configured to adjust the relative motion between the inner and the outer dilators. Between states 3 and states 4, as discussed in relation to FIG. 88 and FIG. 90, the inner dilator remains stationary, and the sheath is released from being held by the inner dilator hub and the outer dilator hub as the pin 9016 to which inner dilator hub 9018 is attached moves freely through slider slot 9014. However, between FIGS. 88 and 90, outer dilator hub 9020 continues to move in the distal direction due to the fact that pin 9016 to which outer dilator hub 9018 is connected is in contact with the proximal end of its corresponding slider slot 9014. This distal motion of outer dilator hub 9018 brings the tip of the delivery system back to a closed position, as shown, for example, in FIG. 87, allowing the inner dilator hub and the outer dilator hub to be withdrawn while leaving the sheath drawn down.

Figure 91:
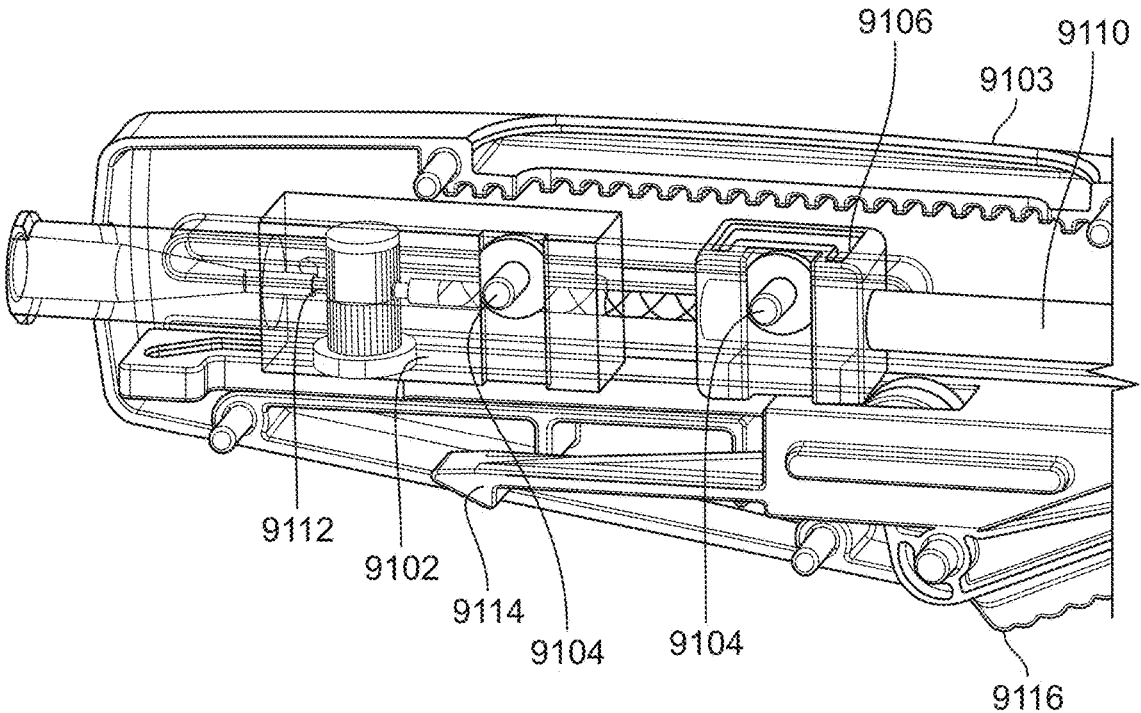
FIG. 91 shows an illustrative cross-sectional view of the hub housing of an illustrative sheath delivery system.

As previously discussed in relation to FIG. 84B, relative motion of the inner and outer dilators is attained by guiding pins attached to each of the inner and outer dilators through slider slots. FIG. 91 shows an illustrative cross-sectional view of hub housing 9100 comprising inner dilator hub 9102, outer dilator hub 9104, inner dilator hub pin 9106, and outer dilator hub 9108. Inner dilator hub pin 9106 and outer dilator hub pin 9108 are configured to slide within the slider slots, as previously discussed, and are also configured to slide up and down within their respective hubs.

Figure 92:
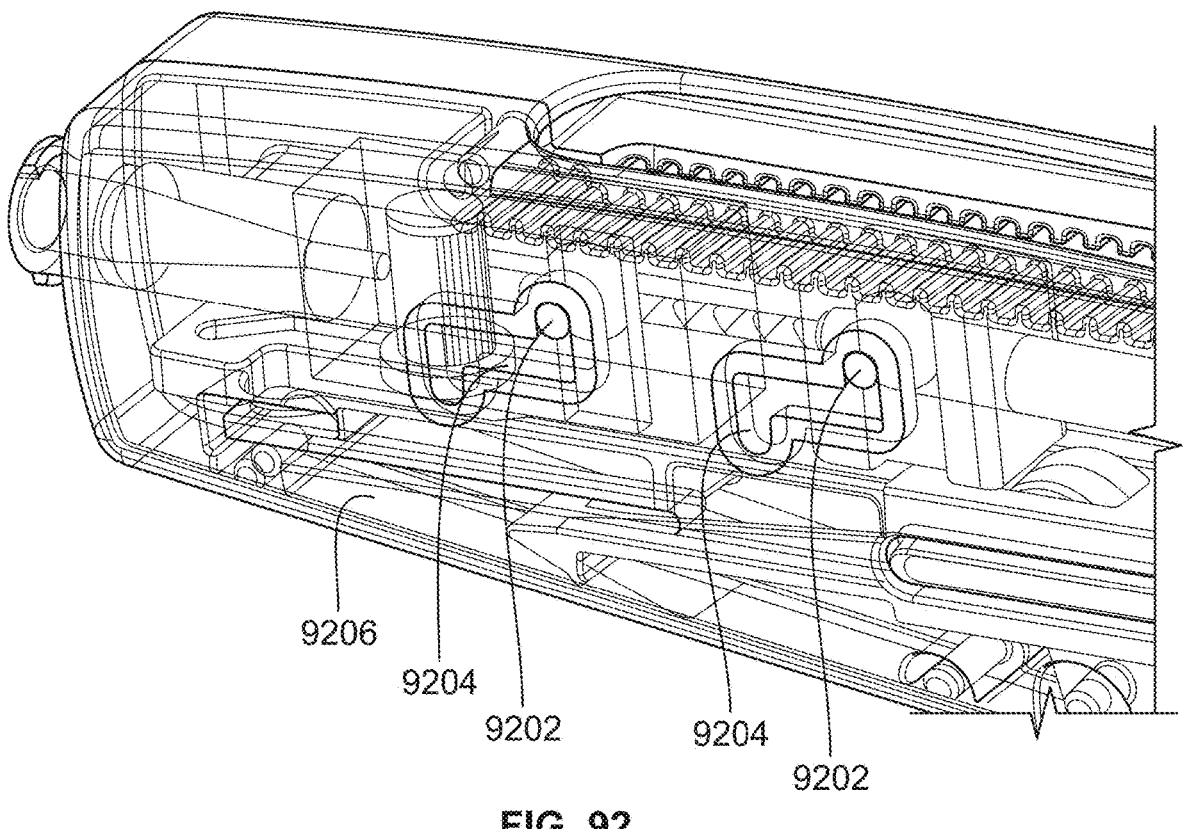
FIG. 92 shows an illustrative internal view of the hub housing of an illustrative sheath delivery system.

FIG. 92 shows an illustrative internal view of the hub housing 9200 of a delivery mechanism for an expandable sheath. Hub housing 9200 houses pins 9202 and slider slots 9204. Movement of the slider (not shown) in the longitudinal direction guides pins 9202 through slider slots 9204. One of pins 9202 is connected to the inner dilator hub, and the other pin is connected to the outer dilator hub. This motion of pins 9202 through slider slots 9204 creates relative motion between the inner and outer dilator hubs, which, in turn, creates relative motion between the inner and outer dilators themselves. Slider slots 9204 may alternatively be disposed within the housing side, as previously discussed in relation to FIGS. 86A-D. The slider slots, the slider, and the channel in the dilator advantageously control the timing, direction, and extent of the movement of the dilators. This facilitates operation of the device for the user, as several specific movements of the components are achieved using a single motion of the slider, ultimately resulting in the release of the sheath tip for the user.

Figure 93A:
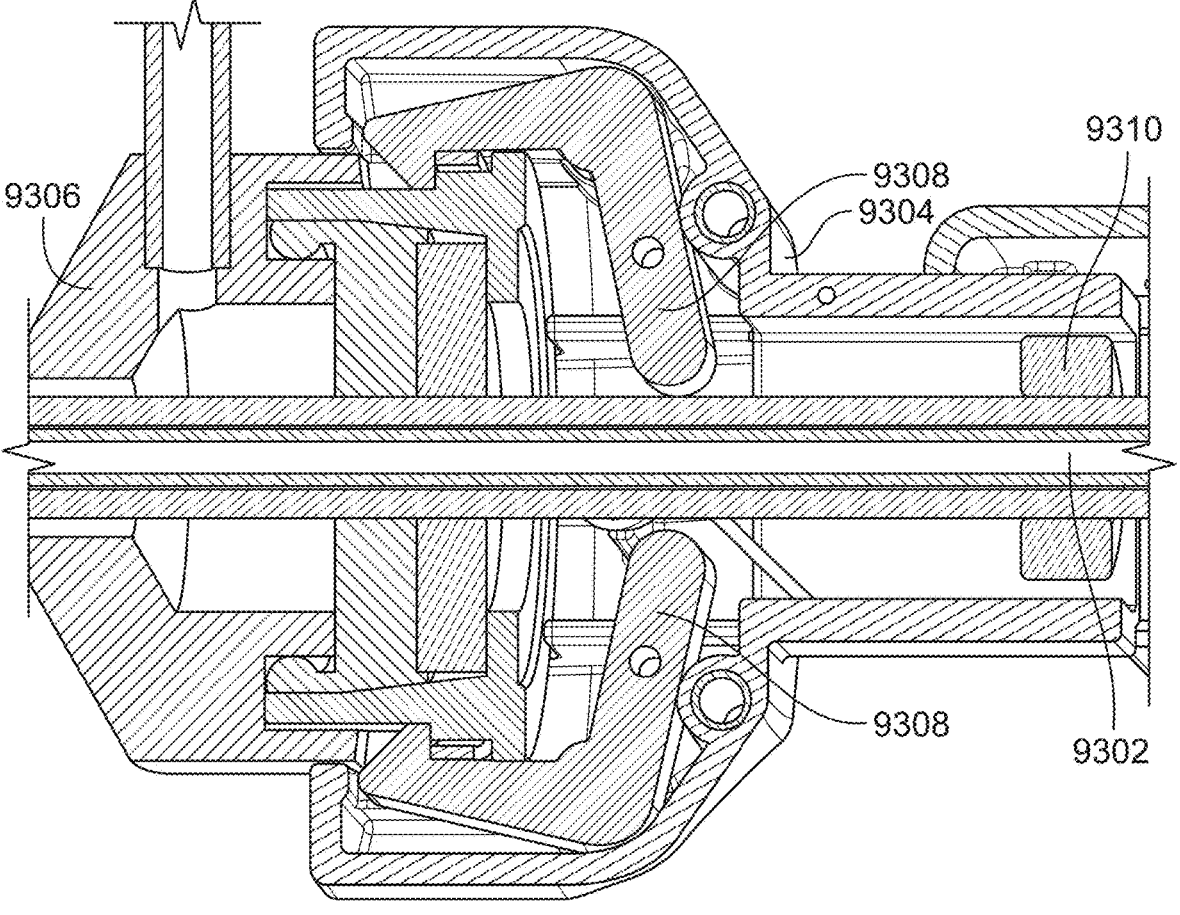
FIG. 93A shows an illustrative cross-sectional view of the hub housing of an illustrative sheath delivery system.
Figure 93B:
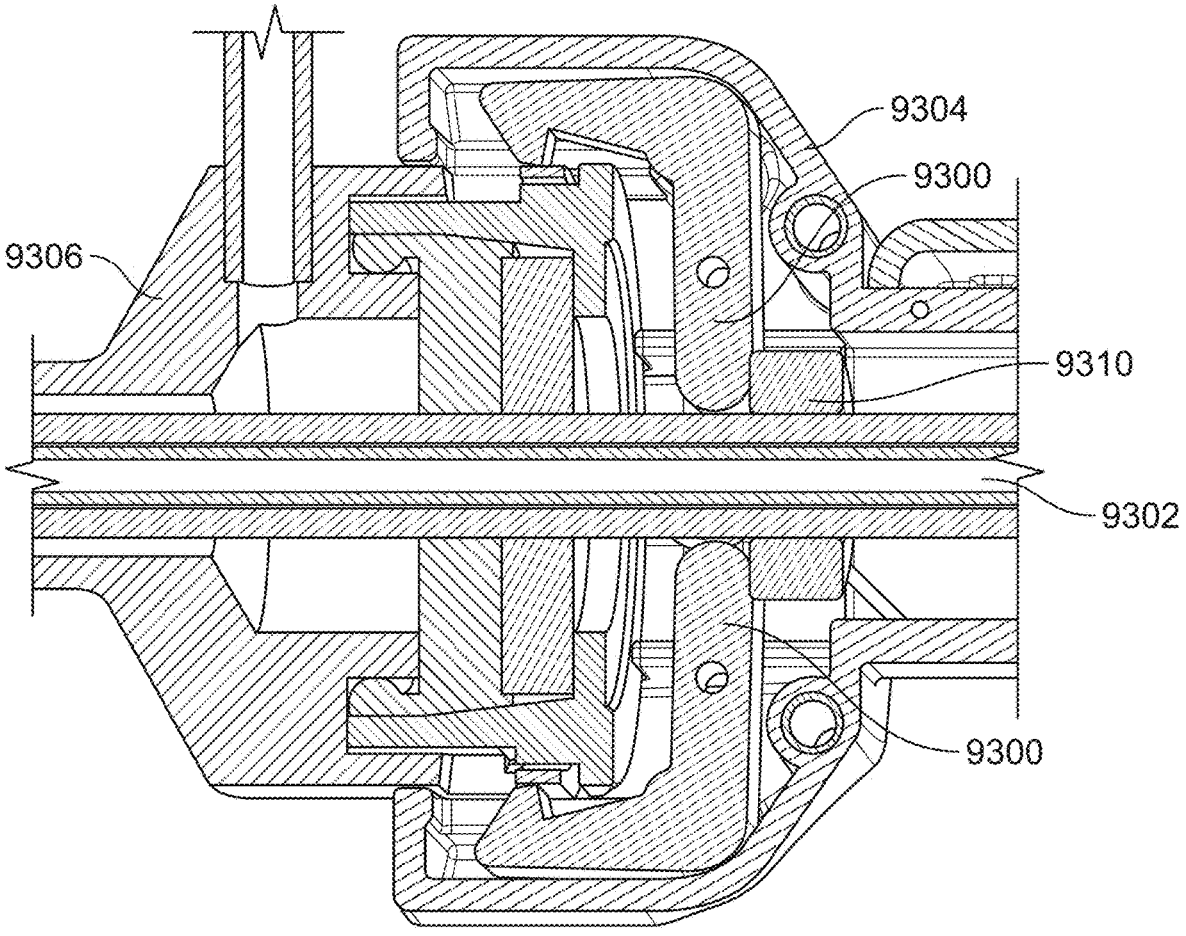
FIG. 93B shows an illustrative cross-sectional view of the hub housing of an illustrative sheath delivery system.

FIGS. 93A and 93B show an illustrative cross-section view of the hub housing of an illustrative delivery mechanism for the insertion of an expandable sheath. FIG. 93A shows the mechanism in the first, second, and third states. FIG. 93B shows the mechanism in the fourth state. FIGS. 93A and 93B FIG. 93A shows an illustrative cross-sectional view of the hub housing 9300, including hub 9302, dilator 9304, clips 9306, and collar 9308. Clips 9306 further comprise securement teeth 9310. Hub housing 9300 is disposed distal of hub 9302. Hub housing 9300 and hub 9302 are configured to receive dilator 9304. In the illustrative implementation showed in FIG. 93, dilator 9304 is an outer dilator. Hub housing 9300 further comprises clips 9306. Clips 9306 secure hub 9302 within hub housing 9300 when the device is in the first state, the second state, and the third state, and discussed previously in relation to FIGS. 83A, 83B, and 88, respectively. Clips 9306 are operated by a spring. Outer dilator 9304 further comprises collar 9308, which, in the first state, the second state, and the third state, is not engaged around outer dilator 9304.

FIG. 93B shows an illustrative cross-sectional view of the hub housing 9300 in the fourth state, as discussed previously in relation to FIG. 90. FIG. 93B includes hub 9302, dilator 9304, clips 9306, collar 9308, and securement teeth 9310. In the fourth state, collar 9308 contacts clips 9306. The contact between clips 9306 and collar 9308 causes clips 9306 to pivot in order to remove securement teeth 9310 from the hub. Removal of the securement teeth 9310 from the hub allows the delivery mechanism to be removed from the hub.

Figure 94A:
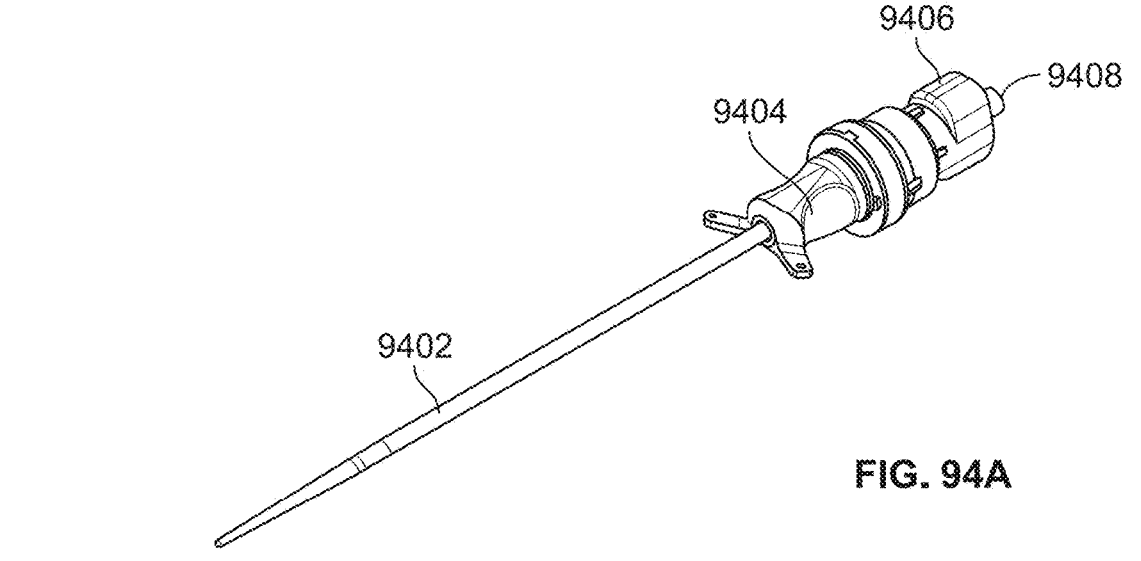
FIG. 94A shows a first isometric view of an illustrative sheath delivery mechanism.
Figure 94B:
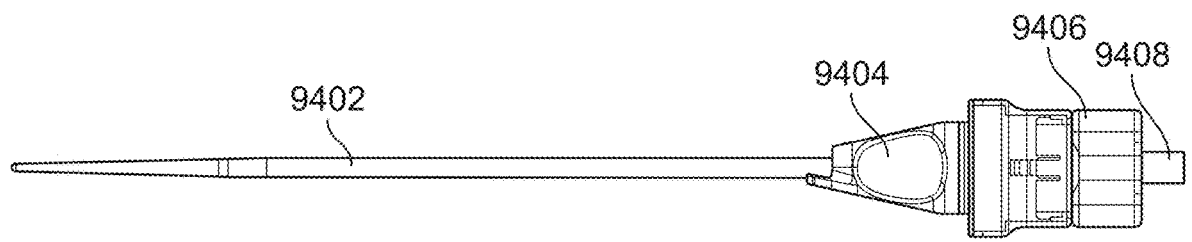
FIG. 94B shows a second isometric view of an illustrative sheath delivery mechanism.
Figure 94C:
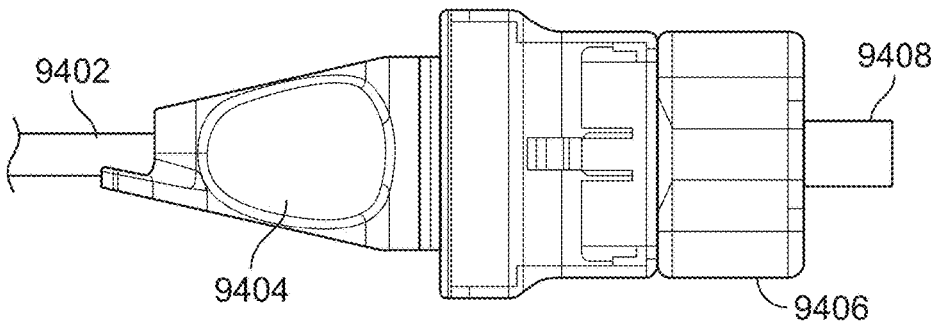
FIG. 94C shows a first isometric view of a hub and a hub housing of an illustrative sheath delivery mechanism.
Figure 94D:
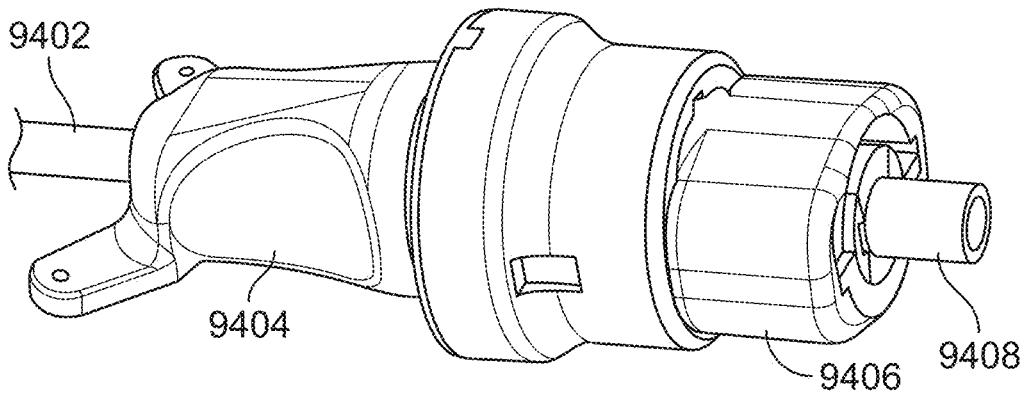
FIG. 94D shows a second isometric view of a hub and a hub housing of an illustrative sheath delivery mechanism.

FIGS. 94A-96C show an alternative embodiment of a delivery mechanism for an expandable sheath. FIG. 94A shows an isometric view of an illustrative delivery mechanism 9400 for an expandable sheath. Delivery mechanism 9400 comprises dilator 9402, hub 9404, hub housing 9406, and keys 9408. FIG. 94B shows delivery mechanism 9400 from a side view. As shown in FIG. 94C, in implementations having the delivery mechanism shown in FIGS. 94A and 94B, the sheath is drawn down into the first state of the device when hub 9404 is pushed into hub housing 9406 in the distal direction. Keys 9408 then snap in place within hub housing 9406 to keep the sheath drawn down. As shown in FIG. 94D, hub housing 9406 is twisted 90 degrees to transition from the second state and third states, in which the tip of the delivery mechanism is deployed, to the fourth state, in which the delivery mechanism can be released from the hub.

Figure 95:
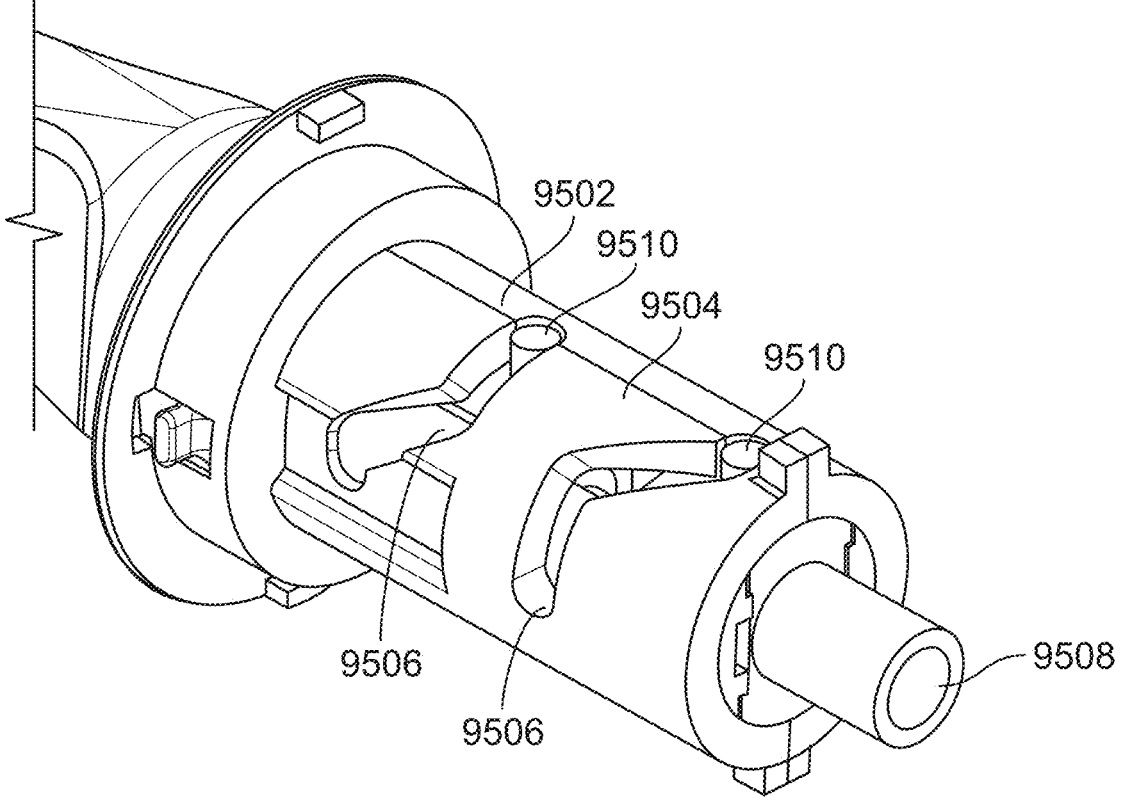
FIG. 95 shows an illustrative barrel of a sheath delivery mechanism.

FIG. 95 shows an illustrative view of the delivery mechanism 9500 comprising hub 9502, barrel 9504, slots 9506, lumen 9508, and pins 9510. Relative motion of the inner and outer dilators along the longitudinal axis of delivery mechanism 9500 is controlled by the interaction between pins 9510 and slots 9506 in barrel 9504. A rigid inner member (not shown) is affixed to the inner dilator and the outer dilator and prevents the dilators from turning as pins 9510 traverse the paths defined by slots 9506 in barrel 9504. This implementation similarly allows for the relative motion of the inner dilator and the outer dilator to be adjusted, while preventing the insertion of the sheath prior to the sheath being drawn down by the proximal motion of hub 9404 into hub housing 9406 by being configured to progress through the first, second, third, and fourth states, as previously discussed in relation to FIGS. 83A, 83B, 88, and 90.

Figure 96A:
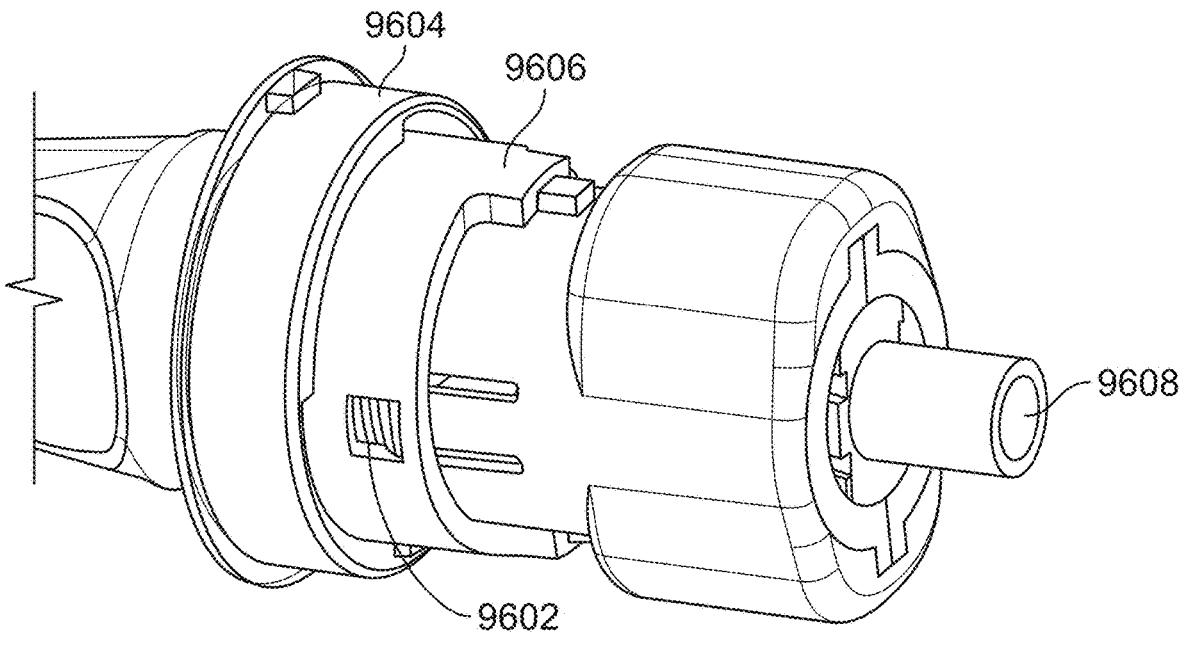
FIG. 96A shows a first isometric view of an illustrative hub release drum of a sheath delivery mechanism.
Figure 96B:
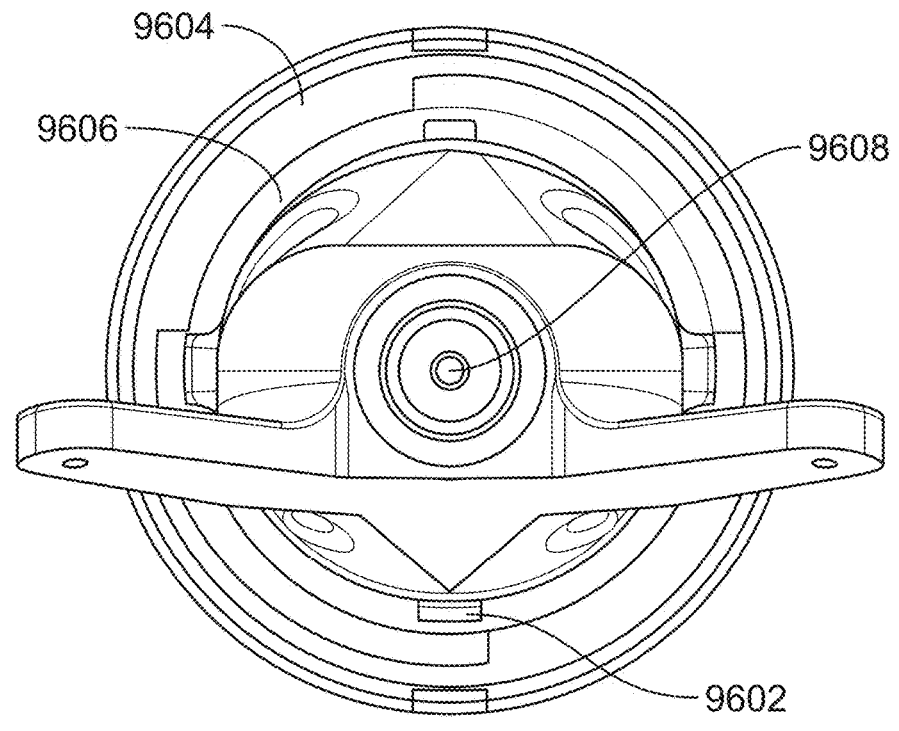
FIG. 96B shows a second isometric view of illustrative hub release drum of a sheath delivery mechanism.
Figure 96C:
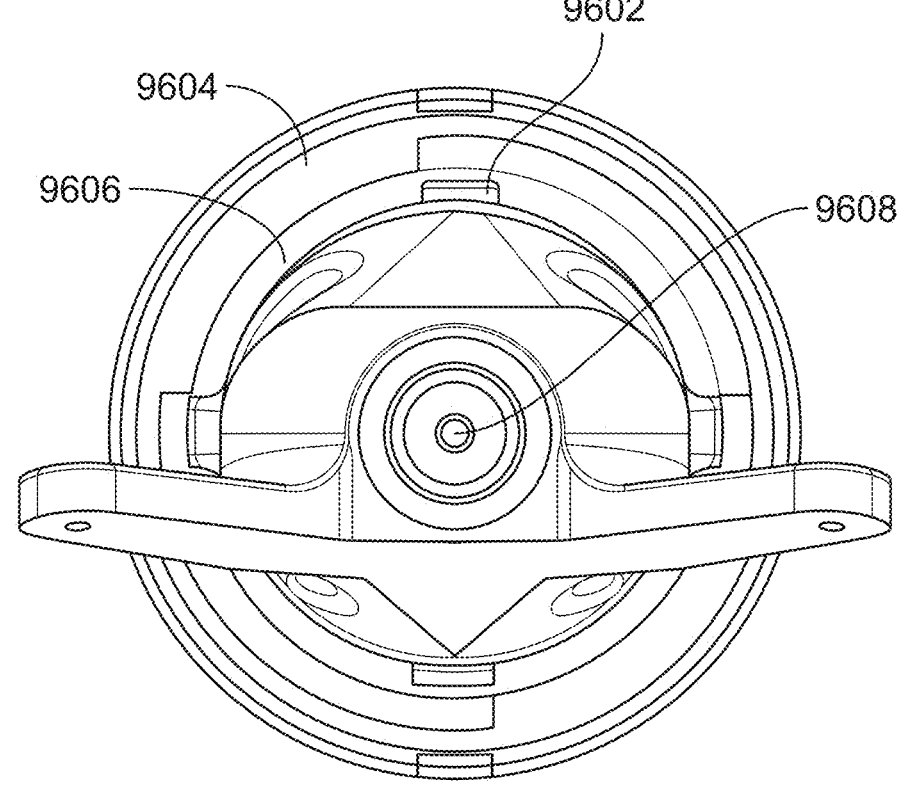
FIG. 96C shows an illustrative hub release drum of a sheath delivery mechanism.

FIGS. 96A-C show an illustrative hub release drum 9600 comprising key 9602, hub 9604, and hub housing 9406. Once the device is drawn down by the pushing of hub 9404 into hub housing 9406, key 9602 interacts with hub release drum 9600 to lock hub 9404 in place with respect to hub release drum 9600. As shown in illustrative FIG. 96B, hub release drum 9600 blocks an outward extending portion of hub 9604, locking hub 9604 in place. Once the device is in the fourth state (i.e., once the device is releasable from hub 9604), hub release drum 9604 aligns with the outward features of hub 9604, allowing the removal of the delivery mechanism from hub 9604.

Figure 46:
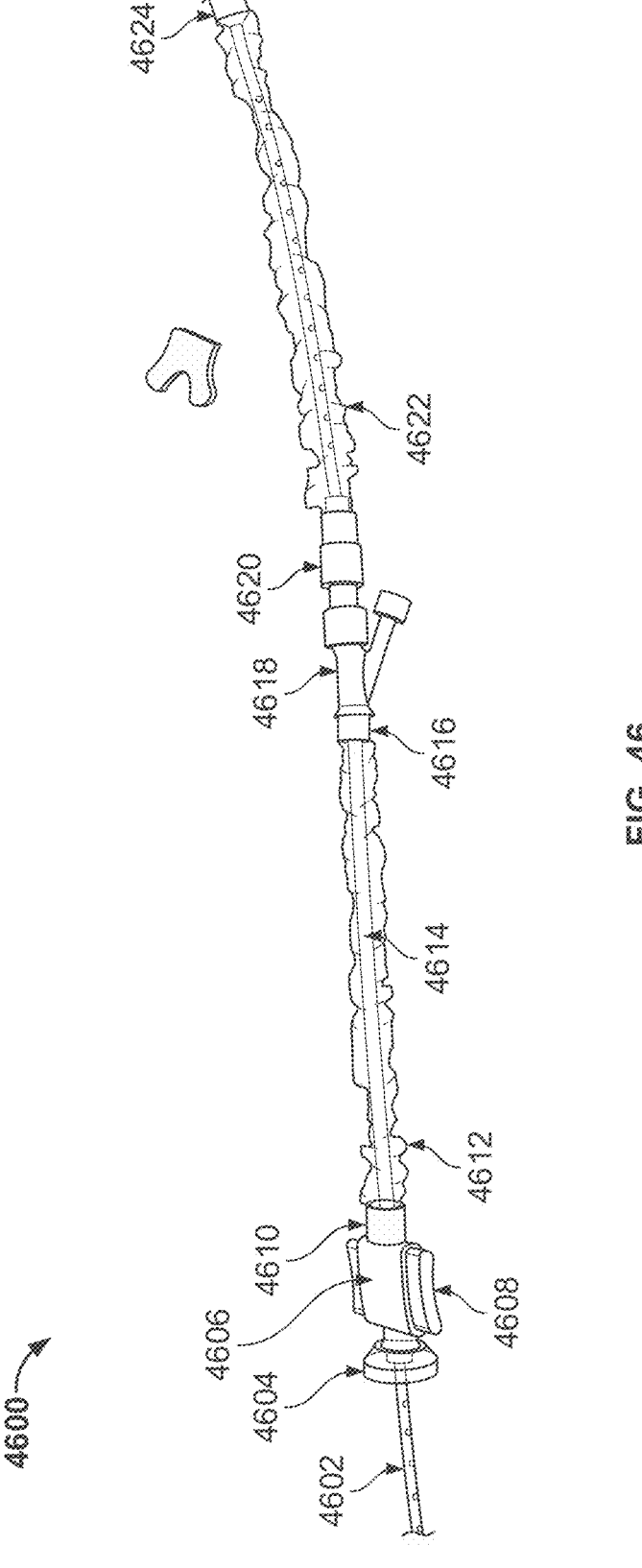
FIG. 46 shows an isometric view of an illustrative hemostasis stylet assembly.

As discussed above in relation to FIG. 1 and sheath assembly 100, and in relation to FIGS. 20-25, the expandable sheath 200 is used in combination with a dilator assembly 2000 to expand the opening of the blood vessel of a patient, and once the dilator assembly 2000 is removed from the expandable sheath 200, the expandable sheath 200 can be used in combination with a hemostasis stylet. A hemostasis stylet assembly can be used to regulate hemostasis between the opening of the blood vessel and the expandable sheath body 202. In some implementations, the hemostasis stylet can be a repositioning sheath, which is also used to control of the blood flow along the expandable sheath and minimize bleeding. A method of regulating hemostasis between the opening of the blood vessel and the expandable sheath body 202 using a hemostasis stylet assembly is described above in relation to FIG. 19. FIG. 1B shows a sheath assembly including an introducer sheath 200 (as described in FIG. 2) connected to the hemostasis stylet assembly 4600 (as described in FIG. 46). FIG. 46 shows a hemostasis stylet assembly 4600 with a catheter 4602 of a pump. The hemostasis stylet assembly 4600 consists of a locking cap 4604, locking hub body 4606 with a set of actuators, e.g. opposing buttons 4608. When the buttons 4608 are compressed inward, the locking hub body 4606 and attached components slide freely on the catheter 4602. When the buttons 4608 are left free, the locking hub body 4606 and attached components are fixed on the catheter 4602. The proximal end of the locking hub body 4606 is connected to an attachment component 4610 of a first sterile layer 4612.

The first sterile layer 4612 is defined by an inner diameter and outer diameter defining a thin layer with a proximal end and a distal end. The hemostasis stylet body 4614 resides within the first sterile layer 4612 and is defined by an outer diameter, inner diameter, and distal and proximal end. The inner diameter of the hemostasis stylet body 4614 aligns axially and clears the catheter 4602. The first sterile layer 4612 is connected to the distal end 4616 of the hemostasis stylet hub 4618. The hemostasis stylet body 4614 is also connected to the distal end 4616 of the hemostasis stylet hub 4618. The hemostasis stylet hub 4618 contains an internal lumen connecting the distal portion in communication with the lumen of the hemostasis stylet body 4614 and proximally with an internal seal component that seals on the outer diameter of the catheter 4602. The hemostasis stylet can slide along the catheter 4602. The proximal portion of the hemostasis stylet hub 4618 is connected to an attachment component 4620 of a second sterile layer 4622. The catheter 4602 is visibly within the second sterile layer 4622. The proximal portion of the second sterile layer 4624 may be attached to another component. In some implementations, the first sterile layer 4612 and second sterile layer 4624 can be sterile sleeves that protect catheter 4602.

Figure 47:
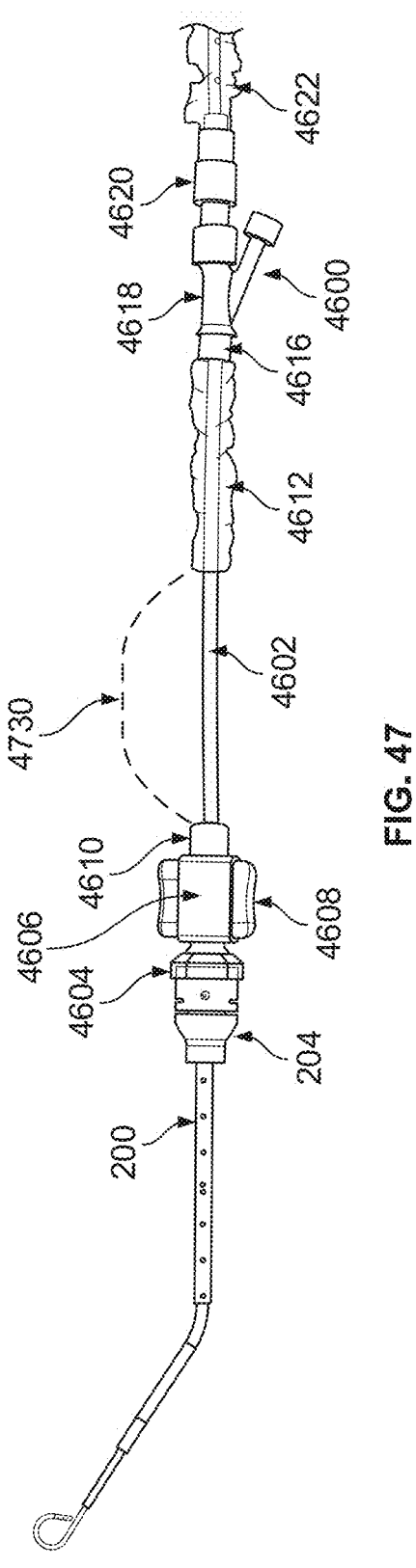
FIG. 47 shows an isometric view of an illustrative hemostasis stylet assembly.

FIG. 47 shows the hemostasis stylet assembly 4600 (as described in FIG. 46) and an introducer sheath 200 (as described in FIG. 2). Also shown in FIG. 47 is a pump after insertion through the introducer sheath 200. In some implementations, the pump and the introducer sheath can be assembled and packaged together prior to insertion in the body of a patient. In FIG. 47, the hemostasis stylet assembly 4600 is not attached to the introducer sheath 200. As shown in FIG. 47, a gap 4730 exists between the hemostasis stylet assembly 4600 and the introducer sheath 200, and catheter 4602 is exposed between the hemostasis stylet assembly 4600 and the introducer sheath 200. In some implementations, gap 4730 can be covered using a sterile layer or a sterile sleeve 4612. In order to keep the catheter 4602 sterile and use the hemostasis stylet assembly 4600 (or repositioning sheath), the portion of exposed catheter 4602 corresponding to gap 4730 is advantageously covered by sterile sleeve 4612. In this configuration, the sterile sleeve extends from the hemostasis stylet hub 4618 to the locking hub body 4606.

Figure 48:
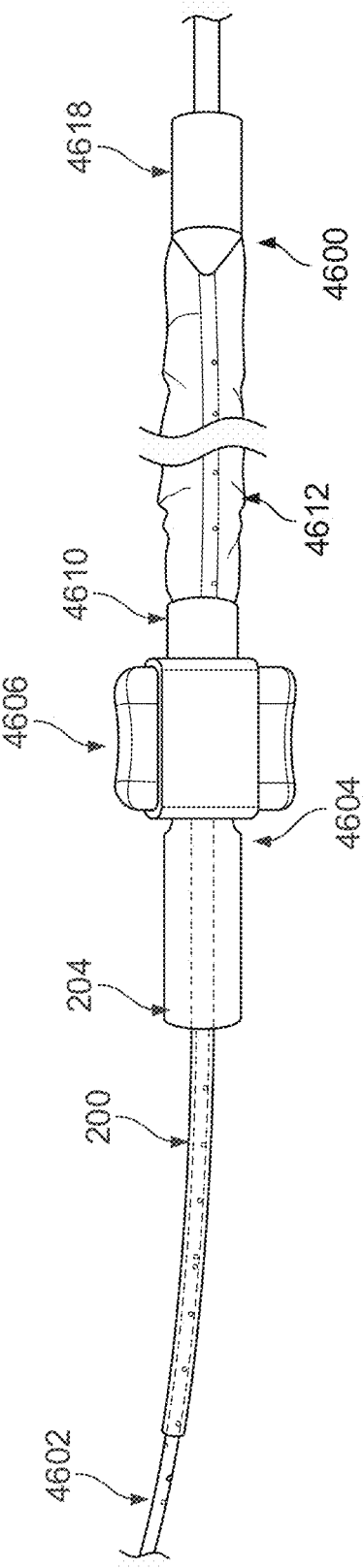
FIG. 48 shows an isometric view of an illustrative hemostasis stylet assembly.

Similar to FIG. 1B, FIG. 48 shows the hemostasis stylet assembly 4600 (as described in FIG. 46) connected to an introducer sheath 200 (as described in FIG. 2). The connection is achieved by locking hub 204 of the introducer sheath 200 to locking cap 4604 of the hemostasis stylet assembly 4600 and locking catheter 4602 to the introducer sheath 200. The locking mechanism between the locking hub 204 and the locking cap 4604 can be, for example, a twist lock, pop, or any comparable locking mechanisms. In some implementations, the locking mechanism between the hemostasis stylet assembly 4600 and the introducer sheath 200 can be different from the locking mechanism between the catheter 4602 and the introducer sheath 200. The proximal end of the sterile layer 4612 is connected to the distal end of the hemostasis stylet hub 4618. The distal end of the sterile layer 4612 is connected to the proximal end 4610 of the locking hub body 4606. As shown in FIG. 48, there is no exposed catheter between the hemostasis stylet assembly 4600 and the introducer sheath 200.

At least one advantage of integrating the hemostasis stylet assembly 4600 with the introducer sheath 200 is that the integration allows for titrated hemostasis at the opening of the blood vessel, e.g. arteriotomy. The diameter of the hemostasis stylet can be specifically chosen to fill the opening of the blood vessel so that distal blood flow is not sacrificed for hemostasis.

In one configuration, the hemostasis stylet assembly 4600 terminates within the body of the introducer sheath 200. In another configuration, the hemostasis valve distal end may terminate outside of the introducer sheath 200. The hemostasis valve may have a constant diameter. The hemostasis valve may have a constant diameter with a short taper at the distal tip. The hemostasis valve may have a long taper along its length. The hemostasis valve may have a first diameter at the distal end, a taper in the middle, and a second diameter at the proximal end with the first diameter smaller than the second diameter. The hemostasis valve may have a locking mechanism to attach the hemostasis stylet assembly 4600 to the introducer sheath hub 204. When the pump 502 is inserted through the expandable sheath body 202 the expanded section passes through and potentially stretches the opening of the blood vessel. If the vessel, e.g. artery cannot recover all of the expansion, the hemostasis stylet assembly 4600 will provide a means of filling the enlarged vessel opening to achieve hemostasis between the vessel and the expandable sheath body 202.

In view of the foregoing, the person of ordinary skill will appreciate that the present disclosure provides a means to fixate mechanical devices in place within an expandable sheath, thereby preventing the migration of the device once inserted into the heart. Medical devices of varying diameters may be used with a single expandable sheath.

The foregoing is merely illustrative of the principles of the disclosure, and the systems, methods, and devices can be practiced by other than the described embodiments, which are presented for purposes of illustration and not of limitation. It is to be understood that the systems, methods, and devices disclosed herein, while shown for use in a system for intracardiac heart pumps, may be applied to systems, methods, and devices for other implantable heart pumps or implantable cardiac assist devices.

Variations and modifications will occur to those of skill in the art after reviewing the present disclosure. The various features described or illustrated above, including any components thereof, may be combined or integrated in other systems. Moreover, certain features may be omitted or not implemented. The various implementations described or illustrated above may be combined in any manner.

Examples of changes, substitutions, and alterations are ascertainable by one skilled in the art and could be made without departing from the scope of the information disclosed herein. All references cited herein are incorporated by reference in their entirety and made part of this application.

ILLUSTRATIVE EMBODIMENTS

1. An introducer sheath for the insertion of a medical device into a blood vessel, the introducer sheath comprising:
   an expandable sheath frame having a length, a first thickness, a proximal end and a distal end;
   the frame comprising a plurality of strands extending longitudinally between the proximal end and the distal end, and having an exterior surface and an interior surface that form an interior lumen along the length of the frame;
   the frame being configured to achieve an expanded state and a contracted state, the expanded state forming an expanded cross-section in the lumen for passing a medical device therethrough; and the frame having a smooth coating about the exterior surface and protrusions extending into the lumen along the interior surface.

2. The introducer sheath of 1, further comprising a polymer layer covering an outer circumference of the frame and forming the smooth coating.

3. The introducer sheath of any of 1 and 2, wherein the expandable sheath frame comprises an expansion mechanism configured to allow the frame to expand and contract.

4. The introducer sheath of 3, wherein the expansion mechanism comprises the plurality of strands configured with a bias to expand or contract from a resting position.

5. The introducer sheath of any of 3 and 4, wherein the expansion mechanism is configured to permit the strands to slide relative to each other when the frame expands and contracts.

6. The introducer sheath of any of 1-5, wherein the plurality of strands comprise first and second overlapping strands, with the second strand extending radially inward from the first strand.

7. The introducer sheath of 6, wherein the second strand overlaps with the first strand and forms a plurality of peaks that project into the lumen.

8. The introducer sheath of any of 1-7, wherein the coating extends about the interior surface.

9. The introducer sheath of any of 1-8, wherein the coating covers the protrusions along the interior surface.

10. The introducer sheath of 9, wherein the coating covering the protrusions has a first thickness and the coating extending about the exterior surface has a second thickness.

11. The introducer sheath of 10, wherein the first thickness is less than the second thickness.

12. The introducer sheath of any of 6-11, wherein the first strand is bounded on an upper side by the smooth exterior surface coating.

13. The introducer sheath of any of 6-12, wherein the coating covers the second strand along a first longitudinal side of the second strand.

14. The introducer sheath of any of 6-13, wherein the coating covers an exterior-facing side of the first strand and an interior facing side of the second strand.

15. The introducer sheath of any of 1-14, wherein the frame comprises a braided mesh formed of a first plurality of strands.

16. The introducer sheath of 15, the first plurality of strands being wrapped in a spiral direction along the length.

17. The introducer sheath of any of 15 and 16, wherein the frame comprises a second plurality of strands.

18. The introducer sheath of 17, wherein the second plurality of strands are wrapped in a counter-clock-wise direction along the length.

19. The introducer sheath of any of 2-18, wherein a thickness of the polymer layer is less than a thickness of the protrusions extending into the lumen along the interior surface.

20. The introducer sheath of 19, wherein a thickness of the coating is less than the thickness of the polymer layer.

1. The introducer sheath of 19, wherein the thickness of the protrusions is less than a thickness of a strand of the first plurality of strands.

22. The introducer sheath of 21, wherein the thickness of the protrusions is less than about 75 or 100 μm.

23. The introducer sheath of any of 1-22, further comprising a sheath tip at the distal end of the expandable sheath frame, the sheath tip having a thickness, wherein the sheath tip thickness is greater than the thickness of the expandable sheath frame.

24. The introducer sheath of 23, wherein at least one of the frame, polymer layer and coating of the sheath tip is thicker than the frame, polymer layer and coating of the sheath.

25. The introducer sheath of any of 23 and 24, wherein the sheath tip is polymer.

26. The introducer sheath of 25, wherein the polymer is co-molded with the coating on the sheath frame.

27. The introducer sheath of any of 23-26, wherein the sheath tip is made of a first material and the expandable sheath is made of a second material different than the first material.

28. The introducer sheath of 27, wherein the first material has a different stiffness than the second material.

29. The introducer sheath of any of 23-28, wherein the distal tip of the sheath is stiffer than the proximal end of the sheath.

30. A dilator assembly for the insertion of a medical device into a blood vessel, the dilator assembly comprising:
an inner dilator having a first length, a lumen between proximal and distal ends of the inner dilator;
an outer dilator having a second length and a lumen between proximal and distal ends of the outer dilator, wherein the outer dilator is coaxial with the inner dilator and the first length is greater than the second length;
the outer dilator and the inner dilator are spaced apart radially by a circumferential gap having a gap thickness.

31. The dilator assembly of 30, wherein the inner dilator comprises:
a shaft extending through the lumen of the outer dilator; and
a distal tip forming a cavity about the distal end of the inner dilator.

32. The dilator assembly of 31, wherein the cavity has an inner wall, a closed end, and an open proximal end sized to receive the distal end of the outer dilator.

33. The dilator assembly of 32, wherein the inner wall has a diameter greater than the diameter of the inner dilator shaft.

34. The dilator assembly of 33, wherein the distal end of the outer dilator extends axially along the inner wall within the cavity to a position between the closed end and the open proximal end, forming a sheath tip receptacle.

35. The dilator assembly of any of 30-34, wherein the outer dilator comprises:
a proximal portion with a first diameter,
a distal portion with a second diameter, wherein the second diameter is smaller than the first diameter, and
a conical transition portion between the proximal portion and the distal portion.

36. The dilator assembly of 35, wherein the second diameter of the outer dilator is substantially equal to an outer diameter of a tip of the inner dilator 37. A sheath assembly comprising an introducer sheath according to any of 1-29, and a dilator assembly according to any of 30-36.

38. The sheath assembly of 37, wherein the inner dilator and outer dilator are configured to be inserted into the first lumen of the expandable sheath frame to adjust a diameter of the expandable sheath frame.

39. The sheath assembly of 38, wherein the head is bonded to the distal end of the dilator.

40. The sheath assembly of 39, wherein the second thickness is greater than the thickness of the sheath frame such that the sheath frame fits within the circumferential gap, the sheath tip fits within the sheath tip receptacle, and the second thickness is smaller than the thickness of the sheath tip such that the sheath tip is retained within the dilator tip.

41. A method of manufacturing an expandable introducer sheath, the method comprising:

priming a sheath frame using a priming solution, wherein the sheath frame is primed for adhesion to a polymer layer;

assembling the polymer layer over the sheath frame;

bonding the polymer layer and the sheath frame by exposing the polymer layer and the sheath frame to air for a duration of time, wherein the air is heated to a first temperature; and coating an inner surface of the polymer layer and the sheath frame with a lubricious material.

42. The method of 41, further comprising coating an outer surface of the polymer layer and the sheath frame with the lubricious material.

43. An introducer sheath for the insertion of a medical device into a blood vessel, the introducer sheath comprising:

an expandable sheath body having a first length, a longitudinal axis, and proximal and distal ends, the expandable sheath body comprising:

a braid forming a first lumen, the first lumen extending between the proximal and distal ends of the expandable sheath body, the first lumen having a first diameter in a first elongated state and a second diameter in a second relaxed state, wherein the second diameter in the second relaxed state is sized to accommodate the medical device, the braid formed of at least one strand of a first material extending from the proximal end of the expandable sheath body at an acute angle relative to the longitudinal axis of the expandable sheath body; and a polymer encapsulating at least a distal portion of the braid, wherein the polymer is configured to expand or collapse along with the braid, the acute angle and the first material selected to allow the medical device to pass through the expandable sheath body in the second relaxed state.

44. The introducer sheath of 43, wherein the braid comprises a first plurality of strands wrapped in a clockwise spiral direction along the first length and a second plurality of strands wrapped in a counter-clock-wise spiral direction along the first length.

45. The introducer sheath of 44, wherein the first plurality of strands and the second plurality of strands are radiopaque.

46. The introducer sheath of any of 44 and 45, wherein an angle between the first plurality of strands and the second plurality of strands is at about 35 degrees, 45 degrees, or 55 degrees.

47. The introducer sheath of any of 44-46, wherein the braid comprises a braid pattern defined by the first plurality of strands and the second plurality of strands.

48. The introducer sheath of 47, wherein the braid pattern defines rhombi, each rhombi comprising a first corner and a second corner adjacent the first corner.

49. The introducer sheath of 48, wherein at least one strand of the first plurality of strands goes over at least one strand of the second plurality of strands at the first corner and the at least one strand of the first plurality of strands goes over the at least one strand of the second plurality of strands at the second corner.

50. The introducer sheath of 48, wherein at least one strand of the first plurality of strands goes over at least one strand of the second plurality of strands at the first corner and the at least one strand of the first plurality of strands goes under the at least one strand of the second plurality of strands at the second corner.

51. The introducer sheath of any of 43-50, wherein the first material of the at least one strand comprises a metal.

52. The introducer sheath of any of 43-51, wherein the first material of the at least one strand comprises at least one of Nitinol round wire, Nitinol flat wire, Stainless steel round wire, stainless steel flat wire, liquid crystal polymer, polyimide, and polyether ether ketone (PEEK).

53. The introducer sheath of any of 43-52, wherein the polymer comprises one of silicone and thermoplastic polyurethane.

54. The introducer sheath of any of 43-53, further comprising a hub having a second length and a second lumen extending between proximal and distal ends of the hub, wherein the distal end of the hub is attached to the proximal end of the expandable sheath body and the second lumen of the hub is in communication with the first lumen of the sheath.

55. The introducer sheath of 54, wherein the hub further comprises a hemostasis valve within the second lumen, wherein the hemostasis valve is configured for insertion of a component.

56. The introducer sheath of any of 54 and 55, wherein the hub further comprises a side-arm that allows for flushing and aspiration of the introducer sheath.

57. The introducer sheath of any of 43-56, wherein the polymer encapsulates the entire braid.

58. The introducer sheath of any of 43-57, further comprising a hydrophilic material coating at least a portion of an inner surface of the polymer.

59. The introducer sheath of 58, wherein the hydrophilic material coats at least a portion of an outer surface of the polymer.

60. The introducer sheath of any of 43-59, wherein an inner surface of the polymer comprises a smooth surface and an outer surface of the polymer comprises at least one trough.

61. The introducer sheath of any of 43-60, wherein an inner surface of the polymer comprises at least one trough and an outer surface of the polymer comprises a smooth surface.

62. The introducer sheath of any of 43-61, wherein the proximal end of the expandable sheath body lies outside of a body of a patient.

63. The introducer sheath of any of 43-62, wherein the introducer sheath is configured for the insertion of a blood pump into a blood vessel.

64. The introducer sheath of any of 43-63, further comprising at the distal end of the expandable sheath body a distal portion of the first lumen shaped such that an inner diameter of the distal portion is different from that of the first lumen.

65. The introducer sheath of any of 43-64, further comprising at the distal end of the expandable sheath body a distal portion of the first lumen, the distal portion shaped to reversibly lock with a distal end of a dilator.

66. An introducer sheath for the insertion of a medical device into a blood vessel, the introducer sheath comprising:

an expandable sheath body having a first length, a longitudinal axis, and proximal and distal ends, the expandable sheath body comprising:

a braid forming a first lumen, the first lumen extending between the proximal and distal ends of the expandable sheath body, the first lumen having a first diameter in a first elongated state, a second diameter in a second relaxed state, and a third diameter in a third expanded state, wherein the first diameter in the first elongated state is sized to insert the expandable sheath body in the blood vessel, and wherein the third diameter in the third expanded state is sized to accommodate the medical device, the braid formed of at least one strand of a first material extending from the proximal end of the expandable sheath body at an acute angle relative to the longitudinal axis of the expandable sheath body; and a polymer encapsulating at least a distal portion of the braid, wherein the polymer is configured to expand or collapse along with the braid, the acute angle and the first material selected to allow the medical device to pass through the expandable sheath body in the third expanded state.

67. An introducer sheath for the insertion of a medical device into a blood vessel, the introducer sheath comprising:

an expandable sheath body having a first length, a longitudinal axis, and proximal and distal ends, the expandable sheath body comprising:

a braid forming a first lumen, the first lumen extending between the proximal and distal ends of the expandable sheath body, the first lumen having a first diameter in a first relaxed state and a second diameter in a second expanded state, wherein the second diameter in the second expanded state is sized to accommodate the medical device, the braid formed of at least one strand of a first material extending from the proximal end of the expandable sheath body at an acute angle relative to the longitudinal axis of the expandable sheath body; and a polymer encapsulating at least a distal portion of the braid, wherein the polymer can expand or collapse along with the braid, the acute angle and the first material selected to allow the medical device to pass through the expandable sheath body in the second expanded state.

68. A sheath assembly for the insertion of a medical device into a blood vessel, the sheath assembly comprising:

an introducer sheath comprising:

an expandable sheath body having a first length, a longitudinal axis, and proximal and distal ends, the expandable sheath body comprising:

a first lumen extending between the proximal and distal ends of the expandable sheath body, the first lumen having a first diameter in a first elongated state and a second diameter in a second relaxed state, wherein the second diameter in the second relaxed state is sized to accommodate the medical device;

a braid forming the first lumen, the braid formed of at least one strand of a first material extending from the proximal end of the expandable sheath body at an acute angle relative to the longitudinal axis of the expandable sheath body; and a polymer encapsulating at least a distal portion of the braid, wherein the polymer can expand or collapse along with the braid, the acute angle and the first material selected to allow the medical device to pass through the expandable sheath body without the expandable sheath body buckling; and a dilator assembly comprising:

an inner dilator having a second length and a second lumen between proximal and distal ends of the inner dilator;

an outer dilator having a third length and a third lumen between proximal and distal ends of the outer dilator, wherein the outer dilator is axially aligned with the inner dilator and the second length is greater than the third length, wherein the inner dilator and outer dilator are configured to be inserted into the first lumen of the expandable sheath body to adjust a diameter of the expandable sheath; and a hub attachment having a third length and a third lumen between proximal and distal ends of the hub attachment, wherein the hub attachment is axially aligned with the outer dilator and inner dilator and the outer dilator and inner dilator lie within the third lumen, wherein the distal end of the hub attachment is attached to a proximal end of the introducer sheath.

69. A sheath assembly for the insertion of a medical device into a blood vessel, the sheath assembly comprising:

an introducer sheath comprising:

an expandable sheath body having a first length, a longitudinal axis, and proximal and distal ends, the expandable sheath body comprising:

a first lumen extending between the proximal and distal ends of the expandable sheath body, the first lumen having a first diameter in a first elongated state and a second diameter in a second relaxed state, wherein the second diameter in the second relaxed state is sized to accommodate the medical device;

a braid forming the first lumen, the braid formed of at least one strand of a first material extending from the proximal end of the expandable sheath body at an acute angle relative to the longitudinal axis of the expandable sheath body; and a polymer encapsulating at least a distal portion of the braid, wherein the polymer can expand or collapse along with the braid, the acute angle and the first material selected to allow the medical device to pass through the expandable sheath body without the expandable sheath body buckling; and a hemostasis stylet assembly comprising:

a locking hub having distal and proximal ends, the distal end configured to attach to a proximal end of the introducer sheath;

a hemostasis stylet having distal and proximal ends, the hemostasis stylet comprising:

a hemostasis stylet body having distal and proximal ends, wherein the distal end of the hemostasis stylet body is configured to be inserted into an expandable sheath of the introducer assembly in order to control hemostasis between the expandable sheath and an opening of a blood vessel; and a first sterile layer having a first length and a first lumen between distal and proximal ends of the first sterile layer, wherein the proximal end of the first sterile layer is attached to the distal end of the locking hub of the hemostasis stylet; and a second sterile layer having a second length and a second lumen between distal and proximal ends of the second sterile layer, wherein the distal end of the second sterile layer is attached to the proximal end of the locking hub of the hemostasis stylet.

70. The introducer sheath of 69, wherein the sheath assembly further comprises:

a hub having a lumen between distal and proximal ends of the hub, wherein the hemostasis stylet body is attached to the proximal end of the hemostasis stylet hub.

71. A sheath assembly for the insertion of a medical device into a blood vessel, the sheath assembly comprising:

an introducer sheath comprising:

an expandable sheath body having a first length, a longitudinal axis, and proximal and distal ends, the expandable sheath body comprising:

a first lumen extending between the proximal and distal ends of the expandable sheath body, the first lumen having a first diameter in a first elongated state and a second diameter in a second relaxed state, wherein the second diameter in the second relaxed state is sized to accommodate the medical device;

a braid forming the first lumen, the braid formed of at least one strand of a first material extending from the proximal end of the expandable sheath body at an acute angle relative to the longitudinal axis of the expandable sheath body; and a polymer encapsulating at least a distal portion of the braid, wherein the polymer can expand or collapse along with the braid, the acute angle and the first material selected to allow the medical device to pass through the expandable sheath body without the expandable sheath body buckling; and a dilator assembly comprising:

an inner dilator having a second length and a second lumen between proximal and distal ends of the inner dilator;

an outer dilator having a third length and a third lumen between proximal and distal ends of the outer dilator, wherein the outer dilator is axially aligned with the inner dilator and the second length is greater than the third length, wherein the inner dilator and outer dilator are configured to be inserted into the first lumen of the expandable sheath body to adjust a diameter of the expandable sheath; and a hub attachment having a third length and a third lumen between proximal and distal ends of the hub attachment, wherein the hub attachment is axially aligned with the outer dilator and the outer dilator lies within the third lumen, wherein the distal end of the hub attachment is attached to a proximal end of the introducer sheath; and a hemostasis stylet assembly comprising:

a locking hub having distal and proximal ends, the distal end configured to attach to a proximal end of the introducer sheath;

a hemostasis stylet having distal and proximal ends, the hemostasis stylet comprising:

a hemostasis stylet hub having a lumen between distal and proximal ends of the hemostasis stylet hub, wherein a first sterile layer and a hemostasis stylet body are attached to the distal end of the hemostasis stylet hub and a second sterile layer is attached to the proximal end of the hemostasis stylet hub; and the hemostasis stylet body having distal and proximal ends, wherein the distal end of the hemostasis stylet body is configured to be inserted into an expandable sheath of the introducer assembly in order to control hemostasis between the expandable sheath and an opening of a blood vessel; and the first sterile layer having a first length and a first lumen between distal and proximal ends of the first sterile layer, wherein the distal end of the first sterile layer is attached to the locking hub; and a second sterile layer having a second length and a second lumen between distal and proximal ends of the second sterile layer.

72. A method of inserting a pump into a blood vessel, the method comprising:

attaching an introducer assembly to a dilator assembly, the introducer assembly comprising an expandable sheath having a first diameter and a first length;

moving the dilator assembly with respect to the introducer assembly in the proximal direction, wherein the expandable sheath of the introducer assembly transitions to a second diameter and a second length, wherein the second diameter is smaller than the first diameter and the second length is greater than the first length;

inserting the introducer assembly and the dilator assembly into a desired location in a blood vessel, wherein an opening of the blood vessel expands to accommodate the second diameter of the expandable sheath;

moving the dilator assembly with respect to the introducer assembly in the distal direction, wherein the expandable sheath of the introducer assembly expands to a third diameter and a third length, wherein the third diameter is greater than the second diameter and the third length is smaller than the second length, wherein the opening of the blood vessel expands to accommodate the third diameter of the expandable sheath;

detaching the dilator assembly from the introducer assembly and removing the dilator assembly from the desired location in the blood vessel;

inserting a pump through the introducer assembly, wherein the expandable sheath expands to a fourth diameter to accommodate the pump as the pump traverses within the introducer assembly, wherein the fourth diameter is greater than the third diameter and the opening of the blood vessel expands to accommodate the fourth diameter of the expandable sheath; and inserting a hemostasis stylet through the introducer assembly, wherein the expandable sheath expands to the fourth diameter sized to accommodate the hemostasis stylet as the hemostasis stylet traverses within the introducer assembly, wherein the fifth diameter is selected to facilitate hemostasis between the opening of the blood vessel and the expandable sheath.

73. A blood pump system, the blood pump system comprising:

a blood pump coupled to a catheter having proximal and distal ends;

an introducer sheath, wherein the introducer sheath is sized to accommodate the blood pump during insertion into the blood vessel; and a repositioning sheath assembly comprising:

a repositioning sheath;

a first sterile sleeve having a first length and a first lumen between distal and proximal ends of the first sterile sleeve, wherein the distal end of the first sterile sleeve is attached to the proximal end of the repositioning sheath;

the repositioning sheath having distal and proximal ends, wherein the distal end of the repositioning sheath is configured to be inserted into the introducer sheath in order to control hemostasis between the introducer sheath and an opening of the blood vessel;

a second sterile sleeve having a second length and a second lumen between distal and proximal ends of the second sterile sleeve, wherein the proximal end of the second sterile sleeve is attached to the proximal end of the repositioning sheath, and the distal end of the second sterile sleeve is attached to a proximal end of the introducer sheath.

74. The blood pump system of 73 further comprising the introducer sheath of any of 1-67.

75. The blood pump system of any of 73 and 74, wherein the first sterile sleeve and the second sterile sleeve are flexible.

76. The blood pump system of any of 73-75, wherein the first sterile sleeve comprises a first plurality of flexible layers and the second sterile sleeve comprises a second plurality of flexible layers.

77. The blood pump system of 73-76, wherein the first and second plurality of flexible layers comprises a flexible material.

78. The blood pump system of any of 73-77, wherein the catheter extends through: the first sterile sleeve, the repositioning sheath, the second sterile sleeve, and the introducer sheath.

79. The blood pump system of 78, wherein the catheter extends slideably through the first sterile sleeve and the second sterile sleeve.

80. The blood pump system of any of 78 and 79, wherein the repositioning sheath is configured to move relative to the catheter.

81. The blood pump system of 80, wherein at least one of the first and second sterile sleeves is configured to be reduced in length when the repositioning sheath is configured to move relative to the catheter.

82. The blood pump system of any of 73-81, wherein the introducer sheath comprises:

an expandable sheath frame having a length, a first thickness, a proximal end and a distal end;

the frame comprising a plurality of strands extending longitudinally between the proximal end and the distal end, and having an exterior surface and an interior surface that form an interior lumen along the length of the frame;

the frame being configured to achieve an expanded state and a contracted state, the expanded state forming an expanded cross-section in the lumen for passing a medical device therethrough; and the frame having a smooth coating about the exterior surface and protrusions extending into the lumen along the interior surface.

The invention claimed is:

1. An introducer sheath for insertion of a medical device into a blood vessel, the introducer sheath comprising:

an expandable sheath frame having a length, a proximal end, and a distal end, the frame comprising a plurality of strands extending longitudinally between the proximal end and the distal end, and having an exterior and an interior that form an interior lumen along the length of the frame, the frame being configured to achieve an expanded state and a contracted state, the expanded state forming an expanded cross-section in the lumen for passing the medical device therethrough; and a coating that forms a smooth exterior surface on the frame, wherein the frame has protrusions extending into the lumen along the interior, wherein the plurality of strands comprise first and second overlapping strands, wherein, at an overlap, one of the first or second overlapping strands extends radially inward from the other of the first or second overlapping strands toward the interior of the frame.

2. The introducer sheath of claim 1, wherein the coating is a polymer layer covering an outer circumference of the frame and forming the smooth exterior surface.

3. The introducer sheath of claim 1, wherein the expandable sheath frame comprises an expansion mechanism configured to allow the frame to expand and contract.

4. The introducer sheath of claim 3, wherein the expansion mechanism comprises the plurality of strands configured with a bias to expand or contract from a resting position.

5. The introducer sheath of claim 4, wherein the expansion mechanism is configured to permit the strands to slide relative to each other when the frame expands and contracts.

6. The introducer sheath of claim 1, wherein at an overlap, the coating covers an exterior-facing side of one of the first overlapping strand or the second overlapping strand and an interior-facing side of the other of the first overlapping strand or the second overlapping strand.

7. The introducer sheath of claim 1, wherein one of the first overlapping strand and the second overlapping strand overlaps with the other of the first overlapping strand or the second overlapping strand to form the protrusions that project into the lumen.

8. The introducer sheath of claim 1, wherein the coating extends about the interior.

9. The introducer sheath of claim 1, wherein the coating covers the protrusions along the interior.

10. The introducer sheath of claim 9, wherein, in a region that the coating covers the protrusions, the coating has a first thickness, and, in a region that the coating extends about the exterior, the coating has a second thickness.

11. The introducer sheath of claim 10, wherein the first thickness is less than the second thickness.

12. The introducer sheath of claim 1, wherein the frame comprises a braided mesh formed of the plurality of strands.

13. The introducer sheath of claim 12, wherein the plurality of strands comprises a first group of strands that are wrapped in a spiral direction along the length.

14. The introducer sheath of claim 13, wherein the plurality of strands comprises a second group of strands.

15. The introducer sheath of claim 2, wherein a thickness of the polymer layer is less than a thickness of the protrusions extending into the lumen along the interior.

16. The introducer sheath of claim 15, wherein the thickness of the protrusions is less than a thickness of a strand of the plurality of strands.

17. The introducer sheath of claim 1, further comprising a sheath tip at the distal end of the expandable sheath frame, the sheath tip having a thickness, wherein the sheath tip thickness is greater than a thickness of the expandable sheath frame.

18. The introducer sheath of claim 17, wherein the sheath tip is made of a first material and the expandable sheath is made of a second material different than the first material.

19. The introducer sheath of claim 17, wherein the distal tip of the sheath is stiffer than the proximal end of the sheath.

\* \* \* \* \*